United States Patent
Dimitrov et al.

(10) Patent No.: US 9,556,254 B2
(45) Date of Patent: Jan. 31, 2017

(54) CROSS-REACTIVE ANTIBODIES AGAINST DENGUE VIRUS AND USES THEREOF

(71) Applicant: The USA, as represented by the Secretary, Dept. of Health and Human Services, Washington, DC (US)

(72) Inventors: Dimiter S. Dimitrov, Frederick, MD (US); Zhongyu Zhu, Frederick, MD (US)

(*) Notice: Subject to any disclaimer, the term of this patent is extended or adjusted under 35 U.S.C. 154(b) by 33 days.

(21) Appl. No.: 14/400,642

(22) PCT Filed: May 14, 2013

(86) PCT No.: PCT/US2013/040966
§ 371 (c)(1),
(2) Date: Nov. 12, 2014

(87) PCT Pub. No.: WO2013/173348
PCT Pub. Date: Nov. 21, 2013

(65) Prior Publication Data
US 2015/0218255 A1    Aug. 6, 2015

Related U.S. Application Data

(60) Provisional application No. 61/646,638, filed on May 14, 2012.

(51) Int. Cl.
| | | |
|---|---|---|
| C07K 16/10 | (2006.01) |
| A61K 39/12 | (2006.01) |
| G01N 33/569 | (2006.01) |
| C07K 14/005 | (2006.01) |
| C07K 16/46 | (2006.01) |

(52) U.S. Cl.
CPC ............ *C07K 16/10* (2013.01); *C07K 14/005* (2013.01); *C07K 16/1081* (2013.01); *C07K 16/468* (2013.01); *G01N 33/56983* (2013.01); *C07K 2317/21* (2013.01); *C07K 2317/31* (2013.01); *C07K 2317/33* (2013.01); *C07K 2317/34* (2013.01); *C07K 2317/35* (2013.01); *C07K 2317/55* (2013.01); *C07K 2317/565* (2013.01); *C07K 2317/622* (2013.01); *C07K 2317/76* (2013.01); *C07K 2317/92* (2013.01); *C12N 2770/24122* (2013.01); *G01N 2333/185* (2013.01); *G01N 2469/10* (2013.01)

(58) Field of Classification Search
None
See application file for complete search history.

(56) References Cited

FOREIGN PATENT DOCUMENTS

WO    WO2010/043977 A2    4/2010

OTHER PUBLICATIONS

Rudikoff et al., PNAS USA, 1982, 79(6):1979-1983.*
MacCallum et al., J. Mol. Biol., 1996, 262(5):732-745.*
De Pascalis et al., The Journal of Immunology, 2002, 169(6):3076-3084.*
Casset et al., BBRC, 2003, 307:198-205.*
Sirivichayakul et al., Virology Journal, 2014, 11:48, 5 pages.*
Zompi and Harris, Viruses, Jan. 2012, 4(1):62-82.*
Beltramello Martina et al: "The Human Immune Response to Dengue Virus is Dominated by Highly Cross-Reactive Antibodies Endowed with Neutralizing and Enhancing Activity", Cell Host & Microbe, vol. 8, No. 3, Sep. 2010 (Sep. 2010), pp. 271,283, XP002700673.
Fischer Nicolas et al: "Bispecific antibodies: Molecules that enable novel therapeutic strategies", Pathobiology, Karger, Basel, CH, vol. 74, No. 1, May 1, 2007 (May 1, 2007), pp. 3-14.
Batra G et al: "Evaluation of envelope domain III-based single chimeric tetravalent antigen and monovalent antigen mixtures for the detection of anti-dengue antibodies in human sera", BMC Infectious Diseases Mar. 15, 2011 Biomed Central Ltd. GBR, vol. 11, Mar. 15, 2011 (Mar. 15, 2011), XP002700674.
Chen Shuiping et al: "Induction of tetravalent protective immunity against four dengue serotypes by the tandem domain III of the envelope protein", DNA and Cell Biology, vol. 26, No. 6, Jun. 2007 (Jun. 2007), pp. 361-367, XP002700675.
International Search Report prepared by the European Patent Office on Jul. 10, 2013, for International Application No. PCT/US2013/040966.
Written Opinion prepared by the European Patent Office on Jul. 10, 2013, for International Application No. PCT/US2013/040966.

* cited by examiner

*Primary Examiner* — Stacy B Chen
(74) *Attorney, Agent, or Firm* — Sheridan Ross P.C.

(57) ABSTRACT

The invention relates to a human anti-dengue virus antibody (an anti-DENV antibody) that binds to a DENV envelope protein and is cross-reactive with DENV serotype 1, DENV serotype 2, DENV serotype 3, and DENV serotype 4. The disclosure provides an anti-DENV antibody that cross-reacts with and neutralizes all four DENV serotypes. Also provided is a nucleic acid molecule that encodes such an anti-DENV antibody. Also provided is a method to produce and use such an antibody or nucleic acid molecule encoding such an antibody.

10 Claims, 11 Drawing Sheets

```
m366-VH     QLQLQESGGGLVQPGGSLRLSCAASGFTFSSYSMNWVRQAPGKRLEWVSSISGSSSYIYYADSVKGRFTIS
IGHV3-21*01 EV...V....K.................................G........S..............
                     10        20        30        40        50        60        70
                                                               a m366-VH     RDNAKNSLYLQMDSLRAEDTAVYYCARYAAGIWTEDIWGQGTTVTVSS
IGHV3-21*01 .........S..N..................
IGHD6-13*01 ------------------------
IGHJ3*02    ----------------------.........
                     80        90        100       110
                      abc                        ab
```

FIG.1A

```
m366-VL     SYELTQPPSVSVAPGKTASISCGGDNIGRKSVHWFQQKPGQAPVLVLYDDSDRPSGIPARFSGSNSGNT
IGLV3-21*01 ..V................R.T..N...S........Y.........I.Y........E........
                     10        20        30        40        50        60        70 m366-VL     ATLTISRVEAGDEADYYCQVWARSSDHPNWVFGGGTKLTVLG
IGLV3-21*01 .........................DS--............
IGLJ3*02    ----------------------------..............
```

FIG.1B

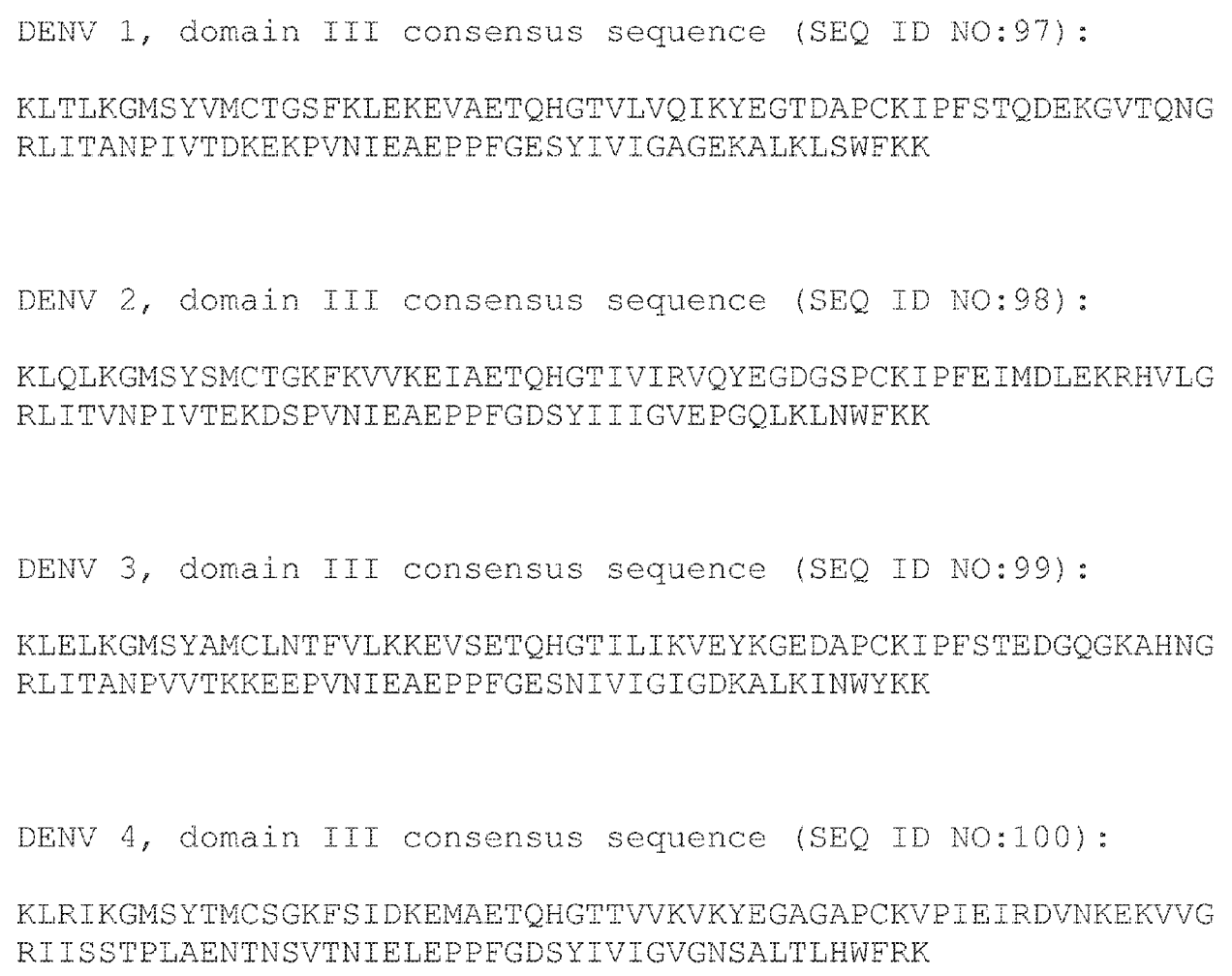

DENV 1, domain III consensus sequence (SEQ ID NO:97):

KLTLKGMSYVMCTGSFKLEKEVAETQHGTVLVQIKYEGTDAPCKIPFSTQDEKGVTQNG
RLITANPIVTDKEKPVNIEAEPPFGESYIVIGAGEKALKLSWFKK

DENV 2, domain III consensus sequence (SEQ ID NO:98):

KLQLKGMSYSMCTGKFKVVKEIAETQHGTIVIRVQYEGDGSPCKIPFEIMDLEKRHVLG
RLITVNPIVTEKDSPVNIEAEPPFGDSYIIIGVEPGQLKLNWFKK

DENV 3, domain III consensus sequence (SEQ ID NO:99):

KLELKGMSYAMCLNTFVLKKEVSETQHGTILIKVEYKGEDAPCKIPFSTEDGQGKAHNG
RLITANPVVTKKEEPVNIEAEPPFGESNIVIGIGDKALKINWYKK

DENV 4, domain III consensus sequence (SEQ ID NO:100):

KLRIKGMSYTMCSGKFSIDKEMAETQHGTTVVKVKYEGAGAPCKVPIEIRDVNKEKVVG
RIISSTPLAENTNSVTNIELEPPFGDSYIVIGVGNSALTLHWFRK

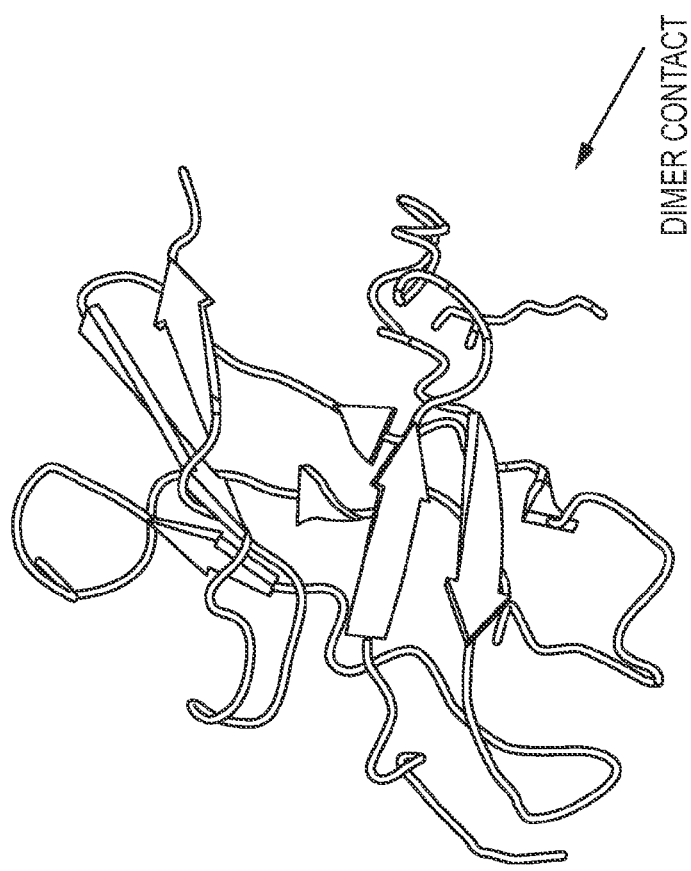
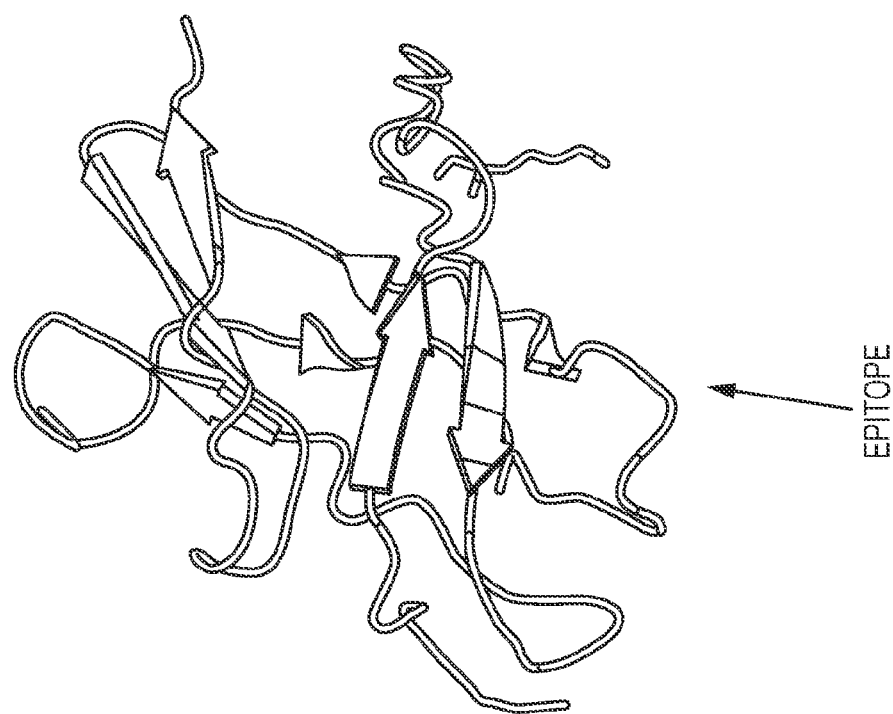
FIG. 7

Sequence comparison of m366VH and mouse mAb 9F12 VH

```
                                              CDR1                              CDR2
9F12VH  ----LQQSGAELVRPGASVKLSCKALGYRFTDYEMYWVKQTPAHGLEWIGGIHPRSGNTAY     57
m366VH  QLQLQESGGGLVQPGGSLRLSCAASGFTFSSYSMNWVRQAPGKRLEWVSSISGSSSYIYY      60
         * **.** ****..*.** ***:* *:***.*:*. :** * :***:.. *.* ::*
                                              CDR3
9F12VH  NQKFKDKATLTADKSSTAYMELSSLTSEDSVVYYCT------TSLYWGQGTTVTVSS         109
m366VH  ADSVKGRFTISRDNAKNSLYLQMDSLRAEDTAVYYCARYAAGIWTEDIWGQGTTVTVSS      119
         :.:*.:::*:::*:.:: *: ::* *:* :****     .*  ************
```

Sequence comparison of m366VL and mouse mAb 9F12 VL

```
                                              CDR1                              CDR2
9F12VL  -------LGDQASISCRSSQSLVHSNGNTYLHWYLQKPGQSPKLLIYSIENRFSGVPDR       52
m366VL  SYELTQPPSVSVAPGKTASISCGGDNIGRKSVHWFQQKPGQAPVLVLYDDSDRPSGIPAR      60
               .*.*: *.:*****..:.:.. ..*:* :*****.*:*:*..:: * :* *
                                              CDR3
9F12VL  FSGSGSGTDFTLKISRVEAEDLGVYFCS------QGTHVPWTFGGGTNLEIKR              99
m366VL  FSGSNSGNTATLTISRVEAGDEADYYCQVWARSSDHPNWVFGGGTKLTVLG                111
         ****.**..:* *******.*  *.*     .   : *.******.*  :
```

FIG. 8

CROSS-REACTIVE ANTIBODIES AGAINST DENGUE VIRUS AND USES THEREOF

CROSS REFERENCE TO RELATED APPLICATIONS

This application is a national stage application under 35 U.S.C. 371 and claims the benefit of PCT Application No. PCT/US2013/040966 having an international filing date of May 14, 2013, which designated the United States, which PCT application claimed the benefit of U.S. Provisional Application No. 61/646,638 filed May 14, 2012, the disclosure of both the above-identified applications are incorporated herein by reference.

REFERENCE TO SEQUENCE LISTING

This application contains a Sequence Listing submitted as an electronic text file named "6137NCI-32-PCT_Sequence_Listing_ST25.txt", having a size in bytes of 115KB, and created on May 14, 2013. The information contained in this electronic file is hereby incorporated by reference in its entirety pursuant to 37 CFR §1.52(e)(5).

FIELD

The invention relates to an antibody against Dengue virus. Such antibody is a human antibody that cross-reacts with all four serotypes of Dengue virus.

BACKGROUND/INTRODUCTION

Dengue virus (DENV) causes the most prevalent mosquito-borne viral disease: over 2.5 billion people are at risk for infection in over 100 countries. Each year, dengue virus infects and exhibits symptoms in about 100 million people worldwide. Of those infected, about 250,000-500,000 develop severe illness, and up to 50,000 die from dengue hemorrhagic fever (DHF) each year (see, e.g., Dengue and dengue hemorrhagic fever, World Health Organization Media center, Fact Sheet No. 117, March 2009; Deen J L et al., 2006, Lancet 368, 170-173; Kyle J L et al., 2008, Annu Rev Microbiol 62, 71-92). In 2010, dengue virus re-entered the US via the Florida Keys, after an absence of sixty-five years (see, e.g., Homeland Security News Wire, 2 Jun. 2010).

There are four closely related, but antigenically distinct, dengue virus serotypes, namely DENV serotype 1 (DENV-1), DENV serotype 2 (DENV-2), DENV serotype 3(DENV-3), and DENV serotype 4 (DENV-4). Each serotype comprises several genotypes that exhibit differences in their infection characteristics in both the mosquito vector and the human host. Recovery from infection by one serotype provides lifelong immunity against that serotype, but confers only partial and transient protection against subsequent infection by other serotypes. One of the confounding problems that has faced vaccine development for decades has been this inability of one serotype to protect against infection by another. Rather, the induced humoral immune response to one DENV serotype as a result of infection can enhance the infection and disease processes brought about by a subsequent infection with another DENV serotype. Such subsequent infection is thought to increase the risk of developing dengue hemorrhagic fever (DHV), a potentially lethal condition. (see, e.g., WHO Fact Sheet No. 117, ibid.; Halstead S B et al., 2007, Lancet 370, 1644-1652; Dejnirattisai W, et al., 2010, Science 328, 745-748.)

Dengue virus is a single positive-stranded RNA virus of the Flaviviridae, genus *Flavivirus*. The viral genome of about 10.7 kilobases is translated as a single polypeptide that is cleaved into three structural proteins (namely a capsid protein (C), a membrane protein (M, prM/M), and an envelope protein (E)), and seven non-structural proteins (namely NS1, NS2a, NS2b, NS3, NS4a, NS4b, and NS5).

The initial step of dengue virus infection is entry of the virus into cells; such entry is mediated by DENV envelope E, a glycoprotein (see, e.g., Dimitrov D S, 2004, Nat. Rev. Microbiol. 2, 109-122). DENV E is a type II fusion protein and consists of three domains (see, e.g., Dimitrov D S, ibid.; Kuhn R J et al., 2002, Cell 108, 717-725). The domains are named ED1, ED2, and ED3, respectively; other names for the envelope domains are domain I (DI), domain II (DII), and domain III (DIII, or Env-DIII), respectively. ED3 has been proposed to contain a receptor binding domain (Huerta V et al., 2008, Virus Res 137, 225-234; Crill W D et al., 2001, J Virol 75, 7769-7773).

Antibodies are important for protective and pathogenic immune responses to dengue virus (see, e.g., Halstead et al., ibid.). Their major target is the DENV E protein (see, e.g., Marasco W A et al., 2007, Nat Biotechnol 25, 1421-1434; Modis Y et al., 2005, J Virol 79, 1223-1231; Roehrig J T et al., 1998, Virology 246, 317-328; Bedouelle H et al., 2006, FEBS J 273, 34-46; Thullier P et al., 2001, J Gen Virol 82, 1885-1892). The amino acid sequences of E proteins for DENV-1, DENV-2, DENV-3, and DENV-4 differ by 25% to 40%; the amino acid sequences of E proteins for genotypes within a DENV serotype vary by up to 3% (see, e.g., Holmes E C et al., 2003, Infect Genet Evol 3, 19-28). Antibodies against ED3 are both serotype specific and cross-reactive; such antibodies are effective DENV neutralizers, typically better than antibodies against ED1 or ED2 (see, e.g., de Alwis R, et al., 2011, PLoS Negl Trop Dis 5, e1188; Balsitis S J, et al., 2010, PLoS Pathog 6, e1000790; Beltramello M et al., 2010, Cell Host Microbe 8, 271-283; Sukupolvi-Petty S et al., 2010, J Virol 84, 9227-9239; Shrestha B et al., 2010, PLoS Pathog 6, e1000823; Rajamanonmani R et al., 2009, J Gen Virol 90, 799-809; Sukupolvi-Petty S et al., 2007, J Virol 81, 12816-12826; Gromowski G D et al., 2010, Virology 407, 237-246; Matsui K et al., 2010, J Gen Virol 91, 2249-2253; Matsui K et al., 2009, Virology 384, 16-20; Gromowski G D et al., 2008, J Virol 82, 8828-8837; Gromowski G D et al., 2007, Virology 366, 349-360; Hiramatsu K et al., 1996, Virology 224, 437-445; Lok S M et al., 2008, Nat Struct Mol Biol 15, 312-317). The cross-reactive antibodies are generally weaker neutralizers than the serotype-specific antibodies (see, e.g., Sukupolvi-Petty S et al, 2007, ibid.; Gromowski G D et al., 2008, ibid.). Anti-ED3 serotype-specific and cross-reactive antibodies are elicited using ED3 as a vaccine immunogen (see, e.g., Guzman M G et al., 2010, Vaccines 9, 137-147; Bernardo L et al., 2011, Vaccine 29, 4256-4263; Bernardo L et al., 2009, Clin Vaccine Immunol 16, 1829-1831; Izquierdo A et al., 2008, Virus Res 138, 135-138; Simmons M et al., 1998, Am J Trop Med Hyg 58, 655-662; Simmons M et al., 2001, Am J Trop Med Hyg 65, 159-161; Srivastava A K et al., 1995, Vaccine 13, 1251-1258) and in infected humans (see, e.g., de Alwis R et al., ibid.; Midgley C M, 2011, J. Virol. 85, 410-421; Rothman A L, 2004, J. Clin. Invest. 113, 946-951; Wahala, W M et al., 2009, Virology 392, 103-113). Recently, several human monoclonal antibodies were selected from immortalized B cells obtained from DENV-infected people, a few of which also exhibited some cross-reactive neutralizing activity against all four serotypes; a cocktail of three of antibodies targeting distinct epitopes and engineered to prevent FcγR binding was successful in a mouse model of disease when administered one day after challenge (Beltramello M et al, 2010, ibid.).

There remains a need for an effective therapeutic, an effective prophylactic, or an effective therapeutic and prophylactic against dengue virus infection, not only to protect an individual from an initial infection, but also to protect that individual from subsequent infection not only by the same DENV serotype but also by any and all other DENV serotypes. As such, there is a need for an anti-DENV antibody that cross-reacts with and neutralizes DENV-1, DENV-2, DENV-3, and DENV-4 dengue virus serotypes. There is also a need for a vaccine that comprises an epitope recognized by such a cross-reactive anti-DENV antibody to protect an individual from dengue virus infection.

SUMMARY

The present disclosure provides a human anti-dengue virus antibody (an anti-DENV antibody) that (a) binds to a DENV envelope protein and (b) is cross-reactive with DENV serotype 1, DENV serotype 2, DENV serotype 3, and DENV serotype 4. In one embodiment, such an anti-DENV antibody neutralizes DENV serotype 1, DENV serotype 2, DENV serotype 3, and DENV serotype 4. Also provided is a nucleic acid molecule that encodes such an anti-DENV antibody. Also provided is a method to produce and use such an antibody or a nucleic acid molecule encoding such an antibody. The present disclosure further provides a protein comprising an epitope that binds to an anti-DENV antibody that (a) binds to a DENV envelope protein and (b) cross-reacts with DENV serotype 1, DENV serotype 2, DENV serotype 3, and DENV serotype 4. Also provided is a nucleic acid molecule that encodes such a protein. Also provided is a method to produce and use such a protein or a nucleic acid molecule encoding such a protein.

The disclosure provides a human anti-dengue virus antibody that binds to domain III of an envelope protein of dengue virus, wherein the antibody is cross-reactive with domain III of dengue virus (DENV) serotype 1 envelope protein, domain III of DENV serotype 2 envelope protein, domain III of DENV serotype 3 envelope protein, and domain III of DENV serotype 4 envelope protein. In some embodiments the antibody does not enhance Dengue virus infection.

The disclosure also provides a human anti-dengue virus bispecific antibody that comprises two antibodies each of which binds to domain III of an envelope protein of dengue virus and at least one of which is cross-reactive with domain III of dengue virus (DENV) serotype 1 envelope protein, domain III of DENV serotype 2 envelope protein, domain III of DENV serotype 3 envelope protein, and domain III of DENV serotype 4 envelope protein. In some embodiments, both antibodies are cross-reactive with domain III of dengue virus (DENV) serotype 1 envelope protein, domain III of DENV serotype 2 envelope protein, domain III of DENV serotype 3 envelope protein, and domain III of DENV serotype 4 envelope protein. In some embodiments, the bispecific antibody does not enhance Dengue virus infection.

The disclosure also provides a human anti-dengue virus antibody that binds to domain III of an envelope protein of dengue virus, wherein the antibody is cross-reactive with domain III of dengue virus (DENV) serotype 1 envelope protein, domain III of DENV serotype 2 envelope protein, domain III of DENV serotype 3 envelope protein, and domain III of DENV serotype 4 envelope protein, and wherein the antibody is selected from the group consisting of: an antibody comprising a complementarity determining region (CDR) having an amino acid sequence selected from the group consisting of amino acid sequences SEQ ID NO:8, SEQ ID NO:10, SEQ ID NO:12, SEQ ID NO:14, SEQ ID NO:16, SEQ ID NO:18, and combinations thereof; an antibody comprising a complementarity determining region (CDR) having an amino acid sequence selected from the group consisting of amino acid sequences SEQ ID NO:28, SEQ ID NO:30, SEQ ID NO:32, SEQ ID NO:34, SEQ ID NO:36, SEQ ID NO:38, and combinations thereof; and an antibody comprising a complementarity determining region (CDR) having an amino acid sequence selected from the group consisting of amino acid sequences SEQ ID NO:48, SEQ ID NO:50, SEQ ID NO:52, SEQ ID NO:54, SEQ ID NO:56, SEQ ID NO:58, and combinations thereof.

The disclosure also provides a human anti-dengue virus antibody that binds to domain III of an envelope protein of dengue virus, wherein the antibody is cross-reactive with domain III of dengue virus (DENV) serotype 1 envelope protein, domain III of DENV serotype 2 envelope protein, domain III of DENV serotype 3 envelope protein, and domain III of DENV serotype 4 envelope protein, and wherein the antibody comprises a CDR-H3 having an amino acid sequence selected from the group consisting of SEQ ID NO:12, SEQ ID NO:32, and SEQ ID NO:52.

In some embodiments, the antibody neutralizes DENV serotype 1, DENV serotype 2, DENV serotype 3, and DENV serotype 4.

In some embodiments, the antibody binds to each of DENV serotype 1, DENV serotype 2, DENV serotype 3, and DENV serotype 4 envelope proteins with a dissociation constant ($K_D$) of no more than about 40 nanomolar (nM).

In some embodiments, such an antibody binds to each of DENV serotype 1, DENV serotype 2, DENV serotype 3, and DENV serotype 4 envelope proteins with a $K_D$ of no more than about 20 nM.

In some embodiments, such an antibody binds to each of DENV serotype 1, DENV serotype 2, DENV serotype 3, and DENV serotype 4 envelope proteins with a $K_D$ of no more than about 1 nM.

In some embodiments, such an antibody binds to each of three DENV serotypes with a $K_D$ of no more than about 1 nM and binds to the fourth DENV serotype with a $K_D$ of no more than about 40 nM.

In some embodiments, such an antibody neutralizes each of DENV serotype 1, DENV serotype 2, DENV serotype 3, and DENV serotype 4 at an $IC_{50}$ of less than about 25 micrograms per ml (µg/ml).

In some embodiments, such an antibody neutralizes each of DENV serotype 1, DENV serotype 2, DENV serotype 3, and DENV serotype 4 at an $IC_{50}$ of less than about 1 µg/ml.

In some embodiments, such an antibody binds to each of DENV serotype 1, DENV serotype 2, DENV serotype 3, and DENV serotype 4 envelope proteins with a $K_D$ of no more than about 1 nM, and wherein the antibody neutralizes each of DENV serotype 1, DENV serotype 2, DENV serotype 3, and DENV serotype 4 at an $IC_{50}$ of less than about 1µg/ml.

In some embodiments, such an antibody is of an isotype selected from the group consisting of IgG, IgM, and IgA.

In some embodiments, such an antibody is not isolated from a human subject.

In some embodiments, such an antibody is selected from the group consisting of a full length Ig antibody, a full-length soluble antibody, a monospecific antibody, a bispecific antibody, a multi-specific antibody, a Fab fragment, a F(ab')$_2$ fragment, a scFv, a scAb, a dAb, a single domain heavy chain antibody, a single domain light chain antibody, and a complementarity determining region (CDR).

In some embodiments, such an antibody is selected from the group consisting of: an antibody comprising an amino acid sequence that is at least about 90 percent identical to an amino acid sequence selected from the group consisting of amino acid sequences SEQ ID NO:4, SEQ ID NO:6, and SEQ ID NO:2; an antibody comprising an amino acid sequence that is at least about 90 percent identical to an amino acid sequence selected from the group consisting of amino acid sequences SEQ ID NO:24, SEQ ID NO:26, and SEQ ID NO:22; and an antibody comprising an amino acid sequence that is at least about 90 percent identical to an amino acid sequence selected from the group consisting of amino acid sequences SEQ ID NO:44, SEQ ID NO:46, and SEQ ID NO:42.

In some embodiments, such an antibody is selected from the group consisting of: an antibody comprising an amino acid sequence selected from the group consisting of amino acid sequences SEQ ID NO:4, SEQ ID NO:6, and SEQ ID NO:2; an antibody comprising an amino acid sequence selected from the group consisting of amino acid sequences SEQ ID NO:24, SEQ ID NO:26, and SEQ ID NO:22; and an antibody comprising an amino acid sequence selected from the group consisting of amino acid sequences SEQ ID NO:44, SEQ ID NO:46, and SEQ ID NO:42.

In some embodiments, such an antibody comprises a $V_H$ chain comprising amino acid sequence SEQ ID NO:4 and a $V_L$ chain comprising amino acid sequence SEQ ID NO:6.

In some embodiments, such an antibody comprises a $V_H$ chain comprising amino acid sequence SEQ ID NO:24 and a $V_L$ chain comprising amino acid sequence SEQ ID NO:26.

In some embodiments, such an antibody comprises a $V_H$ chain comprising amino acid sequence SEQ ID NO:44 and a $V_L$ chain comprising amino acid sequence SEQ ID NO:46.

In some embodiments, such an antibody is selected from the group consisting of: an antibody comprising a first amino acid sequence that is at least about 90 percent identical to amino acid sequence SEQ ID NO:4 and a second amino acid sequence that is at least about 90 percent identical to amino acid sequence SEQ ID NO:6, wherein the first amino acid sequence and second amino acid sequence are joined by a peptide linker; an antibody comprising a first amino acid sequence that is at least about 90 percent identical to amino acid sequence SEQ ID NO:24 and a second amino acid sequence that is at least about 90 percent identical to amino acid sequence SEQ ID NO:26, wherein the first amino acid sequence and second amino acid sequence are joined by a peptide linker; and an antibody comprising a first amino acid sequence that is at least about 90 percent identical to amino acid sequence SEQ ID NO:44 and a second amino acid sequence that is at least about 90 percent identical to amino acid sequence SEQ ID NO:46, wherein the first amino acid sequence and second amino acid sequence are joined by a peptide linker.

In some embodiments, such an antibody is selected from the group consisting of: an antibody comprising amino acid sequence SEQ ID NO:4 and amino acid sequence SEQ ID NO:6, wherein amino acid sequence SEQ ID NO:4 and amino acid sequence SEQ ID NO:6 are joined by a peptide linker; an antibody comprising amino acid sequence SEQ ID NO:24 and amino acid sequence SEQ ID NO:26, wherein amino acid sequence SEQ ID NO:24 and amino acid sequence SEQ ID NO:26 are joined by a peptide linker; and an antibody comprising amino acid sequence SEQ ID NO:44 and amino acid sequence SEQ ID NO:46, wherein amino acid sequence SEQ ID NO:44 and amino acid sequence SEQ ID NO:46 are joined by a peptide linker In some embodiments, the linker is about 10 to about 25 amino acids in length.

In some embodiments, the linker comprises an amino acid sequence selected from the group consisting of amino acid sequences SEQ ID NO:20, SEQ ID NO:40, and SEQ ID NO:60.

In some embodiments, an antibody of the disclosure comprises at least one complementarity determining region (CDR) of an antibody selected from the group consisting of human anti-dengue virus antibody m366, human anti-dengue virus antibody m366.6, and human anti-dengue virus antibody m360.6.

In some embodiments, such an antibody is selected from the group consisting of: an antibody comprising a CDR having an amino acid sequence selected from the group consisting of amino acid sequences SEQ ID NO:8, SEQ ID NO:10, SEQ ID NO:12, SEQ ID NO:14, SEQ ID NO:16, SEQ ID NO:18, and combinations thereof; an antibody comprising a complementarity determining region (CDR) having an amino acid sequence selected from the group consisting of amino acid sequences SEQ ID NO:28, SEQ ID NO:30, SEQ ID NO:32, SEQ ID NO:34, SEQ ID NO:36, SEQ ID NO:38 and combinations thereof; and an antibody comprising a complementarity determining region (CDR) having an amino acid sequence selected from the group consisting of amino acid sequences SEQ ID NO:48, SEQ ID NO:50, SEQ ID NO:52, SEQ ID NO:54, SEQ ID NO:56, SEQ ID NO:58, and combinations thereof.

In some embodiments, such an antibody is selected from the group consisting of: an antibody comprising a CDR-H1 having amino acid sequence SEQ ID NO:8, a CDR-H2 having amino acid sequence SEQ ID NO:10, a CDR-H3 having amino acid sequence SEQ ID NO:12, a CDR-L1 having amino acid sequence SEQ ID NO:14, a CDR-L2 having amino acid sequence SEQ ID NO:16, and a CDR-L3 having amino acid sequence SEQ ID NO:18; an antibody comprising a CDR-H1 having amino acid sequence SEQ ID NO:28, a CDR-H2 having amino acid sequence SEQ ID NO:30, a CDR-H3 having amino acid sequence SEQ ID NO:32, a CDR-L1 having amino acid sequence SEQ ID NO:34, a CDR-L2 having amino acid sequence SEQ ID NO:36, and a CDR-L3 having amino acid sequence SEQ ID NO:38; and an antibody comprising a CDR-H1 having amino acid sequence SEQ ID NO:48, a CDR-H2 having amino acid sequence SEQ ID NO:50, a CDR-H3 having amino acid sequence SEQ ID NO:52, a CDR-L1 having amino acid sequence SEQ ID NO:54, a CDR-L2 having amino acid sequence SEQ ID NO:56, and a CDR-L3 having amino acid sequence SEQ ID NO:58.

In some embodiments, such an antibody comprises an amino acid sequence that is at least about 90 percent identical to an amino acid sequence selected from the group consisting of amino acid sequences SEQ ID NO:2, SEQ ID NO:22, and SEQ ID NO:42.

In some embodiments, such an antibody comprises amino acid sequence SEQ ID NO:2.

In some embodiments, such an antibody comprises amino acid sequence SEQ ID NO:22.

In some embodiments, such an antibody comprises amino acid sequence SEQ ID NO:42.

In some embodiments, such an antibody comprises an Fc domain.

In some embodiments, such an antibody is a bispecific antibody.

In some embodiments, such a bispecific antibody comprises an antibody of any of the embodiments of the disclosure.

In some embodiments, such a bispecific antibody comprises at least one antibody comprises a CDR-H3 having an amino acid sequence selected from the group consisting of SEQ ID NO:12, SEQ ID NO:32, and SEQ ID NO:52. In some embodiments, both antibodies of such a bispecific antibody comprise a CDR-H3 having an amino acid sequence selected from the group consisting of SEQ ID NO:12, SEQ ID NO:32, and SEQ ID NO:52.

In some embodiments, such a bispecific antibody comprises at least one antibody selected from the group consisting of: an antibody comprising a complementarity determining region (CDR) having an amino acid sequence selected from the group consisting of amino acid sequences SEQ ID NO:8, SEQ ID NO:10, SEQ ID NO:12, SEQ ID NO:14, SEQ ID NO:16, SEQ ID NO:18, and combinations thereof; an antibody comprising a complementarity determining region (CDR) having an amino acid sequence selected from the group consisting of amino acid sequences SEQ ID NO:28, SEQ ID NO:30, SEQ ID NO:32, SEQ ID NO:34, SEQ ID NO:36, SEQ ID NO:38, and combinations thereof; and an antibody comprising a complementarity determining region (CDR) having an amino acid sequence selected from the group consisting of amino acid sequences SEQ ID NO:48, SEQ ID NO:50, SEQ ID NO:52, SEQ ID NO:54, SEQ ID NO:56, SEQ ID NO:58, and combinations thereof. In some embodiments, both antibodies of the bispecific antibody comprise such CDRs.

In some embodiments, such a bispecific antibody is selected from the group consisting of: a bispecific antibody comprising (i) an antibody comprising a CDR-H1 having amino acid sequence SEQ ID NO:8, a CDR-H2 having amino acid sequence SEQ ID NO:10, a CDR-H3 having amino acid sequence SEQ ID NO:12, a CDR-L1 having amino acid sequence SEQ ID NO:14, a CDR-L2 having amino acid sequence SEQ ID NO:16, and a CDR-L3 having amino acid sequence SEQ ID NO:18 and (ii) an antibody comprising a CDR-H1 having amino acid sequence SEQ ID NO:28, a CDR-H2 having amino acid sequence SEQ ID NO:30, a CDR-H3 having amino acid sequence SEQ ID NO:32, a CDR-L1 having amino acid sequence SEQ ID NO:34, a CDR-L2 having amino acid sequence SEQ ID NO:36, and a CDR-L3 having amino acid sequence SEQ ID NO:38; a bispecific antibody comprising (i) an antibody comprising a CDR-H1 having amino acid sequence SEQ ID NO:8, a CDR-H2 having amino acid sequence SEQ ID NO:10, a CDR-H3 having amino acid sequence SEQ ID NO:12, a CDR-L1 having amino acid sequence SEQ ID NO:14, a CDR-L2 having amino acid sequence SEQ ID NO:16, and a CDR-L3 having amino acid sequence SEQ ID NO:18 and (ii) an antibody comprising a CDR-H1 having amino acid sequence SEQ ID NO:48, a CDR-H2 having amino acid sequence SEQ ID NO:50, a CDR-H3 having amino acid sequence SEQ ID NO:52, a CDR-L1 having amino acid sequence SEQ ID NO:54, a CDR-L2 having amino acid sequence SEQ ID NO:56, and a CDR-L3 having amino acid sequence SEQ ID NO:58; and a bispecific antibody comprising (i) an antibody comprising a CDR-H1 having amino acid sequence SEQ ID NO:28, a CDR-H2 having amino acid sequence SEQ ID NO:30, a CDR-H3 having amino acid sequence SEQ ID NO:32, a CDR-L1 having amino acid sequence SEQ ID NO:34, a CDR-L2 having amino acid sequence SEQ ID NO:36, and a CDR-L3 having amino acid sequence SEQ ID NO:38 and (ii) an antibody comprising a CDR-H1 having amino acid sequence SEQ ID NO:48, a CDR-H2 having amino acid sequence SEQ ID NO:50, a CDR-H3 having amino acid sequence SEQ ID NO:52, a CDR-L1 having amino acid sequence SEQ ID NO:54, a CDR-L2 having amino acid sequence SEQ ID NO:56, and a CDR-L3 having amino acid sequence SEQ ID NO:58.

In some embodiments, such a bispecific antibody comprises (i) an antibody comprising a CDR-H1 having amino acid sequence SEQ ID NO:28, a CDR-H2 having amino acid sequence SEQ ID NO:30, a CDR-H3 having amino acid sequence SEQ ID NO:32, a CDR-L1 having amino acid sequence SEQ ID NO:34, a CDR-L2 having amino acid sequence SEQ ID NO:36, and a CDR-L3 having amino acid sequence SEQ ID NO:38 and (ii) an antibody comprising a CDR-H1 having amino acid sequence SEQ ID NO:48, a CDR-H2 having amino acid sequence SEQ ID NO:50, a CDR-H3 having amino acid sequence SEQ ID NO:52, a CDR-L1 having amino acid sequence SEQ ID NO:54, a CDR-L2 having amino acid sequence SEQ ID NO:56, and a CDR-L3 having amino acid sequence SEQ ID NO:58.

In some embodiments, such a bispecific antibody comprises an antibody selected from the group consisting of: an antibody comprising a $V_H$ chain comprising amino acid sequence SEQ ID NO:4 and a $V_L$ chain comprising amino acid sequence SEQ ID NO:6; an antibody comprising a $V_H$ chain comprising amino acid sequence SEQ ID NO:24 and a $V_L$ chain comprising amino acid sequence SEQ ID NO:26; an antibody comprising a $V_H$ chain comprising amino acid sequence SEQ ID NO:44 and a $V_L$ chain comprising amino acid sequence SEQ ID NO:46; and combinations thereof.

In some embodiments, such a bispecific antibody comprises an amino acid sequence selected from the group consisting of amino acid sequences SEQ ID NO:2, SEQ ID NO:22, SEQ ID NO:42, and combinations thereof.

In some embodiments, such a bispecific antibody is selected from the group consisting of: a bispecific antibody comprising an antibody comprising a $V_H$ chain comprising amino acid sequence SEQ ID NO:4 and a $V_L$ chain comprising amino acid sequence SEQ ID NO:6 and an antibody comprising a $V_H$ chain comprising amino acid sequence SEQ ID NO:24 and a $V_L$ chain comprising amino acid sequence SEQ ID NO:26; a bispecific antibody comprising an antibody comprising a $V_H$ chain comprising amino acid sequence SEQ ID NO:4 and a $V_L$ chain comprising amino acid sequence SEQ ID NO:6 and an antibody comprising a $V_H$ chain comprising amino acid sequence SEQ ID NO:44 and a $V_L$ chain comprising amino acid sequence SEQ ID NO:46; and a bispecific antibody comprising an antibody comprising a $V_H$ chain comprising amino acid sequence SEQ ID NO:24 and a $V_L$ chain comprising amino acid sequence SEQ ID NO:26; and an antibody comprising a $V_H$ chain comprising amino acid sequence SEQ ID NO:44 and a $V_L$ chain comprising amino acid sequence SEQ ID NO:46.

In some embodiments, such a bispecific antibody is selected from the group consisting of: a bispecific antibody comprising an antibody comprising amino acid sequence SEQ ID NO:2 and an antibody comprising amino acid sequence SEQ ID NO:22; a bispecific antibody comprising an antibody comprising amino acid sequence SEQ ID NO:2 and an antibody comprising amino acid sequence SEQ ID NO:42; and a bispecific antibody comprising an antibody comprising amino acid sequence SEQ ID NO:22 and an antibody comprising amino acid sequence SEQ ID NO:42.

In some embodiments, such a bispecific antibody comprises an antibody comprising a $V_H$ chain comprising amino acid sequence SEQ ID NO:24 and a $V_L$ chain comprising amino acid sequence SEQ ID NO:26 and an antibody comprising a $V_H$ chain comprising amino acid sequence SEQ ID NO:44 and a $V_L$ chain comprising amino acid sequence SEQ ID NO:46.

In some embodiments, such a bispecific antibody comprises an antibody comprising amino acid sequence SEQ ID NO:22 and an antibody comprising amino acid sequence SEQ ID NO:42.

In some embodiments, such a bispecific antibody comprises an Fc domain.

In some embodiments, such an Fc domain comprises an amino acid sequence selected from the group consisting of amino acid sequences SEQ ID NO:92, SEQ ID NO:94, SEQ ID NO:102, AND SEQ ID NO:104.

In some embodiments, such a bispecific antibody comprises amino acid sequences SEQ ID NO:22, SEQ ID NO:94, and SEQ ID NO:42.

In some embodiment, such a bispecific antibody comprises amino acid sequence SEQ ID NO:96.

The disclosure provides a human antibody comprising a variable domain, wherein the variable domain is selected from the group consisting of a variable domain comprising the identifying characteristics of human anti-dengue virus antibody m366, a variable domain comprising the identifying characteristics of human anti-dengue virus antibody m366.6, a variable domain comprising the identifying characteristics of human anti-dengue virus antibody m360, and a variable domain comprising the identifying characteristics of human anti-dengue virus antibody m360.6.

The disclosure provides a human antibody comprising the identifying characteristics of a human anti-dengue virus antibody selected from the group consisting of human anti-dengue virus antibody m366, human anti-dengue virus antibody m366.6, human anti-dengue virus antibody m360, and human anti-dengue virus antibody m360.6.

The disclosure provides a human antibody comprising a variable domain and a constant domain, wherein the human antibody is selected from the group consisting of a human antibody having the identifying characteristics of human anti-dengue virus antibody m366, a human antibody having the identifying characteristics of human anti-dengue virus antibody m366.6, a human antibody having the identifying characteristics of human anti-dengue virus antibody m360, and a human antibody having the identifying characteristics of human anti-dengue virus antibody m360.6.

The disclosure provides a human anti-dengue virus antibody selected from the group consisting of human anti-dengue virus antibody m366, human anti-dengue virus antibody m366.6, human anti-dengue virus antibody m360, and human anti-dengue virus antibody m360.6.

The disclosure provides a bispecific human antibody comprising an antibody comprising a variable domain, wherein the variable domain is selected from the group consisting of a variable domain comprising the identifying characteristics of human anti-dengue virus antibody m366, a variable domain comprising the identifying characteristics of human anti-dengue virus antibody m366.6, a variable domain comprising the identifying characteristics of human anti-dengue virus antibody m360.6, and combinations thereof.

The disclosure provides a bispecific antibody comprising an antibody comprising the identifying characteristics of a human anti-dengue virus antibody selected from the group consisting of human anti-dengue virus antibody m366, human anti-dengue virus antibody m366.6, human anti-dengue virus antibody m360.6, and combinations thereof.

The disclosure provides a bispecific antibody comprising an antibody comprising a variable domain and a constant domain, wherein the antibody is selected from the group consisting of a human antibody having the identifying characteristics of human anti-dengue virus antibody m366, a human antibody having the identifying characteristics of human anti-dengue virus antibody m366.6, a human antibody having the identifying characteristics of human anti-dengue virus antibody m360.6, and combinations thereof.

The disclosure provides a bispecific antibody comprising an antibody selected from the group consisting of human anti-dengue virus antibody m366, human anti-dengue virus antibody m366.6, human anti-dengue virus antibody m360.6, and combinations thereof.

The disclosure provides human anti-dengue virus antibody m366.

The disclosure provides human anti-dengue virus antibody m366.6.

The disclosure provides human anti-dengue virus antibody m360.6.

The disclosure provides human anti-dengue virus antibody m360.

The disclosure provides a bispecific antibody comprising human anti-dengue virus antibody m366 and human anti-dengue virus antibody m366.6.

The disclosure provides a bispecific antibody comprising human anti-dengue virus antibody m366 and human anti-dengue virus antibody m360.6.

The disclosure provides a bispecific antibody comprising human anti-dengue virus antibody m366.6 and human anti-dengue virus antibody m360.6.

The disclosure provides a bispecific antibody having the identifying characteristics of bispecific anti-dengue virus antibody m3666.

The disclosure provides bispecific anti-dengue virus antibody m3666.

The disclosure provides a human antibody that binds an epitope selected from the group consisting of the epitope which human anti-dengue virus antibody m366 binds, the epitope which human anti-dengue virus antibody m366.6 binds, and the epitope which human anti-dengue virus antibody m360.6 binds.

The disclosure provides a human anti-dengue virus antibody, wherein a variable domain of the antibody has a three-dimensional structure similar to that of an antibody selected from the group consisting of human anti-dengue virus antibody m366, human anti-dengue virus antibody m366.6, and human anti-dengue virus antibody m360.6.

The disclosure provides a human anti-dengue virus antibody, wherein CDRs of the antibody are positioned in a three-dimensional structure similar to the positioning of the CDRs of an antibody selected from the groups consisting of human anti-dengue virus antibody m366, human anti-dengue virus antibody m366.6, and human anti-dengue virus antibody m360.6.

The disclosure provides a human anti-dengue virus antibody, wherein a variable domain of the antibody contacts at least amino acid residues 15, 16, 17, 18, 19, 20, 21, 35, 37, 71, 93, and 95 of amino acid sequence SEQ ID NO:82.

The disclosure provides a human anti-dengue virus antibody of the embodiments produced by a method selected from the group consisting of recombinant production and chemical synthesis.

The disclosure provides a nucleic acid molecule that encodes a human anti-dengue virus antibody of the embodiments. Also provided is a recombinant vector comprising such a nucleic acid molecule. Also provided is a recombinant molecule comprising such a nucleic acid molecule.

Also provided is a recombinant cell comprising such a recombinant molecule.

The disclosure provides a pharmaceutical composition comprising a human anti-dengue virus antibody of the embodiments and a pharmaceutically acceptable carrier.

In some embodiments, such a pharmaceutical composition comprises one human anti-dengue virus antibody of the embodiments and a pharmaceutically acceptable carrier.

In some embodiments, such a pharmaceutical composition comprises at least two human anti-dengue virus antibodies of the embodiments and a pharmaceutically acceptable carrier.

In some embodiments, such a pharmaceutical composition comprises at least one antibody selected from the group consisting of human anti-dengue virus antibody m366, human anti-dengue virus antibody m366.6, human anti-dengue virus antibody m360.6, human anti-dengue virus antibody m360, human anti-dengue virus antibody m3666, and combinations thereof.

The disclosure provides a treatment for dengue virus infection comprising a human anti-dengue virus antibody of the embodiments and a pharmaceutically acceptable carrier.

The disclosure provides a preventative composition against dengue virus infection comprising a human anti-dengue virus antibody of the embodiments and a pharmaceutically acceptable carrier.

The disclosure provides a method to protect a subject from dengue virus infection, the method comprising administering to the subject a human anti-dengue virus antibody of the embodiments and a pharmaceutically acceptable carrier. In some embodiments, the subject is a primate. In some embodiments, the subject is a human.

The disclosure provides use of a human anti-dengue virus antibody of the embodiments, or a pharmaceutical composition thereof, to protect a subject from dengue virus infection.

The disclosure provides use of a human anti-dengue virus antibody of the embodiments in the manufacture of a medicament for the protection of a subject from dengue virus infection.

The disclosure provides a method to produce a human anti-dengue virus antibody of the embodiments, the method comprising: (a) screening a yeast display human antibody library for a human antibody cross-reactive with dengue virus (DENV) serotype 1, DENV serotype 2, DENV serotype 3, and DENV serotype 4 in the presence of a non-neutralizing DENV envelope domain III protein; and (b) isolating a clone expressing such an antibody. In some embodiments, the non-neutralizing DENV envelope domain III protein has a mutation at a residue corresponding to amino acid residue 20 of amino acid sequence SEQ ID NO:82. In some embodiments, the mutation is a K310E point mutation, wherein the mutation is at amino acid residue 20 of amino acid sequence SEQ ID NO:82.

The disclosure provides a method to produce a human anti-dengue virus antibody of the embodiments, the method comprising: (a) culturing a recombinant cell encoding the antibody; and (b) recovering the antibody.

The disclosure provides a diagnostic kit comprising a human anti-dengue virus antibody of the embodiments.

The disclosure provides a method to diagnose dengue virus infection in a subject comprising: (a) exposing a human anti-dengue virus antibody of the embodiments to the subject or to a sample collected from the subject; and (b) detecting complex formation between the antibody and an epitope in the subject or in the sample, wherein complex formation indicates that the subject is infected with dengue virus.

The disclosure provides a protein comprising an epitope that binds to an antibody selected from the group consisting of an antibody having the identifying characteristics of human anti-dengue virus antibody m366, an antibody having the identifying characteristics of human anti-dengue virus antibody m366.6, an antibody having the identifying characteristics of human anti-dengue virus antibody m360.6, and an antibody having the identifying characteristics of human anti-dengue virus antibody m3666. In some embodiments, the antibody is selected from the group consisting of human anti-dengue virus antibody m366, human anti-dengue virus antibody m366.6, human anti-dengue virus antibody m360.6, and bispecific anti-dengue virus antibody m3666.

The disclosure provides a protein comprising an epitope that elicits production of an antibody selected from the group consisting of an antibody with identifying characteristics of human anti-dengue virus antibody m366, an antibody having the identifying characteristics of human anti-dengue virus antibody m366.6, and an antibody having the identifying characteristics of human anti-dengue virus antibody m360.6. In some embodiments, the antibody is selected from the group consisting of human anti-dengue virus antibody m366, human anti-dengue virus antibody m366.6, human anti-dengue virus antibody m360.6, and bispecific anti-dengue virus antibody m3666.

In some embodiments, the antibody is selected from the group consisting of: an antibody comprising a CDR-H1 having amino acid sequence SEQ ID NO:8, a CDR-H2 having amino acid sequence SEQ ID NO:10, a CDR-H3 having amino acid sequence SEQ ID NO:12, a CDR-L1 having amino acid sequence SEQ ID NO:14, a CDR-L2 having amino acid sequence SEQ ID NO:16, and a CDR-L3 having amino acid sequence SEQ ID NO:18; an antibody comprising a CDR-H1 having amino acid sequence SEQ ID NO:28, a CDR-H2 having amino acid sequence SEQ ID NO:30, a CDR-H3 having amino acid sequence SEQ ID NO:32, a CDR-L1 having amino acid sequence SEQ ID NO:34, a CDR-L2 having amino acid sequence SEQ ID NO:36, and a CDR-L3 having amino acid sequence SEQ ID NO:38; and an antibody comprising a CDR-H1 having amino acid sequence SEQ ID NO:48, a CDR-H2 having amino acid sequence SEQ ID NO:50, a CDR-H3 having amino acid sequence SEQ ID NO:52, a CDR-L1 having amino acid sequence SEQ ID NO:54, a CDR-L2 having amino acid sequence SEQ ID NO:56, and a CDR-L3 having amino acid sequence SEQ ID NO:58.

In some embodiments, the antibody is selected from the group consisting of: an antibody comprising an amino acid sequence selected from the group consisting of amino acid sequences SEQ ID NO:4, SEQ ID NO:6, and SEQ ID NO:2; an antibody comprising an amino acid sequence selected from the group consisting of amino acid sequences SEQ ID NO:24, SEQ ID NO:26, and SEQ ID NO:22; and an antibody comprising an amino acid sequence selected from the group consisting of amino acid sequences SEQ ID NO:44, SEQ ID NO:46, and SEQ ID NO:42.

In some embodiments, the antibody comprises an amino acid sequence selected from the group consisting of amino acid sequences SEQ ID NO:2, SEQ ID NO:22, SEQ ID NO:42, and SEQ ID NO:96.

In some embodiments, the protein comprises amino acid residues corresponding to amino acid residues 15, 16, 17, 18, 19, 20, 21, 35, 37, 71, 93, and 95 of amino acid sequence SEQ ID NO:82, and wherein the protein comprises a three-dimension structure in which the amino acid residues are localized in positions similar to the positions of corresponding amino acid residues in a natural DENV envelope domain III.2 protein.

The disclosure provides a pharmaceutical composition comprising such an epitope-containing protein of the embodiments and a pharmaceutically acceptable carrier.

The disclosure provides a nucleic acid molecule that encodes such an epitope-containing protein of the embodiments. Also provided is a recombinant vector comprising such a nucleic acid molecule. Also provided is a recombinant molecule comprising such a nucleic acid molecule. Also provided is a recombinant cell comprising such a recombinant molecule.

The disclosure provides a method to produce a protein that binds to an antibody selected from the group consisting of an antibody having the identifying characteristics of human anti-dengue virus antibody m366, an antibody having the identifying characteristics of human anti-dengue virus antibody m366.6, an antibody having the identifying characteristics of human anti-dengue virus antibody m360.6, and an antibody having the identifying characteristics of human anti-dengue virus antibody m3666, the method comprising: (a) culturing a recombinant cell encoding such a protein; and (b) recovering the protein. In some embodiments, the antibody is selected from the group consisting of human anti-dengue virus antibody m366, human anti-dengue virus antibody m366.6, human anti-dengue virus antibody m360.6, and bispecific anti-dengue virus antibody m3666.

The disclosure provides a method to protect a subject from dengue virus infection, the method comprising administering to the subject such an epitope-containing protein of the embodiments, or a pharmaceutical composition thereof. In some embodiments, the subject is a primate. In some embodiments, the subject is a human.

The disclosure provides use of such an epitope-containing protein of the embodiments, or a pharmaceutical composition thereof, to protect a subject from dengue virus infection.

The disclosure provides use of such an epitope-containing protein of the embodiments in the manufacture of a medicament for the protection of a subject from dengue virus infection.

The disclosure provides a diagnostic kit comprising an epitope-containing protein of the embodiments.

The disclosure provides a method to diagnose dengue virus infection in a subject comprising: (a) exposing an epitope-containing protein of the embodiments to the subject or to a sample collected from the subject; and (b) detecting complex formation between the epitope and an antibody in the subject or in the sample, wherein complex formation indicates that the subject is infected with dengue virus.

BRIEF DESCRIPTION OF THE FIGURES

FIG. 1 compares sequences of the heavy and light chains of m366 antibody (having SEQ ID NO:4 and SEQ ID NO:6, respectively) to sequences of corresponding germline precursors. Numbering is according to the IMGT (International ImMunoGene Tics) information system numbering scheme. The six complementarity-determining regions (CDRs) are depicted in bold face. Only mutated residues are shown for the germline sequences.

FIG. 2 provides consensus amino acid sequences for envelope domain III proteins from DENV serotype 1 (DENV1) (SEQ ID NO:97), DENV serotype 2 (DENV2) (SEQ ID NO:98), DENV serotype 3 (DENV3) (SEQ ID NO:99), and DENV serotype 4(DENV 4) (SEQ ID NO:100).

FIG. 7 illustrates that the m366 epitope is at close proximity to or partially overlapping the dimerization interface between domains II and III.

FIG. 8 provides a comparison of the variable heavy chains of mouse anti-dengue virus mAb 9F12 (9F12VH; SEQ ID NO:83) and human anti-dengue virus m366 antibody (m366VH; SEQ ID NO:4). The figure also provides a comparison of the variable light chains of mouse anti-dengue virus mAb 9F12 (9F12VL; SEQ ID NO:84) and human anti-dengue virus m366 antibody (m366VL; SEQ ID NO:6). The respective CDRs are underlined. In the figure, asterisks (*) represent identical amino acids between the two sequences, colons (:) represent conserved substitutions between the two sequences, and periods (.) represent semi-conserved substitution between the two sequences.

DETAILED DESCRIPTION

Figure 3:
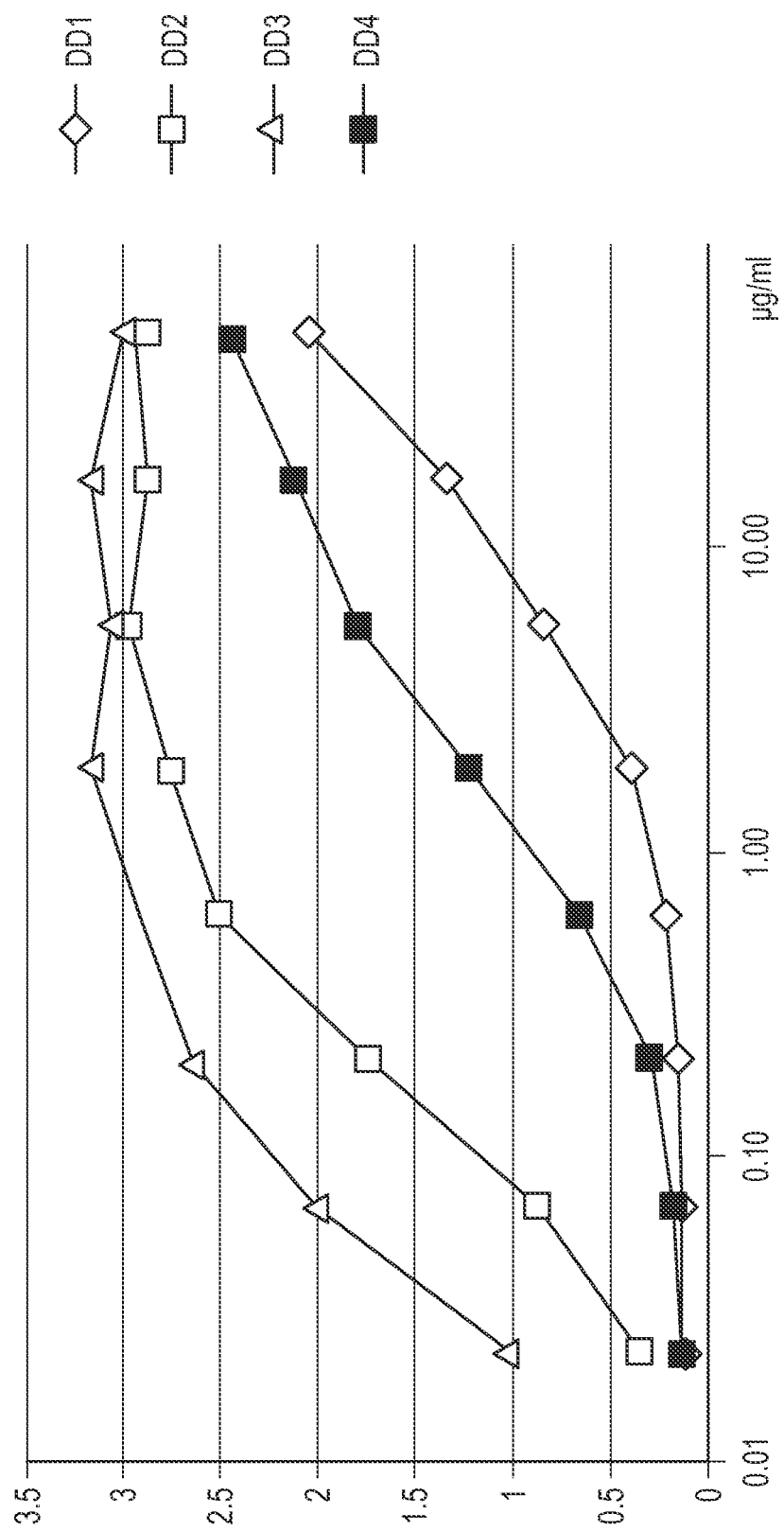
FIG. 3 provides results from an ELISA binding assay that demonstrates cross-reactive binding of antibody D6, the unique clone isolated from the yeast display naïve antibody library, to dengue virus envelope domain III proteins (also referred to herein as ED3 proteins, ED3s, or DDs) from all 4 DENV serotypes, i.e., DENV serotype 1 (DD1), DENV serotype 2 (DD2), DENV serotype 3 (DD3), and DENV serotype 4 (DD4).

The present disclosure describes the novel finding of a human anti-dengue virus antibody that is cross-reactive with all four serotypes of dengue virus (DENV). Such an antibody can also neutralize all four DENV serotypes. In one embodiment, such an antibody can be identified by sequential panning and screening of a naive human antibody library against envelope domain III proteins from all four serotypes. Such an antibody has potential as a therapeutic, and its epitope as a vaccine immunogen.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It should be understood that as used herein, the term "a" entity or "an" entity refers to one or more of that entity. For example, a nucleic acid molecule refers to one or more nucleic acid molecules. As such, the terms "a", "an", "one or more" and "at least one" can be used interchangeably. Similarly the terms "comprising", "including" and "having" can be used interchangeably.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

Human Anti-Dengue Virus Antibodies

The disclosure provides a human anti-dengue virus antibody that cross-reacts with envelope proteins from all four DENV serotypes; such an antibody can also neutralize all four serotypes. One embodiment of such an antibody is antibody m366, which was identified by sequential antigen panning of antibody libraries derived from healthy individuals against the DENV envelope domain III, combined with depletion by entry defective envelope mutants and subsequent in vitro maturation. Human antibody m366 binds with high affinity to DENV envelope proteins of and neutralizes all four serotypes. The inventors localized the m366 epitope by computational analysis of docking models of m366 to domain III and sequence analysis of domain III variants. Antibody m366 has a total of 4 and 10 amino acid changes, respectively, from the closest VH and Vκ germline gene products; see FIG. 1. Additional embodiments of such an antibody are antibody m366.6, antibody m360.6, and bispecific antibody m3666. Antibody m360, from which antibody m360.6 was derived, cross-reacts with envelope proteins from DENV serotype 1, DENV serotype 2, and DENV serotype 3. These antibodies represent promising candidate therapeutics and diagnostics. Appropriately designed vaccine immunogens containing at least one of the epitopes bound by m366, m366.6, m360.6, m360, or m3666, respectively, could elicit antibodies with potent cross-reactive neutralizing activity.

The disclosure provides a human anti-dengue virus antibody that binds to an envelope protein of dengue virus, wherein the antibody is cross-reactive with dengue virus (DENV) serotype 1 envelope protein, DENV serotype 2 envelope protein, DENV serotype 3 envelope protein, and DENV serotype 4 envelope protein. As used herein, a human anti-dengue virus antibody is an antibody that binds to dengue virus. An antibody of the embodiments binds to a DENV envelope protein. A human anti-dengue virus antibody on the embodiments is an isolated antibody in that it is not in the presence of its natural milieu. Although it is a human antibody, it has been isolated from a library comprising human antibodies than having been isolated from a human subject. Such an antibody can be subject to affinity maturation. One embodiment is a human anti-dengue virus antibody that is not isolated from a mammalian subject. One embodiment is a human anti-dengue virus antibody that is not isolated from a primate subject. One embodiment is a human anti-dengue virus antibody that is not isolated from a human subject.

An antibody of the embodiments is a monoclonal antibody. As used herein, a monoclonal antibody is an antibody produced by a group of identical cells, all of which were produced from a single cell by repetitive cellular replication. That is, the clone of cells only produces a single antibody species. While a monoclonal antibody can be produced using hybridoma production technology, other production methods can also be used, such as those described herein and those known to those skilled in the art.

As used herein, an antibody refers to a full-length antibody or a fragment thereof, wherein the fragment retains the ability to bind to an envelope protein of dengue virus (i.e., the fragment retains the antibody binding domain, or paratope, of the full-length antibody) and retains the ability to cross-react with envelope proteins from all four DENV serotypes. Methods to detect and measure antibody binding to an envelope protein of dengue virus are disclosed herein and are known to those skilled in the art. Examples of an antibody of the embodiments include, but are not limited to, a full-length antibody (i.e., a complete antibody, or immunoglobulin, having two full-length heavy chains and two full-length light chains), a full-length soluble antibody (i.e., a complete antibody except that it lacks a transmembrane domain), a monospecific antibody, a bispecific antibody, a multi-specific antibody, a Fab fragment, a F(ab')$_2$ fragment, a scFv, a scAb, a dAb, a single domain heavy chain antibody, a single domain light chain antibody, and a complementarity determining region (CDR). Other antibody forms and non-antibody proteins that bind specifically to the epitopes bound by antibodies of the embodiments, e.g., antibodies m366, m366.6, m360.6, and m3666, are also included herein.

A monospecific antibody is an antibody that has one type of antigen-binding domain, or paratope. A bispecific antibody is an antibody has two types of antigen-binding domains, i.e., two types of paratopes. Monospecific and bispecific antibodies can be full-length soluble antibodies or any fragment thereof that retains the ability to bind to a DENV envelope protein. One embodiment of a bispecific antibody is an antibody that has two paratopes, each of which binds to a different DENV epitope that is cross-reactive with all four DENV serotypes. One embodiment is a multi-specific antibody, such as an antibody that is bispecific, trispecific, or has specificity for four, five, or more antigens.

In some embodiments, an antibody of the disclosure does not enhance Dengue virus infection. As used herein, the phrase "does not enhance Dengue virus infection" means that the antibody does not significantly enhance Dengue virus infection (i.e., antibody-dependent enhancement of infection (ADE)) in a cell or when administered to a subject, and the cell or subject is exposed to Dengue virus. That is, a cell or subject administered an antibody of the embodiments exhibits less than about 50%, less than about 20%, less than about 10%, less than about 5%, less than about 4%, less than about 3%, less than about 2%, less than about 1% enhancement of infection when exposed to Dengue virus compared to enhancement of infection exhibited by other antibodies or as a result of infection after induction of a humoral immune response against a previous Dengue virus infection. This characteristic is surprising because typically an induced humoral immune response to one DENV serotype as a result of infection, or an anti-Dengue virus antibody, can enhance the infection and disease processes brought about by a subsequent infection with another DENV serotype; see, for example, Beltramello et al., ibid. Methods to measure ADE are known to those skilled in the art.

An antibody of the embodiments can be of any isotype that protects a subject from dengue virus. One embodiment is an antibody of an isotype selected from IgA, IgD, IgE, IgG, and IgM. One embodiment is an antibody of an isotype selected from IgG and IgM. One embodiment is an IgA antibody. One embodiment is an IgD antibody. One embodiment is an IgE antibody. One embodiment is an IgG antibody. One embodiment is an IgM antibody.

The disclosure provides a human anti-dengue virus antibody that is cross-reactive with the four known serotypes of dengue virus in that it is cross-reactive with DENV serotype 1 envelope protein, DENV serotype 2 envelope protein, DENV serotype 3 envelope protein, and DENV serotype 4 envelope protein. It is to be appreciated that one or additional DENV serotypes are yet to be discovered. As such, one embodiment is a human anti-dengue virus antibody that is cross-reactive with envelope proteins of serotype 1, serotype 2, serotype 3, and serotype 4 and with an envelope protein from one or more additional DENV serotypes. It is also to be appreciated that DENV serotypes 1, 2, 3 and 4 each include several genotypes. As such, the disclosure provides a human anti-dengue virus antibody that cross-reacts with envelope proteins of DENV genotypes of serotype 1, serotype 2, serotype 3, and serotype 4.

One embodiment of the disclosure is a human anti-dengue virus antibody that binds to a receptor binding domain of a DENV envelope protein, wherein the antibody is cross-reactive with the receptor binding domain of DENV serotype 1, DENV serotype 2, DENV serotype 3, and DENV serotype 4.

One embodiment of the disclosure is a human anti-dengue virus antibody that binds to domain III of a DENV envelope protein (also referred to herein as an envelope domain III protein, an envelope protein domain III, or a domain 3 of a DENV envelope protein), wherein the antibody is cross-reactive with envelope domain III protein of DENV serotype 1, DENV serotype 2, DENV serotype 3, and DENV serotype 4. Without being bound by theory, it is believed that that domain III contains the DENV receptor binding domain that is associated with viral entry, the first step of cellular infection.

One embodiment of the disclosure is a human anti-dengue virus antibody that neutralizes DENV serotype 1, DENV serotype 2, DENV serotype 3, and DENV serotype 4. As used herein, the ability of an antibody to neutralize a DENV serotype refers to the antibody's ability to reduce the ability of a dengue virus serotype to infect a cell. One embodiment is a human anti-dengue virus antibody that neutralizes all four DENV serotypes at an $IC_{50}$ value of less than about 100 micrograms (μg) per milliliter (ml), of less than about 50 μg/ml, or of less than about 25 μg/ml. One embodiment is a human anti-dengue virus antibody that neutralizes all four DENV serotypes at an $IC_{50}$ value of less than about 25 μg/ml. One embodiment is a human anti-dengue virus antibody that neutralizes all four DENV serotypes at an $IC_{50}$ value of less than about 20 μg/ml. One embodiment is a human anti-dengue virus antibody that neutralizes all four DENV serotypes at an $IC_{50}$ value of less than about 15 μg/ml. One embodiment is a human anti-dengue virus antibody that neutralizes all four DENV serotypes at an $IC_{50}$ value of less than about 12.5 μg/ml. One embodiment is a human anti-dengue virus antibody that neutralizes all four DENV serotypes at an $IC_{50}$ value of less than about 10 μg/ml, of less than about 9 μg/ml, of less than about 8 μg/ml, of less than about 7 μg/ml, of less than about 6 μg/ml, of than about 5 μg/ml, of less than about 4 μg/ml, of less than about 3 μg/ml, of less than about 2 μg/ml, or of less than about 1 μg/ml. One embodiment is a human anti-dengue virus antibody that neutralizes all four DENV serotypes at an $IC_{50}$ value of less than about 0.9 μg/ml, of less than about 0.8 μg/ml, of less than about 0.7 μg/ml, of less than about 0.6 μg/ml, of than about 0.5 μg/ml, of less than about 0.4 μg/ml, of less than about 0.3 μg/ml, of less than about 0.2 μg/ml, or of less than about 0.1 μg/ml. One embodiment is a human anti-dengue virus antibody that neutralizes all four DENV serotypes at an $IC_{50}$ value of less than about 5 μg/ml. One embodiment is a human anti-dengue virus antibody that neutralizes all four DENV serotypes at an $IC_{50}$ value of less than about 1 μg/ml. One embodiment is a human anti-dengue virus antibody that neutralizes all four DENV serotypes at an $IC_{50}$ value of less than about 0.5 μg/ml. One embodiment is a human anti-dengue virus antibody that neutralizes all four DENV serotypes at an $IC_{50}$ value of less than about 0.1 μg/ml. One embodiment is a human anti-dengue virus antibody that neutralizes all four DENV serotypes at $IC_{50}$ values as reported for scFv-Fc m360.6 herein. One embodiment is a human anti-dengue virus antibody that neutralizes all four DENV serotypes at $IC_{50}$ values as reported for scFv-Fc m366.6 herein. One embodiment is a human anti-dengue virus antibody that neutralizes all four DENV serotypes at $IC_{50}$ values as reported for m3666 herein. Methods to detect and measure antibody neutralization titers, such as a plaque reduction assay or a reporter gene assay, e.g., a DENV RVP assay, are described herein and are known to those skilled in the art. In one embodiment, a DENV RVP assay as described in Example 9 is used to compare the values obtained from a human anti-dengue virus antibody being tested to values cited above.

One embodiment of the disclosure is a human anti-dengue virus antibody that binds to a receptor binding domain of a DENV envelope protein, wherein the antibody is cross-reactive with the receptor binding domain of DENV serotype 1, DENV serotype 2, DENV serotype 3, and DENV serotype 4, and wherein the antibody neutralizes DENV serotype 1, DENV serotype 2, DENV serotype 3, and DENV serotype 4.

One embodiment of the disclosure is a human anti-dengue virus antibody that binds to domain III of a DENV envelope protein), wherein the antibody is cross-reactive with envelope domain III protein of DENV serotype 1, DENV serotype 2, DENV serotype 3, and DENV serotype 4, and wherein the antibody neutralizes DENV serotype 1, DENV serotype 2, DENV serotype 3, and DENV serotype 4.

One embodiment is a human anti-dengue virus antibody that binds to each of DENV serotype 1, DENV serotype 2, DENV serotype 3, and DENV serotype 4 envelope proteins with a dissociation constant ($K_D$) of no more than about 50 nanomolar (nM). One embodiment is a human anti-dengue virus antibody that binds to each of DENV serotype 1, DENV serotype 2, DENV serotype 3, and DENV serotype 4 envelope proteins with a $K_D$ of no more than about 40 nM. One embodiment is a human anti-dengue virus antibody that binds to each of DENV serotype 1, DENV serotype 2, DENV serotype 3, and DENV serotype 4 envelope proteins with a $K_D$ of no more than about 20 nM. One embodiment is a human anti-dengue virus antibody that binds to each of DENV serotype 1, DENV serotype 2, DENV serotype 3, and DENV serotype 4 envelope proteins with a $K_D$ of no more than about 100 nM, of no more than about 50 nM, of no more than about 20 nM, of no more than about 10 nM, of no more than about 9 nM, of no more than about 8 nM, of no more than about 7 nM, of no more than about 6 nM, of no more than about 5 nM, of no more than about 4 nM of no more than about 3 nM of no more than about 2 nM, of no more than about 1 nM, of no more than about 0.5 nM, of no more than about 0.2 nM, of no more than about 0.1 nM, of no more than about 0.05 nM, of no more than about 0.02 nM, of no more than about 0.01 nM, or of no more than about 0.001 nM. One embodiment is a human anti-dengue virus antibody that binds to each of DENV serotype 1, DENV serotype 2, DENV serotype 3, and DENV serotype 4 envelope proteins with a $K_D$ of no more than about 1 nM. One embodiment is a human anti-dengue virus antibody that binds to each of DENV serotype 1, DENV serotype 2, DENV serotype 3, and DENV serotype 4 envelope proteins with a $K_D$ of no more than about 0.5 nM. One embodiment is a human anti-dengue virus antibody that binds to each of DENV serotype 1, DENV serotype 2, DENV serotype 3, and DENV serotype 4 envelope proteins with a $K_D$ of no more than about 10 picomolar (pM). One embodiment is a human anti-dengue virus antibody that binds to three DENV serotypes with a $K_D$ of no more than about 0.5 nM and binds the fourth DENV serotype with a $K_D$ of no more than about 40 nM.

The disclosure provides a human anti-dengue virus antibody that comprises an amino acid sequence selected from the group consisting of SEQ ID NO:4, SEQ ID NO:6, and SEQ ID NO:2. That is, the disclosure provides a human anti-dengue virus antibody that comprises amino acid sequence SEQ ID NO:4, amino acid sequence SEQ ID NO:6, amino acid sequence SEQ ID NO:2 or an amino acid sequence comprising SEQ ID NO:6 and SEQ ID NO:4. One embodiment is an antibody that comprises amino acid sequence SEQ ID NO:2. Amino acid sequence SEQ ID NO:2 is the amino acid sequence of human anti-dengue virus antibody m366, described in more detail herein. Antibody m366 is a single chain variable fragment (scFv) consisting of a variable heavy chain ($V_H$, having SEQ ID NO:4) and a variable light chain ($V_L$, having SEQ ID NO:6) joined by a linker (L, having SEQ ID NO:20), the order being $V_H$—L—$V_L$.

One embodiment is a human anti-dengue virus antibody comprising an antibody scFv in the order $V_H$—L—$V_L$, a non-limiting example of which is an antibody having an amino acid sequence in the order SEQ ID:4—SEQ ID NO:20—SEQ ID NO:6. Another embodiment is a human anti-dengue virus antibody comprising an antibody scFv in the order $V_L$—L—$V_H$, a non-limiting example of which is an antibody having an amino acid sequence in the order SEQ ID:6—SEQ ID NO:20—SEQ ID NO:4.

One embodiment is an antibody comprising an amino acid sequence that is at least 50 percent identical to amino acid sequence SEQ ID NO:4. One embodiment is an antibody comprising an amino acid sequence that is at least 60 percent identical to amino acid sequence SEQ ID NO:4. One embodiment is an antibody comprising an amino acid sequence that is at least 70 percent identical to amino acid sequence SEQ ID NO:4. One embodiment is an antibody comprising an amino acid sequence that is at least 80 percent identical to amino acid sequence SEQ ID NO:4. One embodiment is an antibody comprising an amino acid sequence that is at least 90 percent identical to amino acid sequence SEQ ID NO:4. One embodiment is an antibody comprising an amino acid sequence that is at least 95 percent identical to amino acid sequence SEQ ID NO:4. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, or at least 99 percent, identical to amino acid sequence SEQ ID NO:4. One embodiment is an antibody comprising amino acid sequence SEQ ID NO:4. Each of these antibodies retains the ability to bind to a DENV envelope protein and to cross-react with envelope proteins from all four DENV serotypes. Such an antibody can be a complete Ig or any fragment thereof.

One embodiment is an antibody comprising an amino acid sequence that is at least 50 percent identical to amino acid sequence SEQ ID NO:6. One embodiment is an antibody comprising an amino acid sequence that is at least 60 percent identical to amino acid sequence SEQ ID NO:6. One embodiment is an antibody comprising an amino acid sequence that is at least 70 percent identical to amino acid sequence SEQ ID NO:6. One embodiment is an antibody comprising an amino acid sequence that is at least 80 percent identical to amino acid sequence SEQ ID NO:6. One embodiment is an antibody comprising an amino acid sequence that is at least 90 percent identical to amino acid sequence SEQ ID NO:6. One embodiment is an antibody comprising an amino acid sequence that is at least 95 percent identical to amino acid sequence SEQ ID NO:6. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, or at least 99 percent, identical to amino acid sequence SEQ ID NO:6. One embodiment is an antibody comprising amino acid sequence SEQ ID NO:6. Each of these antibodies retains the ability to bind to a DENV envelope protein and to cross-react with envelope proteins from all four DENV serotypes. Such an antibody can be a complete Ig or any fragment thereof.

One embodiment is an antibody that comprises amino acid sequences that are at least 50 percent identical to amino acid sequences SEQ ID NO:4 and SEQ ID NO:6. One embodiment is an antibody that comprises amino acid sequences that are at least 60 percent identical to amino acid sequences SEQ ID NO:4 and SEQ ID NO:6. One embodiment is an antibody that comprises amino acid sequences that are at least 70 percent identical to amino acid sequences SEQ ID NO:4 and SEQ ID NO:6. One embodiment is an antibody that comprises amino acid sequences that are at least 80 percent identical to amino acid sequences SEQ ID NO:4 and SEQ ID NO:6. One embodiment is an antibody that comprises amino acid sequences that are at least 90 percent identical to amino acid sequences SEQ ID NO:4 and SEQ ID NO:6. One embodiment is an antibody that comprises amino acid sequences that are at least 95 percent identical to amino acid sequences SEQ ID NO:4 and SEQ ID NO:6. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, or at least 99 percent, identical to amino acid sequences SEQ ID NO:4 and SEQ ID NO:6. One embodiment is an antibody that comprises amino acid sequences SEQ ID NO:4 and SEQ ID NO:6. Each of these antibodies retains the ability to bind to a DENV envelope protein and to cross-react with envelope proteins from all four DENV serotypes. Such an antibody can be a complete Ig or any fragment thereof.

One embodiment is an antibody that comprises amino acid sequences SEQ ID NO:4 and SEQ ID NO:6 wherein SEQ ID NO:4 and SEQ ID NO:6 are joined by a peptide linker. As used herein, two amino acid sequences that are joined by a peptide linker refers to a protein in which one amino acid sequence is joined (i.e., fused by a peptide linkage) to the amino terminus of the peptide linker and the other amino acid sequence is joined (i.e., fused by a peptide linkage) to the carboxyl terminus of the peptide linker. The amino acid composition and length of a peptide linker of the embodiments is typically such to provide flexibility in order to enable the two amino acid sequences in combination to retain the ability to bind to a DENV envelope protein and to cross-react with envelope proteins from all four DENV serotypes. Such a peptide linker typically comprises at least several glycine and/or serine residues. The ability to design such a peptide linker is known to those skilled in the art. One embodiment is a peptide linker of about 10 to about 25 amino acids in length. One embodiment is a peptide linker of 10 to 25 amino acids in length. One embodiment is a linker comprising amino acid sequence SEQ ID NO:20. One embodiment is a linker comprising amino acid sequence SEQ ID NO:40. One embodiment is a linker comprising amino acid sequence SEQ ID NO:60. One embodiment is a linker comprising amino acid sequence SEQ ID NO:80.

One embodiment is an antibody that comprises a first amino acid sequence that is at least 50 percent identical to amino acid sequence SEQ ID NO:4 and a second amino acid sequence that is at least 50 percent identical to amino acid sequence SEQ ID NO:6, wherein the first amino acid sequence and the second amino acid sequence are joined by a peptide linker. One embodiment is an antibody that comprises a first amino acid sequence that is at least 60 percent identical to amino acid sequence SEQ ID NO:4 and a second amino acid sequence that is at least 60 percent identical to amino acid sequence SEQ ID NO:6, wherein the first amino acid sequence and the second amino acid sequence are joined by a peptide linker. One embodiment is an antibody that comprises a first amino acid sequence that is at least 70 percent identical to amino acid sequence SEQ ID NO:4 and a second amino acid sequence that is at least 70 percent identical to amino acid sequence SEQ ID NO:6, wherein the first amino acid sequence and the second amino acid sequence are joined by a peptide linker. One embodiment is an antibody that comprises a first amino acid sequence that is at least 80 percent identical to amino acid sequence SEQ ID NO:4 and a second amino acid sequence that is at least 80 percent identical to amino acid sequence SEQ ID NO:6, wherein the first amino acid sequence and the second amino acid sequence are joined by a peptide linker. One embodiment is an antibody that comprises a first amino acid sequence that is at least 90 percent identical to amino acid sequence SEQ ID NO:4 and a second amino acid sequence that is at least 90 percent identical to amino acid sequence SEQ ID NO:6, wherein the first amino acid sequence and the second amino acid sequence are joined by a peptide linker. One embodiment is an antibody that comprises a first amino acid sequence that is at least 95 percent identical to amino acid sequence SEQ ID NO:4 and a second amino acid sequence that is at least 95 percent identical to amino acid sequence SEQ ID NO:6, wherein the first amino acid sequence and the second amino acid sequence are joined by a peptide linker One embodiment is an antibody that comprises a first amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:4 and a second amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:6, wherein the two amino acid sequences are joined by a peptide linker. One embodiment is an antibody that comprises amino acid sequences SEQ ID NO:4 and SEQ ID NO:6, wherein the two amino acid sequences are joined by a peptide linker. Each of these antibodies retains the ability to bind to a DENV envelope protein and to cross-react with envelope proteins from all four DENV serotypes. Such an antibody can be a complete Ig or any fragment thereof.

One embodiment is an antibody comprising an amino acid sequence that is at least 50 percent identical to amino acid sequence SEQ ID NO:2. One embodiment is an antibody comprising an amino acid sequence that is at least 60 percent identical to amino acid sequence SEQ ID NO:2. One embodiment is an antibody comprising an amino acid sequence that is at least 70 percent identical to amino acid sequence SEQ ID NO:2. One embodiment is an antibody comprising an amino acid sequence that is at least 80 percent identical to amino acid sequence SEQ ID NO:2. One embodiment is an antibody comprising an amino acid sequence that is at least 90 percent identical to amino acid sequence SEQ ID NO:2. One embodiment is an antibody comprising an amino acid sequence that is at least 95 percent identical to amino acid sequence SEQ ID NO:2. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:2. One embodiment is an antibody comprising amino acid sequence SEQ ID NO:2. Each of these antibodies retains the ability to bind to a DENV envelope protein and to cross-react with envelope proteins from all four DENV serotypes. Such an antibody can be a complete Ig or any fragment thereof.

In some embodiments, an antibody of the disclosure comprises at least one complementarity determining region (CDR) of an antibody selected from the group consisting of human anti-dengue virus antibody m366, human anti-dengue virus antibody m366.6, and human anti-dengue virus antibody m360.6. Methods to identify CDRs are known to those skilled in the art. Examples of such methods include those of the IMGT (International ImMunoGene Tics) information system, and methods taught by: Kabat et al., 1977, J. Biol. Chem. 252, 6609-6616; Kabat et al., 1991, U.S. Dept. of Health and Human Services, "Sequences of proteins of immunological interest"; Chothia et al., 1987, J. Mol. Biol. 196, 901-917; and MacCallum et al., 1996, J. Mol. Biol. 262:732-745.

The disclosure provides a human anti-dengue virus antibody that binds to domain III of an envelope protein of dengue virus, wherein the antibody is cross-reactive with domain III of dengue virus (DENV) serotype 1 envelope protein, domain III of DENV serotype 2 envelope protein, domain III of DENV serotype 3 envelope protein, and domain III of DENV serotype 4 envelope protein, and wherein the antibody comprises a CDR-H3 having an amino acid sequence selected from the group consisting of SEQ ID NO:12, SEQ ID NO:32, and SEQ ID NO:52.

The disclosure also provides a human anti-dengue virus antibody that comprises a CDR having an amino acid sequence selected from the group consisting of SEQ ID NO:8, SEQ ID NO:10, SEQ ID NO:12, SEQ ID NO:14, SEQ ID NO:16, SEQ ID NO:18, and combinations thereof. One embodiment is an antibody comprising a CDR having amino acid sequence SEQ ID NO:8. One embodiment is an antibody comprising a CDR having amino acid sequence SEQ ID NO:10. One embodiment is an antibody comprising a CDR having amino acid sequence SEQ ID NO:12. One embodiment is an antibody comprising a CDR having amino acid sequence SEQ ID NO:14. One embodiment is an antibody comprising a CDR having amino acid sequence SEQ ID NO:16. One embodiment is an antibody comprising a CDR having amino acid sequence SEQ ID NO:18. One embodiment is an antibody, the CDR-H1 of which comprises SEQ ID NO:8. One embodiment is an antibody, the CDR-H2 of which comprises SEQ ID NO:10. One embodiment is an antibody, the CDR-H3 of which comprises SEQ ID NO:12. One embodiment is an antibody, the CDR-L1 of which comprises SEQ ID NO:14. One embodiment is an antibody, the CDR-L2 of which comprises SEQ ID NO:16. One embodiment is an antibody, the CDR-L3 of which comprises SEQ ID NO:18. One embodiment is an antibody having any combination of these six CDRs, e.g., comprising two of these CDRs, three of these CDRs, four of these CDRs, five of these CDRs, or all six of these CDRs. One embodiment is an antibody comprising a $V_H$ having a CDR having an amino acid sequence selected from the group consisting of SEQ ID NO:8, SEQ ID NO:10, and SEQ ID NO:12. In one embodiment, such a $V_H$ comprises an amino acid sequence comprising SEQ ID NO:8, SEQ ID NO:10, and SEQ ID NO:12. One embodiment is an antibody comprising a $V_L$ having a CDR having an amino acid sequence selected from the group consisting of SEQ ID NO:14, SEQ ID NO:16, and SEQ ID NO:18. In one embodiment, such a $V_L$ comprises an amino acid sequence comprising SEQ ID NO:14, SEQ ID NO:16, and SEQ ID NO:18. One embodiment is an antibody that comprises CDRs having amino acid sequences SEQ ID NO:8, SEQ ID NO:10, SEQ ID NO:12, SEQ ID NO:14, SEQ ID NO:16, and SEQ ID NO:18. One embodiment is an antibody wherein CDR-H1 has amino acid sequence SEQ ID NO:8, CDR-H2 has amino acid sequence SEQ ID NO:10, CDR-H3 has amino acid sequence SEQ ID NO:12, CDR-L1 has amino acid sequence SEQ ID NO:14, CDR-L2 has amino acid sequence SEQ ID NO:16, and CDR-L3 has amino acid sequence SEQ ID NO:18. One embodiment is an antibody wherein CDR-H3 has amino acid sequence SEQ ID NO:12 and CDR-L1 has amino acid sequence SEQ ID NO:14. Each of these antibodies retains the ability to bind to a DENV envelope protein and to cross-react with envelope proteins from all four DENV serotypes. Such an antibody can be a complete Ig or any fragment thereof.

The disclosure provides a human anti-dengue virus antibody that comprises an amino acid sequence selected from the group consisting of SEQ ID NO:24, SEQ ID NO:26, and SEQ ID NO:22. That is, the disclosure provides a human anti-dengue virus antibody that comprises amino acid sequence SEQ ID NO:24, amino acid sequence SEQ ID NO:26, amino acid sequence SEQ ID NO:22 or an amino acid sequence comprising SEQ ID NO:26 and SEQ ID NO:24. One embodiment is an antibody that comprises amino acid sequence SEQ ID NO:22. Amino acid sequence SEQ ID NO:22 is the amino acid sequence of human anti-dengue virus antibody m366.6, described in more detail herein. Antibody m366.6 is a single chain variable fragment (scFv) consisting of a variable heavy chain ($V_H$, having SEQ ID NO:24) and a variable light chain ($V_L$, having SEQ ID NO:26) joined by a linker (L, having SEQ ID NO:40), the order being $V_H$—L—$V_L$.

One embodiment is a human anti-dengue virus antibody comprising an antibody scFv in the order $V_H$—L—$V_L$, a non-limiting example of which is an antibody having an amino acid sequence in the order SEQ ID NO:24—SEQ ID NO:40—SEQ ID NO:26. Another embodiment is a human anti-dengue virus antibody comprising an antibody scFv in the order VL—L—$V_H$, a non-limiting example of which is an antibody having an amino acid sequence in the order SEQ ID NO:26—SEQ ID NO:40—SEQ ID NO:24.

One embodiment is an antibody comprising an amino acid sequence that is at least 50 percent identical to amino acid sequence SEQ ID NO:24. One embodiment is an antibody comprising an amino acid sequence that is at least 60 percent identical to amino acid sequence SEQ ID NO:24. One embodiment is an antibody comprising an amino acid sequence that is at least 70 percent identical to amino acid sequence SEQ ID NO:24. One embodiment is an antibody comprising an amino acid sequence that is at least 80 percent identical to amino acid sequence SEQ ID NO:24. One embodiment is an antibody comprising an amino acid sequence that is at least 90 percent identical to amino acid sequence SEQ ID NO:24. One embodiment is an antibody comprising an amino acid sequence that is at least 95 percent identical to amino acid sequence SEQ ID NO:24. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:24. One embodiment is an antibody comprising amino acid sequence SEQ ID NO:24. Each of these antibodies retains the ability to bind to a DENV envelope protein and to cross-react with envelope proteins from all four DENV serotypes. Such an antibody can be a complete Ig or any fragment thereof.

One embodiment is an antibody comprising an amino acid sequence that is at least 50 percent identical to amino acid sequence SEQ ID NO:26. One embodiment is an antibody comprising an amino acid sequence that is at least 60 percent identical to amino acid sequence SEQ ID NO:26. One embodiment is an antibody comprising an amino acid sequence that is at least 70 percent identical to amino acid sequence SEQ ID NO:26. One embodiment is an antibody comprising an amino acid sequence that is at least 80 percent identical to amino acid sequence SEQ ID NO:26. One embodiment is an antibody comprising an amino acid sequence that is at least 90 percent identical to amino acid sequence SEQ ID NO:26. One embodiment is an antibody comprising an amino acid sequence that is at least 95 percent identical to amino acid sequence SEQ ID NO:26. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:26. One embodiment is an antibody comprising amino acid sequence SEQ ID NO:26. Each of these antibodies retains the ability to bind to a DENV envelope protein and to cross-react with envelope proteins from all four DENV serotypes. Such an antibody can be a complete Ig or any fragment thereof.

One embodiment is an antibody that comprises amino acid sequences that are at least 50 percent identical to amino acid sequences SEQ ID NO:24 and SEQ ID NO:26. One embodiment is an antibody that comprises amino acid sequences that are at least 60 percent identical to amino acid sequences SEQ ID NO:24 and SEQ ID NO:26. One embodiment is an antibody that comprises amino acid sequences that are at least 70 percent identical to amino acid sequences SEQ ID NO:24 and SEQ ID NO:26. One embodiment is an antibody that comprises amino acid sequences that are at least 80 percent identical to amino acid sequences SEQ ID NO:24 and SEQ ID NO:26. One embodiment is an antibody that comprises amino acid sequences that are at least 90 percent identical to amino acid sequences SEQ ID NO:24 and SEQ ID NO:26. One embodiment is an antibody that comprises amino acid sequences that are at least 95 percent identical to amino acid sequences SEQ ID NO:24 and SEQ ID NO:26. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequences SEQ ID NO:24 and SEQ ID NO:26. One embodiment is an antibody that comprises amino acid sequences SEQ ID NO:24 and SEQ ID NO:26. Each of these antibodies retains the ability to bind to a DENV envelope protein and to cross-react with envelope proteins from all four DENV serotypes. Such an antibody can be a complete Ig or any fragment thereof.

One embodiment is an antibody that comprises amino acid sequences SEQ ID NO:24 and SEQ ID NO:26 wherein SEQ ID NO:224 and SEQ ID NO:26 are joined by a peptide linker. As used herein, two amino acid sequences that are joined by a peptide linker refers to a protein in which one amino acid sequence is joined (i.e., fused by a peptide linkage) to the amino terminus of the peptide linker and the other amino acid sequence is joined (i.e., fused by a peptide linkage) to the carboxyl terminus of the peptide linker. The amino acid composition and length of a peptide linker of the embodiments is typically such to provide flexibility in order to enable the two amino acid sequences in combination to retain the ability to bind to a DENV envelope protein and to cross-react with envelope proteins from all four DENV serotypes. Such a peptide linker typically comprises at least several glycine and/or serine residues. The ability to design such a peptide linker is known to those skilled in the art. One embodiment is a peptide linker of about 10 to about 25 amino acids in length. One embodiment is a peptide linker of 10 to 25 amino acids in length. One embodiment is a linker comprising amino acid sequence SEQ ID N0:40. One embodiment is a linker comprising amino acid sequence SEQ ID NO:20. One embodiment is a linker comprising amino acid sequence SEQ ID NO:60. One embodiment is a linker comprising amino acid sequence SEQ ID NO:80.

One embodiment is an antibody that comprises a first amino acid sequence that is at least 50 percent identical to amino acid sequence SEQ ID NO:24 and a second amino acid sequence that is at least 50 percent identical to amino acid sequence SEQ ID NO:26, wherein the first amino acid sequence and the second amino acid sequence are joined by a peptide linker. One embodiment is an antibody that comprises a first amino acid sequence that is at least 60 percent identical to amino acid sequence SEQ ID NO:24 and a second amino acid sequence that is at least 60 percent identical to amino acid sequence SEQ ID NO:26, wherein the first amino acid sequence and the second amino acid sequence are joined by a peptide linker. One embodiment is an antibody that comprises a first amino acid sequence that is at least 70 percent identical to amino acid sequence SEQ ID NO:24 and a second amino acid sequence that is at least 70 percent identical to amino acid sequence SEQ ID NO:26, wherein the first amino acid sequence and the second amino acid sequence are joined by a peptide linker. One embodiment is an antibody that comprises a first amino acid sequence that is at least 80 percent identical to amino acid sequence SEQ ID NO:24 and a second amino acid sequence that is at least 80 percent identical to amino acid sequence SEQ ID NO:26, wherein the first amino acid sequence and the second amino acid sequence are joined by a peptide linker. One embodiment is an antibody that comprises a first amino acid sequence that is at least 90 percent identical to amino acid sequence SEQ ID NO:24 and a second amino acid sequence that is at least 90 percent identical to amino acid sequence SEQ ID NO:26, wherein the first amino acid sequence and the second amino acid sequence are joined by a peptide linker. One embodiment is an antibody that comprises a first amino acid sequence that is at least 95 percent identical to amino acid sequence SEQ ID NO:24 and a second amino acid sequence that is at least 95 percent identical to amino acid sequence SEQ ID NO:26, wherein the first amino acid sequence and the second amino acid sequence are joined by a peptide linker. One embodiment is an antibody comprising a first amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:24 and a second amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:26, wherein the two amino acid sequences are joined by a peptide linker. One embodiment is an antibody that comprises amino acid sequences SEQ ID NO:24 and SEQ ID NO:26, wherein the two amino acid sequences are joined by a peptide linker. Each of these antibodies retains the ability to bind to a DENV envelope protein and to cross-react with envelope proteins from all four DENV serotypes. Such an antibody can be a complete Ig or any fragment thereof.

One embodiment is an antibody comprising an amino acid sequence that is at least 50 percent identical to amino acid sequence SEQ ID NO:22. One embodiment is an antibody comprising an amino acid sequence that is at least 60 percent identical to amino acid sequence SEQ ID NO:22. One embodiment is an antibody comprising an amino acid sequence that is at least 70 percent identical to amino acid sequence SEQ ID NO:22. One embodiment is an antibody comprising an amino acid sequence that is at least 80 percent identical to amino acid sequence SEQ ID NO:22. One embodiment is an antibody comprising an amino acid sequence that is at least 90 percent identical to amino acid sequence SEQ ID NO:22. One embodiment is an antibody comprising an amino acid sequence that is at least 95 percent identical to amino acid sequence SEQ ID NO:22. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:22. One embodiment is an antibody comprising amino acid sequence SEQ ID NO:22. Each of these antibodies retains the ability to bind to a DENV envelope protein and to cross-react with envelope proteins from all four DENV serotypes. Such an antibody can be a complete Ig or any fragment thereof.

One embodiment is a human anti-dengue virus antibody that comprises a CDR having an amino acid sequence selected from the group consisting of SEQ ID NO:28, SEQ ID NO:30, SEQ ID NO:32, SEQ ID NO:34, SEQ ID NO:36, SEQ ID NO:38, and combinations thereof. One embodiment is an antibody comprising a CDR having amino acid sequence SEQ ID NO:28. One embodiment is an antibody comprising a CDR having amino acid sequence SEQ ID NO:30. One embodiment is an antibody comprising a CDR having amino acid sequence SEQ ID NO:32. One embodiment is an antibody comprising a CDR having amino acid sequence SEQ ID NO:34. One embodiment is an antibody comprising a CDR having amino acid sequence SEQ ID NO:36. One embodiment is an antibody comprising a CDR having amino acid sequence SEQ ID NO:38. One embodiment is an antibody, the CDR-H1 of which comprises SEQ ID NO:28. One embodiment is an antibody, the CDR-H2 of which comprises SEQ ID NO:30. One embodiment is an antibody, the CDR-H3 of which comprises SEQ ID NO:32. One embodiment is an antibody, the CDR-L1 of which comprises SEQ ID NO:34. One embodiment is an antibody, the CDR-L2 of which comprises SEQ ID NO:36. One embodiment is an antibody, the CDR-L3 of which comprises SEQ ID NO:38. One embodiment is an antibody having any combination of these six CDRs, e.g., comprising two of these CDRs, three of these CDRs, four of these CDRs, five of these CDRs, or all six of these CDRs. One embodiment is an antibody comprising a $V_H$ having a CDR having an amino acid sequence selected from the group consisting of SEQ ID NO:28, SEQ ID NO:30, and SEQ ID NO:32. In one embodiment, such a $V_H$ comprises an amino acid sequence comprising SEQ ID NO:28, SEQ ID NO:30, and SEQ ID NO:32. One embodiment is an antibody comprising a $V_L$ having a CDR having an amino acid sequence selected from the group consisting of SEQ ID NO:34, SEQ ID NO:36, and SEQ ID NO:38. In one embodiment, such a $V_L$ comprises an amino acid sequence comprising SEQ ID NO:34, SEQ ID NO:36, and SEQ ID NO:38. One embodiment is an antibody that comprises CDRs having amino acid sequences SEQ ID NO:28, SEQ ID NO:30, SEQ ID NO:32, SEQ ID NO:34, SEQ ID NO:36, and SEQ ID NO:38. One embodiment is an antibody wherein CDR-H1 has amino acid sequence SEQ ID NO:28, CDR-H2 has amino acid sequence SEQ ID NO:30, CDR-H3 has amino acid sequence SEQ ID NO:32, CDR-L1 has amino acid sequence SEQ ID NO:34, CDR-L2 has amino acid sequence SEQ ID NO:36, and CDR-L3 has amino acid sequence SEQ ID NO:38. One embodiment is an antibody wherein CDR-H3 has amino acid sequence SEQ ID NO:32 and CDR-L1 has amino acid sequence SEQ ID NO:34. Each of these antibodies retains the ability to bind to a DENV envelope protein and to cross-react with envelope proteins from all four DENV serotypes. Such an antibody can be a complete Ig or any fragment thereof.

The disclosure provides a human anti-dengue virus antibody that comprises an amino acid sequence selected from the group consisting of SEQ ID NO:44, SEQ ID NO:46, and SEQ ID NO:42. That is, the disclosure provides a human anti-dengue virus antibody that comprises amino acid sequence SEQ ID NO:44, amino acid sequence SEQ ID NO:46, amino acid sequence SEQ ID NO:42 or an amino acid sequence comprising SEQ ID NO:46 and SEQ ID NO:44. One embodiment is an antibody that comprises amino acid sequence SEQ ID NO:42. Amino acid sequence SEQ ID NO:42 is the amino acid sequence of human anti-dengue virus antibody m360.6, described in more detail herein. Antibody m360.6 is a single chain variable fragment (scFv) consisting of a variable heavy chain ($V_H$, having SEQ ID NO:44) and a variable light chain ($V_L$, having SEQ ID NO:46) joined by a linker (L, having SEQ ID NO:60), the order being $V_H$—L—$V_L$.

One embodiment is a human anti-dengue virus antibody comprising an antibody scFv in the order $V_H$—L—$V_L$, a non-limiting example of which is an antibody having an amino acid sequence in the order SEQ ID NO:44—SEQ ID NO:60—SEQ ID NO:46. Another embodiment is a human anti-dengue virus antibody comprising an antibody scFv in the order $V_L$—L—$V_H$, a non-limiting example of which is an antibody having an amino acid sequence in the order SEQ ID NO:46—SEQ ID NO:60—SEQ ID NO:44.

One embodiment is an antibody comprising an amino acid sequence that is at least 50 percent identical to amino acid sequence SEQ ID NO:44. One embodiment is an antibody comprising an amino acid sequence that is at least 60 percent identical to amino acid sequence SEQ ID NO:44. One embodiment is an antibody comprising an amino acid sequence that is at least 70 percent identical to amino acid sequence SEQ ID NO:44. One embodiment is an antibody comprising an amino acid sequence that is at least 80 percent identical to amino acid sequence SEQ ID NO:44. One embodiment is an antibody comprising an amino acid sequence that is at least 90 percent identical to amino acid sequence SEQ ID NO:44. One embodiment is an antibody comprising an amino acid sequence that is at least 95 percent identical to amino acid sequence SEQ ID NO:44. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:44. One embodiment is an antibody comprising amino acid sequence SEQ ID NO:44. Each of these antibodies retains the ability to bind to a DENV envelope protein and to cross-react with envelope proteins from all four DENV serotypes. Such an antibody can be a complete Ig or any fragment thereof.

One embodiment is an antibody comprising an amino acid sequence that is at least 50 percent identical to amino acid sequence SEQ ID NO:46. One embodiment is an antibody comprising an amino acid sequence that is at least 60 percent identical to amino acid sequence SEQ ID NO:46. One embodiment is an antibody comprising an amino acid sequence that is at least 70 percent identical to amino acid sequence SEQ ID NO:46. One embodiment is an antibody comprising an amino acid sequence that is at least 80 percent identical to amino acid sequence SEQ ID NO:46. One embodiment is an antibody comprising an amino acid sequence that is at least 90 percent identical to amino acid sequence SEQ ID NO:46. One embodiment is an antibody comprising an amino acid sequence that is at least 95 percent identical to amino acid sequence SEQ ID NO:46. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:46. One embodiment is an antibody comprising amino acid sequence SEQ ID NO:46. Each of these antibodies retains the ability to bind to a DENV envelope protein and to cross-react with envelope proteins from all four DENV serotypes. Such an antibody can be a complete Ig or any fragment thereof.

One embodiment is an antibody that comprises amino acid sequences that are at least 50 percent identical to amino acid sequences SEQ ID NO:44 and SEQ ID NO:46. One embodiment is an antibody that comprises amino acid sequences that are at least 60 percent identical to amino acid sequences SEQ ID NO:44 and SEQ ID NO:46. One embodiment is an antibody that comprises amino acid sequences that are at least 70 percent identical to amino acid sequences SEQ ID NO:44 and SEQ ID NO:46. One embodiment is an antibody that comprises amino acid sequences that are at least 80 percent identical to amino acid sequences SEQ ID NO:44 and SEQ ID NO:46. One embodiment is an antibody that comprises amino acid sequences that are at least 90 percent identical to amino acid sequences SEQ ID NO:44 and SEQ ID NO:46. One embodiment is an antibody that comprises amino acid sequences that are at least 95 percent identical to amino acid sequences SEQ ID NO:44 and SEQ ID NO:46. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequences SEQ ID NO:44 and SEQ ID NO:46. One embodiment is an antibody that comprises amino acid sequences SEQ ID NO:44 and SEQ ID NO:46. Each of these antibodies retains the ability to bind to a DENV envelope protein and to cross-react with envelope proteins from all four DENV serotypes. Such an antibody can be a complete Ig or any fragment thereof.

One embodiment is an antibody that comprises amino acid sequences SEQ ID NO:44 and SEQ ID NO:46 wherein SEQ ID NO:44 and SEQ ID NO:46 are joined by a peptide linker. As used herein, two amino acid sequences that are joined by a peptide linker refers to a protein in which one amino acid sequence is joined (i.e., fused by a peptide linkage) to the amino terminus of the peptide linker and the other amino acid sequence is joined (i.e., fused by a peptide linkage) to the carboxyl terminus of the peptide linker. The amino acid composition and length of a peptide linker of the embodiments is typically such to provide flexibility in order to enable the two amino acid sequences in combination to retain the ability to bind to a DENV envelope protein and to cross-react with envelope proteins from all four DENV serotypes. Such a peptide linker typically comprises at least several glycine and/or serine residues. The ability to design such a peptide linker is known to those skilled in the art. One embodiment is a peptide linker of about 10 to about 25 amino acids in length. One embodiment is a peptide linker of 10 to 25 amino acids in length. One embodiment is a linker comprising amino acid sequence SEQ ID NO:60. One embodiment is a linker comprising amino acid sequence SEQ ID NO:20. One embodiment is a linker comprising amino acid sequence SEQ ID NO:40. One embodiment is a linker comprising amino acid sequence SEQ ID NO:80.

One embodiment is an antibody that comprises a first amino acid sequence that is at least 50 percent identical to amino acid sequence SEQ ID NO:44 and a second amino acid sequence that is at least 50 percent identical to amino acid sequence SEQ ID NO:46, wherein the first amino acid sequence and the second amino acid sequence are joined by a peptide linker. One embodiment is an antibody that comprises a first amino acid sequence that is at least 60 percent identical to amino acid sequence SEQ ID NO:44 and a second amino acid sequence that is at least 60 percent identical to amino acid sequence SEQ ID NO:46, wherein the first amino acid sequence and the second amino acid sequence are joined by a peptide linker. One embodiment is an antibody that comprises a first amino acid sequence that is at least 70 percent identical to amino acid sequence SEQ ID NO:44 and a second amino acid sequence that is at least 70 percent identical to amino acid sequence SEQ ID NO:46, wherein the first amino acid sequence and the second amino acid sequence are joined by a peptide linker. One embodiment is an antibody that comprises a first amino acid sequence that is at least 80 percent identical to amino acid sequence SEQ ID NO:44 and a second amino acid sequence that is at least 80 percent identical to amino acid sequence SEQ ID NO:46, wherein the first amino acid sequence and the second amino acid sequence are joined by a peptide linker. One embodiment is an antibody that comprises a first amino acid sequence that is at least 90 percent identical to amino acid sequence SEQ ID NO:44 and a second amino acid sequence that is at least 90 percent identical to amino acid sequence SEQ ID NO:46, wherein the first amino acid sequence and the second amino acid sequence are joined by a peptide linker One embodiment is an antibody that comprises a first amino acid sequence that is at least 95 percent identical to amino acid sequence SEQ ID NO:44 and a second amino acid sequence that is at least 95 percent identical to amino acid sequence SEQ ID NO:46, wherein the first amino acid sequence and the second amino acid sequence are joined by a peptide linker. One embodiment is an antibody comprising a first amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:44 and a second amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:46, wherein the two amino acid sequences are joined by a peptide linker. One embodiment is an antibody that comprises amino acid sequences SEQ ID NO:44 and SEQ ID NO:46, wherein the two amino acid sequences are joined by a peptide linker. Each of these antibodies retains the ability to bind to a DENV envelope protein and to cross-react with envelope proteins from all four DENV serotypes. Such an antibody can be a complete Ig or any fragment thereof.

One embodiment is an antibody comprising an amino acid sequence that is at least 50 percent identical to amino acid sequence SEQ ID NO:42. One embodiment is an antibody comprising an amino acid sequence that is at least 60 percent identical to amino acid sequence SEQ ID NO:42. One embodiment is an antibody comprising an amino acid sequence that is at least 70 percent identical to amino acid sequence SEQ ID NO:42. One embodiment is an antibody comprising an amino acid sequence that is at least 80 percent identical to amino acid sequence SEQ ID NO:42. One embodiment is an antibody comprising an amino acid sequence that is at least 90 percent identical to amino acid sequence SEQ ID NO:42. One embodiment is an antibody comprising an amino acid sequence that is at least 95 percent identical to amino acid sequence SEQ ID NO:42. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:42. One embodiment is an antibody comprising amino acid sequence SEQ ID NO:42. Each of these antibodies retains the ability to bind to a DENV envelope protein and to cross-react with envelope proteins from all four DENV serotypes. Such an antibody can be a complete Ig or any fragment thereof.

One embodiment is a human anti-dengue virus antibody that comprises a CDR having an amino acid sequence selected from the group consisting of SEQ ID NO:48, SEQ ID NO:50, SEQ ID NO:52, SEQ ID NO:54, SEQ ID NO:56, SEQ ID NO:58, and combinations thereof. One embodiment is an antibody comprising a CDR having amino acid sequence SEQ ID NO:48. One embodiment is an antibody comprising a CDR having amino acid sequence SEQ ID NO:50. One embodiment is an antibody comprising a CDR having amino acid sequence SEQ ID NO:52. One embodiment is an antibody comprising a CDR having amino acid sequence SEQ ID NO:54. One embodiment is an antibody comprising a CDR having amino acid sequence SEQ ID NO:56. One embodiment is an antibody comprising a CDR having amino acid sequence SEQ ID NO:58. One embodiment is an antibody, the CDR-H1 of which comprises SEQ ID NO:48. One embodiment is an antibody, the CDR-H2 of which comprises SEQ ID NO:50. One embodiment is an antibody, the CDR-H3 of which comprises SEQ ID NO:52. One embodiment is an antibody, the CDR-L1 of which comprises SEQ ID NO:54. One embodiment is an antibody, the CDR-L2 of which comprises SEQ ID NO:56. One embodiment is an antibody, the CDR-L3 of which comprises SEQ ID NO:58. One embodiment is an antibody having any combination of these six CDRs, e.g., comprising two of these CDRs, three of these CDRs, four of these CDRs, five of these CDRs, or all six of these CDRs. One embodiment is an antibody comprising a $V_H$ having a CDR having an amino acid sequence selected from the group consisting of SEQ ID NO:48, SEQ ID NO:50, and SEQ ID NO:52. In one embodiment, such a $V_H$ comprises an amino acid sequence comprising SEQ ID NO:48, SEQ ID NO:50, and SEQ ID NO:52. One embodiment is an antibody comprising a $V_L$ having a CDR having an amino acid sequence selected from the group consisting of SEQ ID NO:54, SEQ ID NO:56, and SEQ ID NO:58. In one embodiment, such a $V_L$ comprises an amino acid sequence comprising SEQ ID NO:54, SEQ ID NO:56, and SEQ ID NO:58. One embodiment is an antibody that comprises CDRs having amino acid sequences SEQ ID NO:48, SEQ ID NO:50, SEQ ID NO:52, SEQ ID NO:54, SEQ ID NO:56, and SEQ ID NO:58. One embodiment is an antibody wherein CDR-H1 has amino acid sequence SEQ ID NO:48, CDR-H2 has amino acid sequence SEQ ID NO:50, CDR-H3 has amino acid sequence SEQ ID NO:52, CDR-L1 has amino acid sequence SEQ ID NO:54, CDR-L2 has amino acid sequence SEQ ID NO:56, and CDR-L3 has amino acid sequence SEQ ID NO:58. One embodiment is an antibody wherein CDR-H3 has amino acid sequence SEQ ID NO:52 and CDR-L1 has amino acid sequence SEQ ID NO:54. Each of these antibodies retains the ability to bind to a DENV envelope protein and to cross-react with envelope proteins from all four DENV serotypes. Such an antibody can be a complete Ig or any fragment thereof.

The disclosure provides a human anti-dengue virus antibody that comprises an amino acid sequence selected from the group consisting of SEQ ID NO:64, SEQ ID NO:66, and SEQ ID NO:62. That is, the disclosure provides a human anti-dengue virus antibody that comprises amino acid sequence SEQ ID NO:64, amino acid sequence SEQ ID NO:66, amino acid sequence SEQ ID NO:62 or an amino acid sequence comprising SEQ ID NO:66 and SEQ ID NO:64. One embodiment is an antibody that comprises amino acid sequence SEQ ID NO:62. Amino acid sequence SEQ ID NO:62 is the amino acid sequence of human anti-dengue virus antibody m360, described in more detail herein. Antibody m360 is a single chain variable fragment (scFv) consisting of a variable heavy chain ($V_H$, having SEQ ID NO:64) and a variable light chain ($V_L$, having SEQ ID NO:66) joined by a linker (L, having SEQ ID NO:80), the order being $V_H$—L—$V_L$.

One embodiment is a human anti-dengue virus antibody comprising an antibody scFv in the order $V_H$—L—$V_L$, a non-limiting example of which is an antibody having an amino acid sequence in the order SEQ ID NO:64—SEQ ID NO:80—SEQ ID NO:66. Another embodiment is a human anti-dengue virus antibody comprising an antibody scFv in the order $V_L$—L—$V_H$, a non-limiting example of which is an antibody having an amino acid sequence in the order SEQ ID NO:66—SEQ ID NO:80—SEQ ID NO:64.

One embodiment is an antibody comprising an amino acid sequence that is at least 50 percent identical to amino acid sequence SEQ ID NO:64. One embodiment is an antibody comprising an amino acid sequence that is at least 60 percent identical to amino acid sequence SEQ ID NO:64. One embodiment is an antibody comprising an amino acid sequence that is at least 70 percent identical to amino acid sequence SEQ ID NO:64. One embodiment is an antibody comprising an amino acid sequence that is at least 80 percent identical to amino acid sequence SEQ ID NO:64. One embodiment is an antibody comprising an amino acid sequence that is at least 90 percent identical to amino acid sequence SEQ ID NO:64. One embodiment is an antibody comprising an amino acid sequence that is at least 95 percent identical to amino acid sequence SEQ ID NO:64. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:64. One embodiment is an antibody comprising amino acid sequence SEQ ID NO:64. Each of these antibodies retains the ability to bind to a DENV envelope protein and to cross-react with envelope proteins from all four DENV serotypes. Such an antibody can be a complete Ig or any fragment thereof.

One embodiment is an antibody comprising an amino acid sequence that is at least 50 percent identical to amino acid sequence SEQ ID NO:66. One embodiment is an antibody comprising an amino acid sequence that is at least 60 percent identical to amino acid sequence SEQ ID NO:66. One embodiment is an antibody comprising an amino acid sequence that is at least 70 percent identical to amino acid sequence SEQ ID NO:66. One embodiment is an antibody comprising an amino acid sequence that is at least 80 percent identical to amino acid sequence SEQ ID NO:66. One embodiment is an antibody comprising an amino acid sequence that is at least 90 percent identical to amino acid sequence SEQ ID NO:66. One embodiment is an antibody comprising an amino acid sequence that is at least 95 percent identical to amino acid sequence SEQ ID NO:66. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:66. One embodiment is an antibody comprising amino acid sequence SEQ ID NO:66. Each of these antibodies retains the ability to bind to a DENV envelope protein and to cross-react with envelope proteins from all four DENV serotypes. Such an antibody can be a complete Ig or any fragment thereof.

One embodiment is an antibody that comprises amino acid sequences that are at least 50 percent identical to amino acid sequences SEQ ID NO:64 and SEQ ID NO:66. One embodiment is an antibody that comprises amino acid sequences that are at least 60 percent identical to amino acid sequences SEQ ID NO:64 and SEQ ID NO:66. One embodiment is an antibody that comprises amino acid sequences that are at least 70 percent identical to amino acid sequences SEQ ID NO:64 and SEQ ID NO:66. One embodiment is an antibody that comprises amino acid sequences that are at least 80 percent identical to amino acid sequences SEQ ID NO:64 and SEQ ID NO:66. One embodiment is an antibody that comprises amino acid sequences that are at least 90 percent identical to amino acid sequences SEQ ID NO:64 and SEQ ID NO:66. One embodiment is an antibody that comprises amino acid sequences that are at least 95 percent identical to amino acid sequences SEQ ID NO:64 and SEQ ID NO:66. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequences SEQ ID NO:64 and SEQ ID NO:66. One embodiment is an antibody that comprises amino acid sequences SEQ ID NO:64 and SEQ ID NO:66. Each of these antibodies retains the ability to bind to a DENV envelope protein and to cross-react with envelope proteins from all four DENV serotypes. Such an antibody can be a complete Ig or any fragment thereof.

One embodiment is an antibody that comprises amino acid sequences SEQ ID NO:64 and SEQ ID NO:66 wherein SEQ ID NO:64 and SEQ ID NO:66 are joined by a peptide linker. As used herein, two amino acid sequences that are joined by a peptide linker refers to a protein in which one amino acid sequence is joined (i.e., fused by a peptide linkage) to the amino terminus of the peptide linker and the other amino acid sequence is joined (i.e., fused by a peptide linkage) to the carboxyl terminus of the peptide linker. The amino acid composition and length of a peptide linker of the embodiments is typically such to provide flexibility in order to enable the two amino acid sequences in combination to retain the ability to bind to a DENV envelope protein and to cross-react with envelope proteins from all four DENV serotypes. Such a peptide linker typically comprises at least several glycine and/or serine residues. The ability to design such a peptide linker is known to those skilled in the art. One embodiment is a peptide linker of about 10 to about 25 amino acids in length. One embodiment is a peptide linker of 10 to 25 amino acids in length. One embodiment is a linker comprising amino acid sequence SEQ ID NO:80. One embodiment is a linker comprising amino acid sequence SEQ ID NO:20. One embodiment is a linker comprising amino acid sequence SEQ ID NO:40. One embodiment is a linker comprising amino acid sequence SEQ ID NO:60.

One embodiment is an antibody that comprises a first amino acid sequence that is at least 50 percent identical to amino acid sequence SEQ ID NO:64 and a second amino acid sequence that is at least 50 percent identical to amino acid sequence SEQ ID NO:66, wherein the first amino acid sequence and the second amino acid sequence are joined by a peptide linker. One embodiment is an antibody that comprises a first amino acid sequence that is at least 60 percent identical to amino acid sequence SEQ ID NO:64 and a second amino acid sequence that is at least 60 percent identical to amino acid sequence SEQ ID NO:66, wherein the first amino acid sequence and the second amino acid sequence are joined by a peptide linker. One embodiment is an antibody that comprises a first amino acid sequence that is at least 70 percent identical to amino acid sequence SEQ ID NO:64 and a second amino acid sequence that is at least 70 percent identical to amino acid sequence SEQ ID NO:66, wherein the first amino acid sequence and the second amino acid sequence are joined by a peptide linker. One embodiment is an antibody that comprises a first amino acid sequence that is at least 80 percent identical to amino acid sequence SEQ ID NO:64 and a second amino acid sequence that is at least 80 percent identical to amino acid sequence SEQ ID NO:66, wherein the first amino acid sequence and the second amino acid sequence are joined by a peptide linker. One embodiment is an antibody that comprises a first amino acid sequence that is at least 90 percent identical to amino acid sequence SEQ ID NO:64 and a second amino acid sequence that is at least 90 percent identical to amino acid sequence SEQ ID NO:66, wherein the first amino acid sequence and the second amino acid sequence are joined by a peptide linker One embodiment is an antibody that comprises a first amino acid sequence that is at least 95 percent identical to amino acid sequence SEQ ID NO:64 and a second amino acid sequence that is at least 95 percent identical to amino acid sequence SEQ ID NO:66, wherein the first amino acid sequence and the second amino acid sequence are joined by a peptide linker. One embodiment is an antibody comprising a first amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:64 and a second amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:66, wherein the two amino acid sequences are joined by a peptide linker. One embodiment is an antibody that comprises amino acid sequences SEQ ID NO:64 and SEQ ID NO:66, wherein the two amino acid sequences are joined by a peptide linker. Each of these antibodies retains the ability to bind to a DENV envelope protein and to cross-react with envelope proteins from all four DENV serotypes. Such an antibody can be a complete Ig or any fragment thereof.

One embodiment is an antibody comprising an amino acid sequence that is at least 50 percent identical to amino acid sequence SEQ ID NO:62. One embodiment is an antibody comprising an amino acid sequence that is at least 60 percent identical to amino acid sequence SEQ ID NO:62. One embodiment is an antibody comprising an amino acid sequence that is at least 70 percent identical to amino acid sequence SEQ ID NO:62. One embodiment is an antibody comprising an amino acid sequence that is at least 80 percent identical to amino acid sequence SEQ ID NO:62. One embodiment is an antibody comprising an amino acid sequence that is at least 90 percent identical to amino acid sequence SEQ ID NO:62. One embodiment is an antibody comprising an amino acid sequence that is at least 95 percent identical to amino acid sequence SEQ ID NO:62. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, at least 99 percent identical to amino acid sequence SEQ ID NO:62. One embodiment is an antibody comprising amino acid sequence SEQ ID NO:62. Each of these antibodies retains the ability to bind to a DENV envelope protein and to cross-react with envelope proteins from all four DENV serotypes. Such an antibody can be a complete Ig or any fragment thereof.

One embodiment is a human anti-dengue virus antibody that comprises a CDR having an amino acid sequence selected from the group consisting of SEQ ID NO:68, SEQ ID NO:70, SEQ ID NO:72, SEQ ID NO:74, SEQ ID NO:76, SEQ ID NO:78, and combinations thereof. One embodiment is an antibody comprising a CDR having amino acid sequence SEQ ID NO:68. One embodiment is an antibody comprising a CDR having amino acid sequence SEQ ID NO:70. One embodiment is an antibody comprising a CDR having amino acid sequence SEQ ID NO:72. One embodiment is an antibody comprising a CDR having amino acid sequence SEQ ID NO:74. One embodiment is an antibody comprising a CDR having amino acid sequence SEQ ID NO:76. One embodiment is an antibody comprising a CDR having amino acid sequence SEQ ID NO:78. One embodiment is an antibody, the CDR-H1 of which comprises SEQ ID NO:68. One embodiment is an antibody, the CDR-H2 of which comprises SEQ ID NO:70. One embodiment is an antibody, the CDR-H3 of which comprises SEQ ID NO:72. One embodiment is an antibody, the CDR-L1 of which comprises SEQ ID NO:74. One embodiment is an antibody, the CDR-L2 of which comprises SEQ ID NO:76. One embodiment is an antibody, the CDR-L3 of which comprises SEQ ID NO:78. One embodiment is an antibody having any combination of these six CDRs, e.g., comprising two of these CDRs, three of these CDRs, four of these CDRs, five of these CDRs, or all six of these CDRs. One embodiment is an antibody comprising a $V_H$ having a CDR having an amino acid sequence selected from the group consisting of SEQ ID NO:68, SEQ ID NO:70, and SEQ ID NO:72. In one embodiment, such a $V_H$ comprises an amino acid sequence comprising SEQ ID NO:68, SEQ ID NO:70, and SEQ ID NO:72. One embodiment is an antibody comprising a $V_L$ having a CDR having an amino acid sequence selected from the group consisting of SEQ ID NO:74, SEQ ID NO:76, and SEQ ID NO:78. In one embodiment, such a $V_L$ comprises an amino acid sequence comprising SEQ ID NO:74, SEQ ID NO:76, and SEQ ID NO:78. One embodiment is an antibody that comprises CDRs having amino acid sequences SEQ ID NO:68, SEQ ID NO:70, SEQ ID NO:72, SEQ ID NO:74, SEQ ID NO:76, and SEQ ID NO:78. One embodiment is an antibody wherein CDR-H1 has amino acid sequence SEQ ID NO:68, CDR-H2 has amino acid sequence SEQ ID NO:70, CDR-H3 has amino acid sequence SEQ ID NO:72, CDR-L1 has amino acid sequence SEQ ID NO:74, CDR-L2 has amino acid sequence SEQ ID NO:76, and CDR-L3 has amino acid sequence SEQ ID NO:78. One embodiment is an antibody wherein CDR-H3 has amino acid sequence SEQ ID NO:72 and CDR-L1 has amino acid sequence SEQ ID NO:74. Each of these antibodies retains the ability to bind to a DENV envelope protein and to cross-react with envelope proteins from all four DENV serotypes. Such an antibody can be a complete Ig or any fragment thereof.

The disclosure provides a human anti-dengue virus antibody of the embodiments that comprises a constant (Fc) domain. In such an embodiment the antibody domain (which includes the antigen-binding domain) is joined to an Fc domain. As used herein, an antibody domain joined to an Fc domain is an antibody domain that is fused directly to the Fc domain or that is joined to the Fc domain by a linker. In one embodiment, such a linker is a cleavable linker. In one embodiment, such a linker is a non-cleavable linker. Typically, the Fc domain is joined to the carboxyl terminus of the antibody-binding domain by genetic engineering techniques. An Fc domain can be a full-length constant domain or any fragment thereof. Typically, a constant domain is glycosylated and binds to an Fc gamma receptor. One embodiment is an Fc domain that has modified affinity to one or more Fc receptors. One embodiment of the disclosure is a glycosylated Fc domain that binds to an Fc gamma receptor. One embodiment is an Fc domain that has modified affinity to one or more Fc receptors. One embodiment is an Fc domain that exhibits reduced binding to an Fc gamma receptor. Such reduction in binding can range from less than one percent reduction to hundred percent reduction (i.e., from a slight reduction in receptor binding to inability to bind to the receptor). One embodiment is a non-glycosylated Fc domain. One embodiment is a non-glycosylated Fc domain that exhibits reduced binding to an Fc gamma receptor.

The disclosure also provides a human anti-dengue virus antibody of the embodiments that comprises a fusion segment. In such an embodiment, the antibody domain is joined to the fusion segment to form a fusion protein. As used herein, an antibody domain joined to a fusion segment is an antibody domain that is fused directly to the fusion segment or that is joined to the fusion segment by a linker. In one embodiment, such a linker is a cleavable linker. In one embodiment, such a linker is a non-cleavable linker. In one embodiment, the fusion segment is joined to the carboxyl terminus of the antibody domain. In one embodiment, the fusion segment is joined to the amino terminus of the antibody domain. Typically, the antibody domain and fusion segment are joined by genetic engineering techniques. A fusion segment can provide one or more benefits to the antibody. Non-limiting examples of fusion segments include fusion segments that aid in purification (e.g., a His tag, an Avi Tag, a c-Myc tag, a Flag tag, and a HA tag), fusion segments that are detectable markers (e.g., can be used to detect the antibody in an in vivo, ex vivo, or in vitro diagnostic assay), fusion segments that are agents to combat dengue virus infection, and fusion segments that increase the half-life of the fusion protein.

One embodiment of the disclosure is a human anti-dengue virus antibody that comprises an Fc domain joined to a fusion segment. As used herein, an Fc domain joined to a fusion segment is an Fc domain that is fused directly to the fusion segment or that is joined to the fusion segment by a linker. In one embodiment, such a linker is a cleavable linker. In one embodiment, such a linker is a non-cleavable linker. Typically, the fusion segment is joined to the carboxyl terminus of the Fc domain by genetic engineering techniques. The disclosure also provides an antibody in which the fusion segment is joined to the amino terminus of the Fc domain. Non-limiting examples of fusion segments and their benefits are provided herein and are known to those skilled in the art.

The disclosure provides a bispecific human anti-dengue virus antibody (also referred to herein as a bispecific anti-dengue virus antibody) that comprises at least one monospecific antibody of the embodiments. Such a bispecific antibody binds to domain III of the envelope protein of dengue virus and is cross-reactive with domain III of dengue virus (DENV) serotype 1 envelope protein, domain III of DENV serotype 2 envelope protein, domain III of DENV serotype 3 envelope protein, and domain III of DENV serotype 4 envelope protein. Such a bispecific antibody neutralizes DENV serotype 1, DENV serotype 2, DENV serotype 3, and DENV serotype 4.

One embodiment is a bispecific anti-dengue virus antibody that comprises two monospecific human anti-dengue virus antibodies of the embodiments. In one embodiment, the monospecific antibodies are the same human anti-dengue virus antibody. In one embodiment, the monospecific antibodies are different human anti-dengue virus antibodies that recognize different DENV virus epitopes. In one embodiment, the bispecific antibody comprises a monospecific human anti-dengue virus antibody of the embodiments and an antibody against another target. In one embodiment, both antibodies of the bispecific antibody are cross-reactive with domain III of dengue virus (DENV) serotype 1 envelope protein, domain III of DENV serotype 2 envelope protein, domain III of DENV serotype 3 envelope protein, and domain III of DENV serotype 4 envelope protein.

The disclosure provides a bispecific anti-dengue virus antibody that neutralizes each of DENV serotype 1, DENV serotype 2, DENV serotype 3, and DENV serotype 4 at an $IC_{50}$ of less than 25 micrograms per ml (µg/ml), less than 20 µg/ml, less than 15 µg/ml, less than 10 µg/ml, less than 5 µg/ml, less than 1 µg/ml, less than 0.5 µg/ml, less than 0.1 µg/ml, less than 0.05 µg/ml, or less than 0.01 µg/ml in a DENV RVP assay as set forth in the Examples. In one embodiment, a bispecific anti-dengue virus antibody neutralizes each of DENV serotype 1, DENV serotype 2, DENV serotype 3, and DENV serotype 4 at an $IC_{50}$ of less than 1 µg/ml. In one embodiment, a bispecific anti-dengue virus antibody neutralizes two of the DENV serotypes at an $IC_{50}$ of less than 1 µg/ml and two of the DENV serotypes at an $IC_{50}$ of less than 0.1 µg/ml.

The disclosure provides a bispecific anti-dengue virus antibody that comprises a human anti-dengue virus antibody that binds to each of DENV serotype 1, DENV serotype 2, DENV serotype 3, and DENV serotype 4 envelope proteins with a dissociation constant ($K_D$) of no more than 50 nanomolar (nM), no more than 40 nM, no more than 35 nM, no more than 30 nM, no more than 25 nM, no more than 20 nM, no more than 15 nM. no more than 10 nM, no more than 5 nM, no more than 1 nM, no more than 0.5 nM, no more than 0.1 nM, no more than 0.05 nM, no more than 0.01 nM, no more than 5 pM or no more than 1 pM. One embodiment is a bispecific antibody comprising a human anti-dengue virus antibody that binds to each of DENV serotype 1, DENV serotype 2, DENV serotype 3, and DENV serotype 4 envelope proteins with a $K_D$ of no more than 40 nM. One embodiment is a bispecific antibody comprising a human anti-dengue virus antibody that binds to each of DENV serotype 1, DENV serotype 2, DENV serotype 3, and DENV serotype 4 envelope proteins with a $K_D$ of no more than 20 nM. One embodiment is a bispecific antibody comprising a human anti-dengue virus antibody that binds to each of DENV serotype 1, DENV serotype 2, DENV serotype 3, and DENV serotype 4 envelope proteins with a $K_D$ of no more than 1 nM. One embodiment is a bispecific antibody comprising a human anti-dengue virus antibody that binds to three DENV serotypes with a $K_D$ of no more than 0.5 nM and binds the fourth DENV serotype with a $K_D$ of no more than 40 nM.

In some embodiments, such a bispecific antibody is selected from the group consisting of: a bispecific antibody comprising (i) an antibody comprising a CDR-H1 having amino acid sequence SEQ ID NO:8, a CDR-H2 having amino acid sequence SEQ ID NO:10, a CDR-H3 having amino acid sequence SEQ ID NO:12, a CDR-L1 having amino acid sequence SEQ ID NO:14, a CDR-L2 having amino acid sequence SEQ ID NO:16, and a CDR-L3 having amino acid sequence SEQ ID NO:18 and (ii) an antibody comprising a CDR-H1 having amino acid sequence SEQ ID NO:28, a CDR-H2 having amino acid sequence SEQ ID NO:30, a CDR-H3 having amino acid sequence SEQ ID NO:32, a CDR-L1 having amino acid sequence SEQ ID NO:34, a CDR-L2 having amino acid sequence SEQ ID NO:36, and a CDR-L3 having amino acid sequence SEQ ID NO:38; a bispecific antibody comprising (i) an antibody comprising a CDR-H1 having amino acid sequence SEQ ID NO:8, a CDR-H2 having amino acid sequence SEQ ID NO:10, a CDR-H3 having amino acid sequence SEQ ID NO:12, a CDR-L1 having amino acid sequence SEQ ID NO:14, a CDR-L2 having amino acid sequence SEQ ID NO:16, and a CDR-L3 having amino acid sequence SEQ ID NO:18 and (ii) an antibody comprising a CDR-H1 having amino acid sequence SEQ ID NO:48, a CDR-H2 having amino acid sequence SEQ ID NO:50, a CDR-H3 having amino acid sequence SEQ ID NO:52, a CDR-L1 having amino acid sequence SEQ ID NO:54, a CDR-L2 having amino acid sequence SEQ ID NO:56, and a CDR-L3 having amino acid sequence SEQ ID NO:58; and a bispecific antibody comprising (i) an antibody comprising a CDR-H1 having amino acid sequence SEQ ID NO:28, a CDR-H2 having amino acid sequence SEQ ID NO:30, a CDR-H3 having amino acid sequence SEQ ID NO:32, a CDR-L1 having amino acid sequence SEQ ID NO:34, a CDR-L2 having amino acid sequence SEQ ID NO:36, and a CDR-L3 having amino acid sequence SEQ ID NO:38 and (ii) an antibody comprising a CDR-H1 having amino acid sequence SEQ ID NO:48, a CDR-H2 having amino acid sequence SEQ ID NO:50, a CDR-H3 having amino acid sequence SEQ ID NO:52, a CDR-L1 having amino acid sequence SEQ ID NO:54, a CDR-L2 having amino acid sequence SEQ ID NO:56, and a CDR-L3 having amino acid sequence SEQ ID NO:58.

In some embodiments, such a bispecific antibody comprises (i) an antibody comprising a CDR-H1 having amino acid sequence SEQ ID NO:28, a CDR-H2 having amino acid sequence SEQ ID NO:30, a CDR-H3 having amino acid sequence SEQ ID NO:32, a CDR-L1 having amino acid sequence SEQ ID NO:34, a CDR-L2 having amino acid sequence SEQ ID NO:36, and a CDR-L3 having amino acid sequence SEQ ID NO:38 and (ii) an antibody comprising a CDR-H1 having amino acid sequence SEQ ID NO:48, a CDR-H2 having amino acid sequence SEQ ID NO:50, a CDR-H3 having amino acid sequence SEQ ID NO:52, a CDR-L1 having amino acid sequence SEQ ID NO:54, a CDR-L2 having amino acid sequence SEQ ID NO:56, and a CDR-L3 having amino acid sequence SEQ ID NO:58.

One embodiment is a bispecific anti-dengue virus antibody that comprises a $V_H$ chain comprising amino acid sequence SEQ ID NO:4 and a $V_L$ chain comprising amino acid sequence SEQ ID NO:6. One embodiment is a bispecific anti-dengue virus antibody that comprises a $V_H$ chain comprising amino acid sequence SEQ ID NO:24 and a $V_L$ chain comprising amino acid sequence SEQ ID NO:26. One embodiment is a bispecific anti-dengue virus antibody that comprises a $V_H$ chain comprising amino acid sequence SEQ ID NO:44 and a $V_L$ chain comprising amino acid sequence SEQ ID NO:46. One embodiment is a bispecific anti-dengue virus antibody that comprises amino acid sequence SEQ ID NO:2. One embodiment is a bispecific anti-dengue virus antibody that comprises amino acid sequence SEQ ID NO:22. One embodiment is a bispecific anti-dengue virus antibody that comprises amino acid sequence SEQ ID NO:42.

The disclosure provides a bispecific anti-dengue virus antibody that comprises: an antibody comprising a $V_H$ chain comprising amino acid sequence SEQ ID NO:4 and a $V_L$ chain comprising amino acid sequence SEQ ID NO:6; and an antibody comprising a $V_H$ chain comprising amino acid sequence SEQ ID NO:24 and a $V_L$ chain comprising amino acid sequence SEQ ID NO:26. The disclosure also provides a bispecific anti-dengue virus antibody that comprises: an antibody comprising a $V_H$ chain comprising amino acid sequence SEQ ID NO:4 and a $V_L$ chain comprising amino acid sequence SEQ ID NO:6; and an antibody comprising a $V_H$ chain comprising amino acid sequence SEQ ID NO:44 and a $V_L$ chain comprising amino acid sequence SEQ ID NO:46. The disclosure also provides a bispecific anti-dengue virus antibody that comprises: an antibody comprising a $V_H$ chain comprising amino acid sequence SEQ ID NO:24 and a $V_L$ chain comprising amino acid sequence SEQ ID NO:26; and an antibody comprising a $V_H$ chain comprising amino acid sequence SEQ ID NO:44 and a $V_L$ chain comprising amino acid sequence SEQ ID NO:46. One embodiment is a bispecific antibody comprising an antibody comprising amino acid sequence SEQ ID NO:2 and an antibody comprising amino acid sequence SEQ ID NO:22. One embodiment is a bispecific antibody comprising an antibody comprising amino acid sequence SEQ ID NO:2 and an antibody comprising amino acid sequence SEQ ID NO:42. One embodiment is a bispecific antibody comprising an antibody comprising amino acid sequence SEQ ID NO:22 and an antibody comprising amino acid sequence SEQ ID NO:42.

The disclosure also provides a bispecific anti-dengue virus antibody comprising an Fc domain. In one embodiment, the Fc domain is glycosylated. In one embodiment, the Fc domain is non-glycosylated. In one embodiment, the Fc domain has modified affinity to one or more Fc receptors. In one embodiment, the Fc domain exhibits reduced binding to an Fc gamma receptor. One embodiment is an Fc domain flanked by linkers. One embodiment is a bispecific anti-dengue antibody having an Fc domain comprising amino acid sequence SEQ ID NO:102. One embodiment is a bispecific anti-dengue antibody having an Fc domain comprising amino acid sequence SEQ ID NO:104; such an Fc domain exhibits reduced binding to an Fc gamma receptor.

One embodiment is a bispecific anti-dengue antibody comprising amino acid sequence SEQ ID NO:92; such an Fc domain comprises amino acid sequence SEQ ID NO:102 flanked by linkers. One embodiment is a bispecific anti-dengue antibody comprising amino acid sequence SEQ ID NO:94; such an Fc domain comprises amino acid sequence SEQ ID NO:104 flanked by linkers.

The disclosure provides a bispecific anti-dengue virus antibody comprising amino acid sequences SEQ ID NO:2, SEQ ID NO:102, and SEQ ID NO:22. The disclosure provides a bispecific anti-dengue virus antibody comprising amino acid sequences SEQ ID NO:2, SEQ ID NO:104, and SEQ ID NO:22. The disclosure provides a bispecific anti-dengue virus antibody comprising amino acid sequences SEQ ID NO:2, SEQ ID NO:92, and SEQ ID NO:22. The disclosure also provides a bispecific anti-dengue virus antibody comprising amino acid sequences SEQ ID NO:2, SEQ ID NO:94, and SEQ ID NO:22. In one embodiment, the bispecific antibody has an amino acid sequence in the order SEQ ID:2—SEQ ID NO:94—SEQ ID NO:22. In one embodiment, the bispecific antibody has an amino acid sequence in the order SEQ ID:22—SEQ ID NO:94—SEQ ID NO:2.

The disclosure provides a bispecific anti-dengue virus antibody comprising amino acid sequences SEQ ID NO:2, SEQ ID NO:102, and SEQ ID NO:42. The disclosure provides a bispecific anti-dengue virus antibody comprising amino acid sequences SEQ ID NO:2, SEQ ID NO:104, and SEQ ID NO:42. The disclosure provides a bispecific anti-dengue virus antibody comprising amino acid sequences SEQ ID NO:2, SEQ ID NO:92, and SEQ ID NO:42. The disclosure also provides a bispecific anti-dengue virus antibody comprising amino acid sequences SEQ ID NO:2, SEQ ID NO:94, and SEQ ID NO:42. In one embodiment, the bispecific antibody has an amino acid sequence in the order SEQ ID:2—SEQ ID NO:94—SEQ ID NO:42. In one embodiment, the bispecific antibody has an amino acid sequence in the order SEQ ID:42—SEQ ID NO:94—SEQ ID NO:2.

Figure 10:
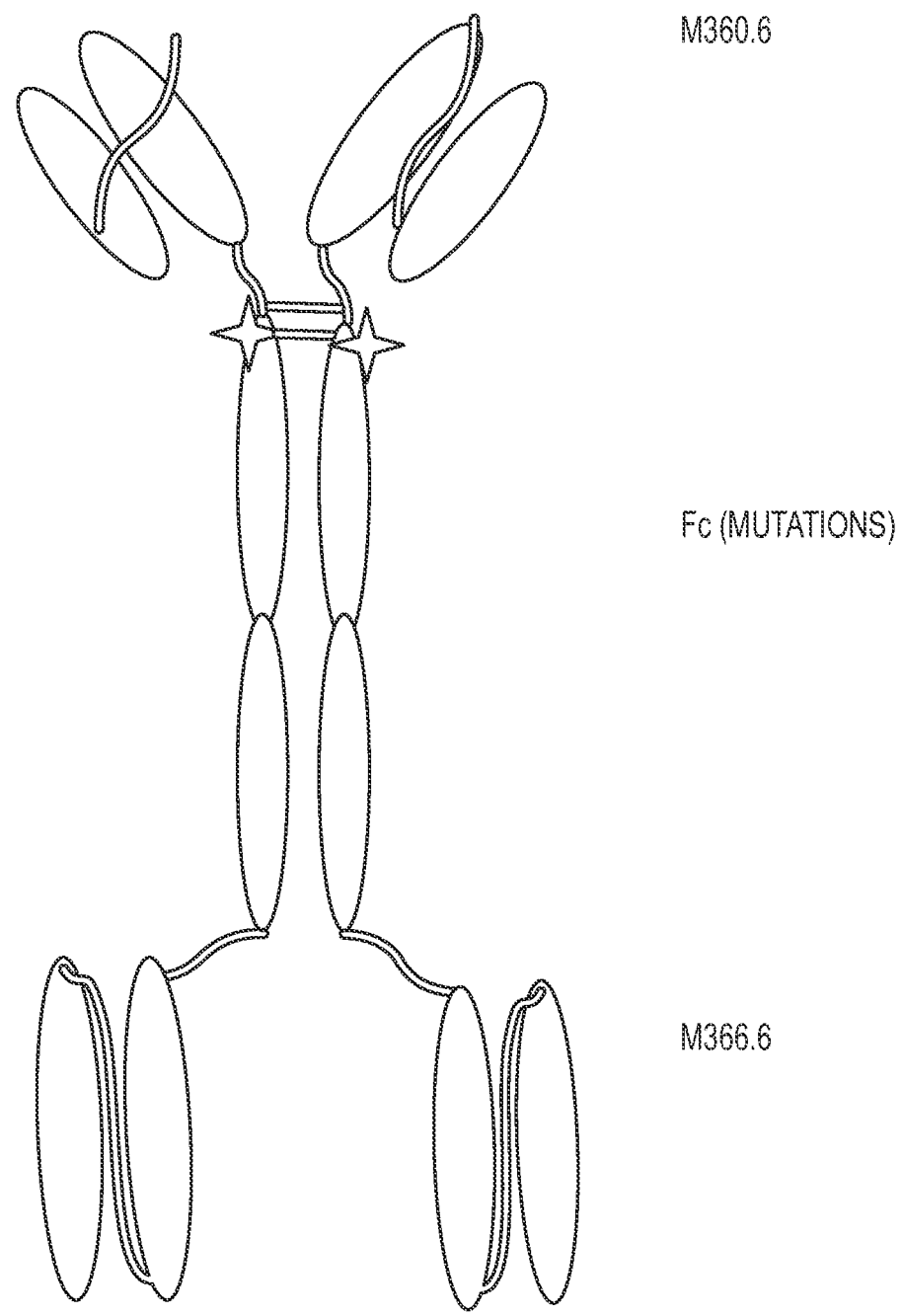
FIG. 10 provides a schematic of human anti-dengue virus bispecific antibody m3666, which comprises human anti-dengue virus antibodies m360.6 and m366.6 linked by an Fc domain comprising amino acid sequence SEQ ID NO:94. The term "Fc (mutations)" refers to an Fc region in which the two leucines positioned at amino acid residues 21 and 22 of SEQ ID NO:92 have been deleted, as indicated by the two stars.

The disclosure provides a bispecific anti-dengue virus antibody comprising amino acid sequences SEQ ID NO:22, SEQ ID NO:102, and SEQ ID NO:42. The disclosure provides a bispecific anti-dengue virus antibody comprising amino acid sequences SEQ ID NO:22, SEQ ID NO:104, and SEQ ID NO:42. The disclosure provides a bispecific anti-dengue virus antibody comprising amino acid sequences SEQ ID NO:22, SEQ ID NO:92, and SEQ ID NO:42. The disclosure also provides a bispecific anti-dengue virus antibody comprising amino acid sequences SEQ ID NO:22, SEQ ID NO:94, and SEQ ID NO:42. In one embodiment, the bispecific antibody has an amino acid sequence in the order SEQ ID:22—SEQ ID NO:94—SEQ ID NO:42. In one embodiment, the bispecific antibody has an amino acid sequence in the order SEQ ID:42—SEQ ID NO:94—SEQ ID NO:22. One embodiment is a bispecific anti-dengue virus antibody comprising amino acid sequence SEQ ID NO:96. One embodiment of such a bispecific antibody is depicted in FIG. 10.

One embodiment is a bispecific antibody comprising an amino acid sequence that is at least 50 percent identical to amino acid sequence SEQ ID NO:96. One embodiment is an antibody comprising an amino acid sequence that is at least 60 percent identical to amino acid sequence SEQ ID NO:96. One embodiment is an antibody comprising an amino acid sequence that is at least 70 percent identical to amino acid sequence SEQ ID NO:96. One embodiment is an antibody comprising an amino acid sequence that is at least 80 percent identical to amino acid sequence SEQ ID NO:96. One embodiment is an antibody comprising an amino acid sequence that is at least 90 percent identical to amino acid sequence SEQ ID NO:96. One embodiment is an antibody comprising an amino acid sequence that is at least 95 percent identical to amino acid sequence SEQ ID NO:96. One embodiment is an antibody comprising an amino acid sequence that is at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:96. One embodiment is an antibody comprising amino acid sequence SEQ ID NO:96. Each of these bispecific antibodies retains the ability to bind to a DENV envelope protein and to cross-react with envelope proteins from all four DENV serotypes.

The disclosure provides a bispecific antibody comprising human anti-dengue virus antibody m366. The disclosure provides a bispecific antibody comprising human anti-dengue virus antibody m366.6. The disclosure provides a bispecific antibody comprising human anti-dengue virus antibody m360.6. The disclosure provides a bispecific antibody comprising human anti-dengue virus antibody m360. The disclosure provides a bispecific antibody comprising human anti-dengue virus antibodies m366 and m366.6. The disclosure provides a bispecific antibody comprising human anti-dengue virus antibodies m366 and m360.6. The disclosure provides a bispecific antibody comprising human anti-dengue virus antibodies m366 and m360. The disclosure provides a bispecific antibody comprising human anti-dengue virus antibodies m366.6 and m360.6. The disclosure provides a bispecific antibody comprising human anti-dengue virus antibodies m366.6 and m360. The disclosure provides a bispecific antibody comprising human anti-dengue virus antibodies m360.6 and m360.

The disclosure provides a bispecific antibody comprising human anti-dengue virus antibody m366 and an Fc domain, such as an Fc domain comprising amino acid sequence SEQ ID NO:92 or SEQ ID NO:94, such as an Fc domain comprising amino acid sequence SEQ ID NO:94. The disclosure provides a bispecific antibody comprising human anti-dengue virus antibody m366.6 and an Fc domain, such as an Fc domain comprising amino acid sequence SEQ ID NO:92 or SEQ ID NO:94, such as an Fc domain comprising amino acid sequence SEQ ID NO:94. The disclosure provides a bispecific antibody comprising human anti-dengue virus antibody m360.6 and an Fc domain, such as an Fc domain comprising amino acid sequence SEQ ID NO:92 or SEQ ID NO:94, such as an Fc domain comprising amino acid sequence SEQ ID NO:94. The disclosure provides a bispecific antibody comprising human anti-dengue virus antibody m360 and an Fc domain, such as an Fc domain comprising amino acid sequence SEQ ID NO:92 or SEQ ID NO:94, such as an Fc domain comprising amino acid sequence SEQ ID NO:94.

The disclosure provides a bispecific antibody comprising human anti-dengue virus antibodies m366 and m366.6 and an Fc domain, such as an Fc domain comprising amino acid sequence SEQ ID NO:92 or SEQ ID NO:94, such as an Fc domain comprising amino acid sequence SEQ ID NO:94. The disclosure provides a bispecific antibody comprising human anti-dengue virus antibodies m366 and m360.6 and an Fc domain, such as an Fc domain comprising amino acid sequence SEQ ID NO:92 or SEQ ID NO:94, such as an Fc domain comprising amino acid sequence SEQ ID NO:94. The disclosure provides a bispecific antibody comprising human anti-dengue virus antibodies m366 and m360 and an Fc domain, such as an Fc domain comprising amino acid sequence SEQ ID NO:92 or SEQ ID NO:94, such as an Fc domain comprising amino acid sequence SEQ ID NO:94. The disclosure provides a bispecific antibody comprising human anti-dengue virus antibodies m366.6 and m360.6 and an Fc domain, such as an Fc domain comprising amino acid sequence SEQ ID NO:92 or SEQ ID NO:94, such as an Fc domain comprising amino acid sequence SEQ ID NO:94. The disclosure provides a bispecific antibody comprising human anti-dengue virus antibodies m366.6 and m360 and an Fc domain, such as an Fc domain comprising amino acid sequence SEQ ID NO:92 or SEQ ID NO:94, such as an Fc domain comprising amino acid sequence SEQ ID NO:94. The disclosure provides a bispecific antibody comprising human anti-dengue virus antibodies m360.6 and m360 and an Fc domain, such as an Fc domain comprising amino acid sequence SEQ ID NO:92 or SEQ ID NO:94, such as an Fc domain comprising amino acid sequence SEQ ID NO:94.

The disclosure also provides a human anti-dengue virus antibody of the embodiments that comprises a secretory segment (i.e., a secretory sequence) joined to the amino terminus of the antibody domain. A secretory segment enables an expressed antibody to be secreted from the cell that produces it. Suitable secretory segments include an antibody secretory segment or any heterologous secretory segment capable of directing the secretion of an antibody of the embodiments. Examples of secretory segments include, but are not limited to, tissue plasminogen activator (t-PA), interferon, interleukin, growth hormone, histocompatibility, viral envelope glycoprotein, and antibody secretory segments. In one embodiment, the secretory segment is an antibody secretory segment.

The disclosure provides an antibody comprising a variable domain having the identifying characteristics of human anti-dengue virus antibody m366. Identifying characteristics of human anti-dengue virus antibody m366 include (a) derivation from a human antibody, (b) binding to a DENV envelope domain III protein, (c) cross-reactive with DENV serotype 1, DENV serotype 2, DENV serotype 3, and DENV serotype 4, (d) binding to each of DENV serotype 1, DENV serotype 2, DENV serotype 3, and DENV serotype 4 envelope proteins with a dissociation constant ($K_D$) of no more than 20 nanomolar (nM), as determined by a Biocore assay as set forth in the Examples, (e) neutralization of DENV serotype 1, DENV serotype 2, DENV serotype 3, and DENV serotype 4, and (f) interaction with amino acid residue 20 of DENV envelope domain III.2 protein having SEQ ID NO:82 (i.e., interaction with amino acid residue 310 of DENV envelope serotype 2 protein having SEQ ID NO:81). In one embodiment, such an antibody also has the identifying characteristic of binding to each of the DENV serotypes with a $K_D$ of no more than 2, 5, 10, and 15 nM, respectively, as determined by a Biocore assay as set forth in the Examples. In one embodiment, such an antibody also has the identifying characteristic of neutralizing each of the DENV serotypes at no more than 25 µg/ml, as determined in a plaque reduction assay as set forth in the Examples. SEQ ID NO:81 represents the amino acid sequence of Swiss Prot: P143338.1: DENV envelope serotype 2, except that several amino acids have been changed to correspond to SEQ ID NO:82: i.e., residue 310 has been changed from E to K; residue 337 has been changed from L to F; residue 343 has been changed from D to E; residue 344 has been changed from N to K; residue 367 has been changed from V to I; and residue 373 has been changed from L to F.

Without being bound by theory, it is believed that antibody m366 interacts with amino acid residues 15, 16, 17, 18, 19, 20, 21, 35, 37, 71, 93 and 95 of DENV envelope domain III.2 protein having amino acid sequence SEQ ID NO:82; these residues correspond to amino acid residues 305, 306, 307, 308, 309, 310, 311, 325, 327, 361, 383, and 385 of DENV envelope serotype 2 protein having amino acid sequence SEQ ID NO:81.

One embodiment is a human anti-dengue virus antibody comprising a variable domain having the identifying characteristics of antibody m366. One embodiment is a human anti-dengue virus antibody comprising a variable domain and a constant domain, wherein the antibody has the identifying characteristics of antibody m366. One embodiment of the disclosure is human anti-dengue virus antibody m366, also referred to herein as human DENV antibody m366, human antibody m366, antibody m366, and m366. One embodiment of the disclosure is a human anti-dengue virus antibody comprising amino acid sequence SEQ ID NO:2. One embodiment is an antibody that comprises an antibody m366 paratope. One embodiment is an antibody that binds the epitope which antibody m366 binds.

The disclosure provides a human anti-dengue virus antibody, the variable domain of which has a three-dimensional structure that is similar to that of antibody m366. Such a three-dimensional structure enables binding of such an antibody to the epitope which antibody m366 binds. One embodiment is an antibody in which the CDRs of the antibody are positioned in a three-dimensional structure similar to the positioning of the CDRs of antibody m366, i.e., such that the antibody can bind to the epitope which antibody m366 binds. One embodiment is an antibody comprising a variable domain that contacts at least one of the following amino acid residues of the DENV envelope domain III.2 protein having amino acid sequence SEQ ID NO:82: amino acid residue 15, 16, 17, 18, 19, 20, 21, 35, 37, 71, 93 or 95 of amino acid sequence SEQ ID NO:82. One embodiment is an antibody comprising a variable domain that contacts at least one of the following amino acid residues of the DENV envelope serotype 2 protein having amino acid sequence SEQ ID NO:81: i.e., amino acid residue 305, 306, 307, 308, 309, 310, 311, 325, 327, 361, 383, or 385 of amino acid sequence SEQ ID NO:81.

One embodiment is an antibody comprising a variable domain that contacts amino acid residue 15 of amino acid sequence SEQ ID NO:82. One embodiment is an antibody comprising a variable domain that contacts amino acid residue 16 of amino acid sequence SEQ ID NO:82. One embodiment is an antibody comprising a variable domain that contacts amino acid residue 17 of amino acid sequence SEQ ID NO:82. One embodiment is an antibody comprising a variable domain that contacts amino acid residue 18 of amino acid sequence SEQ ID NO:82. One embodiment is an antibody comprising a variable domain that contacts amino acid residue 19 of amino acid sequence SEQ ID NO:82. One embodiment is an antibody comprising a variable domain that contacts amino acid residue 20 of amino acid sequence SEQ ID NO:82. One embodiment is an antibody comprising a variable domain that contacts amino acid residue 21 of amino acid sequence SEQ ID NO:82. One embodiment is an antibody comprising a variable domain that contacts amino acid residue 35 of amino acid sequence SEQ ID NO:82. One embodiment is an antibody comprising a variable domain that contacts amino acid residue 37 of amino acid sequence SEQ ID NO:82. One embodiment is an antibody comprising a variable domain that contacts amino acid residue 71 of amino acid sequence SEQ ID NO:82. One embodiment is an antibody comprising a variable domain that contacts amino acid residue 93 of amino acid sequence SEQ ID NO:82. One embodiment is an antibody comprising a variable domain that contacts amino acid residue 95 of amino acid sequence SEQ ID NO:82. The disclosure provides for an antibody comprising a variable domain that contacts any combination of amino acid residues 15, 16, 17, 18, 19, 20, 21, 35, 37, 71, 93 and 95 of amino acid sequence SEQ ID NO:82. The disclosure provides for an antibody comprising a variable domain that contacts amino acid residues 71, 93 and 95 of amino acid sequence SEQ ID NO:82. Without being bound by theory, it is believed that these residues are only contacted by antibodies of the disclosure.

One embodiment is an antibody comprising a variable domain that contacts amino acid residue 305 of amino acid sequence SEQ ID NO:81. One embodiment is an antibody comprising a variable domain that contacts amino acid residue 306 of amino acid sequence SEQ ID NO:81. One embodiment is an antibody comprising a variable domain that contacts amino acid residue 307 of amino acid sequence SEQ ID NO:81. One embodiment is an antibody comprising a variable domain that contacts amino acid residue 308 of amino acid sequence SEQ ID NO:81. One embodiment is an antibody comprising a variable domain that contacts amino acid residue 309 of amino acid sequence SEQ ID NO:81. One embodiment is an antibody comprising a variable domain that contacts amino acid residue 310 of amino acid sequence SEQ ID NO:81. One embodiment is an antibody comprising a variable domain that contacts amino acid residue 311 of amino acid sequence SEQ ID NO:81. One embodiment is an antibody comprising a variable domain that contacts amino acid residue 325 of amino acid sequence SEQ ID NO:81. One embodiment is an antibody comprising a variable domain that contacts amino acid residue 327 of amino acid sequence SEQ ID NO:81. One embodiment is an antibody comprising a variable domain that contacts amino acid residue 361 of amino acid sequence SEQ ID NO:81. One embodiment is an antibody comprising a variable domain that contacts amino acid residue 383 of amino acid sequence SEQ ID NO:81. One embodiment is an antibody comprising a variable domain that contacts amino acid residue 385 of amino acid sequence SEQ ID NO:81. The disclosure provides for an antibody comprising a variable domain that contacts amino acid residues 361, 383 and 385 of amino acid sequence SEQ ID NO:81. Without being bound by theory, it is believed that these residues are only contacted by antibodies of the disclosure.

The disclosure provides an antibody comprising a variable domain having the identifying characteristics of human anti-dengue virus antibody m366.6. Identifying characteristics of human anti-dengue virus antibody m366.6 include (a) derivation from a human antibody, (b) binding to a DENV envelope domain III protein, (c) cross-reactive with DENV serotype 1, DENV serotype 2, DENV serotype 3, and DENV serotype 4, (d) binding to each of DENV serotype 1, DENV serotype 2, DENV serotype 3, and DENV serotype 4 envelope proteins with a dissociation constant ($K_D$) of no more than 1 nanomolar (nM), as determined by a Biocore assay as set forth in the Examples, (e) neutralization of DENV serotype 1, DENV serotype 2, DENV serotype 3, and DENV serotype 4 at an $IC_{50}$ of less than 25 µg/ml, as determined by a DENV RVP assay as set forth in the Examples, and (f) interaction with amino acid residue 20 of DENV envelope domain III.2 protein having SEQ ID NO:82 (i.e., interaction with amino acid residue 310 of DENV envelope serotype 2 protein having SEQ ID NO:81). In one embodiment, such an antibody also has the identifying characteristic of neutralizing each of the DENV serotypes at an $IC_{50}$ of no more than 0.5. 1, 3, and 25 µg/ml, respectively, as determined by a DENV RVP assay as set forth in the Examples.

One embodiment is a human anti-dengue virus antibody comprising a variable domain having the identifying characteristics of antibody m366.6. One embodiment is a human anti-dengue virus antibody comprising a variable domain and a constant domain, wherein the antibody has the identifying characteristics of antibody m366.6. One embodiment of the disclosure is human anti-dengue virus antibody m366.6, also referred to herein as human DENV antibody m366.6, human antibody m366.6, antibody m366.6, and m366.6. One embodiment of the disclosure is a human anti-dengue virus antibody comprising amino acid sequence SEQ ID NO:22. One embodiment is an antibody that comprises an antibody m366.6 paratope. One embodiment is an antibody that binds the epitope which antibody m366.6 binds.

The disclosure provides a human anti-dengue virus antibody, the variable domain of which has a three-dimensional structure that is similar to that of antibody m366.6. Such a three-dimensional structure enables binding of such an antibody to the epitope which antibody m366.6 binds. One embodiment is an antibody in which the CDRs of the antibody are positioned in a three-dimensional structure similar to the positioning of the CDRs of antibody m366.6, i.e., such that the antibody can bind to the epitope which antibody m366.6 binds.

The disclosure provides an antibody comprising a variable domain having the identifying characteristics of human anti-dengue virus antibody m360.6. Identifying characteristics of human anti-dengue virus antibody m360.6 include (a) derivation from a human antibody, (b) binding to a DENV envelope domain III protein, (c) cross-reactive with DENV serotype 1, DENV serotype 2, DENV serotype 3, and DENV serotype 4, (d) binding to each of DENV serotype 1, DENV serotype 2, DENV serotype 3, and DENV serotype 4 envelope proteins with a dissociation constant ($K_D$) of no more than 40 nanomolar (nM), as determined by a Biocore assay as set forth in the Examples, (e) neutralization of DENV serotype 1, DENV serotype 2, DENV serotype 3, and DENV serotype 4 at an $IC_{50}$ of less than 25 µg/ml, as determined by a DENV RVP assay as set forth in the Examples, and (f) interaction with amino acid residue 20 of DENV envelope domain III.2 protein having SEQ ID NO:82 (i.e., interaction with amino acid residue 310 of DENV envelope serotype 2 protein having SEQ ID NO:81). In one embodiment, such an antibody also has the identifying characteristic of binding to each of the DENV serotypes with a $K_D$ of no more than 1, 1, 1, and 40 nM, respectively, as determined by a Biocore assay as set forth in the Examples. In one embodiment, such an antibody also has the identifying characteristic of neutralizing each of the DENV serotypes at an $IC_{50}$ of no more than 2, 5, 15, and 25 µg/ml, respectively, as determined by a DENV RVP assay as set forth in the Examples.

One embodiment is a human anti-dengue virus antibody comprising a variable domain having the identifying characteristics of antibody m360.6. One embodiment is a human anti-dengue virus antibody comprising a variable domain and a constant domain, wherein the antibody has the identifying characteristics of antibody m360.6. One embodiment of the disclosure is human anti-dengue virus antibody m360.6, also referred to herein as human DENV antibody m360.6, human antibody m360.6, antibody m360.6, and m360.6. One embodiment of the disclosure is a human anti-dengue virus antibody comprising amino acid sequence SEQ ID NO:42. One embodiment is an antibody that comprises an antibody m360.6 paratope. One embodiment is an antibody that binds the epitope which antibody m360.6 binds.

The disclosure provides a human anti-dengue virus antibody, the variable domain of which has a three-dimensional structure that is similar to that of antibody m360.6. Such a three-dimensional structure enables binding of such an antibody to the epitope which antibody m360.6 binds. One embodiment is an antibody in which the CDRs of the antibody are positioned in a three-dimensional structure similar to the positioning of the CDRs of antibody m360.6, i.e., such that the antibody can bind to the epitope which antibody m360.6 binds.

The disclosure provides an antibody comprising a variable domain having the identifying characteristics of human anti-dengue virus antibody m360. Identifying characteristics of human anti-dengue virus antibody m360 include (a) derivation from a human antibody, (b) binding to a DENV envelope domain III protein, (c) cross-reactive with DENV serotype 1, DENV serotype 2, and DENV serotype 3, (d) binding to each of DENV serotype 1, DENV serotype 2, and DENV serotype 3 envelope proteins with a dissociation constant ($K_D$) of no more than 10 nM nanomolar (nM), (e) neutralization of three serotypes of DENV, and (f) interaction with amino acid residue 20 of DENV envelope domain III.2 protein having SEQ ID NO:82 (i.e., interaction with amino acid residue 310 of DENV envelope serotype 2 protein having SEQ ID NO:81). In one embodiment, such an antibody also has the identifying characteristic of binding to each of the DENV serotypes with a $K_D$ of no more than 0.1, 10, 10, and 100 nM, respectively, as determined by a Biocore assay as set forth in the Examples.

One embodiment is a human anti-dengue virus antibody comprising a variable domain having the identifying characteristics of antibody m360. One embodiment is a human anti-dengue virus antibody comprising a variable domain and a constant domain, wherein the antibody has the identifying characteristics of antibody m360. One embodiment of the disclosure is human anti-dengue virus antibody m360, also referred to herein as human DENV antibody m360, human antibody m360, antibody m360, and m360. One embodiment of the disclosure is a human anti-dengue virus antibody comprising amino acid sequence SEQ ID NO:62. One embodiment is an antibody that comprises an antibody m360 paratope. One embodiment is an antibody that binds the epitope which antibody m360 binds.

The disclosure provides a human anti-dengue virus antibody, the variable domain of which has a three-dimensional structure that is similar to that of antibody m360. Such a three-dimensional structure enables binding of such an antibody to the epitope which antibody m360 binds. One embodiment is an antibody in which the CDRs of the antibody are positioned in a three-dimensional structure similar to the positioning of the CDRs of antibody m360, i.e., such that the antibody can bind to the epitope which antibody m360 binds.

The disclosure provides a bispecific antibody having the identifying characteristics of human anti-dengue virus antibody m3666. Identifying characteristics of bispecific antidengue virus antibody m3666 include (a) comprising human anti-dengue virus antibodies having the identifying characteristics of antibodies m360.6 and m366.6, (b) binding to a DENV envelope domain III protein, (c) cross-reactive with DENV serotype 1, DENV serotype 2, DENV serotype 3, and DENV serotype 4, (d) binding to each of DENV serotype 1, DENV serotype 2, DENV serotype 3, and DENV serotype 4 envelope proteins with a dissociation constant ($K_D$) of no more than 40 nanomolar (nM), as determined by a Biocore assay as set forth in the Examples, (e) neutralization of DENV serotype 1, DENV serotype 2, DENV serotype 3, and DENV serotype 4 at an $IC_{50}$ of less than 1 µg/ml, as determined by a DENV RVP assay as set forth in the Examples, and (f) interaction with amino acid residue 20 of DENV envelope domain III.2 protein having SEQ ID NO:82 (i.e., interaction with amino acid residue 310 of DENV envelope serotype 2 protein having SEQ ID NO:81). In one embodiment, such a bispecific antibody also has the identifying characteristic of neutralizing two of the DENV serotypes at an $IC_{50}$ of less than 1 µg/ml and two of the DENV serotypes at an $IC_{50}$ of less than 0.1 µg/ml, as determined by a DENV RVP assay as set forth in the Examples.

One embodiment of the disclosure is bispecific anti-dengue virus antibody m3666, also referred to herein as bispecific DENV antibody m3666, bispecific antibody m3666, antibody m3666, and m3666. One embodiment of the disclosure is a bispecific anti-dengue virus antibody comprising amino acid sequence SEQ ID NO:96. One embodiment is an antibody that comprises antibody m3666 paratopes. One embodiment is an antibody that binds the epitopes which antibody m3666 binds.

The disclosure provides a bispecific anti-dengue virus antibody, the variable domains of which have three-dimensional structures that are similar to those of bispecific antibody m3666. Such three-dimensional structure enables binding of such a bispecific antibody to the epitopes which bispecific antibody m3666 binds. One embodiment is an antibody in which the CDRs of the antibody are positioned in a three-dimensional structure similar to the positioning of the CDRs of bispecific antibody m3666, i.e., such that the antibody can bind to the epitopes which antibody m3666 binds.

The disclosure also provides human anti-dengue virus antibody conjugates comprising an anti-dengue virus antibody of the embodiments conjugated to an agent. Any of the human anti-dengue virus antibodies disclosed herein, including monospecific, bispecific and multispecific antibodies can be used to form an antibody-agent conjugate. The agent can be conjugated to the antibody directly or via a linker using techniques known to those skilled in the art. The linker can be cleavable or non-cleavable. The agent can be a therapeutic agent, a toxic agent, or a detectable marker. Examples of such therapeutic agents (e.g., for use in therapy), toxic agents (such as a cytotoxic agent), or detectable markers (e.g., for use as a diagnostic) are known to those skilled in the art.

Epitope-Containing Proteins

The disclosure provides a protein comprising an epitope that binds to an antibody having the identifying characteristics of human anti-dengue virus antibody m366. Such a protein can have utility as an immunogen against dengue virus infection. Identifying characteristics of human anti-dengue virus antibody m366 are disclosed herein. One embodiment is a protein comprising an epitope that binds to an antibody comprising amino acid sequence SEQ ID NO:2. One embodiment is a protein comprising an epitope that binds to human anti-dengue virus antibody m366. In one embodiment, the epitope contacts at least one residue in amino acid sequence SEQ ID NO:2 that corresponds to at least one residue contacted by DENV Env-DIII.2. In one embodiment, the epitope contacts at least one residue in amino acid sequence SEQ ID NO:2 that corresponds to at least one residue contacted by DENV envelope proteins from serotype 1, serotype 2, serotype 3, and serotype 4.

The disclosure provides a protein comprising an epitope that binds to an antibody having the identifying characteristics of human anti-dengue virus antibody m366.6. Such a protein can have utility as an immunogen against dengue virus infection. Identifying characteristics of human anti-dengue virus antibody m366.6 are disclosed herein. One embodiment is a protein comprising an epitope that binds to an antibody comprising amino acid sequence SEQ ID NO:22. One embodiment is a protein comprising an epitope that binds to human anti-dengue virus antibody m366.6. In one embodiment, the epitope contacts at least one residue in amino acid sequence SEQ ID NO:22 that corresponds to at least one residue contacted by DENV Env-DIII.2. In one embodiment, the epitope contacts at least one residue in amino acid sequence SEQ ID NO:22 that corresponds to at least one residue contacted by DENV envelope proteins from serotype 1, serotype 2, serotype 3, and serotype 4.

The disclosure provides a protein comprising an epitope that binds to an antibody having the identifying characteristics of human anti-dengue virus antibody m360.6. Such a protein can have utility as an immunogen against dengue virus infection. Identifying characteristics of human anti-dengue virus antibody m360.6 are disclosed herein. One embodiment is a protein comprising an epitope that binds to an antibody comprising amino acid sequence SEQ ID NO:42. One embodiment is a protein comprising an epitope that binds to human anti-dengue virus antibody m360.6. In one embodiment, the epitope contacts at least one residue in amino acid sequence SEQ ID NO:42 that corresponds to at least one residue contacted by DENV Env-DIII.2. In one embodiment, the epitope contacts at least one residue in amino acid sequence SEQ ID NO:42 that corresponds to at least one residue contacted by DENV envelope proteins from serotype 1, serotype 2, serotype 3, and serotype 4.

The disclosure provides a protein comprising an epitope that binds to an antibody having the identifying characteristics of human anti-dengue virus antibody m360. Such a protein can have utility as an immunogen against dengue virus infection. Identifying characteristics of human anti-dengue virus antibody m360 are disclosed herein. One embodiment is a protein comprising an epitope that binds to an antibody comprising amino acid sequence SEQ ID NO:62. One embodiment is a protein comprising an epitope that binds to human anti-dengue virus antibody m360. In one embodiment, the epitope contacts at least one residue in amino acid sequence in SEQ ID NO:62 that corresponds to at least one residue contacted by DENV Env-DIII.2. In one embodiment, the epitope contacts at least one residue in amino acid sequence SEQ ID NO:62 that corresponds to at least one residue contacted by DENV envelope proteins from serotype 1, serotype 2, and serotype 3.

The disclosure provides a protein comprising an epitope that binds to an antibody having the identifying characteristics of bispecific human anti-dengue virus antibody m3666. Such a protein can have utility as an immunogen against dengue virus infection. Identifying characteristics of bispecific anti-dengue virus antibody m3666 are disclosed herein. One embodiment is a protein comprising an epitope that binds to an antibody comprising amino acid sequence SEQ ID NO:96. One embodiment is a protein comprising an epitope that binds to human anti-dengue virus antibody m3666. In one embodiment, the epitope contacts at least one residue in amino acid sequence in SEQ ID NO:96 that corresponds to at least one residue contacted by DENV Env-DIII.2. In one embodiment, the epitope contacts at least one residue in amino acid sequence SEQ ID NO:96 that corresponds to at least one residue contacted by DENV envelope proteins from serotype 1, serotype 2, serotype 3, and serotype 4.

One embodiment is a protein comprising an epitope that elicits production of an antibody having the identifying characteristics of a human anti-dengue virus antibody selected from the group consisting of anti-dengue virus antibody m366, anti-dengue virus antibody m366.6, anti-dengue virus antibody m360.6, and anti-dengue virus antibody m360. One embodiment is a protein comprising an epitope that elicits production of an antibody having the identifying characteristics of human anti-dengue virus antibody m366. One embodiment is a protein comprising an epitope that elicits production of an antibody having the identifying characteristics of human anti-dengue virus antibody m366.6. One embodiment is a protein comprising an epitope that elicits production of an antibody having the identifying characteristics of human anti-dengue virus antibody m360.6. One embodiment is a protein comprising an epitope that elicits production of an antibody having the identifying characteristics of human anti-dengue virus antibody m360. One embodiment is a protein comprising an epitope that elicits production of an antibody that binds to DENV envelope proteins from serotype 1, serotype 2, serotype 3, and serotype 4. One embodiment is a protein comprising an epitope that elicits production of an antibody that neutralizes DENV serotype 1, DENV serotype 2, DENV serotype 3, and DENV serotype 4.

The disclosure provides a protein that comprises at least one amino acid residue corresponding to at least one of amino acid residues 15, 16, 17, 18, 19, 20, 21, 35, 37, 71, 93, and 95 of amino acid sequence SEQ ID NO:82, wherein the protein comprises a three-dimensional structure in which the at least one amino acid residue is localized in a position similar to the position of the corresponding at least one amino acid residue in a natural DENV envelope domain III.2 protein. The disclosure provides a protein that comprises amino acid residues corresponding to amino acid residues 15, 16, 17, 18, 19, 20, 21, 35, 37, 71, 93, and 95 of amino acid sequence SEQ ID NO:82, wherein the protein comprises a three-dimensional structure in which the amino acid residues are localized in positions similar to the positions of the corresponding amino acid residues in a natural DENV envelope domain III.2 protein.

Nucleic Acid Molecules and Uses Thereof

The disclosure provides a nucleic acid molecule that encodes a human anti-dengue virus antibody of the embodiments. The disclosure also provides a nucleic acid molecule that encodes a protein comprising an epitope that binds to an antibody having the identifying characteristics of human anti-dengue virus antibody m366. The disclosure also provides a nucleic acid molecule that encodes a protein comprising an epitope that binds to an antibody having the identifying characteristics of human anti-dengue virus antibody m366.6. The disclosure also provides a nucleic acid molecule that encodes a protein comprising an epitope that binds to an antibody having the identifying characteristics of human anti-dengue virus antibody m360.6. The disclosure also provides a nucleic acid molecule that encodes a protein comprising an epitope that binds to an antibody having the identifying characteristics of human anti-dengue virus antibody m360. The disclosure also provides a nucleic acid molecule that encodes a protein comprising an epitope that binds to an antibody having the identifying characteristics of human anti-dengue virus antibody m3666.

One embodiment is a nucleic acid molecule that encodes a human anti-dengue virus antibody that binds to an envelope protein of dengue virus, wherein the antibody is cross-reactive with dengue virus (DENV) serotype 1 envelope protein, DENV serotype 2 envelope protein, DENV serotype 3 envelope protein, and DENV serotype 4 envelope protein. In one embodiment, the antibody encoded by the nucleic acid molecule neutralizes DENV serotype 1, DENV serotype 2, DENV serotype 3, and DENV serotype 4. In one embodiment, the antibody encoded by the nucleic acid molecule binds to a receptor binding domain of the envelope protein. In one embodiment, the antibody encoded by the nucleic acid molecule binds to a receptor binding domain of the envelope protein and neutralizes DENV serotype 1, DENV serotype 2, DENV serotype 3, and DENV serotype 4. In one embodiment, the antibody encoded by the nucleic acid molecule binds to domain III of the envelope protein. In one embodiment, the antibody encoded by the nucleic acid molecule binds to domain III of the envelope protein and neutralizes DENV serotype 1, DENV serotype 2, DENV serotype 3, and DENV serotype 4. In one embodiment, the antibody encoded by the nucleic acid molecule binds to each of DENV serotype 1, DENV serotype 2, DENV serotype 3, and DENV serotype 4 envelope proteins with a dissociation constant ($K_D$) of no more than 20 nanomolar (nM)

In one embodiment, the antibody encoded by the nucleic acid molecule is not isolated from a human subject.

The disclosure provides a nucleic acid molecule that encodes an antibody comprising amino acid sequence SEQ ID NO:4, an antibody comprising amino acid sequence SEQ ID NO:6, an antibody comprising amino acid sequences SEQ ID NO:4 and SEQ ID NO:6, or an antibody comprising amino acid sequence SEQ ID NO:2. One embodiment is a nucleic acid molecule that encodes an antibody comprising amino acid sequence SEQ ID NO:4. One embodiment is a nucleic acid molecule that encodes an antibody comprising amino acid sequence SEQ ID NO:6. One embodiment is a nucleic acid molecule that encodes an antibody comprising amino acid sequences SEQ ID NO:4 and SEQ ID NO:6. One embodiment is a nucleic acid molecule that encodes an antibody comprising amino acid sequence SEQ ID NO:2. One embodiment is a nucleic acid molecule that encodes an antibody comprising an amino acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to an amino acid sequence selected from the group consisting of SEQ ID NO:4, SEQ ID NO:6, and SEQ ID NO:2. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule comprising nucleic acid sequence SEQ ID NO:3, comprising nucleic acid sequence SEQ ID NO:5, comprising nucleic acid sequences SEQ ID NO:3 and SEQ ID NO:5, or comprising nucleic acid sequence SEQ ID NO:1. One embodiment is a nucleic acid molecule comprising nucleic acid sequence SEQ ID NO:3. One embodiment is a nucleic acid molecule comprising nucleic acid sequence SEQ ID NO:5. One embodiment is a nucleic acid molecule comprising nucleic acid sequences SEQ ID NO:3 and SEQ ID NO:5. One embodiment is a nucleic acid molecule comprising nucleic acid sequence SEQ ID NO:1. One embodiment is a nucleic acid molecule comprising a nucleic acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to a nucleic acid sequence selected from the group consisting of SEQ ID NO:3, SEQ ID NO:5, and SEQ ID NO:1. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule that encodes an antibody of the embodiments that comprises amino acid sequences SEQ ID NO:4 and SEQ ID NO:6 joined by a peptide linker. One embodiment is a nucleic acid molecule that encodes an antibody comprising amino acid sequences SEQ ID NO:4 and SEQ ID NO:6 joined by a peptide linker comprising amino acid sequence SEQ ID NO:20. In one embodiment the order of the amino acid sequences from N-terminus to C-terminus is SEQ ID NO:4—SEQ ID NO:20—SEQ ID NO:6. One embodiment is a nucleic acid molecule that encodes an antibody comprising an amino acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to amino acid sequences SEQ ID NO:4 and SEQ ID NO:6 joined by a peptide linker comprising amino acid sequence SEQ ID NO:20. In one embodiment the order of the amino acid sequences from N-terminus to C-terminus is SEQ ID NO:4—SEQ ID NO:20—SEQ ID NO:6. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule that comprises nucleic acid sequences SEQ ID NO:3 and SEQ ID NO:5 joined by a nucleic acid sequence encoding a peptide linker. One embodiment is a nucleic acid molecule comprising nucleic acid sequences SEQ ID NO:3 and SEQ ID NO:5 joined by nucleic acid sequence SEQ ID NO:19. In one embodiment, the order of the nucleic acid sequences from 5' to 3' is SEQ ID NO:3—SEQ ID NO:19—SEQ ID NO:5. One embodiment is a nucleic acid molecule comprising a nucleic acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to nucleic acid sequences SEQ ID NO:3 and SEQ ID NO:5 joined by nucleic acid sequence SEQ ID NO:19. In one embodiment, the order of the nucleic acid sequences from 5' to 3' is SEQ ID NO:3—SEQ ID NO:19—SEQ ID NO:5. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule that encodes an antibody comprising amino acid sequence SEQ ID NO:2. One embodiment is a nucleic acid molecule that encodes an antibody comprising an amino acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:2. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule comprising nucleic acid sequence SEQ ID NO:1. One embodiment is a nucleic acid molecule comprising a nucleic acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to nucleic acid sequence SEQ ID NO:1. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule that encodes an antibody comprising a CDR having an amino acid sequence selected from the group consisting of SEQ ID NO:8, SEQ ID NO:10, SEQ ID NO:12, SEQ ID NO:14, SEQ ID NO:16, SEQ ID NO:18, and combinations thereof. One embodiment is a nucleic acid molecule that encodes a $V_H$ having a CDR having an amino acid sequence selected from the group consisting of SEQ ID NO:8, SEQ ID NO:10, and SEQ ID NO:12, and combinations thereof. One embodiment is a nucleic acid molecule that encodes a $V_H$, wherein CDR-H1 has amino acid sequence SEQ ID NO:8, CDR-H2 has amino acid sequence SEQ ID NO:10, and CDR-H3 has amino acid sequence SEQ ID NO:12. One embodiment is a nucleic acid molecule that encodes a $V_L$, wherein CDR-L1 has amino acid sequence SEQ ID NO:14, CDR-L2 has amino acid sequence SEQ ID NO:16, and CDR-L3 has amino acid sequence SEQ ID NO:18. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

One embodiment is a nucleic acid molecule comprising a nucleic acid sequence selected from the group consisting of SEQ ID NO:7, SEQ ID NO:9, SEQ ID NO:11, SEQ ID NO:13, SEQ ID NO:15, SEQ ID NO:17, and combinations thereof. One embodiment is a nucleic acid molecule comprising nucleic acid sequences SEQ ID NO:7, SEQ ID NO:9 and SEQ ID NO:11. One embodiment is a nucleic acid molecule comprising nucleic acid sequences SEQ ID NO:13, SEQ ID NO:15, and SEQ ID NO:17. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

A nucleic acid molecule of the embodiments can include a nucleic acid sequence that encodes an Fc domain of the embodiments. In one embodiment, such an encoded Fc domain can be joined to a fusion segment of the embodiments.

The disclosure provides a nucleic acid molecule that encodes an antibody comprising a variable domain having the identifying characteristics of human anti-dengue virus antibody m366. One embodiment is a nucleic acid molecule that encodes a scFv comprising a variable domain having the identifying characteristics of human anti-dengue virus antibody m366. One embodiment is a first nucleic acid molecule that encodes a heavy chain of an antibody comprising a variable domain having the identifying characteristics of human anti-dengue virus antibody m366 and a second nucleic acid molecule that encodes a light chain of an antibody comprising a variable domain having the identifying characteristics of human anti-dengue virus antibody m366.

The disclosure provides a nucleic acid molecule that encodes a protein comprising an epitope that binds to an antibody having the identifying characteristics of human anti-dengue virus antibody m366. Examples of such epitope-containing proteins are provided herein.

The disclosure provides a nucleic acid molecule that encodes an antibody comprising amino acid sequence SEQ ID NO:24, an antibody comprising amino acid sequence SEQ ID NO:26, an antibody comprising amino acid sequences SEQ ID NO:24 and SEQ ID NO:26, or an antibody comprising amino acid sequence SEQ ID NO:22. One embodiment is a nucleic acid molecule that encodes an antibody comprising amino acid sequence SEQ ID NO:24. One embodiment is a nucleic acid molecule that encodes an antibody comprising amino acid sequence SEQ ID NO:26. One embodiment is a nucleic acid molecule that encodes an antibody comprising amino acid sequences SEQ ID NO:24 and SEQ ID NO:26. One embodiment is a nucleic acid molecule that encodes an antibody comprising amino acid sequence SEQ ID NO:22. One embodiment is a nucleic acid molecule that encodes an antibody comprising an amino acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to an amino acid sequence selected from the group consisting of SEQ ID NO:24, SEQ ID NO:26, and SEQ ID NO:22. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule comprising nucleic acid sequence SEQ ID NO:23, comprising nucleic acid sequence SEQ ID NO:25, comprising nucleic acid sequences SEQ ID NO:23 and SEQ ID NO:25, or comprising nucleic acid sequence SEQ ID NO:21. One embodiment is a nucleic acid molecule comprising nucleic acid sequence SEQ ID NO:23. One embodiment is a nucleic acid molecule comprising nucleic acid sequence SEQ ID NO:25. One embodiment is a nucleic acid molecule comprising nucleic acid sequences SEQ ID NO:23 and SEQ ID NO:25. One embodiment is a nucleic acid molecule comprising nucleic acid sequence SEQ ID NO:21. One embodiment is a nucleic acid molecule comprising a nucleic acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to a nucleic acid sequence selected from the group consisting of SEQ ID NO:23, SEQ ID NO:25, and SEQ ID NO:21. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule that encodes an antibody of the embodiments that comprises amino acid sequences SEQ ID NO:24 and SEQ ID NO:26 joined by a peptide linker. One embodiment is a nucleic acid molecule that encodes an antibody comprising amino acid sequences SEQ ID NO:24 and SEQ ID NO:26 joined by a peptide linker comprising amino acid sequence SEQ ID NO:40. In one embodiment the order of the amino acid sequences from N-terminus to C-terminus is SEQ ID NO:24—SEQ ID NO:40—SEQ ID NO:26. In one embodiment the order of the amino acid sequences from N-terminus to C-terminus is SEQ ID NO:26—SEQ ID NO:40—SEQ ID NO:24. One embodiment is a nucleic acid molecule that encodes an antibody comprising an amino acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to amino acid sequences SEQ ID NO:24 and SEQ ID NO:26 joined by a peptide linker comprising amino acid sequence SEQ ID NO:40. In one embodiment the order of the amino acid sequences from N-terminus to C-terminus is SEQ ID NO:24—SEQ ID NO:40—SEQ ID NO:26. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule that comprises nucleic acid sequences SEQ ID NO:23 and SEQ ID NO:25 joined by a nucleic acid sequence encoding a peptide linker. One embodiment is a nucleic acid molecule comprising nucleic acid sequences SEQ ID NO:23 and SEQ ID NO:25 joined by nucleic acid sequence SEQ ID NO:39. In one embodiment, the order of the nucleic acid sequences from 5' to 3' is SEQ ID NO:23—SEQ ID NO:39—SEQ ID NO:25. One embodiment is a nucleic acid molecule comprising a nucleic acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to nucleic acid sequences SEQ ID NO:23 and SEQ ID NO:25 joined by nucleic acid sequence SEQ ID NO:39. In one embodiment, the order of the nucleic acid sequences from 5' to 3' is SEQ ID NO:23—SEQ ID NO:39—SEQ ID NO:25. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule that encodes an antibody comprising amino acid sequence SEQ ID NO:22. One embodiment is a nucleic acid molecule that encodes an antibody comprising an amino acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:22. Each of these nucleic acid molecules encodes an antibody that retains the ability to bind to a DENV envelope protein and to cross-react with envelope proteins from all four DENV serotypes.

Such an encoded antibody can be a complete Ig or any fragment thereof.

The disclosure provides a nucleic acid molecule comprising nucleic acid sequence SEQ ID NO:21. One embodiment is a nucleic acid molecule comprising a nucleic acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to nucleic acid sequence SEQ ID NO:21. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule that encodes an antibody comprising a CDR having an amino acid sequence selected from the group consisting of SEQ ID NO:28, SEQ ID NO:30, SEQ ID NO:32, SEQ ID NO:34, SEQ ID NO:36, SEQ ID NO:38, and combinations thereof. One embodiment is a nucleic acid molecule that encodes a $V_H$ having a CDR having an amino acid sequence selected from the group consisting of SEQ ID NO:28, SEQ ID NO:30, and SEQ ID NO:32, and combinations thereof. One embodiment is a nucleic acid molecule that encodes a $V_H$, wherein CDR-H1 has amino acid sequence SEQ ID NO:28, CDR-H2 has amino acid sequence SEQ ID NO:30, and CDR-H3 has amino acid sequence SEQ ID NO:32. One embodiment is a nucleic acid molecule that encodes a $V_L$, wherein CDR-L1 has amino acid sequence SEQ ID NO:34, CDR-L2 has amino acid sequence SEQ ID NO:36, and CDR-L3 has amino acid sequence SEQ ID NO:38. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

One embodiment is a nucleic acid molecule comprising a nucleic acid sequence selected from the group consisting of SEQ ID NO:27, SEQ ID NO:29, SEQ ID NO:31, SEQ ID NO:33, SEQ ID NO:35, SEQ ID NO:37, and combinations thereof. One embodiment is a nucleic acid molecule comprising nucleic acid sequences SEQ ID NO:27, SEQ ID NO:29 and SEQ ID NO:31. One embodiment is a nucleic acid molecule comprising nucleic acid sequences SEQ ID NO:33, SEQ ID NO:35, and SEQ ID NO:37. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

A nucleic acid molecule of the embodiments can include a nucleic acid sequence that encodes an Fc domain of the embodiments. In one embodiment, such an encoded Fc domain can be joined to a fusion segment of the embodiments.

The disclosure provides a nucleic acid molecule that encodes an antibody comprising a variable domain having the identifying characteristics of human anti-dengue virus antibody m366.6. One embodiment is a nucleic acid molecule that encodes a scFv comprising a variable domain having the identifying characteristics of human anti-dengue virus antibody m366.6. One embodiment is a first nucleic acid molecule that encodes a heavy chain of an antibody comprising a variable domain having the identifying characteristics of human anti-dengue virus antibody m366.6 and a second nucleic acid molecule that encodes a light chain of an antibody comprising a variable domain having the identifying characteristics of human anti-dengue virus antibody m366.6.

The disclosure provides a nucleic acid molecule that encodes a protein comprising an epitope that binds to an antibody having the identifying characteristics of human anti-dengue virus antibody m366.6. Examples of such epitope-containing proteins are provided herein.

The disclosure provides a nucleic acid molecule that encodes an antibody comprising amino acid sequence SEQ ID NO:44, an antibody comprising amino acid sequence SEQ ID NO:46, an antibody comprising amino acid sequences SEQ ID NO:44 and SEQ ID NO:46, or an antibody comprising amino acid sequence SEQ ID NO:42. One embodiment is a nucleic acid molecule that encodes an antibody comprising amino acid sequence SEQ ID NO:44. One embodiment is a nucleic acid molecule that encodes an antibody comprising amino acid sequence SEQ ID NO:46. One embodiment is a nucleic acid molecule that encodes an antibody comprising amino acid sequences SEQ ID NO:44 and SEQ ID NO:46. One embodiment is a nucleic acid molecule that encodes an antibody comprising amino acid sequence SEQ ID NO:42. One embodiment is a nucleic acid molecule that encodes an antibody comprising an amino acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to an amino acid sequence selected from the group consisting of SEQ ID NO:44, SEQ ID NO:46, and SEQ ID NO:42. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule comprising nucleic acid sequence SEQ ID NO:43, comprising nucleic acid sequence SEQ ID NO:45, comprising nucleic acid sequences SEQ ID NO:43 and SEQ ID NO:45, or comprising nucleic acid sequence SEQ ID NO:41. One embodiment is a nucleic acid molecule comprising nucleic acid sequence SEQ ID NO:43. One embodiment is a nucleic acid molecule comprising nucleic acid sequence SEQ ID NO:45. One embodiment is a nucleic acid molecule comprising nucleic acid sequences SEQ ID NO:43 and SEQ ID NO:45. One embodiment is a nucleic acid molecule comprising nucleic acid sequence SEQ ID NO:41. One embodiment is a nucleic acid molecule comprising a nucleic acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to a nucleic acid sequence selected from the group consisting of SEQ ID NO:43, SEQ ID NO:45, and SEQ ID NO:41. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule that encodes an antibody of the embodiments that comprises amino acid sequences SEQ ID NO:44 and SEQ ID NO:46 joined by a peptide linker. One embodiment is a nucleic acid molecule that encodes an antibody comprising amino acid sequences SEQ ID NO:44 and SEQ ID NO:46 joined by a peptide linker comprising amino acid sequence SEQ ID NO:60. In one embodiment the order of the amino acid sequences from N-terminus to C-terminus is SEQ ID NO:44—SEQ ID NO:60—SEQ ID NO:46. In one embodiment the order of the amino acid sequences from N-terminus to C-terminus is SEQ ID NO:46—SEQ ID NO:60—SEQ ID NO:44. One embodiment is a nucleic acid molecule that encodes an antibody comprising an amino acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to amino acid sequences SEQ ID NO:44 and SEQ ID NO:46 joined by a peptide linker comprising amino acid sequence SEQ ID NO:60. In one embodiment the order of the amino acid sequences from N-terminus to C-terminus is SEQ ID NO:44—SEQ ID NO:60—SEQ ID NO:46. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule that comprises nucleic acid sequences SEQ ID NO:43 and SEQ ID NO:45 joined by a nucleic acid sequence encoding a peptide linker. One embodiment is a nucleic acid molecule comprising nucleic acid sequences SEQ ID NO:43 and SEQ ID NO:45 joined by nucleic acid sequence SEQ ID NO:59. In one embodiment, the order of the nucleic acid sequences from 5' to 3' is SEQ ID NO:43—SEQ ID NO:59—SEQ ID NO:45. One embodiment is a nucleic acid molecule comprising a nucleic acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to nucleic acid sequences SEQ ID NO:43 and SEQ ID NO:45 joined by nucleic acid sequence SEQ ID NO:59. In one embodiment, the order of the nucleic acid sequences from 5' to 3' is SEQ ID NO:43—SEQ ID NO:59—SEQ ID NO:45. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule that encodes an antibody comprising amino acid sequence SEQ ID NO:42. One embodiment is a nucleic acid molecule that encodes an antibody comprising an amino acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:42. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule comprising nucleic acid sequence SEQ ID NO:41. One embodiment is a nucleic acid molecule comprising a nucleic acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to nucleic acid sequence SEQ ID NO:41. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule that encodes an antibody comprising a CDR having an amino acid sequence selected from the group consisting of SEQ ID NO:48, SEQ ID NO:50, SEQ ID NO:52, SEQ ID NO:54, SEQ ID NO:56, SEQ ID NO:58, and combinations thereof. One embodiment is a nucleic acid molecule that encodes a $V_H$ having a CDR having an amino acid sequence selected from the group consisting of SEQ ID NO:48, SEQ ID NO:50, and SEQ ID NO:52, and combinations thereof. One embodiment is a nucleic acid molecule that encodes a $V_H$, wherein CDR-H1 has amino acid sequence SEQ ID NO:48, CDR-H2 has amino acid sequence SEQ ID NO:50, and CDR-H3 has amino acid sequence SEQ ID NO:52. One embodiment is a nucleic acid molecule that encodes a $V_L$, wherein CDR-L1 has amino acid sequence SEQ ID NO:54, CDR-L2 has amino acid sequence SEQ ID NO:56, and CDR-L3 has amino acid sequence SEQ ID NO:58. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

One embodiment is a nucleic acid molecule comprising a nucleic acid sequence selected from the group consisting of SEQ ID NO:47, SEQ ID NO:49, SEQ ID NO:51, SEQ ID NO:53, SEQ ID NO:55, SEQ ID NO:57, and combinations thereof. One embodiment is a nucleic acid molecule comprising nucleic acid sequences SEQ ID NO:47, SEQ ID NO:49 and SEQ ID NO:51. One embodiment is a nucleic acid molecule comprising nucleic acid sequences SEQ ID NO:53, SEQ ID NO:55, and SEQ ID NO:57. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

A nucleic acid molecule of the embodiments can include a nucleic acid sequence that encodes an Fc domain of the embodiments. In one embodiment, such an encoded Fc domain can be joined to a fusion segment of the embodiments.

The disclosure provides a nucleic acid molecule that encodes an antibody comprising a variable domain having the identifying characteristics of human anti-dengue virus antibody m360.6. One embodiment is a nucleic acid molecule that encodes a scFv comprising a variable domain having the identifying characteristics of human anti-dengue virus antibody m360.6. One embodiment is a first nucleic acid molecule that encodes a heavy chain of an antibody comprising a variable domain having the identifying characteristics of human anti-dengue virus antibody m360.6 and a second nucleic acid molecule that encodes a light chain of an antibody comprising a variable domain having the identifying characteristics of human anti-dengue virus antibody m360.6.

The disclosure provides a nucleic acid molecule that encodes a protein comprising an epitope that binds to an antibody having the identifying characteristics of human anti-dengue virus antibody m360.6. Examples of such epitope-containing proteins are provided herein.

The disclosure provides a nucleic acid molecule that encodes an antibody comprising amino acid sequence SEQ ID NO:64, an antibody comprising amino acid sequence SEQ ID NO:66, an antibody comprising amino acid sequences SEQ ID NO:64 and SEQ ID NO:66, or an antibody comprising amino acid sequence SEQ ID NO:62. One embodiment is a nucleic acid molecule that encodes an antibody comprising amino acid sequence SEQ ID NO:64. One embodiment is a nucleic acid molecule that encodes an antibody comprising amino acid sequence SEQ ID NO:66. One embodiment is a nucleic acid molecule that encodes an antibody comprising amino acid sequences SEQ ID NO:64 and SEQ ID NO:66. One embodiment is a nucleic acid molecule that encodes an antibody comprising amino acid sequence SEQ ID NO:62. One embodiment is a nucleic acid molecule that encodes an antibody comprising an amino acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to an amino acid sequence selected from the group consisting of SEQ ID NO:64, SEQ ID NO:66, and SEQ ID NO:62. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule comprising nucleic acid sequence SEQ ID NO:63, comprising nucleic acid sequence SEQ ID NO:65, comprising nucleic acid sequences SEQ ID NO:63 and SEQ ID NO:65, or comprising nucleic acid sequence SEQ ID NO:61. One embodiment is a nucleic acid molecule comprising nucleic acid sequence SEQ ID NO:63. One embodiment is a nucleic acid molecule comprising nucleic acid sequence SEQ ID NO:65. One embodiment is a nucleic acid molecule comprising nucleic acid sequences SEQ ID NO:63 and SEQ ID NO:65. One embodiment is a nucleic acid molecule comprising nucleic acid sequence SEQ ID NO:61. One embodiment is a nucleic acid molecule comprising a nucleic acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to a nucleic acid sequence selected from the group consisting of SEQ ID NO:63, SEQ ID NO:65, and SEQ ID NO:61. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule that encodes an antibody of the embodiments that comprises amino acid sequences SEQ ID NO:64 and SEQ ID NO:66 joined by a peptide linker. One embodiment is a nucleic acid molecule that encodes an antibody comprising amino acid sequences SEQ ID NO:64 and SEQ ID NO:66 joined by a peptide linker comprising amino acid sequence SEQ ID NO:80. In one embodiment the order of the amino acid sequences from N-terminus to C-terminus is SEQ ID NO:64—SEQ ID NO:80—SEQ ID NO:66. In one embodiment the order of the amino acid sequences from N-terminus to C-terminus is SEQ ID NO:66—SEQ ID NO:80—SEQ ID NO:64. One embodiment is a nucleic acid molecule that encodes an antibody comprising an amino acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to amino acid sequences SEQ ID NO:64 and SEQ ID NO:66 joined by a peptide linker comprising amino acid sequence SEQ ID NO:80. In one embodiment the order of the amino acid sequences from N-terminus to C-terminus is SEQ ID NO:64—SEQ ID NO:80—SEQ ID NO:66. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule that comprises nucleic acid sequences SEQ ID NO:63 and SEQ ID NO:65 joined by a nucleic acid sequence encoding a peptide linker. One embodiment is a nucleic acid molecule comprising nucleic acid sequences SEQ ID NO:63 and SEQ ID NO:65 joined by nucleic acid sequence SEQ ID NO:79. In one embodiment, the order of the nucleic acid sequences from 5' to 3' is SEQ ID NO:63—SEQ ID NO:79—SEQ ID NO:65. One embodiment is a nucleic acid molecule comprising a nucleic acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to nucleic acid sequences SEQ ID NO:63 and SEQ ID NO:65 joined by nucleic acid sequence SEQ ID NO:79. In one embodiment, the order of the nucleic acid sequences from 5' to 3' is SEQ ID NO:63—SEQ ID NO:79—SEQ ID NO:65. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule that encodes an antibody comprising amino acid sequence SEQ ID NO:62. One embodiment is a nucleic acid molecule that encodes an antibody comprising an amino acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:62. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule comprising nucleic acid sequence SEQ ID NO:61. One embodiment is a nucleic acid molecule comprising a nucleic acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to nucleic acid sequence SEQ ID NO:61. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

The disclosure provides a nucleic acid molecule that encodes an antibody comprising a CDR having an amino acid sequence selected from the group consisting of SEQ ID NO:68, SEQ ID NO:70, SEQ ID NO:72, SEQ ID NO:74, SEQ ID NO:76, SEQ ID NO:78, and combinations thereof. One embodiment is a nucleic acid molecule that encodes a $V_H$ having a CDR having an amino acid sequence selected from the group consisting of SEQ ID NO:68, SEQ ID NO:70, and SEQ ID NO:72, and combinations thereof. One embodiment is a nucleic acid molecule that encodes a $V_H$, wherein CDR-H1 has amino acid sequence SEQ ID NO:68, CDR-H2 has amino acid sequence SEQ ID NO:70, and CDR-H3 has amino acid sequence SEQ ID NO:72. One embodiment is a nucleic acid molecule that encodes a $V_L$, wherein CDR-L1 has amino acid sequence SEQ ID NO:74, CDR-L2 has amino acid sequence SEQ ID NO:76, and CDR-L3 has amino acid sequence SEQ ID NO:78. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

One embodiment is a nucleic acid molecule comprising a nucleic acid sequence selected from the group consisting of SEQ ID NO:67, SEQ ID NO:69, SEQ ID NO:71, SEQ ID NO:73, SEQ ID NO:75, SEQ ID NO:77, and combinations thereof. One embodiment is a nucleic acid molecule comprising nucleic acid sequences SEQ ID NO:67, SEQ ID NO:69 and SEQ ID NO:71. One embodiment is a nucleic acid molecule comprising nucleic acid sequences SEQ ID NO:73, SEQ ID NO:75, and SEQ ID NO:77. Each of these nucleic acid molecules encodes an antibody that retains the ability to bind to a DENV envelope protein and to cross-react with envelope proteins from all four DENV serotypes. Such an encoded antibody can be a complete Ig or any fragment thereof.

A nucleic acid molecule of the embodiments can include a nucleic acid sequence that encodes an Fc domain of the embodiments. In one embodiment, such an encoded Fc domain can be joined to a fusion segment of the embodiments.

The disclosure provides a nucleic acid molecule that encodes an antibody comprising a variable domain having the identifying characteristics of human anti-dengue virus antibody m360. One embodiment is a nucleic acid molecule that encodes a scFv comprising a variable domain having the identifying characteristics of human anti-dengue virus antibody m360. One embodiment is a first nucleic acid molecule that encodes a heavy chain of an antibody comprising a variable domain having the identifying characteristics of human anti-dengue virus antibody m360 and a second nucleic acid molecule that encodes a light chain of an antibody comprising a variable domain having the identifying characteristics of human anti-dengue virus antibody m360.

The disclosure provides a nucleic acid molecule that encodes a protein comprising an epitope that binds to an antibody having the identifying characteristics of human anti-dengue virus antibody m360. Examples of such epitope-containing proteins are provided herein.

The disclosure provides a nucleic acid molecule that encodes a bispecific human anti-dengue virus antibody of the embodiments. Such a bispecific antibody binds to domain III of the envelope protein of dengue virus and is cross-reactive with domain III of dengue virus (DENV) serotype 1 envelope protein, domain III of DENV serotype 2 envelope protein, domain III of DENV serotype 3 envelope protein, and domain III of DENV serotype 4 envelope protein. Such a bispecific antibody neutralizes DENV serotype 1, DENV serotype 2, DENV serotype 3, and DENV serotype 4.

One embodiment is a nucleic acid molecule that encodes a bispecific anti-dengue virus antibody that comprises two monospecific human anti-dengue virus antibodies of the embodiments. In one embodiment, such monospecific antibodies are the same human anti-dengue virus antibody. In one embodiment, such monospecific antibodies are different human anti-dengue virus antibodies that recognize different DENV virus epitopes. One embodiment is a nucleic acid molecule that encodes a bispecific antibody comprising a monospecific human anti-dengue virus antibody of the embodiments and an antibody against another target.

The disclosure provides a nucleic acid molecule that encodes a bispecific anti-dengue virus antibody that neutralizes each of DENV serotype 1, DENV serotype 2, DENV serotype 3, and DENV serotype 4 at an $IC_{50}$ of less than 25 micrograms per ml (µg/ml), less than 20 µg/ml, less than 15 µg/ml, less than 10 µg/ml, less than 5 µg/ml, less than 1 µg/ml, less than 0.5 µg/ml, less than 0.1 µg/ml, less than 0.05 µg/ml, or less than 0.01 µg/ml. In one embodiment, such a bispecific anti-dengue virus antibody neutralizes each of DENV serotype 1, DENV serotype 2, DENV serotype 3, and DENV serotype 4 at an $IC_{50}$ of less than 1 µg/ml. In one embodiment, such a bispecific anti-dengue virus antibody neutralizes two of the DENV serotypes at an $IC_{50}$ of less than 1 µg/ml and two of the DENV serotypes at an $IC_{50}$ of less than 0.1 µg/ml. A DENV RVP assay as set forth in the Examples can be used to determine neutralization $IC_{50}$ values.

The disclosure provides a nucleic acid molecule that encodes a bispecific anti-dengue virus antibody that comprises a human anti-dengue virus antibody that binds to each of DENV serotype 1, DENV serotype 2, DENV serotype 3, and DENV serotype 4 envelope proteins with a dissociation constant ($K_D$) of no more than 50 nanomolar (nM), no more than 40 nM, no more than 35 nM, no more than 30 nM, no more than 25 nM, no more than 20 nM, no more than 15 nM, no more than 10 nM, no more than 5 nM, no more than 1 nM, no more than 0.5 nM, no more than 0.1 nM, no more than 0.05 nM, no more than 0.01 nM, no more than 5 pM or no more than 1 pM. In one embodiment, such a bispecific antibody comprises a human anti-dengue virus antibody that binds to each of DENV serotype 1, DENV serotype 2, DENV serotype 3, and DENV serotype 4 envelope proteins with a $K_D$ of no more than 40 nM. In one embodiment such a bispecific antibody comprises a human anti-dengue virus antibody that binds to each of DENV serotype 1, DENV serotype 2, DENV serotype 3, and DENV serotype 4 envelope proteins with a $K_D$ of no more than 20 nM. In one embodiment, such a bispecific antibody comprises a human anti-dengue virus antibody that binds to each of DENV serotype 1, DENV serotype 2, DENV serotype 3, and DENV serotype 4 envelope proteins with a $K_D$ of no more than 1 nM. In one embodiment, such a bispecific antibody comprises a human anti-dengue virus antibody that binds to three DENV serotypes with a $K_D$ of no more than 0.5 nM and binds the fourth DENV serotype with a $K_D$ of no more than 40 nM.

One embodiment is a nucleic acid molecule that encodes a bispecific anti-dengue virus antibody that comprises a $V_H$ chain comprising amino acid sequence SEQ ID NO:4 and a $V_L$ chain comprising amino acid sequence SEQ ID NO:6. One embodiment is a nucleic acid molecule that encodes a bispecific anti-dengue virus antibody that comprises a $V_H$ chain comprising amino acid sequence SEQ ID NO:24 and a $V_L$ chain comprising amino acid sequence SEQ ID NO:26. One embodiment is a nucleic acid molecule that encodes a bispecific anti-dengue virus antibody that comprises a $V_H$ chain comprising amino acid sequence SEQ ID NO:44 and a $V_L$ chain comprising amino acid sequence SEQ ID NO:46. One embodiment is a nucleic acid molecule that encodes a bispecific anti-dengue virus antibody that comprises amino acid sequence SEQ ID NO:2. One embodiment is a nucleic acid molecule that encodes a bispecific anti-dengue virus antibody that comprises amino acid sequence SEQ ID NO:22. One embodiment is a nucleic acid molecule that encodes a bispecific anti-dengue virus antibody that comprises amino acid sequence SEQ ID NO:42.

The disclosure provides a nucleic acid molecule that encodes a bispecific anti-dengue virus antibody that comprises: an antibody comprising a $V_H$ chain comprising amino acid sequence SEQ ID NO:4 and a $V_L$ chain comprising amino acid sequence SEQ ID NO:6; and an antibody comprising a $V_H$ chain comprising amino acid sequence SEQ ID NO:24 and a $V_L$ chain comprising amino acid sequence SEQ ID NO:26. The disclosure also provides a nucleic acid molecule that encodes a bispecific anti-dengue virus antibody that comprises: an antibody comprising a $V_H$ chain comprising amino acid sequence SEQ ID NO:4 and a $V_L$ chain comprising amino acid sequence SEQ ID NO:6; and an antibody comprising a $V_H$ chain comprising amino acid sequence SEQ ID NO:44 and a $V_L$ chain comprising amino acid sequence SEQ ID NO:46. The disclosure also provides a nucleic acid molecule that encodes a bispecific anti-dengue virus antibody that comprises: an antibody comprising a $V_H$ chain comprising amino acid sequence SEQ ID NO:24 and a $V_L$ chain comprising amino acid sequence SEQ ID NO:26; and an antibody comprising a $V_H$ chain comprising amino acid sequence SEQ ID NO:44 and a $V_L$ chain comprising amino acid sequence SEQ ID NO:46. One embodiment is a nucleic acid molecule that encodes a bispecific antibody comprising an antibody comprising amino acid sequence SEQ ID NO:2 and an antibody comprising amino acid sequence SEQ ID NO:22. One embodiment is a nucleic acid molecule that encodes a bispecific antibody comprising an antibody comprising amino acid sequence SEQ ID NO:2 and an antibody comprising amino acid sequence SEQ ID NO:42. One embodiment is a nucleic acid molecule that encodes a bispecific antibody comprising an antibody comprising amino acid sequence SEQ ID NO:22 and an antibody comprising amino acid sequence SEQ ID NO:42.

The disclosure also provides a nucleic acid molecule that encodes a bispecific anti-dengue virus antibody comprising an Fc domain. In one embodiment, the Fc domain is glycosylated. In one embodiment, the Fc domain is non-glycosylated. In one embodiment, an Fc domain has modified affinity to one or more Fc receptors. In one embodiment, the Fc domain exhibits reduced binding to an Fc gamma receptor. In one embodiment, the Fc domain is flanked by linkers. One embodiment is a nucleic acid sequence that encodes a bispecific anti-dengue antibody having an Fc domain comprising amino acid sequence SEQ ID NO:102. One embodiment is a nucleic acid sequence that encodes a bispecific anti-dengue antibody having an Fc domain comprising amino acid sequence SEQ ID NO:104. One embodiment is a nucleic acid molecule that encodes a bispecific anti-dengue antibody having an Fc domain comprising amino acid sequence SEQ ID NO:92. One embodiment is a nucleic acid molecule that encodes a bispecific anti-dengue antibody having an Fc domain comprising amino acid sequence SEQ ID NO:94. One embodiment is a nucleic acid molecule that comprises nucleic acid sequence SEQ ID NO:101. One embodiment is a nucleic acid molecule that comprises nucleic acid sequence SEQ ID NO:103. One embodiment is a nucleic acid molecule that comprises nucleic acid sequence SEQ ID NO:91. One embodiment is a nucleic acid molecule that comprises nucleic acid sequence SEQ ID NO:93.

The disclosure provides a nucleic acid molecule that encodes a bispecific anti-dengue virus antibody comprising amino acid sequences SEQ ID NO:2, SEQ ID NO:102, and SEQ ID NO:22. The disclosure provides a nucleic acid molecule that encodes a bispecific anti-dengue virus antibody comprising amino acid sequences SEQ ID NO:2, SEQ ID NO:104, and SEQ ID NO:22. The disclosure provides a nucleic acid molecule that encodes a bispecific anti-dengue virus antibody comprising amino acid sequences SEQ ID NO:2, SEQ ID NO:92, and SEQ ID NO:22. The disclosure also provides a nucleic acid molecule that encodes a bispecific anti-dengue virus antibody comprising amino acid sequences SEQ ID NO:2, SEQ ID NO:94, and SEQ ID NO:22. In one embodiment, the encoded bispecific antibody has an amino acid sequence in the order SEQ ID:2—SEQ ID NO:94—SEQ ID NO:22. In one embodiment, the encoded bispecific antibody has an amino acid sequence in the order SEQ ID:22—SEQ ID NO:94—SEQ ID NO:2. One embodiment is a nucleic acid molecule comprising SEQ ID NO:1, SEQ ID NO:93, and SEQ ID NO:21.

The disclosure provides a nucleic acid molecule that encodes a bispecific anti-dengue virus antibody comprising amino acid sequences SEQ ID NO:2, SEQ ID NO:102, and SEQ ID NO:42. The disclosure provides a nucleic acid molecule that encodes a bispecific anti-dengue virus antibody comprising amino acid sequences SEQ ID NO:2, SEQ ID NO:104, and SEQ ID NO:42. The disclosure provides a nucleic acid molecule that encodes a bispecific anti-dengue virus antibody comprising amino acid sequences SEQ ID NO:2, SEQ ID NO:92, and SEQ ID NO:42. The disclosure also provides a nucleic acid molecule that encodes a bispecific anti-dengue virus antibody comprising amino acid sequences SEQ ID NO:2, SEQ ID NO:94, and SEQ ID NO:42. In one embodiment, the encoded bispecific antibody has an amino acid sequence in the order SEQ ID:2—SEQ ID NO:94—SEQ ID NO:42. In one embodiment, the encoded bispecific antibody has an amino acid sequence in the order SEQ ID:42—SEQ ID NO:94—SEQ ID NO:2. One embodiment is a nucleic acid molecule comprising SEQ ID NO:1, SEQ ID NO:93, and SEQ ID NO:41.

The disclosure provides a nucleic acid molecule that encodes a bispecific anti-dengue virus antibody comprising amino acid sequences SEQ ID NO:22, SEQ ID NO:102, and SEQ ID NO:42. The disclosure provides a nucleic acid molecule that encodes a bispecific anti-dengue virus antibody comprising amino acid sequences SEQ ID NO:22, SEQ ID NO:104, and SEQ ID NO:42. The disclosure provides a nucleic acid molecule that encodes a bispecific anti-dengue virus antibody comprising amino acid sequences SEQ ID NO:22, SEQ ID NO:92, and SEQ ID NO:42. The disclosure also provides a nucleic acid molecule that encodes a bispecific anti-dengue virus antibody comprising amino acid sequences SEQ ID NO:22, SEQ ID NO:94, and SEQ ID NO:42. In one embodiment, the encoded bispecific antibody has an amino acid sequence in the order SEQ ID:22—SEQ ID NO:94—SEQ ID NO:42. In one embodiment, the encoded bispecific antibody has an amino acid sequence in the order SEQ ID:42—SEQ ID NO:94—SEQ ID NO:22. One embodiment is a nucleic acid molecule comprising SEQ ID NO:21, SEQ ID NO:93, and SEQ ID NO:41. One embodiment is a nucleic acid molecule that has a nucleic acid sequence in the order of SEQ ID NO:41—SEQ ID NO:93—SEQ ID NO:21. One embodiment is a nucleic acid molecule that has a nucleic acid sequence in the order of SEQ ID NO:21—SEQ ID NO:93—SEQ ID NO:41.

One embodiment is a nucleic acid molecule that encodes a bispecific anti-dengue virus antibody comprising amino acid sequence SEQ ID NO:96. One embodiment is a nucleic acid molecule comprising SEQ ID NO:95.

One embodiment is a nucleic acid molecule that encodes a bispecific antibody comprising an amino acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, or at least 99 percent identical to amino acid sequence SEQ ID NO:96. One embodiment is a nucleic acid molecule that encodes a bispecific antibody comprising amino acid sequence SEQ ID NO:96. One embodiment is a nucleic acid molecule comprising a nucleic acid sequence that is at least 50 percent, at least 60 percent, at least 70 percent, at least 80 percent, at least 90 percent, at least 91 percent, at least 92 percent, at least 93 percent, at least 94 percent, at least 95 percent, at least 96 percent, at least 97 percent, at least 98 percent, at least 99 percent, or 100 percent identical to nucleic acid sequence SEQ ID NO:95. Each of these nucleic acid molecules encodes a bispecific antibody that retains the ability to bind to a DENV envelope protein and to cross-react with envelope proteins from all four DENV serotypes.

The disclosure provides a nucleic acid molecule that encodes a bispecific antibody comprising human anti-dengue virus antibody m366. The disclosure provides a nucleic acid molecule that encodes a bispecific antibody comprising human anti-dengue virus antibody m366.6. The disclosure provides a nucleic acid molecule that encodes a bispecific antibody comprising human anti-dengue virus antibody m360.6. The disclosure provides a nucleic acid molecule that encodes a bispecific antibody comprising human anti-dengue virus antibody m360. The disclosure provides a nucleic acid molecule that encodes a bispecific antibody comprising human anti-dengue virus antibodies m366 and m366.6. The disclosure provides a nucleic acid molecule that encodes a bispecific antibody comprising human anti-dengue virus antibodies m366 and m360.6. The disclosure provides a nucleic acid molecule that encodes a bispecific antibody comprising human anti-dengue virus antibodies m366 and m360. The disclosure provides a nucleic acid molecule that encodes a bispecific antibody comprising human anti-dengue virus antibodies m366.6 and m360.6. The disclosure provides a nucleic acid molecule that encodes a bispecific antibody comprising human anti-dengue virus antibodies m366.6 and m360. The disclosure provides a nucleic acid molecule that encodes a bispecific antibody comprising human anti-dengue virus antibodies m360.6 and m360.

The disclosure provides a nucleic acid molecule that encodes a bispecific antibody comprising human anti-dengue virus antibody m366 and an Fc domain, such as an Fc domain comprising amino acid sequence SEQ ID NO:92 or SEQ ID NO:94, such as an Fc domain comprising amino acid sequence SEQ ID NO:94. The disclosure provides a nucleic acid molecule that encodes a bispecific antibody comprising human anti-dengue virus antibody m366.6 and an Fc domain, such as an Fc domain comprising amino acid sequence SEQ ID NO:92 or SEQ ID NO:94, such as an Fc domain comprising amino acid sequence SEQ ID NO:94. The disclosure provides a nucleic acid molecule that encodes a bispecific antibody comprising human anti-dengue virus antibody m360.6 and an Fc domain, such as an Fc domain comprising amino acid sequence SEQ ID NO:92 or SEQ ID NO:94, such as an Fc domain comprising amino acid sequence SEQ ID NO:94. The disclosure provides a nucleic acid molecule that encodes a bispecific antibody comprising human anti-dengue virus antibody m360 and an Fc domain, such as an Fc domain comprising amino acid sequence SEQ ID NO:92 or SEQ ID NO:94, such as an Fc domain comprising amino acid sequence SEQ ID NO:94.

The disclosure provides a nucleic acid molecule that encodes a bispecific antibody comprising human anti-dengue virus antibodies m366 and m366.6 and an Fc domain, such as an Fc domain comprising amino acid sequence SEQ ID NO:92 or SEQ ID NO:94, such as an Fc domain comprising amino acid sequence SEQ ID NO:94. The disclosure provides a nucleic acid molecule that encodes a bispecific antibody comprising human anti-dengue virus antibodies m366 and m360.6 and an Fc domain, such as an Fc domain comprising amino acid sequence SEQ ID NO:92 or SEQ ID NO:94, such as an Fc domain comprising amino acid sequence SEQ ID NO:94. The disclosure provides a nucleic acid molecule that encodes a bispecific antibody comprising human anti-dengue virus antibodies m366 and m360 and an Fc domain, such as an Fc domain comprising amino acid sequence SEQ ID NO:92 or SEQ ID NO:94, such as an Fc domain comprising amino acid sequence SEQ ID NO:94. The disclosure provides a nucleic acid molecule that encodes a bispecific antibody comprising human anti-dengue virus antibodies m366.6 and m360.6 and an Fc domain, such as an Fc domain comprising amino acid sequence SEQ ID NO:92 or SEQ ID NO:94, such as an Fc domain comprising amino acid sequence SEQ ID NO:94. The disclosure provides a nucleic acid molecule that encodes a bispecific antibody comprising human anti-dengue virus antibodies m366.6 and m360 and an Fc domain, such as an Fc domain comprising amino acid sequence SEQ ID NO:92 or SEQ ID NO:94, such as an Fc domain comprising amino acid sequence SEQ ID NO:94. The disclosure provides a nucleic acid molecule that encodes a bispecific antibody comprising human anti-dengue virus antibodies m360.6 and m360 and an Fc domain, such as an Fc domain comprising amino acid sequence SEQ ID NO:92 or SEQ ID NO:94, such as an Fc domain comprising amino acid sequence SEQ ID NO:94.

The disclosure provides a nucleic acid molecule that encodes a bispecific antibody having the identifying characteristics of bispecific anti-dengue virus antibody m3666. The disclosure also provides a nucleic acid molecule that encodes bispecific anti-dengue virus antibody m3666.

The disclosure provides a nucleic acid molecule that encodes a protein comprising an epitope that binds to an antibody having the identifying characteristics of bispecific anti-dengue virus antibody m3666. Examples of such epitope-containing proteins are provided herein.

The disclosure provides a method to produce a human anti-dengue virus antibody of the embodiments. The method comprises: (a) screening a yeast display human antibody library for a human antibody cross-reactive with dengue virus (DENV) serotype 1, DENV serotype 2, DENV serotype 3, and DENV serotype 4 in the presence of a non-neutralizing DENV envelope domain III protein; and (b) isolating a clone expressing the antibody cross-reactive with DENV serotype 1, DENV serotype 2, DENV serotype 3, and DENV serotype 4. In one embodiment, the non-neutralizing DENV envelope domain III protein has a mutation at a residue corresponding to amino acid residue 20 of amino acid sequence SEQ ID NO:82. In one embodiment, the mutation is a K310E point mutation, wherein the mutation is at amino acid residue 310 of amino acid sequence SEQ ID NO:81.

The disclosure also provides a method to produce an human anti-dengue virus antibody of the embodiments, which comprises: (a) culturing a recombinant cell encoding the antibody; and (b) recovering the antibody.

Nucleic acid molecules of the embodiments can be produced using a number of methods known to those skilled in the art; see, for example, Sambrook J et al., 2001, *Molecular Cloning: a Laboratory Manual*, 3$^{rd}$ edition, Cold Spring Harbor Laboratory Press, and Ausubel F et al., 1994, *Current Protocols in Molecular Biology*, John Wiley & Sons. For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecules of the embodiments can be selected from a mixture of modified nucleic acids by screening for the function of the protein encoded by the nucleic acid (e.g., the ability of such a nucleic acid molecule to encode an antibody that retains the ability to bind to a DENV envelope protein and to cross-react with envelope proteins from all four DENV serotypes).

Methods useful for producing antibodies of the embodiments are known to those skilled in the art and are also exemplified in the Examples. Such antibodies can be produced synthetically using techniques known to those skilled in the art. Such antibodies can be produced using recombinant techniques known to those skilled in the art.

The disclosure provides a recombinant vector that comprises a nucleic acid encoding an antibody of the embodiments joined to a vector. Such a vector can be a plasmid vector, a viral vector, or other vector. Such a vector can be DNA, RNA, or a derivative of DNA or RNA The disclosure provides a recombinant molecule that comprises a nucleic acid encoding an antibody of the embodiments operatively linked to at least one transcription control sequence capable of effecting expression of the nucleic acid molecule in a recombinant cell. A recombinant cell is a host cell that is transformed with a recombinant molecule of the embodiments; i.e., a recombinant cell comprises a recombinant molecule. A recombinant molecule can comprise one or more nucleic acid molecules encoding an antibody of the embodiments operatively linked to one or more transcription control sequences. As used herein, the term "operatively linked" refers to the nucleic acid molecule being joined to the transcription control sequence in a manner to enable expression of the nucleic acid molecule in the recombinant cell. A recombinant molecule can also contain other regulatory control sequences known to those skilled in the art. Examples of regulatory control sequences include, but are not limited to, promoters, enhancers, repressors, ribosome binding sites, RNA splice sites, polyadenylation sites, transcriptional terminator sequences, and microRNA binding sites. A recombinant cell can comprise one or more recombinant molecules. Host cells to transform can be selected based on their ability to effect expression of a nucleic acid molecule of the embodiments. Host cells can also be selected that effect post-translational modifications. Methods to select, produce and use recombinant vectors, recombinant molecules, and recombinant cells of the embodiments are known to those skilled in the art. Antibodies of the embodiments can be produced by culturing recombinant cells of the embodiments. Methods to effect such production and recovery of such antibodies are known to those skilled in the art, see for example Sambrook J et al., ibid, and Ausubel, F et al., ibid.

The disclosure provides a method to produce a protein that binds to an antibody having the identifying characteristics of a human anti-dengue virus antibody selected from the group consisting of antibody m366, antibody m366.6, antibody m360.6, antibody m360, or antibody m3666. The method comprises: (a) culturing a recombinant cell encoding an epitope-containing protein of the embodiments; and (b) recovering the protein. The disclosure also provides a recombinant vector comprising a nucleic acid molecule that encodes a protein that binds to an antibody having the identifying characteristics of a human anti-dengue virus antibody selected from the group consisting of antibody m366, antibody m366.6, antibody m360.6, antibody m360, or antibody m3666.One embodiment is a recombinant molecule comprising a nucleic acid molecule that encodes a protein that binds to an antibody having the identifying characteristics of a human anti-dengue virus antibody selected from the group consisting of antibody m366, antibody m366.6, antibody m360.6, antibody m360, or antibody m3666. The disclosure also provides a recombinant cell comprising a recombinant molecule comprising a nucleic acid molecule that encodes a protein that binds to an antibody having the identifying characteristics of a human anti-dengue virus antibody selected from the group consisting of antibody m366, antibody m366.6, antibody m360.6, antibody m360, or antibody m3666. Epitope-containing proteins of the embodiments can be produced using techniques similar to those described for antibodies of the embodiments, as known by those skilled in the art.

The disclosure provides a method to produce a protein comprising an epitope that elicits production of an antibody having the identifying characteristics of a human anti-dengue virus antibody selected from the group consisting of antibody m366, antibody m366.6, antibody m360.6, antibody m360, or antibody m3666, which comprises the steps of: (a) identifying an epitope for the human anti-dengue virus antibody on a DENV envelope protein; (b) engineering the epitope to increase binding to the corresponding germline antibody using mutagenesis and selection techniques; (c) constructing a nucleic acid molecule that expresses the engineered epitope; (d) culturing a recombinant cell expressing the nucleic acid molecule; and (e) recovering epitope. Methods to effect each of the steps are known to those skilled in the art.

Compositions and Methods of Use to Protect a Subject from DENV Infection

The disclosure provides a composition comprising a human anti-dengue virus antibody that binds to an envelope protein of dengue virus, wherein the antibody is cross-reactive with DENV serotype 1 envelope protein, DENV serotype 2 envelope protein, DENV serotype 3 envelope protein, and DENV serotype 4 envelope protein. In one embodiment, the envelope protein is domain III of the envelope protein. Such a composition can also include a carrier. One embodiment is a pharmaceutical composition comprising a human anti-dengue virus antibody that binds to an envelope protein of dengue virus, wherein the antibody is cross-reactive with DENV serotype 1 envelope protein, DENV serotype 2 envelope protein, DENV serotype 3 envelope protein, and DENV serotype 4 envelope protein. In one embodiment, the envelope protein is domain III of the envelope protein. Such a pharmaceutical composition can also include a pharmaceutically acceptable carrier. Carriers and pharmaceutically acceptable carriers are known to those skilled in the art. Examples include, but are not limited to, aqueous solutions, such as a buffer, e.g., a physiologically compatible buffer.

A composition, such as a pharmaceutical composition, of the embodiments is conveniently formulated in a form suitable for administration to a subject. Techniques to formulate such compositions are known to those skilled in the art.

The disclosure provides a method to protect a subject from dengue virus infection. Such a method comprises administering to the subject a human anti-dengue virus antibody that binds to an envelope protein of dengue virus, wherein the antibody is cross-reactive with DENV serotype 1 envelope protein, DENV serotype 2 envelope protein, DENV serotype 3 envelope protein, and DENV serotype 4 envelope protein. In one embodiment, the envelope protein is domain III of the envelope protein. In one embodiment, a pharmaceutical composition comprising such an antibody is administered. As used herein, the ability of an antibody of the embodiments to protect a subject from dengue virus infection refers to the ability of the antibody to treat, prevent, reduce, or ameliorate the symptoms of dengue virus infection. In one embodiment, an antibody of the embodiments prevents dengue virus infection in a subject. In one embodiment, an antibody of the embodiments treats dengue virus infection in a subject. In one embodiment, an antibody of the embodiments does not enhance dengue virus infection when administered to a subject. In one embodiment, an antibody of the embodiments prevents symptoms of dengue virus infection in a subject. In one embodiment, an antibody of the embodiments treats symptoms of dengue virus infection in a subject. In one embodiment, an antibody of the embodiments prevents symptoms of dengue virus infection from worsening in a subject. In one embodiment, an antibody of the embodiments ameliorates symptoms of dengue virus infection in a subject. In one embodiment, an antibody of the embodiments reduces symptoms of dengue virus infection in a subject. Symptoms of dengue virus infection are known to those skilled in the art. Examples of symptoms include, but are not limited to, high fever, severe headache, severe eye pain, joint pain, muscle pain, skin rash, bleeding (e.g., nose or gum bleed, petechiae, easy bruising), low white cell count, low platelet count, blood plasma leakage, low blood pressure due to dengue shock syndrome, and dengue hemorrhagic fever. In some cases, high fever is combined with one or more additional symptoms. Methods to identify and measure such symptoms are known to those skilled in the art.

As used herein, a subject is any animal that is susceptible to dengue virus infection. Subjects include humans and non-human primates. In one embodiment, a subject is a human. In one embodiment, a subject is a non-human primate.

An antibody of the embodiments can be administered in a variety of ways, such as by oral, intranasal, intraocular, conjunctival, intravenous, intraperitoneal, intramuscular, subcutaneous, intradermal, transdermal, topical, aerosol, and rectal administration routes.

The dose of antibodies disclosed herein to be administered to a subject to be effective (i.e., to protect a subject from dengue virus infection) will depend on the subject's condition, manner of administration, and judgment of the prescribing physician. One skilled in the art can determine the dose as well as a dosing regimen that defines the number and scheduling of doses required.

An antibody of the disclosure can be administered alone or in combination with one or more other antibodies. Examples of other antibodies include, but are limited to, other anti-dengue antibodies as well as antibodies against other diseases. Examples of other anti-dengue antibodies include one or more antibodies of the disclosure. One embodiment is a cocktail of antibodies, such as a cocktail of human anti-dengue virus antibodies of the disclosure. An antibody of the disclosure can also be administered in combination with one or more other therapeutic agents. For example, an antibody of the disclosure can be administered in addition to an epitope-containing protein of the disclosure. The antibody and protein can be administered together or one prior to the other separated by a time known to those skilled in the art.

The disclosure provides a treatment for dengue virus infection comprising a human anti-dengue virus antibody that binds to an envelope protein of dengue virus, wherein the antibody is cross-reactive with DENV serotype 1 envelope protein, DENV serotype 2 envelope protein, DENV serotype 3 envelope protein, and DENV serotype 4 envelope protein and a pharmaceutically acceptable carrier. In one embodiment, the envelope protein is domain III of the envelope protein. The disclosure provides a preventative composition against dengue virus infection comprising a human anti-dengue virus antibody that binds to an envelope protein of dengue virus, wherein the antibody is cross-reactive with DENV serotype 1 envelope protein, DENV serotype 2 envelope protein, DENV serotype 3 envelope protein, and DENV serotype 4 envelope protein and a pharmaceutically acceptable carrier.

In one embodiment, the envelope protein is domain III of the envelope protein.

The disclosure provides for a human anti-dengue virus antibody that binds to an envelope protein of dengue virus, wherein the antibody is cross-reactive with DENV serotype 1 envelope protein, DENV serotype 2 envelope protein, DENV serotype 3 envelope protein, and DENV serotype 4 envelope protein to protect a subject from dengue virus infection. In one embodiment, the envelope protein is domain III of the envelope protein. The disclosure provides for a composition comprising a human anti-dengue virus antibody that binds to an envelope protein of dengue virus, wherein the antibody is cross-reactive with DENV serotype 1 envelope protein, DENV serotype 2 envelope protein, DENV serotype 3 envelope protein, and DENV serotype 4 envelope protein to protect a subject from dengue virus infection. In one embodiment, the envelope protein is domain III of the envelope protein.

The disclosure provides for the use of a human anti-dengue virus antibody that binds to an envelope protein of dengue virus, wherein the antibody is cross-reactive with DENV serotype 1 envelope protein, DENV serotype 2 envelope protein, DENV serotype 3 envelope protein, and DENV serotype 4 envelope protein to protect a subject from dengue virus infection. In one embodiment, the envelope protein is domain III of the envelope protein. The disclosure provides for the use of a composition comprising a human anti-dengue virus antibody that binds to an envelope protein of dengue virus, wherein the antibody is cross-reactive with DENV serotype 1 envelope protein, DENV serotype 2 envelope protein, DENV serotype 3 envelope protein, and DENV serotype 4 envelope protein to protect a subject from dengue virus infection. In one embodiment, the envelope protein is domain III of the envelope protein.

The disclosure also provides for use of a human anti-dengue virus antibody that binds to an envelope protein of dengue virus, wherein the antibody is cross-reactive with DENV serotype 1 envelope protein, DENV serotype 2 envelope protein, DENV serotype 3 envelope protein, and DENV serotype 4 envelope protein in the manufacture of a medicament for the protection of a subject from dengue virus infection. In one embodiment, the envelope protein is domain III of the envelope protein. The disclosure also provides for use of a composition comprising a human anti-dengue virus antibody that binds to an envelope protein of dengue virus, wherein the antibody is cross-reactive with DENV serotype 1 envelope protein, DENV serotype 2 envelope protein, DENV serotype 3 envelope protein, and DENV serotype 4 envelope protein in the manufacture of a medicament for the protection of a subject from dengue virus infection. In one embodiment, the envelope protein is domain III of the envelope protein.

The disclosure also provides a composition comprising a protein comprising an epitope that elicits production of an antibody with identifying characteristics of a human anti-dengue virus antibody selected from the group consisting of antibody m366, antibody m366.6, antibody m360.6, and antibody m360. Such a composition can also include a carrier. One embodiment is a pharmaceutical composition comprising a protein comprising an epitope that elicits production of an antibody with identifying characteristics of a human anti-dengue virus antibody selected from the group consisting of antibody m366, antibody m366.6, antibody m360.6, and antibody m360. Such a pharmaceutical composition can also include a pharmaceutically acceptable carrier. Carriers and pharmaceutically acceptable carriers are known to those skilled in the art. Examples include, but are not limited to, aqueous solutions, such as a buffer, such as a physiologically compatible buffer. Such a composition can also include an adjuvant. Adjuvants to select are well known to those skilled in the art. A composition, such as a pharmaceutical composition, of the embodiments is conveniently formulated in a form suitable for administration to a subject. Techniques to formulate such compositions are known to those skilled in the art.

The disclosure provides a method to protect a subject from dengue virus infection, wherein the method comprises administering to the subject a protein comprising an epitope that elicits production of an antibody with identifying characteristics of a human anti-dengue virus antibody selected from the group consisting of antibody m366, antibody m366.6, antibody m360.6, and antibody m360. In one embodiment, a pharmaceutical composition comprising such an antibody is administered. As used herein, the ability of an epitope-containing protein of the embodiments to protect a subject from dengue virus infection refers to the ability of the antibody to treat, prevent, or ameliorate the symptoms of dengue virus infection. In one embodiment, an epitope-containing protein of the embodiments prevents dengue virus infection in a subject. In one embodiment, an epitope-containing protein of the embodiments treats dengue virus infection in a subject. In one embodiment, an epitope-containing protein of the embodiments prevents symptoms of dengue virus infection in a subject. In one embodiment, an epitope-containing protein of the embodiments treats symptoms of dengue virus infection in a subject. In one embodiment, an epitope-containing protein of the embodiments prevents symptoms of dengue virus infection from worsening in a subject. In one embodiment, an epitope-containing protein of the embodiments ameliorates symptoms of dengue virus infection in a subject. In one embodiment, an epitope-containing protein of the embodiments reduces symptoms of dengue virus infection in a subject. Symptoms of dengue virus infection are known to those skilled in the art. Examples of symptoms include, but are not limited to, high fever, severe headache, severe eye pain, joint pain, muscle pain, skin rash, bleeding (e.g., nose or gum bleed, petechiae, easy bruising), low white cell count, low platelet count, blood plasma leakage, low blood pressure due to dengue shock syndrome, and dengue hemorrhagic fever. In some cases, high fever is combined with one or more additional symptoms. Methods to identify and measure such symptoms are known to those skilled in the art.

As described herein, a subject is any animal that is susceptible to dengue virus infection. Subjects include humans and non-human primates. In one embodiment, a subject is a human. In one embodiment, a subject is a non-human primate.

An epitope-containing protein of the embodiments can be administered in a variety of ways, such as by oral, intranasal, intraocular, conjunctival, intravenous, intraperitoneal, intramuscular, subcutaneous, intradermal, transdermal, topical, aerosol, and rectal administration routes.

The dose of an epitope-containing protein disclosed herein to be administered to a subject to be effective (i.e., to protect a subject from dengue virus infection) will depend on the subject's condition, manner of administration, and judgment of the prescribing physician. One skilled in the art can determine the dose as well as a dosing regimen that defines the number and scheduling of doses required. Often a single dose is sufficient; however, the dose can be repeated if desirable.

An epitope-containing protein of the disclosure can be administered alone or in combination with one or more other epitope-containing proteins. Examples of other proteins include, but are limited to, other epitope-containing proteins as well as immunogens against other diseases. Examples of other anti-dengue epitope-containing proteins include one or more epitope-containing proteins of the disclosure. One embodiment is a cocktail of epitope-containing proteins, such as a cocktail of epitope-containing proteins of the disclosure. An epitope-containing protein of the disclosure can also be administered in combination with one or more other therapeutic agents.

The disclosure provides a treatment for dengue virus infection comprising a protein comprising an epitope that elicits production of an antibody with identifying characteristics of a human anti-dengue virus antibody selected from the group consisting of antibody m366, antibody m366.6, antibody m360.6, and antibody m360, and a pharmaceutically acceptable carrier. The disclosure provides a preventative composition against dengue virus infection comprising a protein comprising an epitope that elicits production of an antibody with identifying characteristics of a human anti-dengue virus antibody selected from the group consisting of antibody m366, antibody m366.6, antibody m360.6, and antibody m360, and a pharmaceutically acceptable carrier.

The disclosure provides for a protein comprising an epitope that elicits production of an antibody with identifying characteristics of a human anti-dengue virus antibody selected from the group consisting of antibody m366, antibody m366.6, antibody m360.6, and antibody m360 to protect a subject from dengue virus infection. The disclosure provides for a composition comprising a protein comprising an epitope that elicits production of an antibody with identifying characteristics of a human anti-dengue virus antibody selected from the group consisting of antibody m366, antibody m366.6, antibody m360.6, and antibody m360 to protect a subject from dengue virus infection.

The disclosure provides for the use of a protein comprising an epitope that elicits production of an antibody with identifying characteristics of a human anti-dengue virus antibody selected from the group consisting of antibody m366, antibody m366.6, antibody m360.6, and antibody m360 to protect a subject from dengue virus infection. The disclosure provides for the use of a composition comprising a protein comprising an epitope that elicits production of an antibody with identifying characteristics of a human anti-dengue virus antibody selected from the group consisting of antibody m366, antibody m366.6, antibody m360.6, and antibody m360 to protect a subject from dengue virus infection.

The disclosure also provides for use of a protein comprising an epitope that elicits production of an antibody with identifying characteristics of a human anti-dengue virus antibody selected from the group consisting of antibody m366, antibody m366.6, antibody m360.6, and antibody m360 in the manufacture of a medicament for the protection of a subject from dengue virus infection. The disclosure also provides for use of a composition comprising a protein comprising an epitope that elicits production of an antibody with identifying characteristics of a human anti-dengue virus antibody selected from the group consisting of antibody m366, antibody m366.6, antibody m360.6, and antibody m360 in the manufacture of a medicament for the protection of a subject from dengue virus infection.

Diagnosis of DENV Infection

The disclosure provides a method to diagnose dengue virus infection comprising use of an antibody of the embodiments or an epitope-containing protein of the embodiments. Such a method can be an in vitro, in vivo, or ex vivo diagnostic method. One embodiment is a method to diagnose dengue virus infection in a subject comprising: (a) exposing a human anti-dengue virus antibody that binds to an envelope protein of dengue virus, wherein the antibody is cross-reactive with DENV serotype 1 envelope protein, DENV serotype 2 envelope protein, DENV serotype 3 envelope protein, and DENV serotype 4 envelope protein, to a sample collected from the subject; and (b) detecting complex formation between the antibody and an epitope in the sample, wherein complex formation indicates that the subject is infected with dengue virus. In one embodiment, the envelope protein is domain III of the envelope protein.

One embodiment is a method to diagnose dengue virus infection in a subject comprising: (a) exposing a human anti-dengue virus antibody that binds to an envelope protein of dengue virus, wherein the antibody is cross-reactive with DENV serotype 1 envelope protein, DENV serotype 2 envelope protein, DENV serotype 3 envelope protein, and DENV serotype 4 envelope protein, to the subject; and (b) detecting complex formation between the antibody and an epitope in the subject, wherein complex formation indicates that the subject is infected with dengue virus. In one embodiment, the envelope protein is domain III of the envelope protein.

One embodiment is a method to diagnose dengue virus infection in a subject comprising: (a) exposing a protein comprising an epitope that elicits production of an antibody with identifying characteristics of a human anti-dengue virus antibody selected from the group consisting of antibody m366, antibody m366.6, antibody m360.6, and antibody m360 to a sample collected from the subject; and (b) detecting complex formation between the epitope and an antibody in the sample, wherein complex formation indicates that the subject is infected with dengue virus.

One embodiment is a method to diagnose dengue virus infection in a subject comprising: (a) exposing a protein comprising an epitope that elicits production of an antibody with identifying characteristics of a human anti-dengue virus antibody selected from the group consisting of antibody m366, antibody m366.6, antibody m360.6, and antibody m360 to the subject; and (b) detecting complex formation between the epitope and an antibody in the subject, wherein complex formation indicates that the subject is infected with dengue virus. Methods to use such antibodies and epitope-containing proteins of the embodiments to diagnose dengue virus infection are known to those skilled in the art.

The disclosure provides a diagnostic kit comprising a human anti-dengue virus antibody that binds to an envelope protein of dengue virus, wherein the antibody is cross-reactive with DENV serotype 1 envelope protein, DENV serotype 2 envelope protein, DENV serotype 3 envelope protein, and DENV serotype 4 envelope protein. In one embodiment, the envelope protein is domain III of the envelope protein.

The disclosure also provides a diagnostic kit comprising protein comprising an epitope that elicits production of an antibody with identifying characteristics of a human anti-dengue virus antibody selected from the group consisting of antibody m366, antibody m366.6, antibody m360.6, and antibody m360. Methods to make and use such diagnostic kits are known to those skilled in the art.

The following is a listing of the SEQ ID NOs disclosed in the application. It is to be appreciated that since nucleic acid sequencing technology is not entirely error-free, the nucleic acid sequences and amino acid sequences presented herein represent, respectively, apparent nucleic acid sequences of nucleic acid molecules of the embodiments and apparent amino acid sequences of proteins of the embodiments.

| SEQ ID NO: | Species | Description |
| --- | --- | --- |
| 1 | Synthetic | Nucleic acid sequence encoding human anti-dengue virus antibody m366 (VH-Linker-VL) |
| 2 | Synthetic | Human anti-dengue virus antibody m366 (VH-Linker-VL) |
| 3 | Synthetic | Nucleic acid sequence encoding m366 VH |
| 4 | Synthetic | Human anti-dengue virus antibody m366 VH |
| 5 | Synthetic | Nucleic acid sequence encoding m366 VL |
| 6 | Synthetic | Human anti-dengue virus antibody m366 VL |
| 7 | Synthetic | Nucleic acid sequence encoding m366 CDR-H1 |

-continued

| SEQ ID NO: | Species | Description |
|---|---|---|
| 8 | Synthetic | Human anti-dengue virus antibody m366 CDR-H1 |
| 9 | Synthetic | Nucleic acid sequence encoding m366 CDR-H2 |
| 10 | Synthetic | Human anti-dengue virus antibody m366 CDR-H2 |
| 11 | Synthetic | Nucleic acid sequence encoding m366 CDR-H3 |
| 12 | Synthetic | Human anti-dengue virus antibody m366 CDR-H3 |
| 13 | Synthetic | Nucleic acid sequence encoding m366 CDR-L1 |
| 14 | Synthetic | Human anti-dengue virus antibody m366 CDR-L1 |
| 15 | Synthetic | Nucleic acid sequence encoding m366 CDR-L2 |
| 16 | Synthetic | Human anti-dengue virus antibody m366 CDR-L2 |
| 17 | Synthetic | Nucleic acid sequence encoding m366 CDR-L3 |
| 18 | Synthetic | Human anti-dengue virus antibody m366 CDR-L3 |
| 19 | Synthetic | Nucleic acid sequence encoding m366 linker |
| 20 | Synthetic | m366 linker (Translation of SEQ ID NO: 19) |
| 21 | Synthetic | Nucleic acid sequence encoding human anti-dengue virus antibody m366.6 (VH-Linker-VL) |
| 22 | Synthetic | Human anti-dengue virus antibody m366.6 (VH-Linker-VL) |
| 23 | Synthetic | Nucleic acid sequence encoding m366.6 VH |
| 24 | Synthetic | Human anti-dengue virus antibody m366.6 VH |
| 25 | Synthetic | Nucleic acid sequence encoding m366.6 VL |
| 26 | Synthetic | Human anti-dengue virus antibody m366.6 VL |
| 27 | Synthetic | Nucleic acid sequence encoding m366.6 CDR-H1 |
| 28 | Synthetic | Human anti-dengue virus antibody m366.6 CDR-H1 |
| 29 | Synthetic | Nucleic acid sequence encoding m366.6 CDR-H2 |
| 30 | Synthetic | Human anti-dengue virus antibody m366.6 CDR-H2 |
| 31 | Synthetic | Nucleic acid sequence encoding m366.6 CDR-H3 |
| 32 | Synthetic | Human anti-dengue virus antibody m366.6 CDR-H3 |
| 33 | Synthetic | Nucleic acid sequence encoding m366.6 CDR-L1 |
| 34 | Synthetic | Human anti-dengue virus antibody m366.6 CDR-L1 |
| 35 | Synthetic | Nucleic acid sequence encoding m366.6 CDR-L2 |
| 36 | Synthetic | Human anti-dengue virus antibody m366.6 CDR-L2 |
| 37 | Synthetic | Nucleic acid sequence encoding m366.6 CDR-L3 |
| 38 | Synthetic | Human anti-dengue virus antibody m366.6 CDR-L3 |
| 39 | Synthetic | Nucleic acid sequence encoding m366.6 linker |
| 40 | Synthetic | m366.6 linker (Translation of SEQ ID NO: 39) |
| 41 | Synthetic | Nucleic acid sequence encoding human anti-dengue virus antibody m360.6 (VH-Linker-VL) |
| 42 | Synthetic | Human anti-dengue virus antibody m360.6 (VH-Linker-VL) |
| 43 | Synthetic | Nucleic acid sequence encoding m360.6 VH |
| 44 | Synthetic | Human anti-dengue virus antibody m360.6 VH |
| 45 | Synthetic | Nucleic acid sequence encoding m360.6 VL |
| 46 | Synthetic | Human anti-dengue virus antibody m360.6 VL |
| 47 | Synthetic | Nucleic acid sequence encoding m360.6 CDR-H1 |
| 48 | Synthetic | Human anti-dengue virus antibody m360.6 CDR-H1 |
| 49 | Synthetic | Nucleic acid sequence encoding m360.6 CDR-H2 |
| 50 | Synthetic | Human anti-dengue virus antibody m360.6 CDR-H2 |
| 51 | Synthetic | Nucleic acid sequence encoding m360.6 CDR-H3 |
| 52 | Synthetic | Human anti-dengue virus antibody m360.6 CDR-H3 |
| 53 | Synthetic | Nucleic acid sequence encoding m360.6 CDR-L1 |
| 54 | Synthetic | Human anti-dengue virus antibody m360.6 CDR-L1 |
| 55 | Synthetic | Nucleic acid sequence encoding m360.6 CDR-L2 |
| 56 | Synthetic | Human anti-dengue virus antibody m360.6 CDR-L2 |
| 57 | Synthetic | Nucleic acid sequence encoding m360.6 CDR-L3 |
| 58 | Synthetic | Human anti-dengue virus antibody m360.6 CDR-L3 |
| 59 | Synthetic | Nucleic acid sequence encoding m360.6 linker |
| 60 | Synthetic | m360.6 linker (Translation of SEQ ID NO: 59) |
| 61 | Synthetic | Nucleic acid sequence encoding human anti-dengue virus antibody m360 (VH-Linker-VL) |
| 62 | Synthetic | Human anti-dengue virus antibody m360 (VH-Linker-VL) |
| 63 | Synthetic | Nucleic acid sequence encoding m360 VH |
| 64 | Synthetic | Human anti-dengue virus antibody m360 VH |
| 65 | Synthetic | Nucleic acid sequence encoding m360 VL |
| 66 | Synthetic | Human anti-dengue virus antibody m360 VL |
| 67 | Synthetic | Nucleic acid sequence encoding m360 CDR-H1 |
| 68 | Synthetic | Human anti-dengue virus antibody m360 CDR-H1 |
| 69 | Synthetic | Nucleic acid sequence encoding m360 CDR-H2 |
| 70 | Synthetic | Human anti-dengue virus antibody m360 CDR-H2 |
| 71 | Synthetic | Nucleic acid sequence encoding m360 CDR-H3 |
| 72 | Synthetic | Human anti-dengue virus antibody m360 CDR-H3 |
| 73 | Synthetic | Nucleic acid sequence encoding m360 CDR-L1 |
| 74 | Synthetic | Human anti-dengue virus antibody m360 CDR-L1 |
| 75 | Synthetic | Nucleic acid sequence encoding m360 CDR-L2 |
| 76 | Synthetic | Human anti-dengue virus antibody m360 CDR-L2 |
| 77 | Synthetic | Nucleic acid sequence encoding m360 CDR-L3 |

-continued

| SEQ ID NO: | Species | Description |
|---|---|---|
| 78 | Synthetic | Human anti-dengue virus antibody m360 CDR-L3 |
| 79 | Synthetic | Nucleic acid sequence encoding m360 linker |
| 80 | Synthetic | m360 linker (Translation of SEQ ID NO: 79) |
| 81 | Synthetic | DENV envelope protein, serotype 2 (Swiss-Prot: P14338.1: DENV envelope serotype 2, modified to match SEQ ID NO: 82 between amino acid 291 and amino acid 395) |
| 82 | Synthetic | DENV envelope protein domain III.2 (serotype 2) |
| 83 | Synthetic | Mouse anti-dengue virus antibody 9F12 VH |
| 84 | Synthetic | Mouse anti-dengue virus antibody 9F12 VL |
| 85 | Synthetic | Mouse anti-dengue virus antibody 9F12 CDR-H1 |
| 86 | Synthetic | Mouse anti-dengue virus antibody 9F12 CDR-H2 |
| 87 | Synthetic | Mouse anti-dengue virus antibody 9F12 CDR-H3 |
| 88 | Synthetic | Mouse anti-dengue virus antibody 9F12 CDR-L1 |
| 89 | Synthetic | Mouse anti-dengue virus antibody 9F12 CDR-L2 |
| 90 | Synthetic | Mouse anti-dengue virus antibody 9F12 CDR-L3 |
| 91 | Synthetic | Nucleic acid encoding a human IgG1 Fc with N- and C-terminal linkers |
| 92 | Synthetic | Human IgG1 Fc with linkers |
| 93 | Synthetic | Nucleic acid sequence encoding mutated human IgG1 Fc with N- and C-terminal linkers |
| 94 | Synthetic | Mutated human IgG1 Fc with linkers |
| 95 | Synthetic | Nucleic acid sequence encoding bispecific m3666 |
| 96 | Synthetic | Bispecific anti-dengue virus antibody m3666 |
| 97 | Synthetic | DENV 1, domain III consensus sequence |
| 98 | Synthetic | DENV 2, domain III consensus sequence |
| 99 | Synthetic | DENV 3, domain III consensus sequence |
| 100 | Synthetic | DENV 4, domain III consensus sequence |
| 101 | Synthetic | Nucleic acid sequence encoding human IgG1 Fc |
| 102 | Synthetic | Human IgG1 Fc |
| 103 | Synthetic | Nucleic acid sequence encoding mutated human IgG1 Fc |
| 104 | Synthetic | Mutated human IgG1 Fc |
| 105 | Synthetic | N-terminal linker of SEQ ID NO: 92 and SEQ ID NO: 94 |
| 106 | Synthetic | C-terminal linker of SEQ ID NO: 92 and SEQ ID NO: 94 |

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, and temperature is in degrees Celsius. Standard abbreviations are used.

Example 1

Materials and Methods

This Example provides the materials and methods for the other examples of this section.

A. Yeast Display Naïve Human Antibody Library, Domain III Genes, Antibodies, Biotinylation Kit, Cells.

A large yeast display naïve single chain variable fragment (scFv) human antibody library was constructed using a collection of human antibody gene repertoires, including the genes used for the construction of a phage display Fab library (Zhu Z et al., 2009, Methods Mol Biol 525, 129-142, xv; and unpublished data from Zhu Z and Dimitrov D S laboratory, National Cancer Institute, Frederick, Md.).

All of the nucleic acid molecules encoding envelope domain III proteins (also referred to herein as ED3) were synthesized at Genscript, Inc. (Piscataway, N.J.). These nucleic acid molecules also contained appropriate restriction enzyme recognition sites at the flanking sequences for cloning purposes. Mouse monoclonal anti-c-Myc antibody was purchased from Roche (Pleasanton, Calif.). PE-conjugated streptavidin and Alexa-488 conjugated goat anti-mouse antibody were purchased from Invitrogen (Carlsbad, Calif.). Protein G columns were purchased from GE healthcare (Waukesha, Wis.). Avi-tag specific biotinylation kits were purchased from Avidity (Aurora, Colo.). Yeast plasmid extraction kits were purchased from Zymo Research (Irvine, Calif.). 293 free style protein expression kits were purchased from Invitrogen. An AutoMACS System was purchased from Miltenyi Biotec (Cologne, Germany).

B. Mutant Design, DENV Envelope Domain III-Fc Fusion Protein Expression, Purification and Biotinylation Envelope domain III fusion proteins from each of the four DENV serotypes were produced as described below. These DIII.1, DIII.2, DIII.3, or DIII.4 fusion proteins were fused either to an Avi-tagged human IgG1 Fc or to a c-Myc-tagged human IgG1 Fc to enable efficient purification. A mutant DIII.3 protein fused to an Avi-tagged human IgG1 Fc was also produced.

Nucleic acid molecules encoding dengue envelope domain III proteins from the 4 serotypes were synthesized at Genscript, using consensus gene information for each of the serotypes; the consensus sequences are provided in FIG. 2. Nucleic acid molecules encoding DENV envelope DIII.1, DIII.2, DIII.3, or DIII.4, each with a nucleic acid molecule encoding an Avi- or c-Myc-tagged human IgG Fc domain fused at the 3' end of the DNA encoding the respective DIII protein, were each cloned into a pSecTag vector (Invitrogen), to produce recombinant molecules encoding each respective tagged DIII. These recombinant molecules were named pSecTag:DIII.1-Fc-Avi, pSecTag:DIII.1-Fc-cMyc, pSecTag:DIII.2-Fc-Avi, pSecTag:DIII.2-Fc-cMyc, pSecTag:DIII.3-Fc-Avi, pSecTag:DIII.3-Fc-cMyc, pSecTag:DIII.4-Fc-Avi, and pSecTag:DIII.4-Fc-cMyc.

A nucleic acid molecule encoding a mutant DENV envelope domain III.3 protein with a K310E substitution in the conserved neutralizing epitope of domain III.3 (serotype 3) was produced by introducing a point mutation at the appropriate site of a nucleic acid molecule encoding DIII.3 using overlapping PCR. The 3' end of the resultant nucleic acid molecule was joined to a nucleic acid molecule encoding a Fc-Avi-tag, and cloned into pSecTag to produce a recombinant molecule encoding the mutant DIII.3, named pSecTag:DIII.3(K310E)-Fc-Avi.

Each of the recombinant molecules was transfected into 293 free style cells to produce the respective DIII proteins following the manufacturer's protocol. The respective proteins were purified using a protein G column. Biotinylation of the purified DENV envelope DIII.1-Fc, DIII.2-Fc, DIII.3-Fc, and DIII.4-Fc proteins with Avi-tags was performed using the kit from Avidity following the manufacturer's instructions. The mutant DENV envelope DIII.3-Fc protein was not biotinylated.

C. MACS Sorting Downsize of the Initial Yeast Display Human Antibody Library

Biotinylated DENV envelope domain III.3-Fc was used as the target for three rounds of sorting to downsize the initial yeast display naïve human antibody library. Approximately $10^{10}$ cells from the initial naïve antibody library and 10 µg of biotinylated domain III.3-Fc were incubated in 50 ml PBSA (phosphate-buffered saline containing 1% bovine serum albumin) at room temperature (RT) for 2 hr with rotation; one mg of unrelated antibody (m102.4 IgG1) with the same Fc was also mixed in the mixture to eliminate any Fc-specific antibodies from binding to the Fc domain of the biotinylated domain III.3-Fc. The mixture of biotinylated DIII.3-Fc binding to displayed antibody on cells from the library was washed three times with PBSA and incubated at RT with 100 µl of streptavidin conjugated microbeads from Miltenyi Biotec. The resultant mixture was washed once with PBSA at RT and loaded onto the AutoMACS system for the first round of sorting. The sorted cells were amplified in SDCAA media (20 g dextrose, 6.7 g Difco yeast nitrogen base w/o amino acids, 5 g Bacto casamino acids, 5.4 g $Na_2HPO_4$ and 8.56 g $NaH_2PO_4 \cdot H_2O$ in 1 liter water) at 30° C. and 250 rpm for 24 hr. The culture was then induced in SGCAA media (20 g galactose, 20 g raffinose , 1 g dextrose, 6.7 g Difco yeast nitrogen base w/o amino acids, 5 g Bacto casamino acids, 5.4 g $Na_2HPO_4$ and 8.56 g $NaH_2PO_4 \cdot H_2O$ in 1 liter water) at 20° C. and 250 rpm for 16-18 hr.

The same amounts of antigen, control antibody m102.4 IgG1, and incubation volume were used for the next two rounds of sorting. The cell numbers used for these two rounds of sorting were set at 100 times the size of the sorted pool from the previous round of sorting to keep the diversity of each sorted pool.

D. Competitive Library Panning and Monoclonal Yeast Clone Screening by FACS

The downsized library was further sorted against the biotinylated domain III.3-Fc fusion protein on a FACSAria II cell sorter using the unbiotinylated domain III.3-Fc mutant bearing the point mutation (K310E) in the neutralizing epitope as a competitor. Briefly, $5 \times 10^8$ cells were incubated with 1 µg/ml of biotinylated domain III.3 Fc fusion protein, 10 µg/ml of unbiotinylated domain III.3 mutant Fc fusion protein, and 2 µg/ml of mouse anti-c-Myc antibody in 5 ml of PBSA with rotation for 2 hr at RT followed by three washes with PBSA. A 1:100 diluted PE-conjugated streptavidin and Alexa-488 conjugated goat anti-mouse antibody were then mixed with the cells and incubated at RT for 30 min in the dark, followed by another two washes with PBSA. The stained cells were loaded on the cell sorter for sorting. The gate was set to collect the population with the brightest PE/Alexa signal. The collected cells were amplified in SDCAA media and induced in SGCAA medium as described above. The induced cells were sorted one more time following the same process, and the sorted cells were analyzed on FACS to confirm the specificity of the sorting. The sorted pool, containing only the cells that could not be competed by the mutant, was plated on a SDCAA plate for single yeast clone analysis. Random yeast clones from the plate were inoculated into liquid SDCAA medium for amplification, and induced at 20° C. in 2 ml SGCAA medium for 16 hr. Induced monoclonal yeast cells were stained as described as above without the mutant competitor and analyzed on FACS to select the positive binders.

E. Expression and Purification of scFv-Fc-Avi Proteins

Plasmids were extracted from the identified yeast clones using yeast plasmid extraction kits (Zymo Research), following the manufacturer's instructions. Extracted plasmids were transformed into 10 G chemical competent E. coli (Lucigen , Middleton, Wis.) for further amplification; plasmids extracted from the bacteria were used for DNA sequencing to obtain the nucleic acid sequences encoding the positive binder antibodies. The scFv-encoding inserts of the unique clones were digested with SfiI and ligated into modified pSecTag bearing the same set of SfiI sites and Fc-Avi tag for soluble expression. These constructs were transfected into 293 free style cells for expression following the manufacturer's protocol. After 72 hr of growth, the scFv-Fc fusion proteins were purified from the cell culture medium using protein G columns.

F. ELISA Binding Assay

The purified scFv-Fc proteins were each diluted into PBS at concentration 2 μg/ml; 50 μl of the diluted proteins were coated in a 96-well plate at 4° C. overnight. The c-Myc-tagged DIII proteins from all four serotypes were each serially diluted in 3% milk-PBS and added to the antibody-coated wells for 1 hr after blocking with 3% milk-PBS at RT. After washing, a 1:2000 diluted HRP conjugated anti-c-Myc antibody was added for 1 hr at RT. After washing, 3, 3, 5, 5'-Tetramethylbenzidine (TMB) substrate was added, and the O.D. was read at 450 nm.

G. Mutant Library Construction Through Error-Prone and DNA Shuffling PCR

The scFv D6 mutant library was generated by introducing random point mutations into the DNA encoding scFv D6 through error-prone polymerase chain reaction (PCR), using a GeneMorph II kit (Stratagene, Agilent Technologies, Santa Clara, Calif.) following the manufacturer's protocol with minor modifications. To further diversify the mutation profile, 3 μM of each of the nucleotide analogues 8-oxo-deoxyguanosine triphosphate and 2'-deoxy-p-nucleoside-5'-triphosphate was mixed in the PCR reaction mixture. For the second and third cycle library constructions, an extra step of DNA shuffling PCR was inserted into the regular PCR cycles to combine the beneficial mutations obtained from previous maturation process; see, e.g., Zhao H et al, 1998, Nature Biotechnology 16, 258-261, for a description of DNA shuffling PCR. The DNA shuffling PCR step was performed as following: 20 cycles of denaturation at 94° C. for 15 seconds followed by annealing/extension at 68° C. for 1 second on the Biorad MyCycler (BioRad, Hercules, Calif.).

H. Affinity Determination by Surface Plasmon Resonance

Binding affinities of human anti-DENV scFv m366 to the DENV envelope (E) domain III proteins of the four serotypes were analyzed by surface plasmon resonance technology using a Biacore X100 instrument (GE healthcare). The scFv m366 was covalently immobilized onto a sensor chip (CM5) using carbodiimide coupling chemistry. A control reference surface was prepared for nonspecific binding and refractive index changes. For analysis of the kinetics of interactions, varying concentrations of antigens were injected at a flow rate of 30 μl/min using running buffer containing 10mM HEPES, 150 mM NaCl, 3 mM EDTA, and 0.05% Surfactant P-20 (pH 7.4). The association and dissociation phase data were fitted simultaneously to a 1:1 Langmuir global model, using the nonlinear data analysis program BIAevaluation 3.2. All the experiments were done at 25° C.

I. Plaque Reduction Assay

Serially diluted antibodies in 100 μl L-15 medium (Sigma-Aldrich, St. Louis, Mo.) containing 1% FCS were mixed with 100 μl virus and incubated in a 24-well plate at 37° C. for 1 hr. An 0.5 ml aliquot of PS clone D cells ($4 \times 10^5$/ml) (Sriburia R et al., 2001, J Virological Methods 92, 71) were added and allowed to adhere at 37° C. for 2 hr. Then 0.5 ml of overlay medium (3% carboxymethylcellulose in L15 with 5% FCS) was added and followed by incubation at 37° C. for 5 to 6 days. Cells were stained with naphthalene black.

J. Epitope Mapping of Isolated Antibodies Through Domain III Mutant Library Sorting Random point mutations were introduced into the dengue virus envelope protein domain III.2 coding region (serotype 2) through error-prone PCR using the GeneMorph II mutagenesis kit from Stratagene following the manufacturer's protocol. A repertoire of gel purified gene mutants was re-amplified using YDRDF and YDRDR in regular PCR conditions to add the flanking sequences for in vivo recombination through the Gap repairing process (Zhao Q et al., 2011, Mol Cancer Ther 10, 1677-1685). SfiI digested and gel purified yeast display vector pYD7 (Zhao Q et al., ibid.) was mixed with the mutant gene repertoire and transformed into electroporation-competent yeast cells prepared as described (Perez B et al., 2010, Protein Eng Des 23, 155-159). Yeast display domain III.2 mutant library amplification and induction were performed as described in the Examples herein. The induced mutant library ($5 \times 10^8$ cells) was incubated with 1 μg/ml biotinylated ScFv D6-Fc and 2 μg/ml mouse anti-c-Myc antibody at RT for 2 hr, followed by three washes, and incubation with a mixture of PE-conjugated streptavidin and Alexa-488 conjugated goat anti-mouse antibody as described in the Examples herein. Stained cells were loaded onto the cell sorter; cells that lacked binding to the antigen even though it was still expressed on the yeast cell surface, as demonstrated by Alexa Fluor 488 staining only, were sorted. The sorting process was repeated once under the same conditions. Sorted cells after the second round were amplified; plasmids were extracted from the pool using yeast plasmid extraction kits (Zymo Research), amplified in 10 G E. coli, and sequenced.

K. Computational Docking of Complex Between Env-DIII and scFv Antibody m366

Homology modeling of the variable regions (or domains) of heavy ($V_H$) and light ($V_L$) chains for the scFv antibody m366 was carried out using the SWISS-MODEL workspace by selecting the closest template structures (PDB codes: 3QOS for heavy chain and 2DD8 for light chain), with sequence similarities of 92% and 87% respectively. The $V_H$-$V_L$ orientation of the scFv m366 structure was assigned to be similar to one of the templates (PDB code: 2DD8) that showed minimal steric clash for creating the final scFv m366 model. The crystal structure of the Env-DIII protein of DENV serotype 2 (PDB code: 2R29) was used for docking with the modeled scFv antibody m366. Docking of scFv m366 to the DENV Env-DIII.2 was performed by accessing the ZDOCK server at the University of Massachusetts Medical School's ZLab (Zhiping's Lab) web site. The ZDOCK server uses a fast Fourier transform (FFT)-based rigid-body protein docking algorithm with scoring functions combining pairwise shape complementarity, desolvation and electrostatic energies. Based on the escape mutants that led to the loss of epitopes and available crystal structure of DENV Env-DIII, residues 307, 309, 310, 311, 327, 361 and 383, on the surface of Env-DIII were selected as potential contacting residues for docking constraints. Similarly, one or two residues from each of the CDR-H1, CDR-H3 and CDR-L3 loops were chosen at the docking interface. The CDR-H1 and CDR-H3 loops had dominant hydrophobic residues, whereas CDR-L 1 had a germline mutation, and they all had high antigen-contacting propensities. Results from the top 2000 ZDOCK predictions were filtered using the user-defined residues and a 6-angstrom distance cutoff. Three predicted complexes were only kept as all residues selected come together at the interface and were further examined by PDBePISA (Protein Interfaces, Surfaces and Assemblies). PyMOL (available at the PyMOL website, Schrodinger, N.Y.) was used for the analysis of docked model and graphical illustration.

Example 2

Identification of a Human Anti-Dengue Virus Cross-Reactive Antibody that Binds to Dengue Virus Envelope Domain III Proteins from All 4 Serotypes This Example describes the identification a human anti-dengue virus antibody of the embodiments that is cross-reactive with DENV serotype 1 envelope protein, DENV serotype 2 envelope protein, DENV serotype 3 envelope protein, and DENV serotype 4 envelope protein.

AutoMACS is an ideal platform to quickly sort large numbers of yeast cells and downsize the initial naïve library to make it feasible for the FACS-based cell sorter. Biotinylated DENV envelope domain III.3-Fc (also referred to as DENV Env-DIII.3-Fc, domain III.3-Fc, or DIII.3-Fc) was used for three rounds of sorting of a yeast display naïve antibody library with size at $5 \times 10^9$ on AutoMACS. An excessive amount of an unrelated m102.4 IgG1 with the same Fc fragment as domain III.3-Fc fusion protein was mixed in the library to deplete the potential Fc specific binders. Three rounds of sorting on AutoMACS dramatically enriched the domain III.3-Fc binders. The binding of the entire double positive population to the domain III.3 Fc fusion protein could be competed by a protein that contained only DENV envelope domain III.3 (i.e., without Fc), indicating the binding of the enriched pool was domain III specific, and depletion of potential anti-Fc binding antibodies (Fc binders) using m102.4 IgG1 was efficient.

The downsized pool showed specific binding to the biotinylated DENV envelope domain III.3-Fc with the target antigen at 1 μg/ml. When 10 μg/ml of the unbiotinylated domain III.3-Fc mutant bearing the point mutation (K310E) and 1 μg/ml of the biotinylated wild type domain III.3-Fc were mixed with the yeast pool, the FACS profile obtained from the cell sorter showed the pool divided into several populations, as each was impacted by the mutant competition to a different extent. The first cell population represented those cells that could not bind to the unbiotinylated domain III.3-Fc mutant but still bound well to the biotinylated wild type domain III.3-Fc. The second cell population represented those cells that bound well to epitopes shared by both the wild type and mutant domain III.3. The third cell population, cells that showed no competition by the mutant, were sorted out and plated on a SDCAA plate for single clone screening.

FACS analysis was performed to screen the plated random clones from the sorted yeast pool, which could not be competed by the designed mutant K310E. Plasmids were extracted from the positive yeast clones and sequenced. Two unique clones, designated as D6 and D7, were identified, and nucleic acid molecules encoding their scFv inserts were each introduced into a pSecTag vector encoding the Avi-tagged human IgG1 Fc domain such that the Avi-tagged human IgG1 Fc domain of the resultant protein was at the carboxyl terminus (C terminus) of the scFv fusion protein. The resultant proteins were called scFv D6-Fc-Avi and scFv D7-Fc-Avi.

Human anti-dengue virus antibody scFv D6-Fc-Avi was submitted to an ELISA binding assay as described herein. FIG. 3 shows that the protein encoded by clone D6 (i.e., scFv D6) bound dengue virus envelope domain III proteins from all 4 serotypes.

Example 3

Affinity Maturation Through Random Mutagenesis and Quantitatively Yeast Library Sorting This Example demonstrates that the cross-reactive binding activity of human anti-dengue virus antibody D6 was maintained through the affinity maturation that yielded human anti-dengue virus antibody m366.

After three cycles of mutagenesis and selection of a library encoding scFv D6, one clone was identified from monoclonal yeast display antibody screening of the enriched pool after the final round of sorting, designated as scFv m366. The scFv m366 gene was cloned into a pSecTag vector encoding human IgG1 Fc for scFv m366-Fc fusion protein expression. Biacore analysis showed that the cross-reactive binding activities of scFv m366 to DENV Env domain IIIs from all four DENV serotypes was preserved after the affinity maturation process.

The data are presented in Table 1.

TABLE 1

Binding affinity of scFv m366 to DENV envelope domain IIIs from 4 serotypes measured by Biacore.

| DENV Env Protein Domains | $k_a$ (1/Ms) | $k_d$ (1/s) | $K_D$ (nM) |
|---|---|---|---|
| DIII serotype 1 | 8.601E+5 | 0.02058 | 6.136 |
| DIII serotype 2 | 8.689E+5 | 0.02039 | 2.508 |
| DIII serotype 3 | 1.863E+5 | 2.039E−4 | 1.095 |
| DIII serotype 4 | 2.659E+5 | 0.01032 | 12.38 |

The nucleic acid sequence encoding human anti-dengue virus antibody m366 is provided in nucleic acid sequence SEQ ID NO:1. The amino acid of antibody m366 is provided in amino acid sequence SEQ ID NO:2. The nucleic acid sequences encoding the $V_H$ and $V_L$ chains of antibody m366 are provided in SEQ ID NO:3 and SEQ ID NO:5, respectively. The amino acid sequences of the $V_H$ and $V_L$ chains of antibody m366 are provided in SEQ ID NO:4 and SEQ ID NO:6, respectively. A comparison of the amino acid sequences of the $V_H$ and $V_L$ chains of human anti-dengue virus antibody m366 and mouse anti-dengue virus antibody 9F12, a mouse monoclonal antibody that neutralizes all four dengue virus serotypes (see, e.g., Rajamanonmani R et al., ibid.) indicates that the human and mouse antibodies show less than 50 percent sequence identity, even in their respective CDRs. The amino acid sequence alignment is shown in FIG. 8.

Example 4

Neutralization of Dengue Virus Isolates from All 4 Serotypes by scFv m366-Fc

This Example demonstrates the ability of a human anti-dengue virus antibody of the embodiments to neutralize isolates from DENV serotype 1, DENV serotype 2, DENV serotype 3, and DENV serotype 4.

Figure 4A:
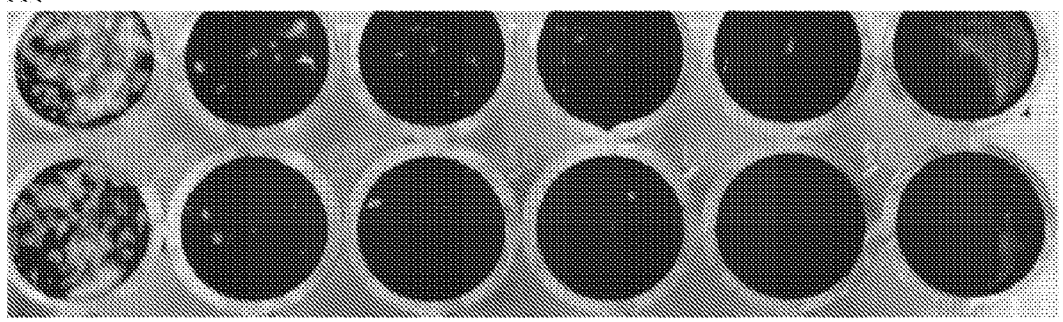
FIG. 4 provides results from a neutralization assay that demonstrates potent neutralization of dengue viruses from serotype 2 (A) and serotype 3 (B) by m366. Serially diluted antibody m366 was tested in duplicates with the final concentration at (from right to left) 200 µg/ml, 100 µg/ml, 50 µg/ml, 25 µg/ml and 12.5 µg/ml. Virus samples without any antibody were plated in duplicates as control.
Figure 4B:
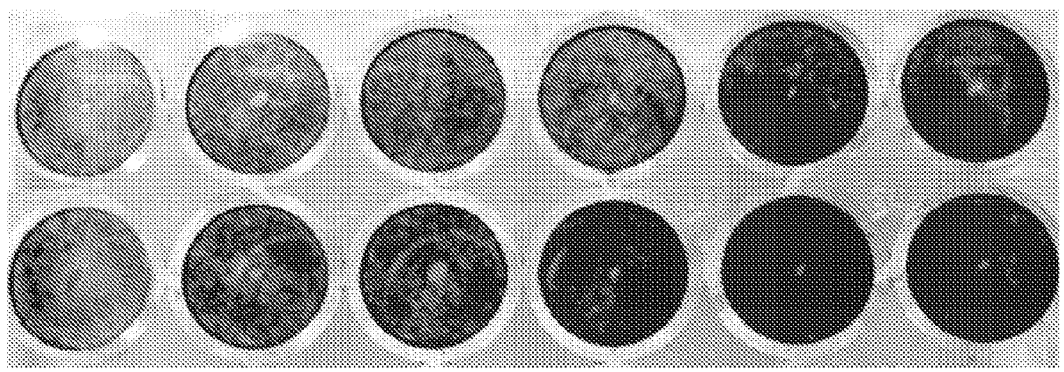

A plaque reduction assay was performed to evaluate the neutralization activity of scFv m366. FIG. 4 provides data demonstrating that scFv m366-Fc potently neutralized the infections of dengue viruses from serotypes 2 and 3. Table 2 provides data indicating that, at 25 μg/ml, scFv m366-Fc fusion proteins neutralized the isolates from 4 all serotypes.

TABLE 2

Summary of the neutralization activity of scFv antibody m366-Fc.

| | Antibodies (25 μg/ml) | | | |
|---|---|---|---|---|
| | D6 | D7 | D3.12 | M366 |
| DENV-1 | − | − | − | + |
| DENV-2 | − | − | − | + |
| DENV-3 | − | − | − | + |
| DENV-4 | − | − | − | + |
| JEV | − | − | − | − |

Example 5

Epitope Mapping Through Yeast Display Domain III Escape Mutant Identification and Sequence Analysis This Example uses epitope mapping analysis to localize the DENV envelope domain III epitope recognized by a human anti-dengue virus antibody of the embodiments. It provides epitope mapping data that shows the position of amino acids mutations in mutant DENV envelope domain III proteins that can no longer bind to a human anti-dengue virus antibody of the embodiments. Such mutated residues are thought to indicate the location of the epitope recognized by the antibody.

A serotype 2 derived DENV envelope domain III consensus gene was used as a template for error-prone PCR. The resulting mutant gene repertoire was cloned into a yeast display vector through gap repairing to construct a yeast display DENV envelope domain III.2 mutant library of $2 \times 10^8$ cells. Two rounds of sorting of yeast cells that expressed mutant forms of DENV envelope DIII.2 protein on the cell surface that lacked binding to the scFv D6-Fc fusion protein were performed. Yeast cells from the second round of sorting were collected; plasmids were extracted from this pool and amplified in 10 G E. coli. Plasmids were extracted from 48 single colonies, and sequenced.

Figure 5:
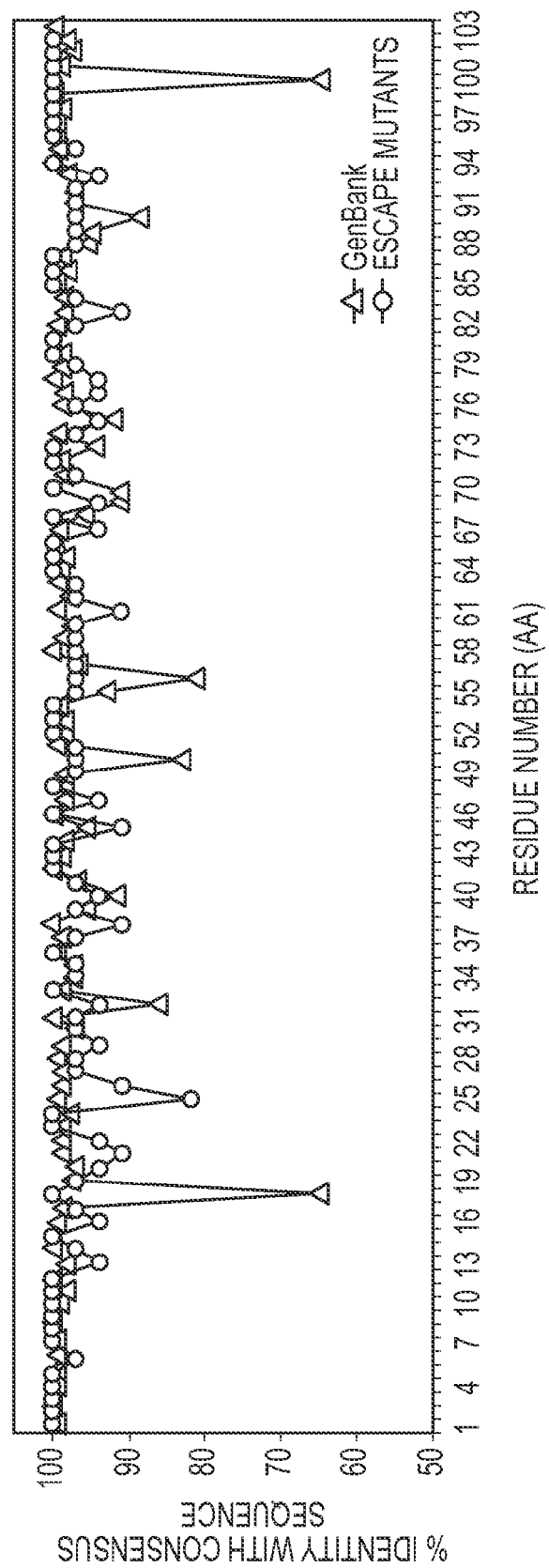
FIG. 5 provides a sequence variation comparison of the domain III.2 (i.e., DIII or ED3 of DENV serotype 2) escape mutants and naturally isolated dengue virus domain IIIs derived from GenBank. The DENV Env-DIII.2 protein shown in this figure is represented by amino acid sequence SEQ ID NO:82, which is a 105-amino acid protein that spans from amino acid 291 through amino acid 395 of the 495-amino acid DENV envelope serotype 2 protein, the amino acid sequence of which represented by SEQ ID NO:81.

Sequence analysis showed that all of the clones encoded complete proteins in the correct reading frame, which is in agreement with the fact that all of the sorted clones expressed mutant DIII.2 proteins on the yeast cell surface. Furthermore, all the clones had at least one mutation encoding a mutated protein, with up to 5 mutations in some clones. Any mutants bearing mutations that occurred in the two cysteine or in solvent inaccessible residues were excluded from sequence analysis. Amino acid sequences from 35 binding escape mutants were aligned with the consensus protein sequence of DENV envelope domain III serotype 2. Mutation frequency at each position was plotted against the amino acid residue position number. Similarly, 193 unique envelope domain III amino acid sequences derived from naturally isolated serotype 2 dengue viruses from GenBank were also aligned with the consensus sequence. The superimposed profiles of the two sets of sequences in FIG. 5 demonstrate that the majority of mutations leading to binding escape mutants are located in regions of Env-DIII.2 that are typically well conserved in nature. Without being bound by theory, this result might explain the broad cross-reactivity of m366 to naturally isolated dengue viruses.

Example 6

Epitope Analysis Using the Docked Model of DENY Env-DIII-scFv Antibody m366 Complex This Example provides additional information regarding the localization of the DENV envelope domain III epitope recognized by a human anti-dengue virus antibody of the embodiments.

Figure 6:
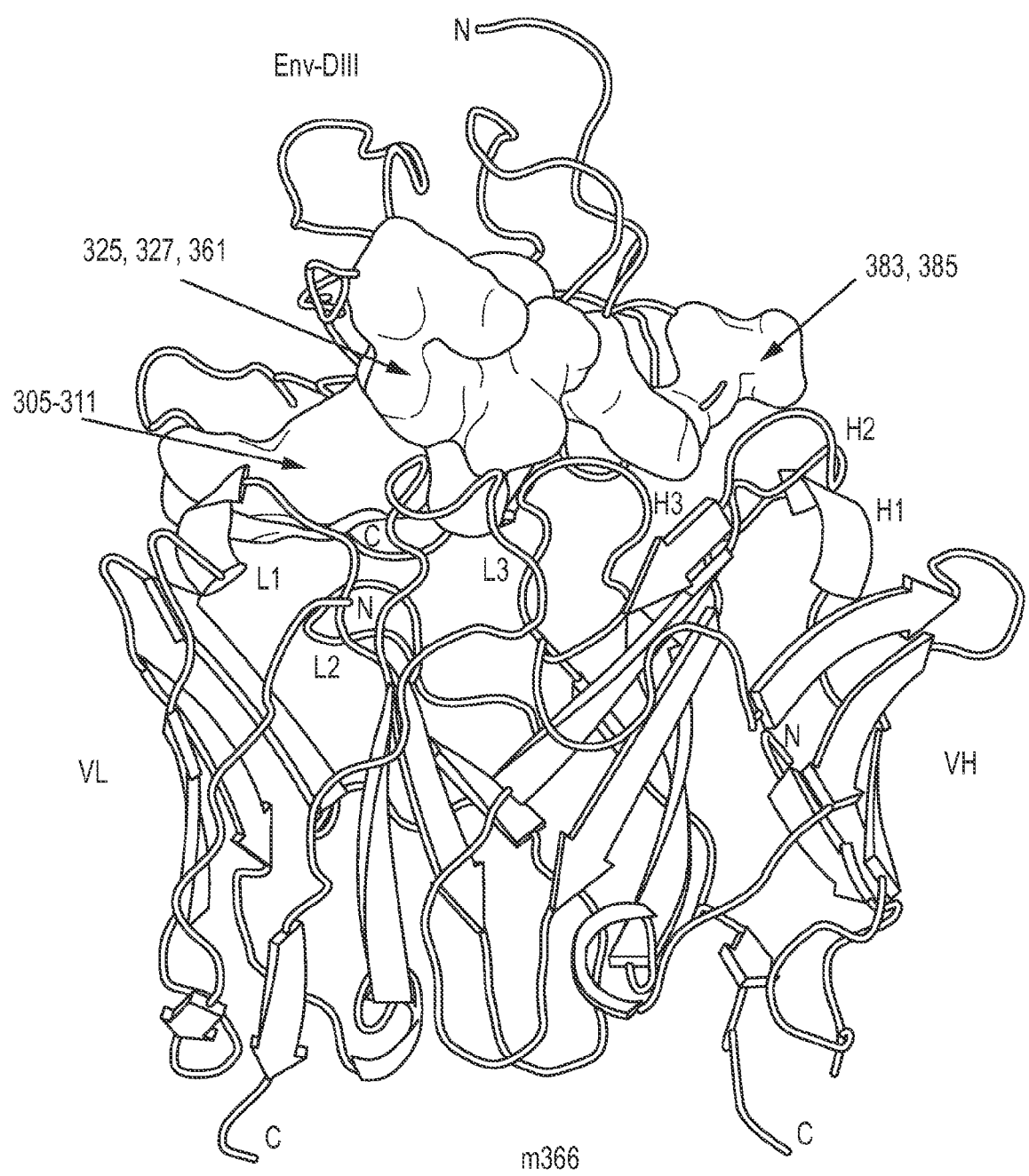
FIG. 6 provides a docking model of the complex between DENV Env-DIII.2 and scFv m366. The model is a ribbon representation of a complex between dengue Env-DIII. 2 and scFv antibody m366 in which the experimentally identified epitope and contacting residues are shown, with complementarity determining regions (CDRs) labeled. Three distinct but structurally proximal epitope regions are labeled with residue numbers (based on the sequence of the entire 495-amino acid DENV envelope serotype 2 protein (SEQ ID NO:81) at putative locations in the model.

Computational docking of the complex between dengue virus Env-DIII and scFv antibody m366 (DENV Env-DIII-scFv antibody m366 complex) was performed using the ZDOCK method. Three docked complexes were selected that contained the key residues identified from the experimental epitope mapping approach described in the Examples herein. One of the top scored docked models exhibited minimum clashes with appropriate protein interface parameters and was used to demonstrate the location of the potential epitopes and their interactions with antibody m366. Without being bound by theory, it is believed that such identification can shed light on the molecular mechanisms of the broadly cross-reactive neutralization of human anti-dengue virus antibodies of the embodiments. FIG. 6 shows the docking model of the Env-DIII-scFv antibody m366 complex in which the epitopes are highlighted. The docking model revealed a different orientation of antibody binding to Env-DIII in the complex structure of FIG. 6 compared to that of Env-DIII with Fab-1A1D-2 previously determined (Lok S M et al., 2008, ibid). The m366 epitope identified herein is comprised of three structurally proximal regions: residues 305-311; 325, 327 and 361; and 383 and 385 at the C-terminal end. One of the key residues, K310, mutation of which of affects epitope formation, contacts the CDR-L1 of m366; CDR-L1 has a germline mutation. In the Env-DIII-Fab-1A1D-2 complex crystal structure, the residue K310 contacts the CDR-H1. Hydrophobic residues, Ile and Trp, of CDR-H3 contact the center part of the epitope and other loops H1, H2, L2 and L3 are also involved in the binding. The surface area of the interface between Env-DIII and scFv antibody m366 is 716 $Å^2$, typical of antibody-antigen interactions. There are six hydrogen bonds likely to form and no salt bridges at the interface. However, the DENV Env-DIII-scFv antibody m366 complex crystal structure would ultimately clarify the precise molecular interactions. Interestingly, protein interface similarity analysis of 1476422 interfaces showed two relevant hits, one is crystal structure of an antibody complexed with anthrax protective antigen domain 4 and the other is the recent structure of influenza A neutralizing antibody in complex with human H3 influenza hemagglutinin (Corti D et al., 2011, Science 333, 850-856).

Example 7

Summary and Conclusions

These Examples describe the identification of a human antibody m366, from a naïve human antibody library, that binds with high (i.e., nanomolar) affinity to envelope domain III from all four DENV serotypes and neutralizes each of those serotypes. There are two major implications from this finding: First is that m366 is a potential candidate therapeutic that could be further developed in preclinical and clinical settings. Second is that the epitope of m366 could be used as a candidate vaccine immunogen capable of eliciting m366 and/or m366-like antibodies.

As of August 2011, twenty-nine monoclonal antibodies have been approved for clinical use in the United States or Europe as well as six Fc fusion proteins (Dimitrov, submitted for publication). Only one of these antibodies, Synagis, is against an infectious disease (caused by RSV), and it is used for prevention, not for therapy (Marasco W A et al., ibid.). Previous studies have identified a candidate therapeutic human monoclonal antibody, m102.4, which potently neutralized both Hendra and Nipah viruses although they differ with respect to their amino acid sequences; the sequence differences are about the same as between any two DENV serotypes (see, for example, Bossart K N et al., 2009, PLoS Pathog. 5, e1000642; Zhu Z et al., 2008, J Infect Dis. 197, 846-853; Zhu Z et al., 2006, J Virol. 80, 891-899). Monoclonal antibody m102.4 was successful as a candidate therapeutic mAb in a monkey disease model where it cured animals treated three days after challenge with infectious virus, while all control monkeys died; M102.4 was also administered to three humans without side effects (Bossart et al., submitted for publication). Antibody m102.4 was produced by good manufacturing practices (GMP) in Australia, and is in stock to be used in future outbreaks.

Human anti-dengue antibody m366 was selected from the same yeast display library as m102.4, and was subjected to affinity maturation light chain shuffling similarly to the maturation of m102.4. The only differences are that (a) m366 was selected by yeast display in a scFv format, while m102.4 was selected by yeast display in an Fab format, (b) there were additional rounds of selection from mutant libraries for m366, and (c) to increase the probability for success, a domain III (D3) mutant corresponding to a non-replicating virus was used to deplete the library from putative non-neutralizing antibodies. Without being bound by theory, it is believed that these differences could further increase the potency and breadth of neutralization by m366. Because m102.4 has been so successful and is likely to get approval for clinical use by FDA based on the positive data from two animal models and lack of side effects, a similarly identified antibody, but with different specificity, could be a promising candidate therapeutic. In progress are experiments in two animal models and with a panel of primary isolates that will provide further information for the potential therapeutic utility of m366.

A combination of computational structural modeling and sequence analysis of mutants has been used to approximately localize the m366 epitope. The epitope appears to overlap to some extent with epitopes previously explored as targets for cross-reactive murine mAbs. This further indicates that the m366 epitope could be an important component of vaccine immunogens intended to elicit cross-reactive neutralizing antibodies. In progress are experiments to crystallize the complex of scFv m366 with DENV envelope domain III that would allow precise determination of the m366 epitope.

Example 8

Identification of Human Anti-Dengue Virus Cross-Reactive Antibody m360

Figure 9:
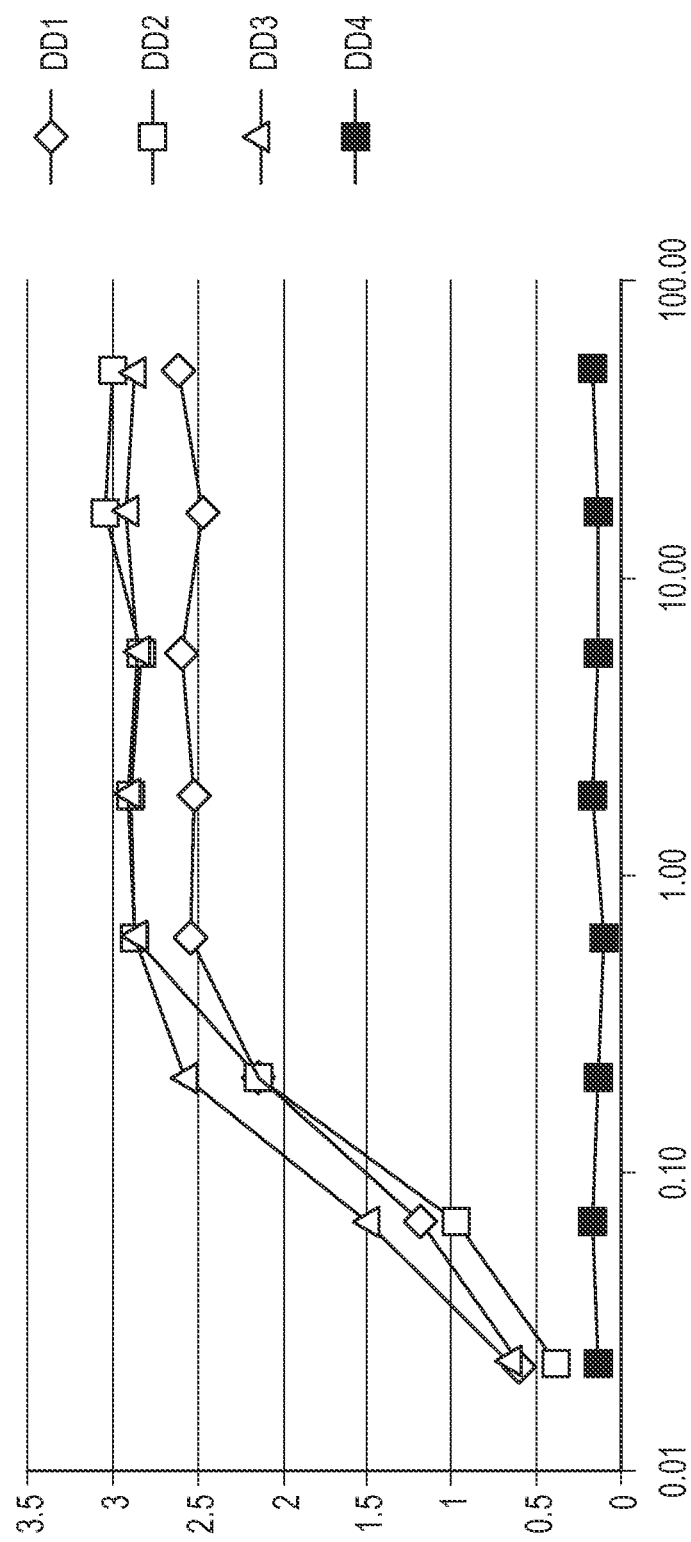
FIG. 9 provides results from an ELISA binding assay that demonstrates cross-reactive binding of m360 to dengue virus envelope domain III proteins from three serotypes.

This Example describes the identification a human anti-dengue virus antibody that is cross-reactive to dengue virus envelope domain III proteins from three serotypes. Human anti-dengue virus antibody scFv D7-Fc-Avi, the production of which was described in Example 2, was submitted to an ELISA binding assay as described herein. FIG. 9 shows that the protein encoded by clone D7 (i.e., scFv D7) bound dengue virus envelope domain III proteins from DENV serotype 1, DENV serotype 2, and DENV serotype 3.

After three cycles of mutagenesis and selection of a library encoding scFv D7, one clone was identified from monoclonal yeast display antibody screening of the enriched pool after the final round of sorting, designated as scFv m360. The scFv m360 gene was cloned into a pSecTag vector encoding human IgG1 Fc for scFv m360-Fc fusion protein expression. Biacore analysis showed that the cross-reactive binding activities of scFv m360 to DENV Env domain IIIs from three of the four DENV serotypes was preserved after the affinity maturation process. The data are presented in Table 3.

TABLE 3

Binding affinity of scFv m360 to DENV envelope domain IIIs measured by Biacore

| DIII Serotype 1 $K_d$ (M) | DIII Serotype 2 $K_d$ (M) | DIII Serotype 3 $K_d$ (M) | DIII Serotype 4 $K_d$ (M) |
|---|---|---|---|
| 5.84E−9 | 5.13E−9 | 1.16E−10 | 8.28E−8 |

The nucleic acid sequence encoding human anti-dengue virus antibody m360 is provided in nucleic acid sequence SEQ ID NO:61. The amino acid of antibody m360 is provided in amino acid sequence SEQ ID NO:62. The nucleic acid sequences encoding the $V_H$ and $V_L$ chains of antibody m360 are provided in SEQ ID NO:63 and SEQ ID NO:65, respectively. The amino acid sequences of the $V_H$ and $V_L$ chains of antibody m360 are provided in SEQ ID NO:64 and SEQ ID NO:66, respectively.

Example 9

Affinity Maturation of Additional Human Anti-Dengue Virus Cross-Reactive Antibodies This Example demonstrates the ability to affinity mature human anti-dengue virus cross-reactive antibodies m360 and m366 to obtain antibodies m360.6 and m366.6, respectively, with enhanced characteristics compared to m360 and m366.

Human anti-dengue virus cross-reactive antibodies m360 and m366 were each affinity matured as described in the Examples herein. For example, a library encoding m360 was mutated, submitted to one round of MACS-based sorting, followed by three rounds of mutagenesis and selection by FACS to specifically isolate the pool of binders with the highest binding activity; typically the sorting gate was set to sort out 0.5%. 0.2% and 0.1% of the pool for rounds 1, 2 and 3 respectively. Then the final yeast pool-derived plasmid was used as template for error-prone and DNA shuffling PCR (as described in the Examples herein) to construct the next mutant library for another cycle of mutagenesis and selection. A total three additional rounds of mutagenesis and selection by FACS were performed, and a single clone was identified after the final round of sorting, designated as antibody m360.6. Antibody m366.6 was affinity matured from antibody m366 in a similar manner. Biacore analysis showed that both scFv m360.6 and scFv m366.6 bound to DENV Env domain IIIs from all four DENV serotypes, as indicated in Table 4.

TABLE 4

Binding affinities of scFv m360.6 and scFv m366.6 to DENV envelope domain IIIs from 4 serotypes measured by Biacore.

| Antibody | DIII Serotype 1 $K_d$ (nM) | DIII Serotype 2 $K_d$ (nM) | DIII Serotype 3 $K_d$ (nM) | DIII Serotype 4 $K_d$ (nM) |
|---|---|---|---|---|
| m360.6 | 0.31 | 0.24 | 0.0023 | 33 |
| m366.6 | 0.44 | 0.29 | 0.27 | 0.75 |

The nucleic acid sequence encoding human anti-dengue virus antibody m360.6 is provided in nucleic acid sequence SEQ ID NO:41. The amino acid of antibody m360.6 is provided in amino acid sequence SEQ ID NO:42. The nucleic acid sequences encoding the $V_H$ and $V_L$ chains of antibody m360.6 are provided in SEQ ID NO:43 and SEQ ID NO:45, respectively. The amino acid sequences of the $V_H$ and $V_L$ chains of antibody m360.6 are provided in SEQ ID NO:44 and SEQ ID NO:46, respectively. The nucleic acid sequence encoding human anti-dengue virus antibody m366.6 is provided in nucleic acid sequence SEQ ID NO:21. The amino acid of antibody m366.6 is provided in amino acid sequence SEQ ID NO:22. The nucleic acid sequences encoding the $V_H$ and $V_L$ chains of antibody m366.6 are provided in SEQ ID NO:23 and SEQ ID NO:25, respectively. The amino acid sequences of the $V_H$ and $V_L$ chains of antibody m366.6 are provided in SEQ ID NO:24 and SEQ ID NO:26, respectively.

Example 10

Production of a Human Dengue Virus Bispecific Antibody, and Comparison of Neutralization Titers of Human Dengue Virus Antibodies of the Embodiments This Example demonstrates the production of a human dengue virus bispecific antibody, denoted m3666, comprising human dengue virus antibodies m360.6 and m366.6. This Example also demonstrates that human dengue virus antibodies m360.6, m366.6 and m3666 were each able to neutralize all four DENV serotypes, i.e., DENV serotype 1, DENV serotype 2, DENV serotype 3, and DENV serotype 4.

Human dengue virus bispecific antibody m3666 was produced by cloning the nucleic acids encoding the scFv of m360.6 at the N terminus and m366.6 at the C-terminus of a mutated human IgG1 Fc into mammalian expression vector pSectag from Invitrogen. The mutant Fc (having amino acid sequence SEQ ID NO:94, encoded by nucleic acid sequence SEQ ID NO:93) was constructed by deleting the two leucines near the N-terminus of CH2 of the non-mutated Fc (having amino acid sequence SEQ ID NO:92, encoded by nucleic acid sequence SEQ ID NO:91). SEQ ID NO:92 and SEQ ID NO:94 contain, respectively, the non-mutated IgG1 Fc (SEQ ID NO:102) and the mutated IgG1 Fc (SEQ ID NO:104), each flanked on the N-terminus by the 7-amino acid linker GQAGQGP (SEQ ID NO:105) and on the C-terminus by the 8-amino acid linker AAAGGGGS (SEQ ID NO:106). The bispecific antibody was expressed and purified from 293 freestyle cells following the vendor provided protocol.

The abilities of human dengue virus antibodies scFv-Fc m360.6, scFv-Fc m366.6 and bispecific m3666 to neutralize all four DENV serotypes was determined by using a reporter system using pseudo-infectious DENV reporter virus particles (DENV RVP assay) as described by Mattia K et al., 2011, PLoS ONE 6 (11): e27252. Table 5 provides DENV neutralization ($IC_{50}$) data for the antibodies m360.6, m366.6 and m3666. Neutralization data for mouse monoclonal antibody 4G2 (available from ATCC CAT #HB-112, ATCC, Manassas, Va.) are also shown for comparison.

TABLE 5

DENV neutralization ($IC_{50}$) data for antibodies m360.6, m366.6, and m3666 measured by a DENV RVP assay.

| Antibody | DIII Serotype 1 (µg/ml) | DIII Serotype 2 (µg/ml) | DIII Serotype 3 (µg/ml) | DIII Serotype 4 (µg/ml) |
|---|---|---|---|---|
| scFv-Fc m360.6 | 12 | 4.2 | 1.5 | 21 |
| scFv-Fc m366.6 | 22 | 2.4 | 0.85 | 0.36 |
| m3666 | 0.80 | 0.22 | 0.07 | 0.01 |
| 4G2 | 2.0 | 2.0 | 1.8 | 0.30 |

Example 11

Enhancement of Infection by Human Anti-Dengue Virus Antibodies of the Embodiments This Example demonstrates that human anti-dengue virus antibodies of the embodiments do not enhance infection by Dengue virus.

Figure 11:
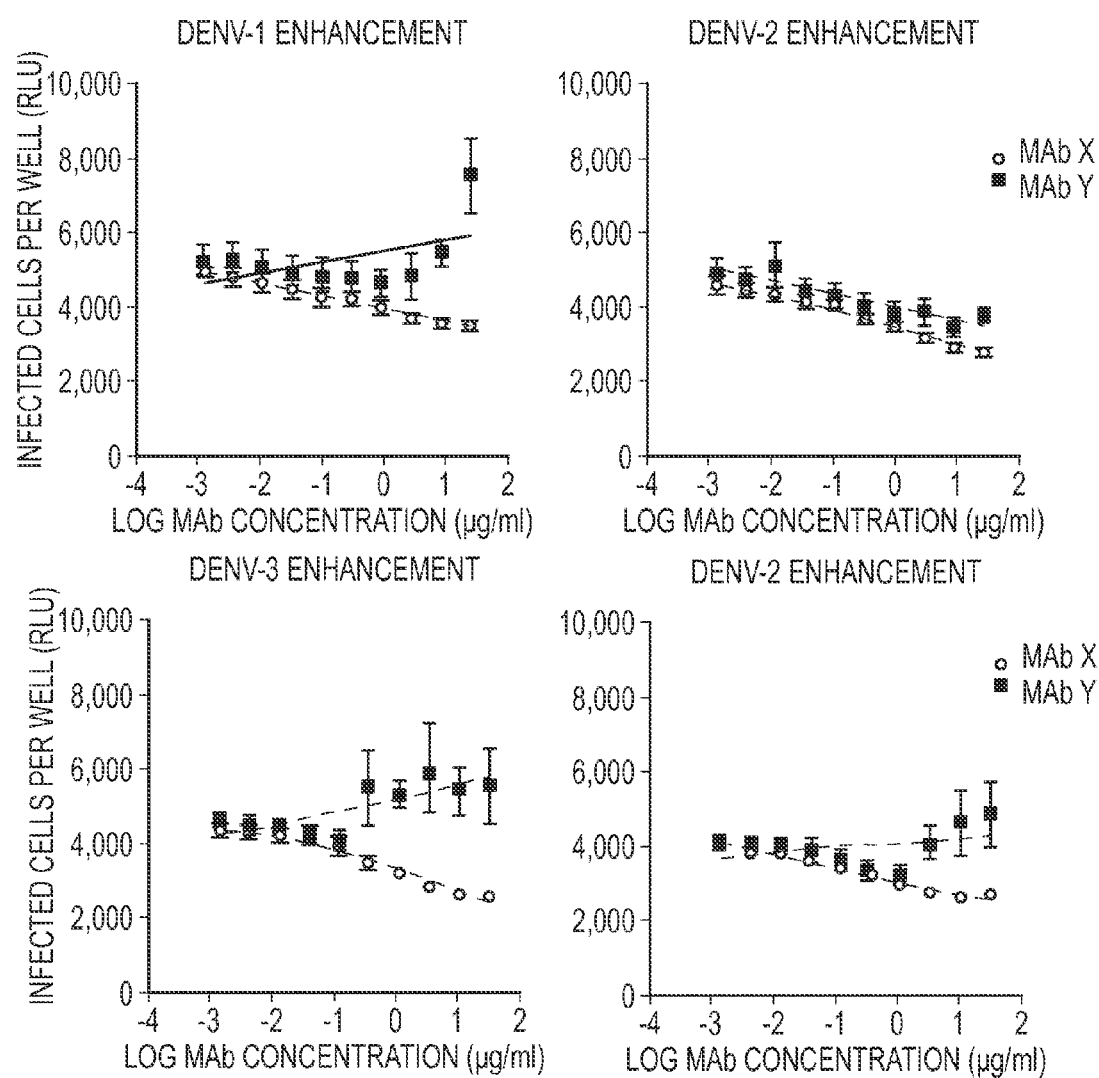
FIG. 11 illustrates that human anti-dengue virus antibody m366 does not significantly enhance Dengue virus infection.

Viral enhancement assays were conducted against all four serotypes of DENV (DENV-1 (WestPac), DENV-2 (S16803), DENV-3 (CH53489) and DENV-4 (TVP360) to measure the potentially pathogenic activity of human anti-dengue virus antibody m366. All enhancements were run in replicates in order to ensure accuracy. DENV RVPs (replication-incompetent virus particles) were pre-incubated with an equal volume of serially diluted antibody (25 µg/ml to 0.00127 µg/ml; all dilutions are pre-dilution) in RPMI complete for 1 hour at room temperature with slow agitation. Following incubation, human erythroleukemic Fc_RIIa-bearing K562 cells were added to each well at a density of 40,000 cells per well followed by incubation at 37oC in 50% CO2 for 72 hours. Cells were subsequently lysed and analyzed for luminescent reporter expression. Raw infection data expressed as luminescence was plotted versus log10 of the antibody dilution, as shown in FIG. 11. mAb X is a negative control, and mAb Y is antibody m366. A dose response curve was applied for curve fitting to determine the titer of antibody that achieved the highest level of infection. No infection level was determined by using a no antibody control. The Figure demonstrates that human anti-dengue virus antibody m366 does not significantly enhance Dengue virus infection.

Human anti-dengue virus antibody m366.6, human anti-dengue virus antibody 360.6, and human anti-dengue virus bispecific antibody m3666 were also evaluated and shown not to significantly enhance Dengue virus infection.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims.

What is claimed is:

1. A human anti-dengue virus bispecific antibody comprising two antibodies each of which binds to domain III of an envelope protein of dengue virus and at least one of which is cross-reactive with domain III of dengue virus (DENV) serotype 1 envelope protein, domain III of DENV serotype 2 envelope protein, domain III of DENV serotype 3 envelope protein, and domain III of DENV serotype 4 envelope protein, wherein the bispecific antibody comprises an antibody selected from the group consisting of:
   an antibody comprising a CDR-H1 having amino acid sequence SEQ ID NO:28, a CDR-H2 having amino acid sequence SEQ ID NO:30, a CDR-H3 having amino acid sequence SEQ ID NO:32, a CDR-L1 having amino acid sequence SEQ ID NO:34, a CDR-L2 having amino acid sequence SEQ ID NO:36, and a CDR-L3 having amino acid sequence SEQ ID NO:38; and
   an antibody comprising a CDR-H1 having amino acid sequence SEQ ID NO:48, a CDR-H2 having amino acid sequence SEQ ID NO:50, a CDR-H3 having amino acid sequence SEQ ID NO:52, a CDR-L1 having amino acid sequence SEQ ID NO:54, a CDR-L2 having amino acid sequence SEQ ID NO:56, and a CDR-L3 having amino acid sequence SEQ ID NO:58; and combinations thereof.

2. A human anti-dengue virus bispecific antibody comprising two antibodies each of which binds to domain III of an envelope protein of dengue virus and at least one of which is cross-reactive with domain III of dengue virus (DENV) serotype 1 envelope protein, domain III of DENV serotype 2 envelope protein, domain III of DENV serotype 3 envelope protein, and domain III of DENV serotype 4 envelope protein, wherein the bispecific antibody comprises (i) an antibody comprising a CDR-H1 having amino acid sequence SEQ ID NO:28, a CDR-H2 having amino acid sequence SEQ ID NO:30, a CDR-H3 having amino acid sequence SEQ ID NO:32, a CDR-L1 having amino acid sequence SEQ ID NO:34, a CDR-L2 having amino acid sequence SEQ ID NO:36, and a CDR-L3 having amino acid sequence SEQ ID NO:38 and (ii) an antibody comprising a CDR-H1 having amino acid sequence SEQ ID NO:48, a CDR-H2 having amino acid sequence SEQ ID NO:50, a CDR-H3 having amino acid sequence SEQ ID NO:52, a CDR-L1 having amino acid sequence SEQ ID NO:54, a CDR-L2 having amino acid sequence SEQ ID NO:56, and a CDR-L3 having amino acid sequence SEQ ID NO:58.

3. The bispecific antibody of claim 1, wherein the bispecific antibody comprises an antibody selected from the group consisting of:
   an antibody comprising a $V_H$ chain comprising amino acid sequence SEQ ID NO:24 and a $V_L$ chain comprising amino acid sequence SEQ ID NO:26; and
   an antibody comprising a $V_H$ chain comprising amino acid sequence SEQ ID NO:44 and a $V_L$ chain comprising amino acid sequence SEQ ID NO:46;
   and combinations thereof.

4. The bispecific antibody of claim 2, wherein the bispecific antibody comprises an antibody comprising a $V_H$ chain comprising amino acid sequence SEQ ID NO:24 and a $V_L$ chain comprising amino acid sequence SEQ ID NO:26; and an antibody comprising a $V_H$ chain comprising amino acid sequence SEQ ID NO:44 and a $V_L$ chain comprising amino acid sequence SEQ ID NO:46.

5. The bispecific antibody of claim 1, wherein the bispecific antibody comprises an antibody comprising amino acid sequence SEQ ID NO:22 and an antibody comprising amino acid sequence SEQ ID NO:42.

6. The bispecific antibody of claim 2, wherein the bispecific antibody comprises amino acid sequence SEQ ID NO:96.

7. A nucleic acid molecule encoding a bispecific antibody of claim 1.

8. An isolated recombinant cell comprising the nucleic acid molecule of claim 7.

9. A composition comprising a bispecific antibody of claim 1 and a pharmaceutically acceptable carrier.

10. A method of inhibiting dengue virus infection in a subject, the method comprising administering to the subject a bispecific antibody of claim 1.

* * * * *

SEQUENCE LISTING

<160> NUMBER OF SEQ ID NOS: 106

<210> SEQ ID NO 1
<211> LENGTH: 735
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(735)

<400> SEQUENCE: 1

```
cag ctg cag ctg cag gag tcg ggg gga ggc ttg gta cag cct gga ggg      48
Gln Leu Gln Leu Gln Glu Ser Gly Gly Gly Leu Val Gln Pro Gly Gly
1               5                   10                  15 tcc ctg aga ctc tcc tgt gca gcc tct gga ttc acc ttc agt agc tat      96
Ser Leu Arg Leu Ser Cys Ala Ala Ser Gly Phe Thr Phe Ser Ser Tyr
            20                  25                  30 agc atg aac tgg gtc cgc cag gct cca ggg aag agg ctg gag tgg gtc     144
Ser Met Asn Trp Val Arg Gln Ala Pro Gly Lys Arg Leu Glu Trp Val
        35                  40                  45 tca tcc att agt ggt agt agt agt tac ata tac tac gca gac tca gtg     192
Ser Ser Ile Ser Gly Ser Ser Ser Tyr Ile Tyr Tyr Ala Asp Ser Val
    50                  55                  60 aag ggc cga ttc acc atc tcc aga gac aac gcc aag aac tca ctg tat     240
Lys Gly Arg Phe Thr Ile Ser Arg Asp Asn Ala Lys Asn Ser Leu Tyr
65                  70                  75                  80 ctg caa atg gac agc ctg aga gcc gag gac acg gct gtg tat tac tgt     288
Leu Gln Met Asp Ser Leu Arg Ala Glu Asp Thr Ala Val Tyr Tyr Cys
                85                  90                  95 gcc aga tac gcg gct ggc att tgg act ttt gat atc tgg ggc caa ggg     336
Ala Arg Tyr Ala Ala Gly Ile Trp Thr Phe Asp Ile Trp Gly Gln Gly
            100                 105                 110 aca acg gtc acc gtc tct tca gga ggt ggc ggg tct ggt ggg ggt gcc     384
Thr Thr Val Thr Val Ser Ser Gly Gly Gly Gly Ser Gly Gly Gly Ala
        115                 120                 125 agc ggt ggt ggc gga tcc tcc tat gag ctg act cag cca ccc tca gtg     432
Ser Gly Gly Gly Gly Ser Ser Tyr Glu Leu Thr Gln Pro Pro Ser Val
    130                 135                 140 tca gtg gcc cca gga aag acg gcc agc att tcc tgt ggg gga gac aac     480
Ser Val Ala Pro Gly Lys Thr Ala Ser Ile Ser Cys Gly Gly Asp Asn
145                 150                 155                 160 att gga agg aaa agt gtg cac tgg ttc cag cag aag cca ggc cag gcc     528
Ile Gly Arg Lys Ser Val His Trp Phe Gln Gln Lys Pro Gly Gln Ala
                165                 170                 175 cct gtg ctg gtc ctc tat gat gat agc gac cgg ccc tca ggg atc cca     576
Pro Val Leu Val Leu Tyr Asp Asp Ser Asp Arg Pro Ser Gly Ile Pro
            180                 185                 190 gcg cga ttc tct ggc tcc aac tct ggg aac acg gcc acc ctg acc atc     624
Ala Arg Phe Ser Gly Ser Asn Ser Gly Asn Thr Ala Thr Leu Thr Ile
        195                 200                 205 agc agg gtc gaa gcc ggg gat gag gcc gac tat tac tgc cag gtg tgg     672
Ser Arg Val Glu Ala Gly Asp Glu Ala Asp Tyr Tyr Cys Gln Val Trp
    210                 215                 220 gcc aga agt agt gat cat cca aat tgg gtg ttc ggc gga ggg acc aag     720
Ala Arg Ser Ser Asp His Pro Asn Trp Val Phe Gly Gly Gly Thr Lys
225                 230                 235                 240 ctg acc gtc cta gga                                                  735
Leu Thr Val Leu Gly
                245
```

<210> SEQ ID NO 2
<211> LENGTH: 245
<212> TYPE: PRT
<213> ORGANISM: Artificial Sequence
<220> FEATURE:
<223> OTHER INFORMATION: Synthetic Construct

<400> SEQUENCE: 2

```
Gln Leu Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ser Met Asn Trp Val Arg Gln Ala Pro Gly Lys Arg Leu Glu Trp Val
         35                  40                  45

Ser Ser Ile Ser Gly Ser Ser Ser Tyr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asp Ser Leu Arg Ala Glu Asp Thr Ala Val Tyr Tyr Cys
                 85                  90                  95

Ala Arg Tyr Ala Ala Gly Ile Trp Thr Phe Asp Ile Trp Gly Gln Gly
            100                 105                 110

Thr Thr Val Thr Val Ser Ser Gly Gly Gly Ser Gly Gly Gly Ala
        115                 120                 125

Ser Gly Gly Gly Gly Ser Ser Tyr Glu Leu Thr Gln Pro Pro Ser Val
    130                 135                 140

Ser Val Ala Pro Gly Lys Thr Ala Ser Ile Ser Cys Gly Gly Asp Asn
145                 150                 155                 160

Ile Gly Arg Lys Ser Val His Trp Phe Gln Gln Lys Pro Gly Gln Ala
                165                 170                 175

Pro Val Leu Val Leu Tyr Asp Asp Ser Asp Arg Pro Ser Gly Ile Pro
            180                 185                 190

Ala Arg Phe Ser Gly Ser Asn Ser Gly Asn Thr Ala Thr Leu Thr Ile
        195                 200                 205

Ser Arg Val Glu Ala Gly Asp Glu Ala Asp Tyr Tyr Cys Gln Val Trp
    210                 215                 220

Ala Arg Ser Ser Asp His Pro Asn Trp Val Phe Gly Gly Gly Thr Lys
225                 230                 235                 240

Leu Thr Val Leu Gly
                245
```

<210> SEQ ID NO 3
<211> LENGTH: 357
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(357)

<400> SEQUENCE: 3

```
cag ctg cag ctg cag gag tcg ggg gga ggc ttg gta cag cct gga ggg      48
Gln Leu Gln Leu Gln Glu Ser Gly Gly Gly Leu Val Gln Pro Gly Gly
 1               5                  10                  15 tcc ctg aga ctc tcc tgt gca gcc tct gga ttc acc ttc agt agc tat      96
Ser Leu Arg Leu Ser Cys Ala Ala Ser Gly Phe Thr Phe Ser Ser Tyr
             20                  25                  30
```

```
agc atg aac tgg gtc cgc cag gct cca ggg aag agg ctg gag tgg gtc      144
Ser Met Asn Trp Val Arg Gln Ala Pro Gly Lys Arg Leu Glu Trp Val
        35                  40                  45 tca tcc att agt ggt agt agt agt tac ata tac tac gca gac tca gtg      192
Ser Ser Ile Ser Gly Ser Ser Ser Tyr Ile Tyr Tyr Ala Asp Ser Val
 50                  55                  60 aag ggc cga ttc acc atc tcc aga gac aac gcc aag aac tca ctg tat      240
Lys Gly Arg Phe Thr Ile Ser Arg Asp Asn Ala Lys Asn Ser Leu Tyr
 65                  70                  75                  80 ctg caa atg gac agc ctg aga gcc gag gac acg gct gtg tat tac tgt      288
Leu Gln Met Asp Ser Leu Arg Ala Glu Asp Thr Ala Val Tyr Tyr Cys
                 85                  90                  95 gcc aga tac gcg gct ggc att tgg act ttt gat atc tgg ggc caa ggg      336
Ala Arg Tyr Ala Ala Gly Ile Trp Thr Phe Asp Ile Trp Gly Gln Gly
            100                 105                 110 aca acg gtc acc gtc tct tca                                          357
Thr Thr Val Thr Val Ser Ser
        115

<210> SEQ ID NO 4
<211> LENGTH: 119
<212> TYPE: PRT
<213> ORGANISM: Artificial Sequence
<220> FEATURE:
<223> OTHER INFORMATION: Synthetic Construct

<400> SEQUENCE: 4

Gln Leu Gln Leu Gln Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Arg Leu Glu Trp Val
        35                  40                  45

Ser Ser Ile Ser Gly Ser Ser Ser Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asp Ser Leu Arg Ala Glu Asp Thr Ala Val Tyr Tyr Cys
                 85                  90                  95

Ala Arg Tyr Ala Ala Gly Ile Trp Thr Phe Asp Ile Trp Gly Gln Gly
            100                 105                 110

Thr Thr Val Thr Val Ser Ser
        115

<210> SEQ ID NO 5
<211> LENGTH: 333
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(333)

<400> SEQUENCE: 5 tcc tat gag ctg act cag cca ccc tca gtg tca gtg gcc cca gga aag       48
Ser Tyr Glu Leu Thr Gln Pro Pro Ser Val Ser Val Ala Pro Gly Lys
 1               5                  10                  15 acg gcc agc att tcc tgt ggg gga gac aac att gga agg aaa agt gtg       96
Thr Ala Ser Ile Ser Cys Gly Gly Asp Asn Ile Gly Arg Lys Ser Val
            20                  25                  30
```

```
cac tgg ttc cag cag aag cca ggc cag gcc cct gtg ctg gtc ctc tat    144
His Trp Phe Gln Gln Lys Pro Gly Gln Ala Pro Val Leu Val Leu Tyr
         35                  40                  45 gat gat agc gac cgg ccc tca ggg atc cca gcg cga ttc tct ggc tcc    192
Asp Asp Ser Asp Arg Pro Ser Gly Ile Pro Ala Arg Phe Ser Gly Ser
 50                  55                  60 aac tct ggg aac acg gcc acc ctg acc atc agc agg gtc gaa gcc ggg    240
Asn Ser Gly Asn Thr Ala Thr Leu Thr Ile Ser Arg Val Glu Ala Gly
 65                  70                  75                  80 gat gag gcc gac tat tac tgc cag gtg tgg gcc aga agt agt gat cat    288
Asp Glu Ala Asp Tyr Tyr Cys Gln Val Trp Ala Arg Ser Ser Asp His
                     85                  90                  95 cca aat tgg gtg ttc ggc gga ggg acc aag ctg acc gtc cta gga        333
Pro Asn Trp Val Phe Gly Gly Gly Thr Lys Leu Thr Val Leu Gly
            100                 105                 110
```

<210> SEQ ID NO 6
<211> LENGTH: 111
<212> TYPE: PRT
<213> ORGANISM: Artificial Sequence
<220> FEATURE:
<223> OTHER INFORMATION: Synthetic Construct

<400> SEQUENCE: 6

```
Ser Tyr Glu Leu Thr Gln Pro Pro Ser Val Ser Val Ala Pro Gly Lys
1               5                   10                  15

Thr Ala Ser Ile Ser Cys Gly Gly Asp Asn Ile Gly Arg Lys Ser Val
            20                  25                  30

His Trp Phe Gln Gln Lys Pro Gly Gln Ala Pro Val Leu Val Leu Tyr
        35                  40                  45

Asp Asp Ser Asp Arg Pro Ser Gly Ile Pro Ala Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Ala Arg Ser Ser Asp His
                85                  90                  95

Pro Asn Trp Val Phe Gly Gly Gly Thr Lys Leu Thr Val Leu Gly
            100                 105                 110
```

<210> SEQ ID NO 7
<211> LENGTH: 24
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(24)

<400> SEQUENCE: 7

```
gga ttc acc ttc agt agc tat agc                                    24
Gly Phe Thr Phe Ser Ser Tyr Ser
1               5
```

<210> SEQ ID NO 8
<211> LENGTH: 8
<212> TYPE: PRT
<213> ORGANISM: Artificial Sequence
<220> FEATURE:
<223> OTHER INFORMATION: Synthetic Construct

<400> SEQUENCE: 8

Gly Phe Thr Phe Ser Ser Tyr Ser

```
<210> SEQ ID NO 9
<211> LENGTH: 24
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(24)

<400> SEQUENCE: 9 att agt ggt agt agt agt tac ata                              24
Ile Ser Gly Ser Ser Ser Tyr Ile
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

Ile Ser Gly Ser Ser Ser Tyr Ile
1               5

<210> SEQ ID NO 11
<211> LENGTH: 36
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(36)

<400> SEQUENCE: 11 gcc aga tac gcg gct ggc att tgg act ttt gat atc              36
Ala Arg Tyr Ala Ala Gly Ile Trp Thr Phe Asp Ile
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic Construct

<400> SEQUENCE: 12

Ala Arg Tyr Ala Ala Gly Ile Trp Thr Phe Asp Ile
1               5                   10

<210> SEQ ID NO 13
<211> LENGTH: 18
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(18)

<400> SEQUENCE: 13 aac att gga agg aaa agt                                      18
Asn Ile Gly Arg Lys Ser
1               5
```

```
<210> SEQ ID NO 14
<211> LENGTH: 6
<212> TYPE: PRT
<213> ORGANISM: Artificial Sequence
<220> FEATURE:
<223> OTHER INFORMATION: Synthetic Construct

<400> SEQUENCE: 14

Asn Ile Gly Arg Lys Ser
1               5

<210> SEQ ID NO 15
<211> LENGTH: 9
<212> TYPE: DNA
<213> ORGANISM: Artificial Sequence
<220> FEATURE:
<223> OTHER INFORMATION: Synthetic Sequence

<400> SEQUENCE: 15 gatgatagc                                                                  9

<210> SEQ ID NO 16
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 16

Asp Asp Ser
1

<210> SEQ ID NO 17
<211> LENGTH: 39
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(39)

<400> SEQUENCE: 17 cag gtg tgg gcc aga agt agt gat cat cca aat tgg gtg              39
Gln Val Trp Ala Arg Ser Ser Asp His Pro Asn Trp Val
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthetic Construct

<400> SEQUENCE: 18

Gln Val Trp Ala Arg Ser Ser Asp His Pro Asn Trp Val
1               5                   10

<210> SEQ ID NO 19
<211> LENGTH: 45
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(45)
```

```
<400> SEQUENCE: 19 gga ggt ggc ggg tct ggt ggg ggt gcc agc ggt ggt ggc gga tcc        45
Gly Gly Gly Gly Ser Gly Gly Gly Ala Ser Gly Gly Gly Gly Ser
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic Construct

<400> SEQUENCE: 20

Gly Gly Gly Gly Ser Gly Gly Gly Ala Ser Gly Gly Gly Gly Ser
1               5                   10                  15

<210> SEQ ID NO 21
<211> LENGTH: 735
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(735)

<400> SEQUENCE: 21 cag ctg cag ctg cag gag tcg ggg gga ggc ttg gta cag cct gga ggg    48
Gln Leu Gln Leu Gln Glu Ser Gly Gly Gly Leu Val Gln Pro Gly Gly
1               5                   10                  15 tcc ctg aga ctc tcc tgt gca gcc tct gga ttc acc ttc agt agc cat    96
Ser Leu Arg Leu Ser Cys Ala Ala Ser Gly Phe Thr Phe Ser Ser His
                20                  25                  30 agc atg aac tgg atc cgc cag gct cca ggg aag agg ctg gag tgg gtc   144
Ser Met Asn Trp Ile Arg Gln Ala Pro Gly Lys Arg Leu Glu Trp Val
            35                  40                  45 tca tcc att agt agt agt agt agt tac ata tac tac gca gac tca gtg   192
Ser Ser Ile Ser Ser Ser Ser Ser Tyr Ile Tyr Tyr Ala Asp Ser Val
        50                  55                  60 agg ggc cga ttc acc atc tcc aga gac aac gcc aag aac tca ctg tat   240
Arg Gly Arg Phe Thr Ile Ser Arg Asp Asn Ala Lys Asn Ser Leu Tyr
65                  70                  75                  80 ctg caa atg gac agc ctg aga gcc gag gac acg gca gtg tat tat tgt   288
Leu Gln Met Asp Ser Leu Arg Ala Glu Asp Thr Ala Val Tyr Tyr Cys
                85                  90                  95 gcc aga tac atg gct ggc atc tgg act ttt gat atc tgg ggc caa ggg   336
Ala Arg Tyr Met Ala Gly Ile Trp Thr Phe Asp Ile Trp Gly Gln Gly
                100                 105                 110 aca atg gtc acc gtc tct tca gga ggc ggc ggg tct ggt gga ggc gct   384
Thr Met Val Thr Val Ser Ser Gly Gly Gly Gly Ser Gly Gly Gly Ala
            115                 120                 125 agt ggt ggt ggc gga tcc tcc tat gag ctg act cag cca ccc tca gtg   432
Ser Gly Gly Gly Gly Ser Ser Tyr Glu Leu Thr Gln Pro Pro Ser Val
        130                 135                 140 tca gtg gcc cca gga aag acg gcc agc att tcc tgt ggg gga gac aac   480
Ser Val Ala Pro Gly Lys Thr Ala Ser Ile Ser Cys Gly Gly Asp Asn
145                 150                 155                 160 att gga agg aaa agt gtg cac tgg ttc cag cag aag cca ggc cag gcc   528
Ile Gly Arg Lys Ser Val His Trp Phe Gln Gln Lys Pro Gly Gln Ala
                165                 170                 175 cct gtg ctg gtc ctc tat gat gat agc gac cgg ccc tca ggg atc cca   576
Pro Val Leu Val Leu Tyr Asp Asp Ser Asp Arg Pro Ser Gly Ile Pro
                180                 185                 190
```

```
gcg cga ttc tct ggc tcc aac tct ggg aac acg gcc acc ctg acc atc    624
Ala Arg Phe Ser Gly Ser Asn Ser Gly Asn Thr Ala Thr Leu Thr Ile
        195                 200                 205 agc ggg gtc gaa gcc ggg gat gag gcc gac tat tac tgt cag gtg tgg    672
Ser Gly Val Glu Ala Gly Asp Glu Ala Asp Tyr Tyr Cys Gln Val Trp
210                 215                 220 gcc aga agt agc gat ctt cca aat tgg gtg ttc ggc gga ggg aca aag    720
Ala Arg Ser Ser Asp Leu Pro Asn Trp Val Phe Gly Gly Gly Thr Lys
225                 230                 235                 240 ctg acc gtc cta gga                                                735
Leu Thr Val Leu Gly
                245
```

<210> SEQ ID NO 22
<211> LENGTH: 245
<212> TYPE: PRT
<213> ORGANISM: Artificial Sequence
<220> FEATURE:
<223> OTHER INFORMATION: Synthetic Construct

<400> SEQUENCE: 22

```
Gln Leu Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ser Met Asn Trp Ile Arg Gln Ala Pro Gly Lys Arg Leu Glu Trp Val
        35                  40                  45

Ser Ser Ile Ser Ser Ser Ser Tyr Ile Tyr Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asp Ser Leu Arg Ala Glu Asp Thr Ala Val Tyr Tyr Cys
                85                  90                  95

Ala Arg Tyr Met Ala Gly Ile Trp Thr Phe Asp Ile Trp Gly Gln Gly
            100                 105                 110

Thr Met Val Thr Val Ser Ser Gly Gly Gly Ser Gly Gly Gly Ala
        115                 120                 125

Ser Gly Gly Gly Gly Ser Ser Tyr Glu Leu Thr Gln Pro Pro Ser Val
    130                 135                 140

Ser Val Ala Pro Gly Lys Thr Ala Ser Ile Ser Cys Gly Gly Asp Asn
145                 150                 155                 160

Ile Gly Arg Lys Ser Val His Trp Phe Gln Gln Lys Pro Gly Gln Ala
                165                 170                 175

Pro Val Leu Val Leu Tyr Asp Asp Ser Asp Arg Pro Ser Gly Ile Pro
            180                 185                 190

Ala Arg Phe Ser Gly Ser Asn Ser Gly Asn Thr Ala Thr Leu Thr Ile
        195                 200                 205

Ser Gly Val Glu Ala Gly Asp Glu Ala Asp Tyr Tyr Cys Gln Val Trp
    210                 215                 220

Ala Arg Ser Ser Asp Leu Pro Asn Trp Val Phe Gly Gly Gly Thr Lys
225                 230                 235                 240

Leu Thr Val Leu Gly
                245
```

<210> SEQ ID NO 23
<211> LENGTH: 357
<212> TYPE: DNA

<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(357)

<400> SEQUENCE: 23

```
cag ctg cag ctg cag gag tcg ggg gga ggc ttg gta cag cct gga ggg      48
Gln Leu Gln Leu Gln Glu Ser Gly Gly Gly Leu Val Gln Pro Gly Gly
1               5                   10                  15 tcc ctg aga ctc tcc tgt gca gcc tct gga ttc acc ttc agt agc cat      96
Ser Leu Arg Leu Ser Cys Ala Ala Ser Gly Phe Thr Phe Ser Ser His
            20                  25                  30 agc atg aac tgg atc cgc cag gct cca ggg aag agg ctg gag tgg gtc     144
Ser Met Asn Trp Ile Arg Gln Ala Pro Gly Lys Arg Leu Glu Trp Val
        35                  40                  45 tca tcc att agt agt agt agt agt tac ata tac tac gca gac tca gtg     192
Ser Ser Ile Ser Ser Ser Ser Ser Tyr Ile Tyr Tyr Ala Asp Ser Val
    50                  55                  60 agg ggc cga ttc acc atc tcc aga gac aac gcc aag aac tca ctg tat     240
Arg Gly Arg Phe Thr Ile Ser Arg Asp Asn Ala Lys Asn Ser Leu Tyr
65                  70                  75                  80 ctg caa atg gac agc ctg aga gcc gag gac acg gca gtg tat tat tgt     288
Leu Gln Met Asp Ser Leu Arg Ala Glu Asp Thr Ala Val Tyr Tyr Cys
                85                  90                  95 gcc aga tac atg gct ggc atc tgg act ttt gat atc tgg ggc caa ggg     336
Ala Arg Tyr Met Ala Gly Ile Trp Thr Phe Asp Ile Trp Gly Gln Gly
            100                 105                 110 aca atg gtc acc gtc tct tca                                         357
Thr Met Val Thr Val Ser Ser
        115
```

<210> SEQ ID NO 24
<211> LENGTH: 119
<212> TYPE: PRT
<213> ORGANISM: Artificial Sequence
<220> FEATURE:
<223> OTHER INFORMATION: Synthetic Construct

<400> SEQUENCE: 24

```
Gln Leu Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ser Met Asn Trp Ile Arg Gln Ala Pro Gly Lys Arg Leu Glu Trp Val
        35                  40                  45

Ser Ser Ile Ser Ser Ser Ser Ser Tyr Ile Tyr Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asp Ser Leu Arg Ala Glu Asp Thr Ala Val Tyr Tyr Cys
                85                  90                  95

Ala Arg Tyr Met Ala Gly Ile Trp Thr Phe Asp Ile Trp Gly Gln Gly
            100                 105                 110

Thr Met Val Thr Val Ser Ser
        115
```

<210> SEQ ID NO 25
<211> LENGTH: 333
<212> TYPE: DNA

<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(333)

<400> SEQUENCE: 25

```
tcc tat gag ctg act cag cca ccc tca gtg tca gtg gcc cca gga aag      48
Ser Tyr Glu Leu Thr Gln Pro Pro Ser Val Ser Val Ala Pro Gly Lys
1               5                   10                  15 acg gcc agc att tcc tgt ggg gga gac aac att gga agg aaa agt gtg      96
Thr Ala Ser Ile Ser Cys Gly Gly Asp Asn Ile Gly Arg Lys Ser Val
            20                  25                  30 cac tgg ttc cag cag aag cca ggc cag gcc cct gtg ctg gtc ctc tat     144
His Trp Phe Gln Gln Lys Pro Gly Gln Ala Pro Val Leu Val Leu Tyr
        35                  40                  45 gat agc gac cgg ccc tca ggg atc cca gcg cga ttc tct ggc tcc         192
Asp Asp Ser Asp Arg Pro Ser Gly Ile Pro Ala Arg Phe Ser Gly Ser
    50                  55                  60 aac tct ggg aac acg gcc acc ctg acc atc agc ggg gtc gaa gcc ggg     240
Asn Ser Gly Asn Thr Ala Thr Leu Thr Ile Ser Gly Val Glu Ala Gly
65                  70                  75                  80 gat gag gcc gac tat tac tgt cag gtg tgg gcc aga agt agc gat ctt     288
Asp Glu Ala Asp Tyr Tyr Cys Gln Val Trp Ala Arg Ser Ser Asp Leu
                85                  90                  95 cca aat tgg gtg ttc ggc gga ggg aca aag ctg acc gtc cta gga         333
Pro Asn Trp Val Phe Gly Gly Gly Thr Lys Leu Thr Val Leu Gly
            100                 105                 110
```

<210> SEQ ID NO 26
<211> LENGTH: 111
<212> TYPE: PRT
<213> ORGANISM: Artificial Sequence
<220> FEATURE:
<223> OTHER INFORMATION: Synthetic Construct

<400> SEQUENCE: 26

```
Ser Tyr Glu Leu Thr Gln Pro Pro Ser Val Ser Val Ala Pro Gly Lys
1               5                   10                  15

Thr Ala Ser Ile Ser Cys Gly Gly Asp Asn Ile Gly Arg Lys Ser Val
            20                  25                  30

His Trp Phe Gln Gln Lys Pro Gly Gln Ala Pro Val Leu Val Leu Tyr
        35                  40                  45

Asp Asp Ser Asp Arg Pro Ser Gly Ile Pro Ala Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Tyr Cys Gln Val Trp Ala Arg Ser Ser Asp Leu
                85                  90                  95

Pro Asn Trp Val Phe Gly Gly Gly Thr Lys Leu Thr Val Leu Gly
            100                 105                 110
```

<210> SEQ ID NO 27
<211> LENGTH: 24
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(24)

-continued

```
<400> SEQUENCE: 27 gga ttc acc ttc agt agc cat agc                                          24
Gly Phe Thr Phe Ser Ser His Ser
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic Construct

<400> SEQUENCE: 28

Gly Phe Thr Phe Ser Ser His Ser
1               5

<210> SEQ ID NO 29
<211> LENGTH: 24
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(24)

<400> SEQUENCE: 29 att agt agt agt agt agt tac ata                                          24
Ile Ser Ser Ser Ser Ser Tyr Ile
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic Construct

<400> SEQUENCE: 30

Ile Ser Ser Ser Ser Ser Tyr Ile
1               5

<210> SEQ ID NO 31
<211> LENGTH: 36
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(36)

<400> SEQUENCE: 31 gcc aga tac atg gct ggc atc tgg act ttt gat atc                          36
Ala Arg Tyr Met Ala Gly Ile Trp Thr Phe Asp Ile
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic Construct

<400> SEQUENCE: 32

Ala Arg Tyr Met Ala Gly Ile Trp Thr Phe Asp Ile
1               5                   10
```

```
<210> SEQ ID NO 33
<211> LENGTH: 18
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(18)

<400> SEQUENCE: 33 aac att gga agg aaa agt                                           18
Asn Ile Gly Arg Lys Ser
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic Construct

<400> SEQUENCE: 34

Asn Ile Gly Arg Lys Ser
1               5

<210> SEQ ID NO 35
<211> LENGTH: 9
<212> TYPE: DNA
<213> ORGANISM: Artificial Sequence
<220> FEATURE:
<223> OTHER INFORMATION: Synthetic Sequence

<400> SEQUENCE: 35 gatgatagc                                                          9

<210> SEQ ID NO 36
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 36

Asp Asp Ser
1

<210> SEQ ID NO 37
<211> LENGTH: 39
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(39)

<400> SEQUENCE: 37 cag gtg tgg gcc aga agt agc gat ctt cca aat tgg gtg               39
Gln Val Trp Ala Arg Ser Ser Asp Leu Pro Asn Trp Val
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Synthetic Construct
```

<400> SEQUENCE: 38

Gln Val Trp Ala Arg Ser Ser Asp Leu Pro Asn Trp Val
1               5                   10

<210> SEQ ID NO 39
<211> LENGTH: 45
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(45)

<400> SEQUENCE: 39

```
gga ggc ggc ggg tct ggt gga ggc gct agt ggt ggt ggc gga tcc     45
Gly Gly Gly Gly Ser Gly Gly Gly Ala Ser Gly Gly Gly Gly Ser
1               5                   10                  15
```

<210> SEQ ID NO 40
<211> LENGTH: 15
<212> TYPE: PRT
<213> ORGANISM: Artificial Sequence
<220> FEATURE:
<223> OTHER INFORMATION: Synthetic Construct

<400> SEQUENCE: 40

Gly Gly Gly Gly Ser Gly Gly Gly Ala Ser Gly Gly Gly Gly Ser
1               5                   10                  15

<210> SEQ ID NO 41
<211> LENGTH: 753
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(753)

<400> SEQUENCE: 41

```
aag gtc aca ttg aag gag tct ggt cct acg ctg gta aaa ccc aga cag     48
Lys Val Thr Leu Lys Glu Ser Gly Pro Thr Leu Val Lys Pro Arg Gln
1               5                   10                  15 acc ctc aca ctg acc tgc acc ttc tct ggg ttc tca ctc agc act agt     96
Thr Leu Thr Leu Thr Cys Thr Phe Ser Gly Phe Ser Leu Ser Thr Ser
                20                  25                  30 gga atg cgt gtg agc tgg gtc cgt cag ccc cca ggg aag gcc ctg gag    144
Gly Met Arg Val Ser Trp Val Arg Gln Pro Pro Gly Lys Ala Leu Glu
            35                  40                  45 tgg atc gca cgc att gat tgg gat gat gat aaa ttc tac agc aca tct    192
Trp Ile Ala Arg Ile Asp Trp Asp Asp Asp Lys Phe Tyr Ser Thr Ser
        50                  55                  60 ctg aag acc agg ctc acc atc tcc aag gac acc ttc aaa aac cag gtg    240
Leu Lys Thr Arg Leu Thr Ile Ser Lys Asp Thr Phe Lys Asn Gln Val
65                  70                  75                  80 gtc ctt aca atg acc aac atg gac cct gtg gac aca gcc atg tat tac    288
Val Leu Thr Met Thr Asn Met Asp Pro Val Asp Thr Ala Met Tyr Tyr
                85                  90                  95 tgt gta cgg aca cct tac aac tgg aac gac ggg ccc cgt ggt gct ctt    336
Cys Val Arg Thr Pro Tyr Asn Trp Asn Asp Gly Pro Arg Gly Ala Leu
            100                 105                 110 gat atc tgg ggc caa gga aca atg gtc acc gtc tct tca gga ggc gac    384
Asp Ile Trp Gly Gln Gly Thr Met Val Thr Val Ser Ser Gly Gly Asp
```

| | | | | | | | | | | | | | | | |
|---|---|---|---|---|---|---|---|---|---|---|---|---|---|---|---|
| | | | 115 | | | | 120 | | | | | 125 | | | |
| agg | tct | gat | gga | ggc | gct | agc | ggt | ggt | ggt | gga | tcc | cag | tct | atg | ttg | 432
| Arg | Ser | Asp | Gly | Gly | Ala | Ser | Gly | Gly | Gly | Gly | Ser | Gln | Ser | Met | Leu |
| | 130 | | | | 135 | | | | | 140 | | | | | |
| acg | cag | tcg | ccc | tca | gtg | tct | gct | gcc | cca | gga | cag | aat | gtc | acc | atc | 480
| Thr | Gln | Ser | Pro | Ser | Val | Ser | Ala | Ala | Pro | Gly | Gln | Asn | Val | Thr | Ile |
| 145 | | | | | 150 | | | | | 155 | | | | | 160 |
| tcc | tgc | tct | gga | gac | tac | ccc | aac | att | aga | aat | aat | tat | gta | tcc | tgg | 528
| Ser | Cys | Ser | Gly | Asp | Tyr | Pro | Asn | Ile | Arg | Asn | Asn | Tyr | Val | Ser | Trp |
| | | | 165 | | | | | 170 | | | | | 175 | | |
| tac | cag | caa | ctc | cca | gga | gca | gcc | ccc | aaa | ctc | ctc | att | tat | gat | aat | 576
| Tyr | Gln | Gln | Leu | Pro | Gly | Ala | Ala | Pro | Lys | Leu | Leu | Ile | Tyr | Asp | Asn |
| | | 180 | | | | | 185 | | | | | 190 | | | |
| aat | aag | cga | ccc | tca | ggg | att | cct | gac | cga | ttc | tct | ggc | tcc | aag | tct | 624
| Asn | Lys | Arg | Pro | Ser | Gly | Ile | Pro | Asp | Arg | Phe | Ser | Gly | Ser | Lys | Ser |
| | 195 | | | | | 200 | | | | | 205 | | | | |
| ggc | acg | tca | gcc | acc | ctg | gac | atc | acc | ggg | ctc | cag | act | ggg | gac | gag | 672
| Gly | Thr | Ser | Ala | Thr | Leu | Asp | Ile | Thr | Gly | Leu | Gln | Thr | Gly | Asp | Glu |
| 210 | | | | | 215 | | | | | 220 | | | | | |
| gcc | gat | tat | tac | tgc | gga | gca | tgg | gat | agc | aga | ctg | agt | gct | gtg | gta | 720
| Ala | Asp | Tyr | Tyr | Cys | Gly | Ala | Trp | Asp | Ser | Arg | Leu | Ser | Ala | Val | Val |
| 225 | | | | 230 | | | | | 235 | | | | | 240 | |
| ttc | ggc | gga | ggg | acc | aag | ctg | acc | gtc | cta | gga | | | | | | 753
| Phe | Gly | Gly | Gly | Thr | Lys | Leu | Thr | Val | Leu | Gly | | | | | |
| | | | | 245 | | | | | 250 | | | | | | |

<210> SEQ ID NO 42
<211> LENGTH: 251
<212> TYPE: PRT
<213> ORGANISM: Artificial Sequence
<220> FEATURE:
<223> OTHER INFORMATION: Synthetic Construct

<400> SEQUENCE: 42

Lys Val Thr Leu Lys Glu Ser Gly Pro Thr Leu Val Lys Pro Arg Gln
1               5                   10                  15

Thr Leu Thr Leu Thr Cys Thr Phe Ser Gly Phe Ser Leu Ser Thr Ser
            20                  25                  30

Gly Met Arg Val Ser Trp Val Arg Gln Pro Pro Gly Lys Ala Leu Glu
        35                  40                  45

Trp Ile Ala Arg Ile Asp Trp Asp Asp Lys Phe Tyr Ser Thr Ser
    50                  55                  60

Leu Lys Thr Arg Leu Thr Ile Ser Lys Asp Thr Phe Lys Asn Gln Val
65                  70                  75                  80

Val Leu Thr Met Thr Asn Met Asp Pro Val Asp Thr Ala Met Tyr Tyr
                85                  90                  95

Cys Val Arg Thr Pro Tyr Asn Trp Asn Asp Gly Pro Arg Gly Ala Leu
            100                 105                 110

Asp Ile Trp Gly Gln Gly Thr Met Val Thr Val Ser Ser Gly Gly Asp
        115                 120                 125

Arg Ser Asp Gly Gly Ala Ser Gly Gly Gly Gly Ser Gln Ser Met Leu
    130                 135                 140

Thr Gln Ser Pro Ser Val Ser Ala Ala Pro Gly Gln Asn Val Thr Ile
145                 150                 155                 160

Ser Cys Ser Gly Asp Tyr Pro Asn Ile Arg Asn Asn Tyr Val Ser Trp
                165                 170                 175

Tyr Gln Gln Leu Pro Gly Ala Ala Pro Lys Leu Leu Ile Tyr Asp Asn
            180                 185                 190

```
Asn Lys Arg Pro Ser Gly Ile Pro Asp Arg Phe Ser Gly Lys Ser
        195                 200                 205
Gly Thr Ser Ala Thr Leu Asp Ile Thr Gly Leu Gln Thr Gly Asp Glu
    210                 215                 220
Ala Asp Tyr Tyr Cys Gly Ala Trp Asp Ser Arg Leu Ser Ala Val Val
225                 230                 235                 240
Phe Gly Gly Gly Thr Lys Leu Thr Val Leu Gly
                245                 250

<210> SEQ ID NO 43
<211> LENGTH: 375
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(375)

<400> SEQUENCE: 43 aag gtc aca ttg aag gag tct ggt cct acg ctg gta aaa ccc aga cag        48
Lys Val Thr Leu Lys Glu Ser Gly Pro Thr Leu Val Lys Pro Arg Gln
1               5                   10                  15 acc ctc aca ctg acc tgc acc ttc tct ggg ttc tca ctc agc act agt        96
Thr Leu Thr Leu Thr Cys Thr Phe Ser Gly Phe Ser Leu Ser Thr Ser
                20                  25                  30 gga atg cgt gtg agc tgg gtc cgt cag ccc cca ggg aag gcc ctg gag       144
Gly Met Arg Val Ser Trp Val Arg Gln Pro Pro Gly Lys Ala Leu Glu
            35                  40                  45 tgg atc gca cgc att gat tgg gat gat gat aaa ttc tac agc aca tct       192
Trp Ile Ala Arg Ile Asp Trp Asp Asp Asp Lys Phe Tyr Ser Thr Ser
        50                  55                  60 ctg aag acc agg ctc acc atc tcc aag gac acc ttc aaa aac cag gtg       240
Leu Lys Thr Arg Leu Thr Ile Ser Lys Asp Thr Phe Lys Asn Gln Val
65                  70                  75                  80 gtc ctt aca atg acc aac atg gac cct gtg gac aca gcc atg tat tac       288
Val Leu Thr Met Thr Asn Met Asp Pro Val Asp Thr Ala Met Tyr Tyr
                85                  90                  95 tgt gta cgg aca cct tac aac tgg aac gac ggg ccc cgt ggt gct ctt       336
Cys Val Arg Thr Pro Tyr Asn Trp Asn Asp Gly Pro Arg Gly Ala Leu
            100                 105                 110 gat atc tgg ggc caa gga aca atg gtc acc gtc tct tca                   375
Asp Ile Trp Gly Gln Gly Thr Met Val Thr Val Ser Ser
        115                 120                 125

<210> SEQ ID NO 44
<211> LENGTH: 125
<212> TYPE: PRT
<213> ORGANISM: Artificial Sequence
<220> FEATURE:
<223> OTHER INFORMATION: Synthetic Construct

<400> SEQUENCE: 44

Lys Val Thr Leu Lys Glu Ser Gly Pro Thr Leu Val Lys Pro Arg Gln
1               5                   10                  15

Thr Leu Thr Leu Thr Cys Thr Phe Ser Gly Phe Ser Leu Ser Thr Ser
                20                  25                  30

Gly Met Arg Val Ser Trp Val Arg Gln Pro Pro Gly Lys Ala Leu Glu
            35                  40                  45

Trp Ile Ala Arg Ile Asp Trp Asp Asp Asp Lys Phe Tyr Ser Thr Ser
        50                  55                  60
```

Leu Lys Thr Arg Leu Thr Ile Ser Lys Asp Thr Phe Lys Asn Gln Val
 65                  70                  75                  80

Val Leu Thr Met Thr Asn Met Asp Pro Val Asp Thr Ala Met Tyr Tyr
             85                  90                  95

Cys Val Arg Thr Pro Tyr Asn Trp Asn Asp Gly Pro Arg Gly Ala Leu
            100                 105                 110

Asp Ile Trp Gly Gln Gly Thr Met Val Thr Val Ser Ser
        115                 120                 125

<210> SEQ ID NO 45
<211> LENGTH: 333
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(333)

<400> SEQUENCE: 45 cag tct atg ttg acg cag tcg ccc tca gtg tct gct gcc cca gga cag       48
Gln Ser Met Leu Thr Gln Ser Pro Ser Val Ser Ala Ala Pro Gly Gln
1               5                   10                  15 aat gtc acc atc tcc tgc tct gga gac tac ccc aac att aga aat aat       96
Asn Val Thr Ile Ser Cys Ser Gly Asp Tyr Pro Asn Ile Arg Asn Asn
            20                  25                  30 tat gta tcc tgg tac cag caa ctc cca gga gca gcc ccc aaa ctc ctc      144
Tyr Val Ser Trp Tyr Gln Gln Leu Pro Gly Ala Ala Pro Lys Leu Leu
        35                  40                  45 att tat gat aat aat aag cga ccc tca ggg att cct gac cga ttc tct      192
Ile Tyr Asp Asn Asn Lys Arg Pro Ser Gly Ile Pro Asp Arg Phe Ser
    50                  55                  60 ggc tcc aag tct ggc acg tca gcc acc ctg gac atc acc ggg ctc cag      240
Gly Ser Lys Ser Gly Thr Ser Ala Thr Leu Asp Ile Thr Gly Leu Gln
65                  70                  75                  80 act ggg gac gag gcc gat tat tac tgc gga gca tgg gat agc aga ctg      288
Thr Gly Asp Glu Ala Asp Tyr Tyr Cys Gly Ala Trp Asp Ser Arg Leu
                85                  90                  95 agt gct gtg gta ttc ggc gga ggg acc aag ctg acc gtc cta gga           333
Ser Ala Val Val Phe Gly Gly Gly Thr Lys Leu Thr Val Leu Gly
            100                 105                 110

<210> SEQ ID NO 46
<211> LENGTH: 111
<212> TYPE: PRT
<213> ORGANISM: Artificial Sequence
<220> FEATURE:
<223> OTHER INFORMATION: Synthetic Construct

<400> SEQUENCE: 46

Gln Ser Met Leu Thr Gln Ser Pro Ser Val Ser Ala Ala Pro Gly Gln
1               5                   10                  15

Asn Val Thr Ile Ser Cys Ser Gly Asp Tyr Pro Asn Ile Arg Asn Asn
            20                  25                  30

Tyr Val Ser Trp Tyr Gln Gln Leu Pro Gly Ala Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Asp Ile Thr Gly Leu Gln
65                  70                  75                  80

```
              Thr Gly Asp Glu Ala Asp Tyr Tyr Cys Gly Ala Trp Asp Ser Arg Leu
                              85                  90                  95

Ser Ala Val Val Phe Gly Gly Gly Thr Lys Leu Thr Val Leu Gly
                          100                 105                 110

<210> SEQ ID NO 47
<211> LENGTH: 30
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(30)

<400> SEQUENCE: 47 ggg ttc tca ctc agc act agt gga atg cgt                                   30
Gly Phe Ser Leu Ser Thr Ser Gly Met Arg
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic Construct

<400> SEQUENCE: 48

Gly Phe Ser Leu Ser Thr Ser Gly Met Arg
1               5                   10

<210> SEQ ID NO 49
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(21)

<400> SEQUENCE: 49 att gat tgg gat gat gat aaa                                               21
Ile Asp Trp Asp Asp Asp Lys
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic Construct

<400> SEQUENCE: 50

Ile Asp Trp Asp Asp Asp Lys
1               5

<210> SEQ ID NO 51
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(51)

<400> SEQUENCE: 51
```

```
gta cgg aca cct tac aac tgg aac gac ggg ccc cgt ggt gct ctt gat    48
Val Arg Thr Pro Tyr Asn Trp Asn Asp Gly Pro Arg Gly Ala Leu Asp
1               5                   10                  15 atc                                                                51
Ile
```

<210> SEQ ID NO 52
<211> LENGTH: 17
<212> TYPE: PRT
<213> ORGANISM: Artificial Sequence
<220> FEATURE:
<223> OTHER INFORMATION: Synthetic Construct

<400> SEQUENCE: 52

```
Val Arg Thr Pro Tyr Asn Trp Asn Asp Gly Pro Arg Gly Ala Leu Asp
1               5                   10                  15

Ile
```

<210> SEQ ID NO 53
<211> LENGTH: 24
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(24)

<400> SEQUENCE: 53

```
tac ccc aac att aga aat aat tat                                    24
Tyr Pro Asn Ile Arg Asn Asn Tyr
1               5
```

<210> SEQ ID NO 54
<211> LENGTH: 8
<212> TYPE: PRT
<213> ORGANISM: Artificial Sequence
<220> FEATURE:
<223> OTHER INFORMATION: Synthetic Construct

<400> SEQUENCE: 54

```
Tyr Pro Asn Ile Arg Asn Asn Tyr
1               5
```

<210> SEQ ID NO 55
<211> LENGTH: 9
<212> TYPE: DNA
<213> ORGANISM: Artificial Sequence
<220> FEATURE:
<223> OTHER INFORMATION: Synthetic Sequence

<400> SEQUENCE: 55

```
gataataat                                                           9
```

<210> SEQ ID NO 56
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 56

```
Asp Asn Asn
1
```

<210> SEQ ID NO 57

```
<211> LENGTH: 33
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(33)

<400> SEQUENCE: 57 gga gca tgg gat agc aga ctg agt gct gtg gta                    33
Gly Ala Trp Asp Ser Arg Leu Ser Ala Val Val
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic Construct

<400> SEQUENCE: 58

Gly Ala Trp Asp Ser Arg Leu Ser Ala Val Val
1               5                   10

<210> SEQ ID NO 59
<211> LENGTH: 45
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(45)

<400> SEQUENCE: 59 gga ggc gac agg tct gat gga ggc gct agc ggt ggt ggt gga tcc    45
Gly Gly Asp Arg Ser Asp Gly Gly Ala Ser Gly Gly Gly Gly Ser
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: Synthetic Construct

<400> SEQUENCE: 60

Gly Gly Asp Arg Ser Asp Gly Gly Ala Ser Gly Gly Gly Gly Ser
1               5                   10                  15

<210> SEQ ID NO 61
<211> LENGTH: 753
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(753)

<400> SEQUENCE: 61 cag gtg acc ctg aaa gaa agc ggc ccg acc ctg gtg aaa cgt acc cag    48
Gln Val Thr Leu Lys Glu Ser Gly Pro Thr Leu Val Lys Arg Thr Gln
1               5                   10                  15 acc ctg acc ctg acc tgc acc ttt ttt ggc ttt agc ctg agc acc agc    96
Thr Leu Thr Leu Thr Cys Thr Phe Phe Gly Phe Ser Leu Ser Thr Ser
            20                  25                  30
```

```
ggc atg cgt gtg agc tgg att cgt cag ccg ccg ggc aaa gcg ctg gaa      144
Gly Met Arg Val Ser Trp Ile Arg Gln Pro Pro Gly Lys Ala Leu Glu
         35                  40                  45 tgg att gcg cgt att gat tgg gat gat gat aaa ttt tat agc att agc      192
Trp Ile Ala Arg Ile Asp Trp Asp Asp Asp Lys Phe Tyr Ser Ile Ser
 50                  55                  60 ctg aaa agc cgt ctg acc att agc aaa gat acc agc aaa aac cag gtg      240
Leu Lys Ser Arg Leu Thr Ile Ser Lys Asp Thr Ser Lys Asn Gln Val
 65                  70                  75                  80 gtg ctg acc atg acc aac atg gat ccg gtg gat acc gcg acc tat tat      288
Val Leu Thr Met Thr Asn Met Asp Pro Val Asp Thr Ala Thr Tyr Tyr
             85                  90                  95 tgc gcg cgt acc ccg tat aac tgg aac gat ggc ccg cgt ggc gcg ttt      336
Cys Ala Arg Thr Pro Tyr Asn Trp Asn Asp Gly Pro Arg Gly Ala Phe
            100                 105                 110 gat att tgg ggc cag ggc acc atg gtg acc gtg agc agc gaa ggc ggc      384
Asp Ile Trp Gly Gln Gly Thr Met Val Thr Val Ser Ser Glu Gly Gly
            115                 120                 125 ggc agc ggc ggc ggc gcg agc agc ggc ggc ggc agc cag agc gtg ctg      432
Gly Ser Gly Gly Gly Ala Ser Ser Gly Gly Gly Ser Gln Ser Val Leu
        130                 135                 140 acc cag ccg ccg agc gtg agc gcg gcg ccg ggc cag aaa gtg acc att      480
Thr Gln Pro Pro Ser Val Ser Ala Ala Pro Gly Gln Lys Val Thr Ile
145                 150                 155                 160 ccg tgc agc ggc agc tat agc aac att cgt aac aac tat gtg agc tgg      528
Pro Cys Ser Gly Ser Tyr Ser Asn Ile Arg Asn Asn Tyr Val Ser Trp
                165                 170                 175 tat cag cag ctg ccg ggc acc gcg ccg aaa ctg ctg att tat gat gat      576
Tyr Gln Gln Leu Pro Gly Thr Ala Pro Lys Leu Leu Ile Tyr Asp Asp
            180                 185                 190 aac aaa cgt ccg agc ggc att ccg gat cgt ttt agc ggc agc aaa agc      624
Asn Lys Arg Pro Ser Gly Ile Pro Asp Arg Phe Ser Gly Ser Lys Ser
        195                 200                 205 ggc acc ctg gcg acc ctg gtg att acc ggc ctg cag agc ggc gat gaa      672
Gly Thr Leu Ala Thr Leu Val Ile Thr Gly Leu Gln Ser Gly Asp Glu
    210                 215                 220 gcg gat tat tat tgc ggc acc tgg gat agc agc ctg agc ggc gtg gtg      720
Ala Asp Tyr Tyr Cys Gly Thr Trp Asp Ser Ser Leu Ser Gly Val Val
225                 230                 235                 240 ttt ggc ggc ggc acc aaa ctg acc gtg ctg ggc                          753
Phe Gly Gly Gly Thr Lys Leu Thr Val Leu Gly
                245                 250

<210> SEQ ID NO 62
<211> LENGTH: 251
<212> TYPE: PRT
<213> ORGANISM: Artificial Sequence
<220> FEATURE:
<223> OTHER INFORMATION: Synthetic Construct

<400> SEQUENCE: 62

Gln Val Thr Leu Lys Glu Ser Gly Pro Thr Leu Val Lys Arg Thr Gln
 1               5                  10                  15

Thr Leu Thr Leu Thr Cys Thr Phe Phe Gly Phe Ser Leu Ser Thr Ser
             20                  25                  30

Gly Met Arg Val Ser Trp Ile Arg Gln Pro Pro Gly Lys Ala Leu Glu
         35                  40                  45

Trp Ile Ala Arg Ile Asp Trp Asp Asp Asp Lys Phe Tyr Ser Ile Ser
 50                  55                  60

Leu Lys Ser Arg Leu Thr Ile Ser Lys Asp Thr Ser Lys Asn Gln Val
```

```
                65                  70                  75                  80
        Val Leu Thr Met Thr Asn Met Asp Pro Val Asp Thr Ala Thr Tyr Tyr
                        85                  90                  95

Cys Ala Arg Thr Pro Tyr Asn Trp Asn Asp Gly Pro Arg Gly Ala Phe
                        100                 105                 110

Asp Ile Trp Gly Gln Gly Thr Met Val Thr Val Ser Ser Glu Gly Gly
                        115                 120                 125

Gly Ser Gly Gly Gly Ala Ser Ser Gly Gly Gly Ser Gln Ser Val Leu
                    130                 135                 140

Thr Gln Pro Pro Ser Val Ser Ala Ala Pro Gly Gln Lys Val Thr Ile
        145                 150                 155                 160

Pro Cys Ser Gly Ser Tyr Ser Asn Ile Arg Asn Asn Tyr Val Ser Trp
                        165                 170                 175

Tyr Gln Gln Leu Pro Gly Thr Ala Pro Lys Leu Leu Ile Tyr Asp Asp
                        180                 185                 190

Asn Lys Arg Pro Ser Gly Ile Pro Asp Arg Phe Ser Gly Ser Lys Ser
                        195                 200                 205

Gly Thr Leu Ala Thr Leu Val Ile Thr Gly Leu Gln Ser Gly Asp Glu
                    210                 215                 220

Ala Asp Tyr Tyr Cys Gly Thr Trp Asp Ser Ser Leu Ser Gly Val Val
        225                 230                 235                 240

Phe Gly Gly Gly Thr Lys Leu Thr Val Leu Gly
                        245                 250

<210> SEQ ID NO 63
<211> LENGTH: 375
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(375)

<400> SEQUENCE: 63 cag gtg acc ctg aaa gaa agc ggc ccg acc ctg gtg aaa cgt acc cag        48
Gln Val Thr Leu Lys Glu Ser Gly Pro Thr Leu Val Lys Arg Thr Gln
1               5                   10                  15 acc ctg acc ctg acc tgc acc ttt ttt ggc ttt agc ctg agc acc agc        96
Thr Leu Thr Leu Thr Cys Thr Phe Phe Gly Phe Ser Leu Ser Thr Ser
            20                  25                  30 ggc atg cgt gtg agc tgg att cgt cag ccg ccg ggc aaa gcg ctg gaa       144
Gly Met Arg Val Ser Trp Ile Arg Gln Pro Pro Gly Lys Ala Leu Glu
        35                  40                  45 tgg att gcg cgt att gat tgg gat gat gat aaa ttt tat agc att agc       192
Trp Ile Ala Arg Ile Asp Trp Asp Asp Asp Lys Phe Tyr Ser Ile Ser
    50                  55                  60 ctg aaa agc cgt ctg acc att agc aaa gat acc agc aaa aac cag gtg       240
Leu Lys Ser Arg Leu Thr Ile Ser Lys Asp Thr Ser Lys Asn Gln Val
65                  70                  75                  80 gtg ctg acc atg acc aac atg gat ccg gtg gat acc gcg acc tat tat       288
Val Leu Thr Met Thr Asn Met Asp Pro Val Asp Thr Ala Thr Tyr Tyr
                85                  90                  95 tgc gcg cgt acc ccg tat aac tgg aac gat ggc ccg cgt ggc gcg ttt       336
Cys Ala Arg Thr Pro Tyr Asn Trp Asn Asp Gly Pro Arg Gly Ala Phe
            100                 105                 110 gat att tgg ggc cag ggc acc atg gtg acc gtg agc agc                   375
Asp Ile Trp Gly Gln Gly Thr Met Val Thr Val Ser Ser
        115                 120                 125
```

<210> SEQ ID NO 64
<211> LENGTH: 125
<212> TYPE: PRT
<213> ORGANISM: Artificial Sequence
<220> FEATURE:
<223> OTHER INFORMATION: Synthetic Construct

<400> SEQUENCE: 64

```
Gln Val Thr Leu Lys Glu Ser Gly Pro Thr Leu Val Lys Arg Thr Gln
1               5                   10                  15

Thr Leu Thr Leu Thr Cys Thr Phe Phe Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Ile Ala Arg Ile Asp Trp Asp Asp Asp Lys Phe Tyr Ser Ile Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Thr Pro Tyr Asn Trp Asn Asp Gly Pro Arg Gly Ala Phe
            100                 105                 110

Asp Ile Trp Gly Gln Gly Thr Met Val Thr Val Ser Ser
            115                 120                 125
```

<210> SEQ ID NO 65
<211> LENGTH: 333
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(333)

<400> SEQUENCE: 65

```
cag agc gtg ctg acc cag ccg ccg agc gtg agc gcg gcg ccg ggc cag      48
Gln Ser Val Leu Thr Gln Pro Pro Ser Val Ser Ala Ala Pro Gly Gln
1               5                   10                  15 aaa gtg acc att ccg tgc agc ggc agc tat agc aac att cgt aac aac      96
Lys Val Thr Ile Pro Cys Ser Gly Ser Tyr Ser Asn Ile Arg Asn Asn
            20                  25                  30 tat gtg agc tgg tat cag cag ctg ccg ggc acc gcg ccg aaa ctg ctg     144
Tyr Val Ser Trp Tyr Gln Gln Leu Pro Gly Thr Ala Pro Lys Leu Leu
        35                  40                  45 att tat gat gat aac aaa cgt ccg agc ggc att ccg gat cgt ttt agc     192
Ile Tyr Asp Asp Asn Lys Arg Pro Ser Gly Ile Pro Asp Arg Phe Ser
    50                  55                  60 ggc agc aaa agc ggc acc ctg gcg acc ctg gtg att acc ggc ctg cag     240
Gly Ser Lys Ser Gly Thr Leu Ala Thr Leu Val Ile Thr Gly Leu Gln
65                  70                  75                  80 agc ggc gat gaa gcg gat tat tat tgc ggc acc tgg gat agc agc ctg     288
Ser Gly Asp Glu Ala Asp Tyr Tyr Cys Gly Thr Trp Asp Ser Ser Leu
                85                  90                  95 agc ggc gtg gtg ttt ggc ggc ggc acc aaa ctg acc gtg ctg ggc         333
Ser Gly Val Val Phe Gly Gly Gly Thr Lys Leu Thr Val Leu Gly
            100                 105                 110
```

<210> SEQ ID NO 66
<211> LENGTH: 111

```
<212> TYPE: PRT
<213> ORGANISM: Artificial Sequence
<220> FEATURE:
<223> OTHER INFORMATION: Synthetic Construct

<400> SEQUENCE: 66

Gln Ser Val Leu Thr Gln Pro Pro Ser Val Ser Ala Ala Pro Gly Gln
1               5                   10                  15

Lys Val Thr Ile Pro Cys Ser Gly Ser Tyr Ser Asn Ile Arg Asn Asn
            20                  25                  30

Tyr Val Ser Trp Tyr Gln Gln Leu Pro Gly Thr Ala Pro Lys Leu Leu
        35                  40                  45

Ile Tyr Asp Asp Asn Lys Arg Pro Ser Gly Ile Pro Asp Arg Phe Ser
    50                  55                  60

Gly Ser Lys Ser Gly Thr Leu Ala Thr Leu Val Ile Thr Gly Leu Gln
65                  70                  75                  80

Ser Gly Asp Glu Ala Asp Tyr Tyr Cys Gly Thr Trp Asp Ser Ser Leu
                85                  90                  95

Ser Gly Val Val Phe Gly Gly Gly Thr Lys Leu Thr Val Leu Gly
            100                 105                 110

<210> SEQ ID NO 67
<211> LENGTH: 30
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(30)

<400> SEQUENCE: 67 ggc ttt agc ctg agc acc agc ggc atg cgt                        30
Gly Phe Ser Leu Ser Thr Ser Gly Met Arg
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthetic Construct

<400> SEQUENCE: 68

Gly Phe Ser Leu Ser Thr Ser Gly Met Arg
1               5                   10

<210> SEQ ID NO 69
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(21)

<400> SEQUENCE: 69 att gat tgg gat gat gat aaa                                    21
Ile Asp Trp Asp Asp Asp Lys
1               5

<210> SEQ ID NO 70
<211> LENGTH: 7
<212> TYPE: PRT
```

<213> ORGANISM: Artificial Sequence
<220> FEATURE:
<223> OTHER INFORMATION: Synthetic Construct

<400> SEQUENCE: 70

Ile Asp Trp Asp Asp Asp Lys
1               5

<210> SEQ ID NO 71
<211> LENGTH: 51
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(51)

<400> SEQUENCE: 71 gcg cgt acc ccg tat aac tgg aac gat ggc ccg cgt ggc gcg ttt gat     48
Ala Arg Thr Pro Tyr Asn Trp Asn Asp Gly Pro Arg Gly Ala Phe Asp
1               5                   10                  15 att                                                                  51
Ile

<210> SEQ ID NO 72
<211> LENGTH: 17
<212> TYPE: PRT
<213> ORGANISM: Artificial Sequence
<220> FEATURE:
<223> OTHER INFORMATION: Synthetic Construct

<400> SEQUENCE: 72

Ala Arg Thr Pro Tyr Asn Trp Asn Asp Gly Pro Arg Gly Ala Phe Asp
1               5                   10                  15

Ile

<210> SEQ ID NO 73
<211> LENGTH: 24
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(24)

<400> SEQUENCE: 73 tat agc aac att cgt aac aac tat                                      24
Tyr Ser Asn Ile Arg Asn Asn Tyr
1               5

<210> SEQ ID NO 74
<211> LENGTH: 8
<212> TYPE: PRT
<213> ORGANISM: Artificial Sequence
<220> FEATURE:
<223> OTHER INFORMATION: Synthetic Construct

<400> SEQUENCE: 74

Tyr Ser Asn Ile Arg Asn Asn Tyr
1               5

<210> SEQ ID NO 75
<211> LENGTH: 9
<212> TYPE: DNA
<213> ORGANISM: Artificial Sequence

```
<220> FEATURE:
<223> OTHER INFORMATION: Synthetic Sequence

<400> SEQUENCE: 75 gatgataac                                                                9

<210> SEQ ID NO 76
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 76

Asp Asp Asn
1

<210> SEQ ID NO 77
<211> LENGTH: 33
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(33)

<400> SEQUENCE: 77 ggc acc tgg gat agc agc ctg agc ggc gtg gtg                             33
Gly Thr Trp Asp Ser Ser Leu Ser Gly Val Val
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Synthetic Construct

<400> SEQUENCE: 78

Gly Thr Trp Asp Ser Ser Leu Ser Gly Val Val
1               5                   10

<210> SEQ ID NO 79
<211> LENGTH: 45
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(45)

<400> SEQUENCE: 79 gaa ggc ggc ggc agc ggc ggc ggc gcg agc agc ggc ggc ggc agc             45
Glu Gly Gly Gly Ser Gly Gly Gly Ala Ser Ser Gly Gly Gly Ser
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic Construct

<400> SEQUENCE: 80

Glu Gly Gly Gly Ser Gly Gly Gly Ala Ser Ser Gly Gly Gly Ser
1               5                   10                  15
```

<210> SEQ ID NO 81
<211> LENGTH: 495
<212> TYPE: PRT
<213> ORGANISM: Artificial Sequence
<220> FEATURE:
<223> OTHER INFORMATION: Synthetic Sequence

<400> SEQUENCE: 81

```
Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Gln Lys Asn Met Glu Gly Lys
        115                 120                 125

Ile Val Gln Pro Glu Asn Leu Glu Tyr Thr Ile Val Val Thr Pro His
130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Asp Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
210                 215                 220

Asp Thr Gln Gly Ser Lys Leu Asp Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365
```

```
Ala Glu Pro Pro Phe Gly Asp Ser Tyr Ile Ile Ile Gly Val Glu Pro
        370                 375                 380

Gly Gln Leu Lys Leu Asn Trp Phe Lys Lys Gly Ser Ser Ile Gly Gln
385                 390                 395                 400

Met Phe Glu Thr Thr Met Ile Arg Ala Lys Arg Met Ala Ile Leu Gly
                405                 410                 415

Asp Thr Ala Trp Asp Phe Arg Ser Leu Gly Gly Val Phe Thr Ser Ile
            420                 425                 430

Gly Lys Ala Leu His Gln Val Phe Gly Ala Ile Tyr Gly Ala Ala Phe
        435                 440                 445

Ser Gly Val Ser Trp Thr Met Lys Ile Leu Ile Gly Val Ile Ile Thr
    450                 455                 460

Trp Ile Gly Met Asn Ser Arg Ser Thr Ser Leu Ser Val Ser Leu Val
465                 470                 475                 480

Leu Val Gly Ile Val Thr Leu Tyr Leu Gly Val Met Val Gln Ala
                485                 490                 495

<210> SEQ ID NO 82
<211> LENGTH: 105
<212> TYPE: PRT
<213> ORGANISM: Artificial Sequence
<220> FEATURE:
<223> OTHER INFORMATION: Synthetic Sequence

<400> SEQUENCE: 82

Lys Leu Gln Leu Lys Gly Met Ser Tyr Ser Met Cys Thr Gly Lys Phe
1               5                   10                  15

Lys Val Val Lys Glu Ile Ala Glu Thr Gln His Gly Thr Ile Val Ile
            20                  25                  30

Arg Val Gln Tyr Glu Gly Asp Gly Ser Pro Cys Lys Ile Pro Phe Glu
        35                  40                  45

Ile Met Asp Leu Glu Lys Arg His Val Leu Gly Arg Leu Ile Thr Val
    50                  55                  60

Asn Pro Ile Val Thr Glu Lys Asp Ser Pro Val Asn Ile Glu Ala Glu
65                  70                  75                  80

Pro Pro Phe Gly Asp Ser Tyr Ile Ile Ile Gly Val Glu Pro Gly Gln
                85                  90                  95

Leu Lys Leu Asn Trp Phe Lys Lys Gly
            100                 105

<210> SEQ ID NO 83
<211> LENGTH: 109
<212> TYPE: PRT
<213> ORGANISM: Artificial Sequence
<220> FEATURE:
<223> OTHER INFORMATION: Synthetic Sequence

<400> SEQUENCE: 83

Leu Gln Gln Ser Gly Ala Glu Leu Val Arg Pro Gly Ala Ser Val Lys
1               5                   10                  15

Leu Ser Cys Lys Ala Leu Gly Tyr Arg Phe Thr Asp Tyr Glu Met Tyr
            20                  25                  30

Trp Val Lys Gln Thr Pro Ala His Gly Leu Glu Trp Ile Gly Gly Ile
        35                  40                  45

His Pro Arg Ser Gly Asn Thr Ala Tyr Asn Gln Lys Phe Lys Asp Lys
    50                  55                  60

Ala Thr Leu Thr Ala Asp Lys Ser Ser Ser Thr Ala Tyr Met Glu Leu
```

```
                65                  70                  75                  80
Ser Ser Leu Thr Ser Glu Asp Ser Val Val Tyr Tyr Cys Thr Thr Ser
                    85                  90                  95
Leu Tyr Trp Gly Gln Gly Thr Thr Val Thr Val Ser Ser
            100                 105

<210> SEQ ID NO 84
<211> LENGTH: 99
<212> TYPE: PRT
<213> ORGANISM: Artificial Sequence
<220> FEATURE:
<223> OTHER INFORMATION: Synthetic Sequence

<400> SEQUENCE: 84

Leu Gly Asp Gln Ala Ser Ile Ser Cys Arg Ser Gln Ser Leu Val
1               5                   10                  15

His Ser Asn Gly Asn Thr Tyr Leu His Trp Tyr Leu Gln Lys Pro Gly
                20                  25                  30

Gln Ser Pro Lys Leu Leu Ile Tyr Ser Ile Phe Asn Arg Phe Ser Gly
            35                  40                  45

Val Pro Asp Arg Phe Ser Gly Ser Gly Ser Gly Thr Asp Phe Thr Leu
        50                  55                  60

Lys Ile Ser Arg Val Glu Ala Glu Asp Leu Gly Val Tyr Phe Cys Ser
65                  70                  75                  80

Gln Gly Thr His Val Pro Trp Thr Phe Gly Gly Gly Thr Asn Leu Glu
                85                  90                  95

Ile Lys Arg

<210> SEQ ID NO 85
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 85

Gly Tyr Arg Phe Thr Asp Tyr Glu
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 86

Ile His Pro Arg Ser Gly Asn Thr
1               5

<210> SEQ ID NO 87
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 87

Thr Thr Ser Leu Tyr
1               5

<210> SEQ ID NO 88
```

-continued

```
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 88

Gln Ser Leu Val His Ser Asn Gly Asn Thr Tyr
1               5                   10

<210> SEQ ID NO 89
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 89

Ser Ile Phe
1

<210> SEQ ID NO 90
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 90

Ser Gln Gly Thr His Val Pro Trp Thr
1               5

<210> SEQ ID NO 91
<211> LENGTH: 726
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(726)

<400> SEQUENCE: 91 ggc cag gcc ggc caa ggg ccc gac aaa act cac aca tgc cca ccg tgc        48
Gly Gln Ala Gly Gln Gly Pro Asp Lys Thr His Thr Cys Pro Pro Cys
1               5                   10                  15 cca gca cct gaa ctc ctg ggg gga ccg tca gtc ttc ctc ttc ccc cca        96
Pro Ala Pro Glu Leu Leu Gly Gly Pro Ser Val Phe Leu Phe Pro Pro
                20                  25                  30 aaa ccc aag gac acc ctc atg atc tcc cgg acc cct gag gtc aca tgc       144
Lys Pro Lys Asp Thr Leu Met Ile Ser Arg Thr Pro Glu Val Thr Cys
            35                  40                  45 gtg gtg gtg gac gtg agc cac gaa gac cct gag gtc aag ttc aac tgg       192
Val Val Val Asp Val Ser His Glu Asp Pro Glu Val Lys Phe Asn Trp
        50                  55                  60 tac gtg gac ggc gtg gag gtg cat aat gcc aag aca aag ccg cgg gag       240
Tyr Val Asp Gly Val Glu Val His Asn Ala Lys Thr Lys Pro Arg Glu
65                  70                  75                  80 gag cag tac aac agc acg tac cgg gtg gtc agc gtc ctc acc gtc ctg       288
Glu Gln Tyr Asn Ser Thr Tyr Arg Val Val Ser Val Leu Thr Val Leu
                85                  90                  95 cac cag gac tgg ctg aat ggc aag gag tac aag tgc aag gtc tcc aac       336
His Gln Asp Trp Leu Asn Gly Lys Glu Tyr Lys Cys Lys Val Ser Asn
            100                 105                 110 aaa gcc ctc cca gcc ccc atc gag aaa acc atc tcc aaa gcc aaa ggg       384
```

```
Lys Ala Leu Pro Ala Pro Ile Glu Lys Thr Ile Ser Lys Ala Lys Gly
            115                 120                 125 cag ccc cga gaa cca cag gtg tac acc ctg ccc cca tcc cgg gat gag     432
Gln Pro Arg Glu Pro Gln Val Tyr Thr Leu Pro Pro Ser Arg Asp Glu
            130                 135                 140 ctg acc aag aac cag gtc agc ctg acc tgc ctg gtc aaa ggc ttc tat     480
Leu Thr Lys Asn Gln Val Ser Leu Thr Cys Leu Val Lys Gly Phe Tyr
145                 150                 155                 160 ccc agc gac atc gcc gtg gag tgg gag agc aat ggg cag ccg gag aac     528
Pro Ser Asp Ile Ala Val Glu Trp Glu Ser Asn Gly Gln Pro Glu Asn
                165                 170                 175 aac tac aag acc acg cct ccc gtg ctg gac tcc gac ggc tcc ttc ttc     576
Asn Tyr Lys Thr Thr Pro Pro Val Leu Asp Ser Asp Gly Ser Phe Phe
            180                 185                 190 ctc tac agc aag ctc acc gtg gac aag agc agg tgg cag cag ggg aac     624
Leu Tyr Ser Lys Leu Thr Val Asp Lys Ser Arg Trp Gln Gln Gly Asn
            195                 200                 205 gtc ttc tca tgc tcc gtg atg cat gag gct ctg cac aac cac tac acg     672
Val Phe Ser Cys Ser Val Met His Glu Ala Leu His Asn His Tyr Thr
210                 215                 220 cag aag agc ctc tcc ctg tct ccg ggt aaa gcg gcc gct gga ggt gga     720
Gln Lys Ser Leu Ser Leu Ser Pro Gly Lys Ala Ala Ala Gly Gly Gly
225                 230                 235                 240 ggc agc                                                              726
Gly Ser <210> SEQ ID NO 92
<211> LENGTH: 242
<212> TYPE: PRT
<213> ORGANISM: Artificial Sequence
<220> FEATURE:
<223> OTHER INFORMATION: Synthetic Construct

<400> SEQUENCE: 92

Gly Gln Ala Gly Gln Gly Pro Asp Lys Thr His Thr Cys Pro Pro Cys
1               5                   10                  15

Pro Ala Pro Glu Leu Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Gly
            115                 120                 125

Gln Pro Arg Glu Pro Gln Val Tyr Thr Leu Pro Pro Ser Arg Asp Glu
            130                 135                 140

Leu Thr Lys Asn Gln Val Ser Leu Thr Cys Leu Val Lys Gly Phe Tyr
145                 150                 155                 160

Pro Ser Asp Ile Ala Val Glu Trp Glu Ser Asn Gly Gln Pro Glu Asn
                165                 170                 175

Asn Tyr Lys Thr Thr Pro Pro Val Leu Asp Ser Asp Gly Ser Phe Phe
            180                 185                 190
```

-continued

```
Leu Tyr Ser Lys Leu Thr Val Asp Lys Ser Arg Trp Gln Gln Gly Asn
        195                 200                 205
Val Phe Ser Cys Ser Val Met His Glu Ala Leu His Asn His Tyr Thr
210                 215                 220
Gln Lys Ser Leu Ser Leu Ser Pro Gly Lys Ala Ala Gly Gly Gly
225                 230                 235                 240
Gly Ser
```

```
<210> SEQ ID NO 93
<211> LENGTH: 720
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(720)
```

<400> SEQUENCE: 93

```
ggc cag gcc ggc caa ggg ccc gac aaa act cac aca tgc cca ccg tgc        48
Gly Gln Ala Gly Gln Gly Pro Asp Lys Thr His Thr Cys Pro Pro Cys
1               5                   10                  15 cca gca cct gaa ggg gga ccg tca gtc ttc ctc ttc ccc cca aaa ccc        96
Pro Ala Pro Glu Gly Gly Pro Ser Val Phe Leu Phe Pro Pro Lys Pro
            20                  25                  30 aag gac acc ctc atg atc tcc cgg acc cct gag gtc aca tgc gtg gtg       144
Lys Asp Thr Leu Met Ile Ser Arg Thr Pro Glu Val Thr Cys Val Val
        35                  40                  45 gtg gac gtg agc cac gaa gac cct gag gtc aag ttc aac tgg tac gtg       192
Val Asp Val Ser His Glu Asp Pro Glu Val Lys Phe Asn Trp Tyr Val
    50                  55                  60 gac ggc gtg gag gtg cat aat gcc aag aca aag ccg cgg gag gag cag       240
Asp Gly Val Glu Val His Asn Ala Lys Thr Lys Pro Arg Glu Glu Gln
65                  70                  75                  80 tac aac agc acg tac cgg gtg gtc agc gtc ctc acc gtc ctg cac cag       288
Tyr Asn Ser Thr Tyr Arg Val Val Ser Val Leu Thr Val Leu His Gln
                85                  90                  95 gac tgg ctg aat ggc aag gag tac aag tgc aag gtc tcc aac aaa gcc       336
Asp Trp Leu Asn Gly Lys Glu Tyr Lys Cys Lys Val Ser Asn Lys Ala
            100                 105                 110 ctc cca gcc ccc atc gag aaa acc atc tcc aaa gcc aaa ggg cag ccc       384
Leu Pro Ala Pro Ile Glu Lys Thr Ile Ser Lys Ala Lys Gly Gln Pro
        115                 120                 125 cga gaa cca cag gtg tac acc ctg ccc cca tcc cgg gat gag ctg acc       432
Arg Glu Pro Gln Val Tyr Thr Leu Pro Pro Ser Arg Asp Glu Leu Thr
    130                 135                 140 aag aac cag gtc agc ctg acc tgc ctg gtc aaa ggc ttc tat ccc agc       480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac       528
Asp Ile Ala Val Glu Trp Glu Ser Asn Gly Gln Pro Glu Asn Asn Tyr
                165                 170                 175 aag acc acg cct ccc gtg ctg gac tcc gac ggc tcc ttc ttc ctc tac       576
Lys Thr Thr Pro Pro Val Leu Asp Ser Asp Gly Ser Phe Phe Leu Tyr
            180                 185                 190 agc aag ctc acc gtg gac aag agc agg tgg cag cag ggg aac gtc ttc       624
Ser Lys Leu Thr Val Asp Lys Ser Arg Trp Gln Gln Gly Asn Val Phe
        195                 200                 205 tca tgc tcc gtg atg cat gag gct ctg cac aac cac tac acg cag aag       672
Ser Cys Ser Val Met His Glu Ala Leu His Asn His Tyr Thr Gln Lys
```

```
                210                 215                 220
agc ctc tcc ctg tct ccg ggt aaa gcg gcc gct gga ggt gga ggc agc      720
Ser Leu Ser Leu Ser Pro Gly Lys Ala Ala Ala Gly Gly Gly Gly Ser
225                 230                 235                 240

<210> SEQ ID NO 94
<211> LENGTH: 240
<212> TYPE: PRT
<213> ORGANISM: Artificial Sequence
<220> FEATURE:
<223> OTHER INFORMATION: Synthetic Construct

<400> SEQUENCE: 94

Gly Gln Ala Gly Gln Gly Pro Asp Lys Thr His Thr Cys Pro Pro Cys
1               5                   10                  15

Pro Ala Pro Glu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys Ala Ala Ala Gly Gly Gly Gly Ser
225                 230                 235                 240

<210> SEQ ID NO 95
<211> LENGTH: 2208
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(2208)

<400> SEQUENCE: 95 aag gtc aca ttg aag gag tct ggt cct acg ctg gta aaa ccc aga cag      48
Lys Val Thr Leu Lys Glu Ser Gly Pro Thr Leu Val Lys Pro Arg Gln
1               5                   10                  15 acc ctc aca ctg acc tgc acc ttc tct ggg ttc tca ctc agc act agt      96
```

|  |  |  |  |  |  |  |  |  |  |  |  |  |  |  |  |
|---|---|---|---|---|---|---|---|---|---|---|---|---|---|---|---|
| Thr | Leu | Thr | Leu<br>20 | Thr | Cys | Thr | Phe | Ser<br>25 | Gly | Phe | Ser | Leu | Ser<br>30 | Thr | Ser |

```
gga atg cgt gtg agc tgg gtc cgt cag ccc cca ggg aag gcc ctg gag      144
Gly Met Arg Val Ser Trp Val Arg Gln Pro Pro Gly Lys Ala Leu Glu
     35                  40                  45 tgg atc gca cgc att gat tgg gat gat gat aaa ttc tac agc aca tct      192
Trp Ile Ala Arg Ile Asp Trp Asp Asp Asp Lys Phe Tyr Ser Thr Ser
 50                  55                  60 ctg aag acc agg ctc acc atc tcc aag gac acc ttc aaa aac cag gtg      240
Leu Lys Thr Arg Leu Thr Ile Ser Lys Asp Thr Phe Lys Asn Gln Val
 65                  70                  75                  80 gtc ctt aca atg acc aac atg gac cct gtg gac aca gcc atg tat tac      288
Val Leu Thr Met Thr Asn Met Asp Pro Val Asp Thr Ala Met Tyr Tyr
                 85                  90                  95 tgt gta cgg aca cct tac aac tgg aac gac ggg ccc cgt ggt gct ctt      336
Cys Val Arg Thr Pro Tyr Asn Trp Asn Asp Gly Pro Arg Gly Ala Leu
            100                 105                 110 gat atc tgg ggc caa gga aca atg gtc acc gtc tct tca gga ggc gac      384
Asp Ile Trp Gly Gln Gly Thr Met Val Thr Val Ser Ser Gly Gly Asp
        115                 120                 125 agg tct gat gga ggc gct agc ggt ggt ggt gga tcc cag tct atg ttg      432
Arg Ser Asp Gly Gly Ala Ser Gly Gly Gly Gly Ser Gln Ser Met Leu
130                 135                 140 acg cag tcg ccc tca gtg tct gct gcc cca gga cag aat gtc acc atc      480
Thr Gln Ser Pro Ser Val Ser Ala Ala Pro Gly Gln Asn Val Thr Ile
145                 150                 155                 160 tcc tgc tct gga gac tac ccc aac att aga aat aat tat gta tcc tgg      528
Ser Cys Ser Gly Asp Tyr Pro Asn Ile Arg Asn Asn Tyr Val Ser Trp
                165                 170                 175 tac cag caa ctc cca gga gca gcc ccc aaa ctc ctc att tat gat aat      576
Tyr Gln Gln Leu Pro Gly Ala Ala Pro Lys Leu Leu Ile Tyr Asp Asn
            180                 185                 190 aat aag cga ccc tca ggg att cct gac cga ttc tct ggc tcc aag tct      624
Asn Lys Arg Pro Ser Gly Ile Pro Asp Arg Phe Ser Gly Ser Lys Ser
        195                 200                 205 ggc acg tca gcc acc ctg gac atc acc ggg ctc cag act ggg gac gag      672
Gly Thr Ser Ala Thr Leu Asp Ile Thr Gly Leu Gln Thr Gly Asp Glu
210                 215                 220 gcc gat tat tac tgc gga gca tgg gat agc aga ctg agt gct gtg gta      720
Ala Asp Tyr Tyr Cys Gly Ala Trp Asp Ser Arg Leu Ser Ala Val Val
225                 230                 235                 240 ttc ggc gga ggg acc aag ctg acc gtc cta gga ggc cag gcc ggc caa      768
Phe Gly Gly Gly Thr Lys Leu Thr Val Leu Gly Gly Gln Ala Gly Gln
                245                 250                 255 ggg ccc gac aaa act cac aca tgc cca ccg tgc cca gca cct gaa ggg      816
Gly Pro Asp Lys Thr His Thr Cys Pro Pro Cys Pro Ala Pro Glu Gly
            260                 265                 270 gga ccg tca gtc ttc ctc ttc ccc cca aaa ccc aag gac acc ctc atg      864
Gly Pro Ser Val Phe Leu Phe Pro Pro Lys Pro Lys Asp Thr Leu Met
        275                 280                 285 atc tcc cgg acc cct gag gtc aca tgc gtg gtg gtg gac gtg agc cac      912
Ile Ser Arg Thr Pro Glu Val Thr Cys Val Val Val Asp Val Ser His
290                 295                 300 gaa gac cct gag gtc aag ttc aac tgg tac gtg gac ggc gtg gag gtg      960
Glu Asp Pro Glu Val Lys Phe Asn Trp Tyr Val Asp Gly Val Glu Val
305                 310                 315                 320 cat aat gcc aag aca aag ccg cgg gag gag cag tac aac agc acg tac     1008
His Asn Ala Lys Thr Lys Pro Arg Glu Glu Gln Tyr Asn Ser Thr Tyr
                325                 330                 335
```

```
cgg gtg gtc agc gtc ctc acc gtc ctg cac cag gac tgg ctg aat ggc   1056
Arg Val Val Ser Val Leu Thr Val Leu His Gln Asp Trp Leu Asn Gly
            340             345                 350 aag gag tac aag tgc aag gtc tcc aac aaa gcc ctc cca gcc ccc atc   1104
Lys Glu Tyr Lys Cys Lys Val Ser Asn Lys Ala Leu Pro Ala Pro Ile
                355             360             365 gag aaa acc atc tcc aaa gcc aaa ggg cag ccc cga gaa cca cag gtg   1152
Glu Lys Thr Ile Ser Lys Ala Lys Gly Gln Pro Arg Glu Pro Gln Val
    370             375             380 tac acc ctg ccc cca tcc cgg gat gag ctg acc aag aac cag gtc agc   1200
Tyr Thr Leu Pro Pro Ser Arg Asp Glu Leu Thr Lys Asn Gln Val Ser
385             390             395             400 ctg acc tgc ctg gtc aaa ggc ttc tat ccc agc gac atc gcc gtg gag   1248
Leu Thr Cys Leu Val Lys Gly Phe Tyr Pro Ser Asp Ile Ala Val Glu
                405             410             415 tgg gag agc aat ggg cag ccg gag aac aac tac aag acc acg cct ccc   1296
Trp Glu Ser Asn Gly Gln Pro Glu Asn Asn Tyr Lys Thr Thr Pro Pro
            420             425             430 gtg ctg gac tcc gac ggc tcc ttc ttc ctc tac agc aag ctc acc gtg   1344
Val Leu Asp Ser Asp Gly Ser Phe Phe Leu Tyr Ser Lys Leu Thr Val
        435             440             445 gac aag agc agg tgg cag cag ggg aac gtc ttc tca tgc tcc gtg atg   1392
Asp Lys Ser Arg Trp Gln Gln Gly Asn Val Phe Ser Cys Ser Val Met
450             455             460 cat gag gct ctg cac aac cac tac acg cag aag agc ctc tcc ctg tct   1440
His Glu Ala Leu His Asn His Tyr Thr Gln Lys Ser Leu Ser Leu Ser
465             470             475             480 ccg ggt aaa gcg gcc gct gga ggt gga ggc agc cag ctg cag ctg cag   1488
Pro Gly Lys Ala Ala Ala Gly Gly Gly Gly Ser Gln Leu Gln Leu Gln
                485             490             495 gag tcg ggg gga ggc ttg gta cag cct gga ggg tcc ctg aga ctc tcc   1536
Glu Ser Gly Gly Gly Leu Val Gln Pro Gly Gly Ser Leu Arg Leu Ser
            500             505             510 tgt gca gcc tct gga ttc acc ttc agt agc cat agc atg aac tgg atc   1584
Cys Ala Ala Ser Gly Phe Thr Phe Ser Ser His Ser Met Asn Trp Ile
        515             520             525 cgc cag gct cca ggg aag agg ctg gag tgg gtc tca tcc att agt agt   1632
Arg Gln Ala Pro Gly Lys Arg Leu Glu Trp Val Ser Ser Ile Ser Ser
530             535             540 agt agt agt tac ata tac tac gca gac tca gtg agg ggc cga ttc acc   1680
Ser Ser Ser Tyr Ile Tyr Tyr Ala Asp Ser Val Arg Gly Arg Phe Thr
545             550             555             560 atc tcc aga gac aac gcc aag aac tca ctg tat ctg caa atg gac agc   1728
Ile Ser Arg Asp Asn Ala Lys Asn Ser Leu Tyr Leu Gln Met Asp Ser
                565             570             575 ctg aga gcc gag gac acg gca gtg tat tat tgt gcc aga tac atg gct   1776
Leu Arg Ala Glu Asp Thr Ala Val Tyr Tyr Cys Ala Arg Tyr Met Ala
            580             585             590 ggc atc tgg act ttt gat atc tgg ggc caa ggg aca atg gtc acc gtc   1824
Gly Ile Trp Thr Phe Asp Ile Trp Gly Gln Gly Thr Met Val Thr Val
        595             600             605 tct tca gga ggc ggc ggg tct ggt gga ggc gct agt ggt ggt ggc gga   1872
Ser Ser Gly Gly Gly Gly Ser Gly Gly Gly Ala Ser Gly Gly Gly Gly
610             615             620 tcc tcc tat gag ctg act cag cca ccc tca gtg tca gtg gcc cca gga   1920
Ser Ser Tyr Glu Leu Thr Gln Pro Pro Ser Val Ser Val Ala Pro Gly
625             630             635             640 aag acg gcc agc att tcc tgt ggg gga gac aac att gga agg aaa agt   1968
Lys Thr Ala Ser Ile Ser Cys Gly Gly Asp Asn Ile Gly Arg Lys Ser
                645             650             655
```

```
gtg cac tgg ttc cag cag aag cca ggc cag gcc cct gtg ctg gtc ctc      2016
Val His Trp Phe Gln Gln Lys Pro Gly Gln Ala Pro Val Leu Val Leu
            660                 665                 670 tat gat gat agc gac cgg ccc tca ggg atc cca gcg cga ttc tct ggc      2064
Tyr Asp Asp Ser Asp Arg Pro Ser Gly Ile Pro Ala Arg Phe Ser Gly
                675                 680                 685 tcc aac tct ggg aac acg gcc acc ctg acc atc agc ggg gtc gaa gcc      2112
Ser Asn Ser Gly Asn Thr Ala Thr Leu Thr Ile Ser Gly Val Glu Ala
        690                 695                 700 ggg gat gag gcc gac tat tac tgt cag gtg tgg gcc aga agt agc gat      2160
Gly Asp Glu Ala Asp Tyr Tyr Cys Gln Val Trp Ala Arg Ser Ser Asp
705                 710                 715                 720 ctt cca aat tgg gtg ttc ggc gga ggg aca aag ctg acc gtc cta gga      2208
Leu Pro Asn Trp Val Phe Gly Gly Gly Thr Lys Leu Thr Val Leu Gly
                725                 730                 735

<210> SEQ ID NO 96
<211> LENGTH: 736
<212> TYPE: PRT
<213> ORGANISM: Artificial Sequence
<220> FEATURE:
<223> OTHER INFORMATION: Synthetic Construct

<400> SEQUENCE: 96

Lys Val Thr Leu Lys Glu Ser Gly Pro Thr Leu Val Lys Pro Arg Gln
1               5                   10                  15

Thr Leu Thr Leu Thr Cys Thr Phe Ser Gly Phe Ser Leu Ser Thr Ser
            20                  25                  30

Gly Met Arg Val Ser Trp Val Arg Gln Pro Pro Gly Lys Ala Leu Glu
        35                  40                  45

Trp Ile Ala Arg Ile Asp Trp Asp Asp Lys Phe Tyr Ser Thr Ser
    50                  55                  60

Leu Lys Thr Arg Leu Thr Ile Ser Lys Asp Thr Phe Lys Asn Gln Val
65                  70                  75                  80

Val Leu Thr Met Thr Asn Met Asp Pro Val Asp Thr Ala Met Tyr Tyr
                85                  90                  95

Cys Val Arg Thr Pro Tyr Asn Trp Asn Asp Gly Pro Arg Gly Ala Leu
            100                 105                 110

Asp Ile Trp Gly Gln Gly Thr Met Val Thr Val Ser Ser Gly Gly Asp
        115                 120                 125

Arg Ser Asp Gly Gly Ala Ser Gly Gly Gly Ser Gln Ser Met Leu
130                 135                 140

Thr Gln Ser Pro Ser Val Ser Ala Ala Pro Gly Gln Asn Val Thr Ile
145                 150                 155                 160

Ser Cys Ser Gly Asp Tyr Pro Asn Ile Arg Asn Asn Tyr Val Ser Trp
                165                 170                 175

Tyr Gln Gln Leu Pro Gly Ala Ala Pro Lys Leu Leu Ile Tyr Asp Asn
            180                 185                 190

Asn Lys Arg Pro Ser Gly Ile Pro Asp Arg Phe Ser Gly Ser Lys Ser
        195                 200                 205

Gly Thr Ser Ala Thr Leu Asp Ile Thr Gly Leu Gln Thr Gly Asp Glu
    210                 215                 220

Ala Asp Tyr Tyr Cys Gly Ala Trp Asp Ser Arg Leu Ser Ala Val Val
225                 230                 235                 240

Phe Gly Gly Gly Thr Lys Leu Thr Val Leu Gly Gly Gln Ala Gly Gln
                245                 250                 255
```

```
Gly Pro Asp Lys Thr His Thr Cys Pro Pro Cys Pro Ala Pro Glu Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
    290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
    370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
        435                 440                 445

Asp Lys Ser Arg Trp Gln Gln Gly Asn Val Phe Ser Cys Ser Val Met
    450                 455                 460

His Glu Ala Leu His Asn His Tyr Thr Gln Lys Ser Leu Ser Leu Ser
465                 470                 475                 480

Pro Gly Lys Ala Ala Ala Gly Gly Gly Gly Ser Gln Leu Gln Leu Gln
                485                 490                 495

Glu Ser Gly Gly Gly Leu Val Gln Pro Gly Gly Ser Leu Arg Leu Ser
            500                 505                 510

Cys Ala Ala Ser Gly Phe Thr Phe Ser Ser His Ser Met Asn Trp Ile
        515                 520                 525

Arg Gln Ala Pro Gly Lys Arg Leu Glu Trp Val Ser Ser Ile Ser Ser
    530                 535                 540

Ser Ser Ser Tyr Ile Tyr Tyr Ala Asp Ser Val Arg Gly Arg Phe Thr
545                 550                 555                 560

Ile Ser Arg Asp Asn Ala Lys Asn Ser Leu Tyr Leu Gln Met Asp Ser
                565                 570                 575

Leu Arg Ala Glu Asp Thr Ala Val Tyr Tyr Cys Ala Arg Tyr Met Ala
            580                 585                 590

Gly Ile Trp Thr Phe Asp Ile Trp Gly Gln Gly Thr Met Val Thr Val
        595                 600                 605

Ser Ser Gly Gly Gly Gly Ser Gly Gly Gly Ala Ser Gly Gly Gly Gly
    610                 615                 620

Ser Ser Tyr Glu Leu Thr Gln Pro Pro Ser Val Ser Val Ala Pro Gly
625                 630                 635                 640

Lys Thr Ala Ser Ile Ser Cys Gly Gly Asp Asn Ile Gly Arg Lys Ser
                645                 650                 655

Val His Trp Phe Gln Gln Lys Pro Gly Gln Ala Pro Val Leu Val Leu
            660                 665                 670

Tyr Asp Asp Ser Asp Arg Pro Ser Gly Ile Pro Ala Arg Phe Ser Gly
```

675                 680                 685

Ser Asn Ser Gly Asn Thr Ala Thr Leu Thr Ile Ser Gly Val Glu Ala
    690                 695                 700

Gly Asp Glu Ala Asp Tyr Tyr Cys Gln Val Trp Ala Arg Ser Ser Asp
705                 710                 715                 720

Leu Pro Asn Trp Val Phe Gly Gly Gly Thr Lys Leu Thr Val Leu Gly
                725                 730                 735

<210> SEQ ID NO 97
<211> LENGTH: 104
<212> TYPE: PRT
<213> ORGANISM: Artificial Sequence
<220> FEATURE:
<223> OTHER INFORMATION: Synthetic Sequence

<400> SEQUENCE: 97

Lys Leu Thr Leu Lys Gly Met Ser Tyr Val Met Cys Thr Gly Ser Phe
1               5                   10                  15

Lys Leu Glu Lys Glu Val Ala Glu Thr Gln His Gly Thr Val Leu Val
                20                  25                  30

Gln Ile Lys Tyr Glu Gly Thr Asp Ala Pro Cys Lys Ile Pro Phe Ser
            35                  40                  45

Thr Gln Asp Glu Lys Gly Val Thr Gln Asn Gly Arg Leu Ile Thr Ala
        50                  55                  60

Asn Pro Ile Val Thr Asp Lys Glu Lys Pro Val Asn Ile Glu Ala Glu
65                  70                  75                  80

Pro Pro Phe Gly Glu Ser Tyr Ile Val Ile Gly Ala Gly Glu Lys Ala
                85                  90                  95

Leu Lys Leu Ser Trp Phe Lys Lys
            100

<210> SEQ ID NO 98
<211> LENGTH: 104
<212> TYPE: PRT
<213> ORGANISM: Artificial Sequence
<220> FEATURE:
<223> OTHER INFORMATION: Synthetic Sequence

<400> SEQUENCE: 98

Lys Leu Gln Leu Lys Gly Met Ser Tyr Ser Met Cys Thr Gly Lys Phe
1               5                   10                  15

Lys Val Val Lys Glu Ile Ala Glu Thr Gln His Gly Thr Ile Val Ile
                20                  25                  30

Arg Val Gln Tyr Glu Gly Asp Gly Ser Pro Cys Lys Ile Pro Phe Glu
            35                  40                  45

Ile Met Asp Leu Glu Lys Arg His Val Leu Gly Arg Leu Ile Thr Val
        50                  55                  60

Asn Pro Ile Val Thr Glu Lys Asp Ser Pro Val Asn Ile Glu Ala Glu
65                  70                  75                  80

Pro Pro Phe Gly Asp Ser Tyr Ile Ile Ile Gly Val Glu Pro Gly Gln
                85                  90                  95

Leu Lys Leu Asn Trp Phe Lys Lys
            100

<210> SEQ ID NO 99
<211> LENGTH: 104
<212> TYPE: PRT
<213> ORGANISM: Artificial Sequence
<220> FEATURE:

<223> OTHER INFORMATION: Synthetic Sequence

<400> SEQUENCE: 99

Lys Leu Glu Leu Lys Gly Met Ser Tyr Ala Met Cys Leu Asn Thr Phe
1               5                   10                  15

Val Leu Lys Lys Glu Val Ser Glu Thr Gln His Gly Thr Ile Leu Ile
            20                  25                  30

Lys Val Glu Tyr Lys Gly Glu Asp Ala Pro Cys Lys Ile Pro Phe Ser
        35                  40                  45

Thr Glu Asp Gly Gln Gly Lys Ala His Asn Gly Arg Leu Ile Thr Ala
    50                  55                  60

Asn Pro Val Val Thr Lys Lys Glu Glu Pro Val Asn Ile Glu Ala Glu
65                  70                  75                  80

Pro Pro Phe Gly Glu Ser Asn Ile Val Ile Gly Ile Gly Asp Lys Ala
                85                  90                  95

Leu Lys Ile Asn Trp Tyr Lys Lys
            100

<210> SEQ ID NO 100
<211> LENGTH: 104
<212> TYPE: PRT
<213> ORGANISM: Artificial Sequence
<220> FEATURE:
<223> OTHER INFORMATION: Synthetic Sequence

<400> SEQUENCE: 100

Lys Leu Arg Ile Lys Gly Met Ser Tyr Thr Met Cys Ser Gly Lys Phe
1               5                   10                  15

Ser Ile Asp Lys Glu Met Ala Glu Thr Gln His Gly Thr Thr Val Val
            20                  25                  30

Lys Val Lys Tyr Glu Gly Ala Gly Ala Pro Cys Lys Val Pro Ile Glu
        35                  40                  45

Ile Arg Asp Val Asn Lys Glu Lys Val Val Gly Arg Ile Ile Ser Ser
    50                  55                  60

Thr Pro Leu Ala Glu Asn Thr Asn Ser Val Thr Asn Ile Glu Leu Glu
65                  70                  75                  80

Pro Pro Phe Gly Asp Ser Tyr Ile Val Ile Gly Val Gly Asn Ser Ala
                85                  90                  95

Leu Thr Leu His Trp Phe Arg Lys
            100

<210> SEQ ID NO 101
<211> LENGTH: 681
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(681)

<400> SEQUENCE: 101 gac aaa act cac aca tgc cca ccg tgc cca gca cct gaa ctc ctg ggg         48
Asp Lys Thr His Thr Cys Pro Pro Cys Pro Ala Pro Glu Leu Leu Gly
1               5                   10                  15 gga ccg tca gtc ttc ctc ttc ccc cca aaa ccc aag gac acc ctc atg         96
Gly Pro Ser Val Phe Leu Phe Pro Pro Lys Pro Lys Asp Thr Leu Met
            20                  25                  30 atc tcc cgg acc cct gag gtc aca tgc gtg gtg gtg gac gtg agc cac        144
Ile Ser Arg Thr Pro Glu Val Thr Cys Val Val Val Asp Val Ser His

```
gaa gac cct gag gtc aag ttc aac tgg tac gtg gac ggc gtg gag gtg      192
Glu Asp Pro Glu Val Lys Phe Asn Trp Tyr Val Asp Gly Val Glu Val
    50                  55                  60 cat aat gcc aag aca aag ccg cgg gag gag cag tac aac agc acg tac      240
His Asn Ala Lys Thr Lys Pro Arg Glu Glu Gln Tyr Asn Ser Thr Tyr
65                  70                  75                  80 cgg gtg gtc agc gtc ctc acc gtc ctg cac cag gac tgg ctg aat ggc      288
Arg Val Val Ser Val Leu Thr Val Leu His Gln Asp Trp Leu Asn Gly
                85                  90                  95 aag gag tac aag tgc aag gtc tcc aac aaa gcc ctc cca gcc ccc atc      336
Lys Glu Tyr Lys Cys Lys Val Ser Asn Lys Ala Leu Pro Ala Pro Ile
            100                 105                 110 gag aaa acc atc tcc aaa gcc aaa ggg cag ccc cga gaa cca cag gtg      384
Glu Lys Thr Ile Ser Lys Ala Lys Gly Gln Pro Arg Glu Pro Gln Val
        115                 120                 125 tac acc ctg ccc cca tcc cgg gat gag ctg acc aag aac cag gtc agc      432
Tyr Thr Leu Pro Pro Ser Arg Asp Glu Leu Thr Lys Asn Gln Val Ser
    130                 135                 140 ctg acc tgc ctg gtc aaa ggc ttc tat ccc agc gac atc gcc gtg gag      480
Leu Thr Cys Leu Val Lys Gly Phe Tyr Pro Ser Asp Ile Ala Val Glu
145                 150                 155                 160 tgg gag agc aat ggg cag ccg gag aac aac tac aag acc acg cct ccc      528
Trp Glu Ser Asn Gly Gln Pro Glu Asn Asn Tyr Lys Thr Thr Pro Pro
                165                 170                 175 gtg ctg gac tcc gac ggc tcc ttc ttc ctc tac agc aag ctc acc gtg      576
Val Leu Asp Ser Asp Gly Ser Phe Phe Leu Tyr Ser Lys Leu Thr Val
            180                 185                 190 gac aag agc agg tgg cag cag ggg aac gtc ttc tca tgc tcc gtg atg      624
Asp Lys Ser Arg Trp Gln Gln Gly Asn Val Phe Ser Cys Ser Val Met
        195                 200                 205 cat gag gct ctg cac aac cac tac acg cag aag agc ctc tcc ctg tct      672
His Glu Ala Leu His Asn His Tyr Thr Gln Lys Ser Leu Ser Leu Ser
    210                 215                 220 ccg ggt aaa                                                          681
Pro Gly Lys
225

<210> SEQ ID NO 102
<211> LENGTH: 227
<212> TYPE: PRT
<213> ORGANISM: Artificial Sequence
<220> FEATURE:
<223> OTHER INFORMATION: Synthetic Construct

<400> SEQUENCE: 102

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
```

```
                    100                 105                 110
Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 103
<211> LENGTH: 675
<212> TYPE: DNA
<213> ORGANISM: Artificial Sequence
<220> FEATURE:
<223> OTHER INFORMATION: Synthetic Sequence
<220> FEATURE:
<221> NAME/KEY: CDS
<222> LOCATION: (1)..(675)

<400> SEQUENCE: 103 gac aaa act cac aca tgc cca ccg tgc cca gca cct gaa ggg gga ccg      48
Asp Lys Thr His Thr Cys Pro Pro Cys Pro Ala Pro Glu Gly Gly Pro
1               5                   10                  15 tca gtc ttc ctc ttc ccc cca aaa ccc aag gac acc ctc atg atc tcc     96
Ser Val Phe Leu Phe Pro Pro Lys Pro Lys Asp Thr Leu Met Ile Ser
            20                  25                  30 cgg acc cct gag gtc aca tgc gtg gtg gtg gac gtg agc cac gaa gac    144
Arg Thr Pro Glu Val Thr Cys Val Val Val Asp Val Ser His Glu Asp
        35                  40                  45 cct gag gtc aag ttc aac tgg tac gtg gac ggc gtg gag gtg cat aat    192
Pro Glu Val Lys Phe Asn Trp Tyr Val Asp Gly Val Glu Val His Asn
    50                  55                  60 gcc aag aca aag ccg cgg gag gag cag tac aac agc acg tac cgg gtg    240
Ala Lys Thr Lys Pro Arg Glu Glu Gln Tyr Asn Ser Thr Tyr Arg Val
65                  70                  75                  80 gtc agc gtc ctc acc gtc ctg cac cag gac tgg ctg aat ggc aag gag    288
Val Ser Val Leu Thr Val Leu His Gln Asp Trp Leu Asn Gly Lys Glu
                85                  90                  95 tac aag tgc aag gtc tcc aac aaa gcc ctc cca gcc ccc atc gag aaa    336
Tyr Lys Cys Lys Val Ser Asn Lys Ala Leu Pro Ala Pro Ile Glu Lys
            100                 105                 110 acc atc tcc aaa gcc aaa ggg cag ccc cga gaa cca cag gtg tac acc    384
Thr Ile Ser Lys Ala Lys Gly Gln Pro Arg Glu Pro Gln Val Tyr Thr
        115                 120                 125 ctg ccc cca tcc cgg gat gag ctg acc aag aac cag gtc agc ctg acc    432
Leu Pro Pro Ser Arg Asp Glu Leu Thr Lys Asn Gln Val Ser Leu Thr
    130                 135                 140 tgc ctg gtc aaa ggc ttc tat ccc agc gac atc gcc gtg gag tgg gag    480
Cys Leu Val Lys Gly Phe Tyr Pro Ser Asp Ile Ala Val Glu Trp Glu
145                 150                 155                 160
```

```
agc aat ggg cag ccg gag aac aac tac aag acc acg cct ccc gtg ctg      528
Ser Asn Gly Gln Pro Glu Asn Asn Tyr Lys Thr Thr Pro Pro Val Leu
            165                 170                 175 gac tcc gac ggc tcc ttc ttc ctc tac agc aag ctc acc gtg gac aag      576
Asp Ser Asp Gly Ser Phe Phe Leu Tyr Ser Lys Leu Thr Val Asp Lys
        180                 185                 190 agc agg tgg cag cag ggg aac gtc ttc tca tgc tcc gtg atg cat gag      624
Ser Arg Trp Gln Gln Gly Asn Val Phe Ser Cys Ser Val Met His Glu
    195                 200                 205 gct ctg cac aac cac tac acg cag aag agc ctc tcc ctg tct ccg ggt      672
Ala Leu His Asn His Tyr Thr Gln Lys Ser Leu Ser Leu Ser Pro Gly
210                 215                 220 aaa                                                                   675
Lys
225

<210> SEQ ID NO 104
<211> LENGTH: 225
<212> TYPE: PRT
<213> ORGANISM: Artificial Sequence
<220> FEATURE:
<223> OTHER INFORMATION: Synthetic Construct

<400> SEQUENCE: 104

Asp Lys Thr His Thr Cys Pro Pro Cys Pro Ala Pro Glu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Asp Glu Leu Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 105
<211> LENGTH: 7
<212> TYPE: PRT
```

```
<213> ORGANISM: Artificial Sequence
<220> FEATURE:
<223> OTHER INFORMATION: Synthetic Sequence

<400> SEQUENCE: 105

Gly Gln Ala Gly Gln Gly Pro
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 106

Ala Ala Ala Gly Gly Gly Gly Ser
1               5
```